(12) United States Patent
Wassell et al.

(10) Patent No.: US 7,718,408 B2
(45) Date of Patent: May 18, 2010

(54) METHOD

(75) Inventors: Paul Wassell, Århus (DK); Jørn Borch Søe, Tilst (DK); Jørn Dalgaard Mikkelsen, Hvidovre (DK); Anna Cecilie Jentoft Kristensen, Århus (DK)

(73) Assignee: Danisco A/S, Copenhagen (DK)

(*) Notice: Subject to any disclaimer, the term of this patent is extended or adjusted under 35 U.S.C. 154(b) by 1207 days.

(21) Appl. No.: 10/898,775

(22) Filed: Jul. 26, 2004

(65) Prior Publication Data

US 2005/0142647 A1 Jun. 30, 2005

(30) Foreign Application Priority Data

| Dec. 24, 2003 | (GB) | ................................ 0330016.7 |
| Jan. 15, 2004 | (WO) | ................. PCT/IB2004/000655 |
| Jul. 16, 2004 | (GB) | ................................ 0416023.0 |

(51) Int. Cl.
*C12P 7/64* (2006.01)
*C12Q 1/48* (2006.01)
*C12N 9/10* (2006.01)
*C12P 21/06* (2006.01)
*C07H 21/04* (2006.01)

(52) U.S. Cl. .................. 435/134; 435/15; 435/193; 536/23.2

(58) Field of Classification Search ................. 435/134, 435/193, 69.1, 252.3; 426/35, 601; 536/23.2
See application file for complete search history.

(56) References Cited

U.S. PATENT DOCUMENTS

| 2,888,385 | A | 5/1959 | Grandel |
| 3,260,606 | A | 7/1966 | Azuma |
| 3,368,903 | A | 2/1968 | Johnson |
| 3,520,702 | A | 7/1970 | Menzi |
| 3,634,195 | A | 1/1972 | Melaschouris |
| 3,652,397 | A | 3/1972 | Pardun |
| 3,677,902 | A | 7/1972 | Aunstrup |
| 3,852,260 | A | 12/1974 | Knutsen |
| 3,973,042 | A | 8/1976 | Kosikowski |
| 4,034,124 | A | 7/1977 | Van Dam |
| 4,065,580 | A | 12/1977 | Feldman |
| 4,160,848 | A | 7/1979 | Vidal |
| 4,202,941 | A | 5/1980 | Terada |
| 4,399,218 | A | 8/1983 | Gauhl |
| 4,567,046 | A | 1/1986 | Inoue |
| 4,683,202 | A | 7/1987 | Mullis |
| 4,689,297 | A | 8/1987 | Good |
| 4,707,291 | A | 11/1987 | Thom |
| 4,707,364 | A | 11/1987 | Barach |
| 4,708,876 | A | 11/1987 | Yokoyama |
| 4,798,793 | A | 1/1989 | Eigtved |
| 4,808,417 | A | 2/1989 | Masuda |
| 4,810,414 | A | 3/1989 | Huge-Jensen |
| 4,814,331 | A | 3/1989 | Kerkenaar |
| 4,818,695 | A | 4/1989 | Eigtved |
| 4,826,767 | A | 5/1989 | Hansen |
| 4,865,866 | A | 9/1989 | Moore |
| 4,904,483 | A | 2/1990 | Christensen |
| 4,916,064 | A | 4/1990 | Derez |
| 5,112,624 | A | 5/1992 | Johna |
| 5,213,968 | A | 5/1993 | Castle |
| 5,219,733 | A | 6/1993 | Myojo |
| 5,219,744 | A | 6/1993 | Kurashige |
| 5,232,846 | A | 8/1993 | Takeda |
| 5,264,367 | A | 11/1993 | Aalrust |
| 5,273,898 | A | 12/1993 | Ishii |
| 5,288,619 | A | 2/1994 | Brown |
| 5,290,694 | A | 3/1994 | Nakanishi |
| 5,378,623 | A | 1/1995 | Hattori |
| 5,523,237 | A | 6/1996 | Budtz |
| 5,536,661 | A | 7/1996 | Boel |
| 5,558,781 | A | 9/1996 | Buchold |

(Continued)

FOREIGN PATENT DOCUMENTS

AR 331094 2/1995

(Continued)

OTHER PUBLICATIONS

Brumlik, M., Identification of the Catalytic Triad of the Lipase/Acyltransferase from *Aeromonas hydrophila* (1996) Journal of Bacteriology vol. 178(7): 2060-2064.

(Continued)

*Primary Examiner*—Richard Hutson
*Assistant Examiner*—Iqbal H Chowdhury
(74) *Attorney, Agent, or Firm*—Frommer Lawrence & Haug LLP; Thomas J. Kowalski; Smitha B. Uthaman

(57) ABSTRACT

The present application provides a method of reducing and/or removing diglyceride from an edible oil, comprising admixing an edible oil with an acyl acceptor substrate and a diglyceride: glycerol acyltransferase, wherein the diglyceride:glycerol acyltransferase is characterized as an enzyme which in an edible oil is capable of transferring an acyl group from a diglyceride to glycerol. The diglyceride:glycerol acyltransferase can comprise the amino acid sequence motif GDSX. The present invention also relates to the use of a diglyceride:glycerol acyltransferase in the manufacture of an edible oil, for reducing and/or removing diglyceride from said edible oil and to the use of said enzyme in the manufacture of a foodstuff comprising an edible oil for improving the crystallization properties of said foodstuff.

12 Claims, 44 Drawing Sheets

U.S. PATENT DOCUMENTS

| | | |
|---|---|---|
| 5,650,188 A | 7/1997 | Gaubert |
| 5,677,160 A | 10/1997 | Oester |
| 5,695,802 A | 12/1997 | Van Den Ouweland |
| 5,763,383 A | 6/1998 | Hashida |
| 5,766,912 A | 6/1998 | Boel |
| 5,776,741 A | 7/1998 | Pedersen |
| 5,814,501 A | 9/1998 | Becker |
| 5,821,102 A | 10/1998 | Berka |
| 5,827,719 A | 10/1998 | Sandal |
| 5,830,736 A | 11/1998 | Oxenboll |
| 5,834,280 A | 11/1998 | Oxenboll |
| 5,856,163 A | 1/1999 | Hashida |
| 5,863,759 A | 1/1999 | Boel |
| 5,869,438 A | 2/1999 | Svendsen |
| 5,874,558 A | 2/1999 | Boel |
| 5,879,920 A | 3/1999 | Dale |
| 5,892,013 A | 4/1999 | Svendsen |
| 5,914,306 A | 6/1999 | Svendsen |
| 5,916,619 A | 6/1999 | Miyazaki |
| 5,919,746 A | 7/1999 | Hirayama |
| 5,929,017 A | 7/1999 | Gormsen |
| 5,965,384 A | 10/1999 | Boel |
| 5,965,422 A | 10/1999 | Loffler |
| 5,976,855 A | 11/1999 | Svendsen |
| 5,989,599 A | 11/1999 | Chmiel |
| 5,990,069 A | 11/1999 | Andre |
| 6,001,586 A | 12/1999 | Schellenberger |
| 6,001,640 A | 12/1999 | Loeffler |
| 6,020,180 A | 2/2000 | Svendsen |
| 6,066,482 A | 5/2000 | Steffens |
| 6,074,863 A | 6/2000 | Svendsen |
| 6,103,505 A | 8/2000 | Clausen |
| 6,110,508 A | 8/2000 | Olesen |
| 6,140,094 A | 10/2000 | Loffler |
| 6,143,543 A | 11/2000 | Michelsen |
| 6,143,545 A | 11/2000 | Clausen |
| 6,146,869 A | 11/2000 | Harris |
| 6,156,548 A | 12/2000 | Christensen |
| 6,180,406 B1 | 1/2001 | Stemmer |
| 6,254,645 B1 | 7/2001 | Kellis |
| 6,344,328 B1 | 2/2002 | Short |
| 6,350,604 B1 | 2/2002 | Hirayama |
| 6,358,543 B1 | 3/2002 | Soe |
| 6,361,974 B1 | 3/2002 | Short |
| 6,365,204 B1 | 4/2002 | Spendler |
| 6,432,898 B1 | 8/2002 | Rey |
| 6,495,357 B1 | 12/2002 | Fuglsang |
| 6,506,588 B2 | 1/2003 | Tsutsumi |
| 6,509,182 B2 | 1/2003 | Tsutsumi |
| 6,511,837 B2 | 1/2003 | Tsutsumi |
| 6,514,739 B1 | 2/2003 | Udagawa |
| 6,558,715 B1 | 5/2003 | Rey |
| 6,582,942 B1 | 6/2003 | Christensen |
| 6,624,129 B1 | 9/2003 | Borch |
| 6,645,749 B2 | 11/2003 | Vind |
| 6,682,922 B2 | 1/2004 | Berka |
| 6,686,189 B2 | 2/2004 | Rey |
| 6,726,942 B2 | 4/2004 | Søe et al. |
| 6,730,346 B2 | 5/2004 | Rey |
| 6,815,190 B1 | 11/2004 | Abo |
| 6,852,346 B2 | 2/2005 | Søe |
| 6,936,289 B2 | 8/2005 | Olsen et al. |
| 6,967,035 B2 | 11/2005 | Bojsen et al. |
| 7,226,771 B2 | 6/2007 | Gramatikova et al. |
| 2002/0098536 A1 | 7/2002 | Norinobu |
| 2002/0110854 A1 | 8/2002 | Tsutsumi |
| 2002/0142434 A1 | 10/2002 | Tsutsumi |
| 2002/0168746 A1 | 11/2002 | Tsutsumi |
| 2003/0003561 A1 | 1/2003 | Vind |
| 2003/0028923 A1 | 2/2003 | Lardizabal et al. |
| 2003/0040450 A1 | 2/2003 | Rey |
| 2003/0074695 A1 | 4/2003 | Farese, Jr. et al. |
| 2003/0100092 A1 | 5/2003 | Berka |
| 2003/0119164 A1 | 6/2003 | Udagawa |
| 2003/0148495 A1 | 8/2003 | Hastrup |
| 2003/0180418 A1 | 9/2003 | Rey |
| 2003/0185939 A1 | 10/2003 | Nielsen |
| 2003/0215544 A1 | 11/2003 | Nielsen |
| 2004/0005399 A1 | 1/2004 | Chakrabarti |
| 2004/0142441 A1 | 7/2004 | Weiss et al. |
| 2004/0235106 A1 | 11/2004 | Kapeller-Libermann |
| 2005/0059130 A1 | 3/2005 | Bojsen |
| 2005/0059131 A1 | 3/2005 | Bisgard-Frantzen |
| 2005/0118697 A1 | 6/2005 | Budolfsen |
| 2005/0142647 A1 | 6/2005 | Wassell |
| 2006/0040357 A1 | 2/2006 | Bandaru et al. |

FOREIGN PATENT DOCUMENTS

| | | |
|---|---|---|
| AR | 249546 | 12/1996 |
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 754470 | 11/1999 |
| BR | 8404421-7 | 4/1984 |
| CA | 1270781 | 6/1990 |
| CA | 2012723 | 9/1990 |
| CA | 2134597 | 10/1994 |
| CA | 2224143 | 12/1996 |
| CA | 2 403 025 | 4/2004 |
| CN | 036151 | 2/2002 |
| CN | 172509 | 6/2003 |
| CN | 97181706 | 10/2003 |
| DE | 2817087 | 11/1978 |
| DE | 19620649 | 11/1997 |
| DE | 69129988 | 3/1999 |
| DE | 69330066 | 10/2001 |
| DE | 69527835 | 4/2003 |
| DE | 69528070 | 6/2003 |
| DE | 69333065 | 7/2003 |
| DE | 69904161 | 7/2003 |
| DE | 69716711 | 9/2003 |
| DE | 69531538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |
| DK | PA1096/95 | 9/1995 |
| DK | 152763 | 3/1998 |
| DK | PA0543/98 | 4/1998 |
| DK | PA199801572 | 11/1998 |
| DK | PA5677000 | 12/1998 |
| DK | PA199801604 | 12/1998 |
| DK | PA199901736 | 12/1999 |
| DK | PA200000989 | 6/2000 |
| DK | PA200000991 | 6/2000 |
| DK | PA200100285 | 2/2001 |
| DK | PA200100843 | 5/2001 |
| DK | EP659049 | 6/2001 |
| DK | EP0784674 | 11/2002 |
| DK | EP0869167 | 1/2003 |
| DK | EP1073339 | 1/2003 |
| DK | PA200300634 | 4/2003 |
| DK | 5559215 | 7/2003 |
| DK | EP0746608 | 10/2003 |
| DK | EP1042458 | 3/2004 |
| EP | 0064855 | 11/1982 |
| EP | 0010296 | 12/1982 |
| EP | 0109244 | 5/1984 |
| EP | 0130064 | 1/1985 |

| | | | | | |
|---|---|---|---|---|---|
| EP | 0140542 | 5/1985 | EP | 0977869 | 7/2004 |
| EP | 0167309 | 1/1986 | EP | 0743017 | 9/2004 |
| EP | 0171995 | 2/1986 | EP | 0675949 | 10/2004 |
| EP | 0205208 | 12/1986 | EP | 0880590 | 10/2004 |
| EP | 0206390 | 12/1986 | EP | 0897423 | 10/2004 |
| EP | 0 257 388 A1 | 3/1988 | EP | 1466980 | 10/2004 |
| EP | 0257388 | 3/1988 | EP | 0839186 | 11/2004 |
| EP | 0260573 | 3/1988 | EP | 1162889 | 2/2005 |
| EP | 0334462 | 9/1989 | EP | 1559788 | 8/2005 |
| EP | 0195311 | 6/1990 | EP | 1363506 | 11/2005 |
| EP | 0375102 | 6/1990 | EP | 1 624 047 A1 | 2/2006 |
| EP | 0426211 | 5/1991 | EP | 1 624 047 B1 | 10/2006 |
| EP | 0445692 | 9/1991 | ES | 535608 | 9/1984 |
| EP | 0449375 | 10/1991 | ES | 535602 | 10/1984 |
| EP | 0468731 | 1/1992 | ES | 535609 | 3/1985 |
| EP | 0513709 | 11/1992 | GB | 1086550 | 10/1967 |
| EP | 0542351 | 5/1993 | GB | 1442418 | 7/1976 |
| EP | 0 558 112 A1 | 9/1993 | GB | 1577933 | 10/1980 |
| EP | 0558112 | 9/1993 | GB | 2 264 429 | 9/1993 |
| EP | 0258068 | 11/1993 | GB | 0028701.1 | 11/2000 |
| EP | 0238023 | 12/1993 | GB | 2358784 | 8/2001 |
| EP | 0575133 | 12/1993 | GB | 0301117.8 | 1/2003 |
| EP | 0580252 | 1/1994 | GB | 0301118.6 | 1/2003 |
| EP | 0258068 | 8/1994 | GB | 0301119.4 | 1/2003 |
| EP | 0622446 | 11/1994 | GB | 0301120.2 | 1/2003 |
| EP | 0 652 289 A1 | 5/1995 | GB | 0301121.0 | 1/2003 |
| EP | 0652289 | 5/1995 | GB | 0301122.8 | 1/2003 |
| EP | 0654527 | 5/1995 | GB | 2379165 | 3/2003 |
| EP | 0396162 | 9/1995 | GB | 2267033 | 11/2003 |
| EP | 0585988 | 3/1996 | GB | 0330016.7 | 12/2003 |
| EP | 0721981 | 7/1996 | JP | 59183881 | 4/1960 |
| EP | 0776604 | 6/1997 | JP | 48016612 | 12/1970 |
| EP | 0531104 | 8/1997 | JP | 54-76892 | 6/1979 |
| EP | 0808903 | 11/1997 | JP | 55131340 | 10/1980 |
| EP | 0682116 | 12/1997 | JP | 60078529 | 5/1985 |
| EP | 0812910 | 12/1997 | JP | 62118883 | 11/1985 |
| EP | 0305216 | 3/1998 | JP | 63042691 | 8/1986 |
| EP | 0847701 | 6/1998 | JP | 62061590 | 3/1987 |
| EP | 0548228 | 8/1998 | JP | 62285749 | 12/1987 |
| EP | 0702712 | 12/1998 | JP | 10203974 | 8/1988 |
| EP | 0882797 | 12/1998 | JP | 1252294 | 10/1989 |
| EP | 0897667 | 2/1999 | JP | 2-49593 | 2/1990 |
| EP | 0913092 | 5/1999 | JP | 2-153997 | 6/1990 |
| EP | 0913468 | 5/1999 | JP | 04075592 | 3/1992 |
| EP | 0321811 | 12/1999 | JP | 6014773 | 3/1992 |
| EP | 1131416 | 6/2000 | JP | 4121186 | 4/1992 |
| EP | 0739985 | 11/2000 | JP | 15626492 | 6/1992 |
| EP | 1057415 | 12/2000 | JP | 04200339 | 7/1992 |
| EP | 1071734 | 1/2001 | JP | 4300839 | 10/1992 |
| EP | 1073339 | 2/2001 | JP | 4327536 | 11/1992 |
| EP | 0659049 | 3/2001 | JP | 04 370055 | 12/1992 |
| EP | 1103606 | 5/2001 | JP | 5211852 | 8/1993 |
| EP | 1108360 | 6/2001 | JP | 6345800 | 12/1994 |
| EP | 1138763 | 10/2001 | JP | 07 079687 | 3/1995 |
| EP | 1145637 | 10/2001 | JP | 8268882 | 4/1995 |
| EP | 0191217 | 2/2002 | JP | 7231788 | 9/1995 |
| EP | 0869167 | 2/2002 | JP | 7330794 | 12/1995 |
| EP | 1193314 | 4/2002 | JP | 8143457 | 6/1996 |
| EP | 0746618 | 8/2002 | JP | 8266213 | 10/1996 |
| EP | 1233676 | 8/2002 | JP | 9040689 | 2/1997 |
| EP | 0648263 | 9/2002 | JP | 10155493 | 6/1998 |
| EP | 0784674 | 9/2002 | JP | 10155493 A | 6/1998 |
| EP | 1275711 | 1/2003 | JP | 11290078 | 10/1999 |
| EP | 1285969 | 2/2003 | JP | 2000226335 | 8/2000 |
| EP | 1298205 | 4/2003 | JP | 3553958 | 5/2004 |
| EP | 0635053 | 6/2003 | KR | 93-700773 | 3/1993 |
| EP | 0675944 | 6/2003 | KR | 94-10252 | 10/1994 |
| EP | 0817838 | 6/2003 | KR | 95-700043 | 1/1995 |
| EP | 1280919 | 6/2003 | KR | 95-702583 | 6/1995 |
| EP | 0746608 | 8/2003 | KR | 96-704602 | 8/1996 |
| EP | 0851913 | 5/2004 | KR | 2001-7012115 | 9/2001 |
| EP | 1262562 | 6/2004 | KR | 2003-7008997 | 10/2003 |
| EP | 1433852 | 6/2004 | NL | 0784674 | 12/2002 |

| | | | | | |
|---|---|---|---|---|---|
| NL | 0869167 | 1/2003 | WO | 00/05396 | 2/2000 |
| NL | 1073339 | 2/2003 | WO | WO 00/05396 | 2/2000 |
| NL | 0746608 | 11/2003 | WO | 00/28044 | 5/2000 |
| RU | 2140751 | 6/1997 | WO | 00/32758 | 6/2000 |
| RU | 2235775 | 11/1999 | WO | 00/34450 | 6/2000 |
| RU | 2001117497 | 6/2001 | WO | 00/36114 | 6/2000 |
| SE | 9802548 | 7/1998 | WO | WO 00/36114 | 6/2000 |
| TR | 200101551 | 12/1999 | WO | 00/43036 | 7/2000 |
| WO | 88/02775 | 4/1988 | WO | 00/49164 | 8/2000 |
| WO | 88/03365 | 5/1988 | WO | 00/58517 | 10/2000 |
| WO | 98/50532 | 11/1988 | WO | 00/59307 | 10/2000 |
| WO | 89/01969 | 3/1989 | WO | 00/60063 | 10/2000 |
| WO | 89/06803 | 7/1989 | WO | 00/61771 | 10/2000 |
| WO | 91/00920 | 1/1991 | WO | 00/71808 | 11/2000 |
| WO | 91/06661 | 5/1991 | WO | 00/75295 | 12/2000 |
| WO | 91/14772 | 10/1991 | WO | 01/16308 | 3/2001 |
| WO | 92/05249 | 4/1992 | WO | 01/27251 | 4/2001 |
| WO | 92/14830 | 9/1992 | WO | 01/29222 | 4/2001 |
| WO | 92/18645 | 10/1992 | WO | 01/34835 | 5/2001 |
| WO | 93/01285 | 1/1993 | WO | 01/39602 | 6/2001 |
| WO | 93/11249 | 6/1993 | WO | 01/42433 | 6/2001 |
| WO | 93/12812 | 7/1993 | WO | 01/47363 | 7/2001 |
| WO | 94/01541 | 1/1994 | WO | 01/66711 | 9/2001 |
| WO | 94/04035 | 3/1994 | WO | 01/78524 | 10/2001 |
| WO | 94/14940 | 7/1994 | WO | 01/83559 | 11/2001 |
| WO | 94/14951 | 7/1994 | WO | 01/83770 | 11/2001 |
| WO | 94/26883 | 11/1994 | WO | 01/92502 | 12/2001 |
| WO | 95/06720 | 3/1995 | WO | 02/00852 | 1/2002 |
| WO | 95/09909 | 4/1995 | WO | 02/03805 | 1/2002 |
| WO | 95/22606 | 8/1995 | WO | 02/06457 | 1/2002 |
| WO | 95/22615 | 8/1995 | WO | 02/14490 | 2/2002 |
| WO | 95/22625 | 8/1995 | WO | 02/24881 | 3/2002 |
| WO | 95/29996 | 11/1995 | WO | 02/30207 | 4/2002 |
| WO | 95/30744 | 11/1995 | WO | 02/055679 | 7/2002 |
| WO | 96/09772 | 4/1996 | WO | 02/062973 | 8/2002 |
| WO | 96/13578 | 5/1996 | WO | 02/065854 | 8/2002 |
| WO | 96/13579 | 5/1996 | WO | 02/066622 | 8/2002 |
| WO | 96/13580 | 5/1996 | WO | 02/094123 | 11/2002 |
| WO | 96/27002 | 9/1996 | WO | WO 200306644 | 1/2003 |
| WO | 96/28542 | 9/1996 | WO | 03/020923 | 3/2003 |
| WO | 96/30502 | 10/1996 | WO | 03/040091 | 5/2003 |
| WO | 96/32472 | 10/1996 | WO | 03/060112 | 7/2003 |
| WO | 96/39851 | 12/1996 | WO | 03/070013 | 8/2003 |
| WO | 97/04079 | 2/1997 | WO | 03/089260 | 10/2003 |
| WO | 97/05219 | 2/1997 | WO | WO 03/089620 | 10/2003 |
| WO | 97/07202 | 2/1997 | WO | 03/097825 | 11/2003 |
| WO | 97/07205 | 2/1997 | WO | 03/099016 | 12/2003 |
| WO | 97/11083 | 3/1997 | WO | 03/100044 | 12/2003 |
| WO | 97/14713 | 4/1997 | WO | 03/102118 | 12/2003 |
| WO | 97/27237 | 7/1997 | WO | 2003/100044 | 12/2003 |
| WO | 97/27276 | 7/1997 | WO | 2004/004467 | 1/2004 |
| WO | 97/41212 | 11/1997 | WO | 2004/018660 | 3/2004 |
| WO | 97/41735 | 11/1997 | WO | 2004/053039 | 6/2004 |
| WO | 97/41736 | 11/1997 | WO | 2004/053152 | 6/2004 |
| WO | 98/08939 | 3/1998 | WO | 2004059075 | 7/2004 |
| WO | 98/14594 | 4/1998 | WO | 2004/064537 | 8/2004 |
| WO | 98/18912 | 5/1998 | WO | 2004/064987 | 8/2004 |
| WO | 98/26057 | 6/1998 | WO | WO 2004/064537 | 8/2004 |
| WO | 98/31790 | 7/1998 | WO | 2004/097012 | 11/2004 |
| WO | WO 98 31790 | 7/1998 | WO | 2004/111216 | 12/2004 |
| WO | 98/41623 | 9/1998 | WO | 2005/003339 | 1/2005 |
| WO | 98/44804 | 10/1998 | WO | 2005/005977 | 1/2005 |
| WO | 98/45453 | 10/1998 | WO | 2005/056782 | 6/2005 |
| WO | 98/51163 | 11/1998 | WO | 2005/066347 | 7/2005 |
| WO | 98/59028 | 12/1998 | WO | 2005/066351 | 7/2005 |
| WO | 99/33964 | 7/1999 | WO | WO 2005069762 | 8/2005 |
| WO | 99/34011 | 7/1999 | WO | 2005/080540 | 9/2005 |
| WO | 99/37782 | 7/1999 | WO | 2005/087918 | 9/2005 |
| WO | 99/42566 | 8/1999 | WO | 2006/008508 | 1/2006 |
| WO | 99/50399 | 10/1999 | WO | 2006/008653 | 1/2006 |
| WO | 99/53001 | 10/1999 | WO | WO 200618205 | 2/2006 |
| WO | 99/53769 | 10/1999 | WO | 2006/032279 | 3/2006 |
| WO | 99/55883 | 11/1999 | | | |

| WO | WO 2008 094847 | 8/2008 |

OTHER PUBLICATIONS

Upton, et al.; "A New Family of Lipolytic Enzymes"; Tibs Trends in Biochemical Science, Elsevier Publication (1995); vol. 20 (5); pp. 178-179.
U.S. Appl. No. 60/039,791, filed Mar. 4, 1997, Clausen.
U.S. Appl. No. 60/189,780, filed Mar. 16, 2000, Soe.
U.S. Appl. No. 60/489,441, filed Jul. 23, 2003, Kreij.
Acker, L. "Die Lipide des Getreides, ihre Zusammense und inre Bedeutung", Getreide Mehl Brot (1974) 28:181-187.
Agarwal et al., "Lipase Activity of Some Fungi Isolated from Groundnut", Current Science, Dec. 5, 1984, vol. 53, No. 23.
Aisaka, Kazuo et al., "Production of Lipoprotein Lipase and Lipase by *Rhizopus japonicu*", Agri. Biol. Chem., vol. 43, No. 10, pp. 2125-2129, 1979.
Akoh, Casimir C., et al., "GDSL family of serine esterases/lipases" Progress in Lipid Research, vol. 43, 2004, pp. 534-552.
Allan Svendsen et al., "Biochemical properties of cloned lipases from the *Pseudomonas* family", Biochimica et Biophysica Acta, vol. 1259, 1995, pp. 9-17.
Amin, Neelam S., et al., "Direct transformation of site-saturation libraries in *Bacillus subtilis*", BioTechniques, Dec. 2003, 35:1134-1140.
Andersson, L., et al., "Hydrolysis of galactolipids by human pancreatic lipolytic enzymes and duidenal contents", Journal of Lipid Research, 1995, vol. 36, pp. 1392-1400.
Andreas Sander, Eberhand Eilers, Andrea Heilemann, Edith von Kreis.Fett/lipid 99 (1997) Nr. 4, 115-120.
An-I Yeh et al., "Effects of Oxido-reductants on rheological properties of wheat flour dough and comparison with some characteristics of extruded noodles", Cereal Chemistry, 1999, vol. 76, No. 5, pp. 614-620.
Archer, David B., et al., "Proteolytic degradation of heterologous proteins expressed in *Aspergillus niger*", Biotechnology Letter, vol. 14, No. 5, May 1992, pp. 357-362.
Arcos J.A. et al, "Quantative Enzymatic Production of 6.O-Acylglucose Esters", Biotechnology and Bioengineering 1998 57(5).
Arpigny Jean Louis et al, "Bacterial lipolytic enzymes: Classification and properties", Biochemical Journal, vol. 343, No. 1, Oct. 1, 1999, pp. 177-183, XP002375631.
August C.A.P.A. et al. "The use of genetic engineering to obtain efficient production of porcine pancreatic phospholipase A2", Biochimica et Biophysica Acta, vol. 1089, 1991, pp. 345-351.
Ballance, D.J., et al., "Transformation of *Aspergillus nidulans* by the orotidine-5'-phosphate decarboxylase gene of *Neurospora crassa*", Biochemical and biophysical Research Communications, vol. 112, No. 1, 1983, pp. 284-289.
Ballance, Molecular Industrial Mycology, Systems and Applications for Filamentous Fungi, Leong and Berka (eds.), Marcel Dekker Inc, New York 1991, pp. 1-29.
Barbesgaard, Peder et al Applied Microbiology and Biotechnology (1992) 36: 569-572.
Barnes, P.J., "Lipids in Cereal Technology", Food and Science Technology, Academic Press, 1983.
Basrl, M., et al., "Amidination of Lipase with Hyrdophobic Imidoesters", JAOCS, vol. 69, No. 6, Jun. 1992.
Bateman A and Haft DH (2002) Brief Bioinform 3, 236-245.
Bateman A et al, (2002) Nucleic Acids Res. 30, 276-280.
Bekkers et al, The use of genetic engineering to obtain efficient production of porcine pancreatic phospholipase A2 by *Saccharomyces cerevisiae*, (1991) Biochim Biophys Acta 1089(3), 345-51.
Bentley S D et al, Complete genome sequence of the model actinomycete *Streptomyces coelicolor* A3(2), Nature vol. 417, 2002, pp. 141-147.
Berger K.G. (1990) Recent developments in palm oil. In Oleagineux 45:437-443.
Berks, Ben C., "A common export pathway for proteins binding complex redox cofactors?" Molecular Microbiology, 1996, vol. 22, pp. 393-404.
Beucage S.L. et al, (1981) Tetrahedron Letters 22, p. 1859-1869.

Bilyk, Alexander, et al., "Lipase-catalyzed triglyceride Hydrolysis in Organic Solvent", pp. 320-323, JAOCS, vol. 68, No. 5, May 1991.
Birgitte Hugh-Jensen et al., "*Rhizomucor miehei* Triglyceride Lipase is Processed and Secreted from Transformed *Aspergillus oryzae*", Lipids, vol. 24, No. 9, 1989.
Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.
Bjorkling, F., et al., "Lipase Catalyzed Organic Synthesis", S. Servie (ed.), Microbial Reagents in Organic Synthesis, pp. 249-260, 1992.
Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.
Bjorkling, Frederik, et al., "Lipase -mediated Formation of Peroxycarboxylic acids used in Catalytic Epoxidation of Alkenes", J. Chem. Soc., Chemical Communications, Issue 19, 1990.
Bjurlin et al. Identification of carboxylesterase activites of commercial triacylglycerol hydrolase (lipase) preparations, Eur. J. Lipid Sci. Technol. 104 (2002) 143-155.
Blain JA et al, The Nature of Mycelial Lipolytic enzymes in filamentous fungi, Fems Microbiol. Lett., 1978, vol. 3, 85-87.
Blecker et al, Improved emulsifying and foaming of whey proteins after enzymic fat hydrolysis, (1997) J Food Science, vol. 62, No. 1.
Blumenthal, Cynthia Z., "Production of toxic metabolites in *Aspergillus niger*, *Apergillus oryzae*, and *Trichoderma reesei*: justification of mycotoxin testing in food grade enzyme preparations derived from the three fungi", Regulatory Toxicology and Pharmacology, vol. 39, 2004, p. 214-228.
Boel, Esper, et al.; "*Rhizomucor miehei* Triglyceride Lipase is Synthesized as a Precursor"; Novo Research Institute; vol. 23; No. 7; Jul. 1988.
Bornscheuer U T et al, Trends in Biotechnology, Elsevier Publications, Cambridge GB, vol. 20, No. 10, Oct. 1, 2002, pp. 433-437.
Bornscheuer, Uwe T., Lipase-catalyzed syntheses of monoacylglycerols, Enzyme and Microbiol Technology, vol. 17, pp. 578-586, 1995.
Brady, Leo, et al., "A serine protease triad forms the catalytic centre of a triacylglycerol lipase", Nature, vol. 343, 1990.
Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.
Brzozowski, A.M., et al., "A model for interfacial activation in lipases from the structure of a fungal lipase-inhibitor comples", Nature, vol. 351, 1991.
Buckley J. Thomas et al, Journal of Biological Chemistry, vol. 257, No. 6, pp. 3320-3325, 1982.
Bulkacz J et al, Biochim. Biophys. Acta (1981) vol. 664, pp. 148-155.
Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.
Butcher, Bronwyn G., et al., Microbiology, 2002, vol. 148, pp. 3983-3992.
Buxton et al, Gene, 1985, 37:207-214.
Carriere et al, "Pancreatic Lipase Structure- Function Relationships by Domain Exchange", American Chemical Society-Biochemistry (1997), 36, pp. 239-248.
Carriére, Frédéric, et al., "Structural basis for the substrate selectivity of pancreatic lipases and some related proteins", Biochemica et Biophysica Acta, vol. 1376, pp. 417-432, 1998.
Casimir C A et al Progress in Lipid Research, 2004, pp. 534-552.
Castello, Phillippe, et al., "Effect of exogenous lipase on dough lipids during mixing of wheat flours", Cereal Chemistry, 1998, vol. 75, No. 5, pp. 595-601.
Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.
Chakravarti DN et al, Biol. Abstracts, 1981, vol. 72, abstract No. 012592.

Cheng Cheng et al., "Transformation of *Trichoderma viride* using the *Neurospora crassa* pyr4 gene and its use in the expression of a Taka-amylase A gene from *Aspergillus oryzae*", Curr. Genet., 18: 453-456, 1990.

Christensen et al, "A new and simple method to immobilise lipases by means of granulation", 1998 Nachwachsende Rohstoff 10, 98-105.

Christie, William et al., "New Procedures for Rapid Screening of Leaf Lipid Components from *Arabidopsis*", Phytochemical Analysis, vol. 9, pp. 53-57, 1998.

Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.

Ciuffreda, Pierangela, et al., "Spectrophotometric Assay of Lipase Activity: A New 40nitrophenyl Ester of a Dialkylglycerol Suitable as a Chromogenic Substrate of *Pseudomonas cepacia* Lipase", Biocatalysis and Biotransformation, vol. 21, No. 3, pp. 123-127, 2003.

Claesson et al., "Techniques for measuring surface forces", Advances in Colloid and Interface Science, vol. 67, 1996, pp. 119-183.

Clausen, Kim, "Enzymatic oil-degumming by a novel microbial phospholipase", European Journal of Lipid Science And Technology, vol. 103, 2001, pp. 333-340.

Clausen, Kim, "New enzyme for degumming", Oils and Fats International, vol. 17, No. 4, Jun. 2001, pp. 24-25.

Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.

Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.

Cordle et al, "The hydrophobic surface of colipase influences lipase activity at an oil-water interface", Journal of Lipid Research, vol. 39 (1998), 1759-1767.

Council Regulation (EC) No. 2991/94 May 12, 1994 Official Journal of the European Communities, Sep. 12, 1994, No. L316/2-7.

Creveld, Lucia D, et al., "Identification of Functional and Unfolding Motions of Cutinase as Obtained from Molecular Dynamics Computer Simulations", Proteins: Structure, Function, and Genetics, 33:253-264, 1998.

Cui et al., "Purification and characterization of an intracellular carboxylesterase from *Arthrobacter viscosus* NRRL B-1973", Enzyme and Microbial Technology, vol. 24, pp. 200-208, 1999.

Daboussi et al, Heterologous expression of the *Aspergillus nidulans* regulatory gene nirA in *Fusarium oxysporum*, (1991) Gene 109(1), 155-60.

Daboussi et al., "Transformation of seven species of filamentous fungi using the nitrate reductase gene of *Aspergillus nidulans*", Curr. Genet., 15:453-456, 1989.

Daftary, R.D., et al., "Functional Bread-Making Properties of Wheat Flour Lipids", Food Technology, vol. 22, No. 237, Mar. 1968-1979.

Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.

Dalrymple, Brian D., et al., "Three Neocallimastic patriciarum esterases associated with the degradation of complex polysaccharides are members of a new family of hydrolases", Microbiology, vol. 142, pp. 2605-2614, 1997.

Database accession No. P10480 -& Database UniProt 'Online!, Jul. 1, 1989.

Database accession No. Q44268 -& Database UniProt 'Online! Nov. 1, 1996.

Database accession No. Q9F7Y6 Database UniProt 'Online!, Mar. 1, 2001.

Database FSTA International Food Information Service (IFIS), Frankfurt/Main, De Mine Y:"Application of the enzymatic methods to the determination of contaminated yolk in egg white." XP002077295 see abstract & Food Research International, vol. 29, No. 1, 19976, pp. 81-84.

Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.

Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.

Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl und Brot, vol. 26, No. 10, 1972, pp. 275-280.

Database UNIPROTKB Jun. 1, 2003, S. Omura et al: "putative secreted hydrolase from *Streptomyces avermitilis*" XP002376340 retrieved from EBI, Hinxton, UK Database accession No. Q828T4 abstract.

Database UNIPROTKB May 1, 2000, S.D. Bentley et al: "Putative Secreted Hydrolase from *Streptomyces coelicolor*" XP002376339 retrieved from EBI, Hinxton, UK Database accession No. Q9S2A5 abstract.

Davies, Progress in Industrial Microbiology, Martinelli and Kinghorn (eds.), Elsevier, Amsterdam 1994, 29:525-560.

De Haas GH et al, "Purification and Properties of Phospholipase A from Porcine Pancreas" Biochim. Biophys. ACTA, 1968, vol. 139, pp. 103-117.

Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.

Dellaporta, et al.; "A Plant DNA Minipreparation Version II"; Plant Molecular Biology Reporter(1983); vol. 1(4); pp. 19-21.

Derewenda et al, "The crystal and molecular structure of the *Rhizomuxor miehei* Triacylglyceride Lipase at 1•9 Å Resolution", J. Mol. Biol. 1992, 227:818-839.

Derewenda, Urszula, et al., "Catalysis at the Interface: The Anatomy of a Conformational Change in a Triglyceride Lipase", Biochemistry, vol. 31, pp. 1532-1541, 1992.

Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.

Dugi KA et al, "Human hepatic and lipoprotein lipase: the loop covering the catalytic site mediates lipase substrate specificity", Journal of Biological Chemistry (1995), vol. 270, pp. 25, 396-pp. 25, 401.

Dutilh & Groger, "Improvement of Product Attributes of Mayonnaise by Enzymic Hydrolysis of Egg Yolk with Phospholipase A2", 1981 J. Sci. Food Agric. 32, 451-458.

Eddine et al, "Cloning and expression analysis of NhL1, a gene encoding an extracellular lipase from the fungal pea pathogen *Nextria haematococca* MP VI (*Fusarium solani* f. sp. *pisi*) that is expressed in planta", Mol. Genet. Genomics (2001) 265: 215-224.

Ellaiah et al., "Production of lipase by immobilized cells of *Aspergillus niger*", Process Biochemistry, vol. 39, 2004, pp. 525-528.

Elyk, Alexander, et al., "Lipase-Catalyzed—", JAOCS, vol. 08, No. 5, May 1991, pp. 320-323.

Engelhorn and Raab, "Rapid Electroblotting of Small DNA Fragments from Polyacrylamide Gels", Biotechniques (1991) 11(5):594-6.

Engelhorn et al., "Rapid Electroblotting of Small DNA Fragments from Polyacrylamide Gels"; Biotechniques(1991); vol. 11(5); pp. 594-596.

EPO, Mobay Chemical Corporation—Decision of the Technical Board of Appeal 3.3.1 dated Jul. 1, 1982, *Official Journal EPO*, Oct. 1982, pp. 394-402.

Ettinger, William F. et al., "Structure of Cutinase Gene, cDNA, and the Derived Amino Acid Sequence from Phytopathogenic Fungi", Biochemistry, vol. 26, pp. 7883-7892, 1987.

Ezra, David, et al., "Coronamycins, peptide antibiotics produced by a verticillate *Streptomyces* sp. (MSU-2110) endophytic on *Monstera* sp.", Microbiology, 2004, vol. 150, p. 785-793.

Fauvel, et al.; "Purification of Two Lipases with High Phospholipase A, Activity from Guinea-Pig Pancreas", Biochimica et Biophysica Acta(1981); vol. 663; pp. 446-456.

Fernandez-Garcia et al., "The use of lipolytic and proteolytic enzymes in the manufacture of manchego type cheese from ovine and bovine milk", 1994 J. Dairy Sci. 77: 2139-2149.

Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.

Ferrer et al, 2000, J. Chem. Technol. Biotechnol. 75, 569-576.

Fox, et al.; "Isolation and some Properties of Extracellular Heat-Stable Lipases: from *Pseudomonas fluorescens* Strain AFT 36", Journal of Dairy Research (1988); vol. 50; pp. 77-89.

Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.

Fugman, Douglas A et al Biochemica et Biophysica acia 795 (1984),191-195.

Galliard T and Dennis S (1974) Phytochemistry vol. 13, pp. 1731-1735.

Galliard, "The Enzymic Breakdown of Lipids in Potato Tuber by Phospholipid- And Galactolipid- Acyl Hydrolase Activities and by Lipoxygenase", Phytochemistry, 1970, vol. 9, pp. 1725-1734.

Gan, Z. et al., "Rapid Communication- Antisera agains: Wheat Diacylgalactosylglycerol (MGDG) and Diacyldigalactosylglycerol (DGDG)", Journal of Cereal Science, vol. 18, pp. 207-210, 1993.

Ganghro AB & Dahot MU, Sci Int. (Lahore), 1992, vol. 4, pp. 169-172.

Geus et al (1987) Nucleic Acids Research 15(9) p. 3743-3759.

Gilbert, E. Jane, et al., "Purification and properties of extracellular lipase from *Pseudomonal aeruginosa* EF2", Journal of General Microbiology, 1991, vol. 137, pp. 2223-2229.

Gillian, B., Turgeon et al., "*Cochliobolus heterostrophus* using the *Aspergillus nidulans* amdS gene", Mol Gen Genet, 201: 450-453, 1985.

Goodey et al, Yeast Biotechnology, Berry et al (eds.), Allen and Unwin, London 1987, pp. 401-429.

Graille J, Lipid Technology, vol. 5, No. 1, 1993, pp. 11-16.

Greenough et al (1996) Food Chem Toxicology 34:161-166 and PubMed abstract in respect thereof.

Greenough R J et al, Food and Chemical Toxicology, vol. 34(2), 1996, pp. 161-166.

Haas and Berka, 1991 Gene, 109:107-113.

Haas, et al., "Enzymatic Phosphatidylcholine Hydrolysis in Organic Solvents: An Examination of Selected Commercially Available Lipases", JAOCS, vol. 71, No. 5, May 1994, pp. 483-490.

Haas, et al.; "Lipases of the Genera *Rhizopus* and *Rhizomucor*. Versatile Catalysts in Nature and the Laboratory"; Food Biotechnology Micro-organisms (1995); pp. 549-588.

Haggag H F et al. Egypt J Food Sci vol. 22, No. 1, pp. 99-107 (1994).

Hara, et al.; "Comparative Study of Comercially Available Lipases in Hydrolysis Reaction of Phosphatidylcholine"; JAOCS (1997); vol. 74; No. 9, pp. 1129-1132.

Hawker, Kim L., et al., "Heterologous expression and regulation of the *Neurospora crassa* nit-4 pathway-specific regulartory gene for nitrate assimilation in *Aspergillus nidulans*", Gene., vol. 100, pp. 237-240, 1991.

Helmsing, "Purification and Properties of Galactolipase", Biochem., Biophys., Acta, vol. 178, pp. 519-533, 1969.

Henderson, H.E., et al., "Structure-function relationships of lipoprotein lipase: mutation analysis and mutagenesis of the loop region", Journal of Lipid Research, vol. 34, 1993, pp. 1593-1602.

Hernquist L & Anjou K (1993) Diglycerides as a stabilizer of the β'-crystal form in margarines and fats, in Fette Seifen Anstrichmittel 2:64-66.

Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.

Hilton S et al, Biochemistry vol. 29, No. 38, 1990, pp. 9072-9078.

Hilton S, Buckley JT, J Biol Chem. Jan. 15, 1991; 266(2): 997-1000.

Hirayama O et al, Biochim Biophys Acta. 1975, vol. 384(1), p. 127-37.

Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.

Höfelmann et al, J. Food Sci., 1985, 50:1721-1731.

Holmquist et al., "Probing a Functional Role of Glu87 and Trp89 in the Lid of *Humicola lanuginosa* Lipase through Transesterification Reactions in Organic Solvent", Journal of Protein Chemistry, 1995, vol. 14, No. 4, pp. 217-224.

Hoshino, et al.; "Calcium Ion Regulates the Release of Lipase of *Fusarium oxysporum*"; J. Biochem (1991); vol. 110; pp. 457-461.

Hoshino, et al.; "Purification and Some Characteristics of Extracellular Lipase from *Fusarium oxysporum* f. sp. *lini*"; Biosci. Biotech. Biochem (1992); pp. 660-664.

Hoshino, Tamotsu, et al., "Purfication and Some Characteristics of Extracellular Lipase from *Fusarium oxysporum*", Biosci. Biotech. Biochem., vol. 56, No. 4, pp. 660-664, 1992.

Hossen, Monjur and Hernandez, Ernesto, Lipids, vol. 39, Aug. 2004, pp. 777-782.

Hou Ching T, Journal of Industrial Microbiology, vol. 13, No. 4, 1994, pp. 242-248.

Hübner et al., "Interactions at the lipid-water interface", Chemistry and physics of Lipids, vol. 96, 1998, pp. 99-123.

Icard-Verniere, Christele, et al., "Effects of mixing conditions on pasta dough development on biochemical changes", Cereal Chemistry, 1999, vol. 76, No. 4, pp. 558-565.

Igrejas, Gilberto, et al., "Genetic and Environmental Effects on Puroindoline-a and Puroindoline -b Content and their Relationship to Technological Properties in French Bread Wheats", Journal of Cereal Science, vol. 34, 2001, pp. 37-47.

Ikeda H et al, Nature Biotech, vol. 21, 2003, p. 526-531.

Ishihara et al Biochimica et Biophysica Acta 388 (1975) 413-422.

Isobe and Nokihara, Febs. Lett., 1993, 320:101-106.

Isobe K et al, Journal of Molecular Catalysis B: Enzymatic 1 (1995), pp. 37-43.

Iwai and Tsujisaka (in Lipases, Borgström and Brockman (eds.), Elsevier, Amsterdam, 1984, pp. 443-468.

Izco et al. Adv Food Sci vol. 21 N 3/4, (10-116) 1999.

Jacob, Jules S., et al., "The Effects of Galactolipid Depletion on the Structure of a Photosynthetic Membrane", The Journal of Cell Biology, vol. 103, Oct. 1986, pp. 1337-1347.

Jacobsberg B. & Oh C.H. (1976) Studies in Palm Oil Crystallisation, in Journal of the American Oil Chemist Society 53:609-616.

Jan-Willem F. A. Simons et al., "Cloning, purification and characterisation of the lipase from *Staphylococcus epidermidis*", Eur. J. Biochem., vol. 253, pp. 675-683, 1998.

Jeng-yen Lin, Matthew, "Wheat Polar Lipids- A Theseis Submitted to the Graduate Faculty of the North Dakota State University of Agriculture and Applied Science", May 1972.

Joerger et al., "Alteration of Chain Length Selectivity of a *Rhizopus delemar* Lipase through Site-Directed Mutagenesis", Lipids, vol. 29, No. 6, 1994, pp. 377-384.

Joshi, et al.; "Specificity of Fungal Lipase in Hydrolytic Cleavage of Oil"; Acta Microbiologica Hungarica (1987); vol. 34(2); pp. 111-114.

Joshi, Sunita, et al., "Specificity of Lipase isolated from *Fusarium oxysporum*", Department of Chemistry, Indian Institute of Technology, vol. 25, No. 1 & 2, pp. 76-78.

Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.

Jurgens, Catharina, et al., "Directed evolution of a (βα)8-barrel enzyme to catalyze related reactions in two different metabolic pathways", PNAS, Aug. 29, 2000, vol. 97, No. 18, pp. 9925-9930.

Kaniuga Z, Acta Biochim Pol. (1997), vol. 44(1), p. 21-35.

Kapur J & Sood ML, J. Parasit., 1986, vol. 72, pp. 346-347.

Kasai, Naoya, et al., "Chiral C3 epoxides and halophydrins: Their preparation and synthetic application", Journal of Molecular Catalysis B: Enzymatic, vol. 4, 1998, pp. 237-252.

Kasai, Naoya, et al., "Optically Active Chlorohydrins as Chiral C3 and C4 Building Units: Microbial Resolution and Synthetic Applications", Chirality, vol. 10, pp. 682-692.

Kawamura and Doi, J. of Bacteriology Oct. 1984, p. 442-444.

Keller, R.C.A., et al., "Competitive Adsorption Behaviour of Wheat Flour Components and Emulsifiers at an Air-Water Interface", Journal of Cereal Science, vol. 25, 1997, pp. 175-183.

Keum J S et al. Korean J Dairy Sci 15 (2): 103-117, 1993.

Kim, Hyung Kwoun, et al., Expression and characterization of Ca2+-independent lipase from *Bacillus pumilus* B26, Biochimica et Biophysica Acta, vol. 1583, 2002, pp. 205-212.

Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.

Kimura, Yoshiharu, et al., "Application of Immobilized Lipase to Hydrolysis of Triacylglyceride", Eur J. Appl Microbiol Biotechnol, 1983, vol. 17, pp. 107-112.

King et al, Molecular and Cell Biology of Yeasts, Walton and Yarronton (eds.), Blackie, Glasgow, 1989, pp. 107-133.

Kirk, Ole, et al., "Fatty Acid Specificity in Lipase-Catalyzed Synthesis of Glucoside Esters" Biocatalysis, 1992, vol. 6, pp. 127-134.

Klein, Robert R., et al., "Altered Acyl Chain Length Specificity of *Rhizopus delemar* Lipase Through Mutagenesis and Molecular Modeling", Lipids, 1997, vol. 32, No. 2, pp. 123-130.

Kochubei S M et al, Biophysics (1981), vol. 26(2), p. 299-304.

Kochubei S M et al, Mol Biol (Mosk) (1975), vol. 9(2), (p. 190-3) p. 150-153.

Kochubei SM et al, Mol Biol (Mosk) (1978),(vol. 1, p. 47-54) p. 32-37.

Kouker, et al.; "Specific and Sensitive Plate Assay for Bacterial Lipases"; Applied and Environmental Microbiology (1987); vol. 53(1); pp. 211-213.

Krishna, Sajja Hari, et al., "Enantioselective transesterification of a tertiary alcohol by lipase A from *Candida antarctica*", Tetrahedron: Asymmetry, vol. 13, 2002, pp. 2693-2696.

Krog, Cereal Foods World, The American Association of Cereal Chemists, p. 10, Jan. 1979, vol. 24, No. 1, pp. 10-11.

Krupa, Zbigniew et al., "Requirement of Galactolipids for Photosystem J Activity In Lyophilized Spinach Chloroplasts", Biochimica et Biophysica Acta, 408, pp. 26-34, 1975.

Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.

Kuwabara, et al., "Purification and Some Properties of Water-soluble Phospholipase B from *Torulaspora delbrueckii*", J. Biochem., vol. 104, pp. 236-241, 1988.

Kuwabara, et al., "Purification and Some Properties of Water-soluble Phospholipase", Agric. Biol. Chem., vol. 52, No. 10, pp. 2451-2458, 1988.

Larsen N G et al, Journal of Cereal Science (1990), vol. 12(2), p. 155-164.

Lee, Keun Hyeung, et al., "Identification and characterization of the antimicrobial peptide corresponding to C-terminal B-sheet domain of tenecin 1, an antibacterial protein of larvae of *Tenebrio molitor*", Biochem. J., 1996, vol. 334, pp. 99-105.

Li, W., et al., "Surface properties and locations of gluten proteins and lipids revealed using confocal scanning laser microscopy in bread dough", Journal of Cereal Science, vol. 39, 2004, pp. 403-411.

Lih-ling Wang et al, J Agric. Food. Chem. (1993), 41, 1000-1005.

Lima, Vera L.M., et al., "Lecithin-cholesterol acyltransferase (LCAT) as a plasma glycoprotein: an overview", Carbohydrate Polymers, vol. 55, 2004, pp. 179-191.

Lin M J Y et al, Cereal Chemistry (1974), vol. 51(1), p. 34-45.

Lin S et al, Enzyme and Microbial Technology 18 (1996), pp. 383-387.

Litthauer, Derek, et al., "*Pseudomonas luteola* lipase: A new member of the 320- residue *Pseudomonas* lipase family", Enzyme and Microbial Technology, vol. 30, pp. 209-215, 2002.

Llustenberger, Cornelia, et al., "Application of Noopazyme in Asian Noodles and Non-Durum Pasta", Cereal Food, 2002-18584-01, p. 1, vol. 11.

Llustenberger, Cornelia, et al., "Enzymes in Frozen Dough and Parbaked Bread", Cereal Food, 2001-17056-01, p. 1, vol. 19.

Lo Y-C et al. Crystal structure of *Escherichia coli* Thioesterase I/Proteasel/Lysophospholipase L1: Consensus sequence blocks constitute the catalytic center of SGNH-hydrolases through a conserved hydrogen bond network. Journal of Molecular Biology, London, GB, vol. 330, No. 3, 539-551.

Longhi, Sonia, et al., "Atomic Resolution (1.0 ↑) Crystal Structure of *Fusarium solani* Cutinase: Stereochemical Analysis" J. Mol. Biol. vol. 268, pp. 779-799, 1997.

Lozano et al., "Over-stabilization of *Candida antarctica* lipase B by ionic liquids in ester synthesis", Biotechnology Letters, vol. 23, pp. 1529-1533, 2001.

Luzi, Paola et al, Genomics (1995), vol. 26(2), p. 407-9.

Madsen J.S. & Qvist K.B. (1997) J. Food Sci. 62, 579-582.

Mao, Cungui, et al., "Cloning and Characterization of a *Saccharomyces cerevisiae* Alkaline Ceramidase with Specificity for Dihydroceramide", The Journal of Biological Chemistry, vol. 275, No. 40, 2000, pp. 31369-31378.

Marion D et al—Chapter 6, pp. 131-167 of "Interactions The Keys to Cereal Quality" 1998 ISBN 0913250-99-6 (ed. Hamer & Hoseney).

Marion D et al pp. 245-160 of Wheat Structure Biochemistry & Functionality (ed Schofield JP) ISBN 085404777-8 published in 2000—(It states that it is the Proceedings of Conference organised by Royal Soc of Chemistry Food Chemistry Group held on Apr. 10-12, 1995, in Reading, UK. However, it is unclear why there was such a delay).

Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.

Martinelle et al., "The Role of Glu87 and Trp89 in the lid of *Humicola lanuginosa* lipase", Protein Engineering, vol. 9, No. 6, 1996, pp. 519-524.

Martinez, Chrislaine, et al., "Engineering cysteine mutants to obtain crystallographic phases with a cutinase from *Fusarium solani pisi*", Protein Engineering, vol. 6, No. 2, pp. 157-165, 1993.

Mase et al., "Purification and Characterization of a new Lipase from *Fusarium* sp. TM-30", Biosci. Biotech. Biochem., vol. 59, No. 9, pp. 1771-1772, 1995.

Mason, Research Disclosure, Kenneth Mason Publications, Westbourne GB No. 390, Oct. 1996, pp. 661-662.

Masuda, Naoko, et al., "Primary structure of protein moiety of *Penicillum notatum* phospholipase B deduced from the Cdna", Eur. J. Biochem., vol. 202, pp. 783-787, 1991.

Matos AR, Lipid Catabolism: Lipid Degradation, 2000, p. 779-781.

Matos, AR et al, Febs Letters, 491 (2001) p. 188-192.

Matsuda H et al, Biochim Biophys Acta, (1979), vol. 573(1), p. 155-65.

Matsuoka, et al.; "Purification and properties of a Phospholipase C That has High Activity toward Sphingomyelin from *Aspergillus saitoi*"; Biotiechonology and Applied Biochemistry (1987); vol. 9, pp. 401-409.

Matthes et al, (1984) EMBO J. 3, p. 801-805.

McAuley, Katherine E., et al., "Structure of a feruloyl esterase from *Aspergillus niger*", Acta Crystallographica, Section D, pp. 878-887, 2004.

McCoy M G et al, Journal of Lipid Research (2002), vol. 43, pp. 921-929.

McNeill G.P. & Berger R.G. (1993) Enzymatic glycerolysis of palm oil fractions and palm oil based model mixture: Relationship between fatty acid composition and monoglyceride yield, in Food Biotechnology 7: 75-87.

McNeill, Gerald P., et al., "High-Yield Enzymatic Glycerolysis of Fats and Oils", JAOCS, vol. 68, No. 1, Jan. 1991.

Meyer, V., et al., "Transcriptional regulation of the Antifungal Protein in *Aspergillus giganteus*", Mol Genet Genomics, 2002, vol. 266, pp. 747-757.

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al., "Covalent immobilisation of manganese peroxidases (MnP) from *Phanerochaete chrysosporium* and *Bjerkandera* sp. BOS55", Enzyme and Microbial Technology, vol. 32, 2003, pp. 769-775.

Mine Y, Food Research International, 29(1), 1996, pp. 81-84.

Mogensen, Jesper E., et al., "Activation, Inhibition, and Destabilization of *Thermomyces lanuginosus* Lipase by Detergents", Biochemistry, vol. 44, pp. 1719-1730, 2005.

Mohsen et al., "Specificity of Lipase Produced by *Rhyopus delemar* and Its Utilization in Bread Making", Egypt. J Food. Sci. vol. 14, No. 1, pp. 175-182.

Moore, Charles M., et al., "Metal ion homeostasis in *Bacillus subtilis*", Current Opinion in Microbiology, 2005, vol. 8, pp. 188-195.

Morgan, Keith R., et al., "Stalling in Starch Breads: The Effect of Antistaling α-Amylase", Starch/Stärke, vol. 49, 1997, pp. 59-66.

Morgan-Jones, Gareth; "Notes on Coelomycetes.II. Concerning the *Fusicoccum anamorph* of *Botryosphaneria ribis*"; vol. Xxx, pp. 117-125; Oct.-Dec. 1987.

Morinaga et al Biotechnology (1984) 2, p. 636-639.

Mukherjee, Kumar D. et al., "Enrichment of y-linolenic acid from fungal oil by lipase-catalysed reactions", Appl. Microbiol Biotechnol (1991), vol. 35, pp. 579-584.

Murakami, Nobutoshi, et al., "Enzymatic Transformation of Glyceroglycolipids into sn-1 and sn-2 Lysoglyceroglycolipids by use of *Rhizopus arrhizus* Lipase", Tetrahedron, vol. 50, No. 7, pp. 1993-2002, 1994.

Mustranta, Annikka, et al., "Comparison of Lipases and Phosphlipases in the Hydrolysis of Phospholipids", Process Biochemistry, vol. 30, No. 5, pp. 393-401, 1995.

Nagano, et al.; "Cloning and Nucleotide Sequence of cDNA Encoding a Lipase from *Fusarium keteroporum*"; J. Biochem (1994); vol. 116; pp. 535-540.

Nagao et al, J. Biochem 124, 1124-1129, 1998.

Nagao et al, J. of Bioscience and Bioengineering vol. 89, No. 5, 446-450, 2000.

Nagao et al, J. of Molecular Catalysis B: Enzymatic 17 (2002) 125-132.

Nagao, Toshihiro et al., "Cloning and Nucleotide Sequence of CDNA Encoding a Lipase from *Fusarium heterosporum*", J. Biochem., vol. 116, pp. 535-540, 1994.

Nagao, Toshihiro et al., "Expression of Lipase cDNA from *Fusarium heterosporum* by *Saccharomyces cereviisiae*: High-Level Production and Purification", Journal of Fermentation and Bioengineering, 1996, vol. 81, No. 6, pp. 488-492.

National Research Council (U.S.) Committee on Specifications of the Food Chemicals Codex, "Lipase Activity" in *Food Chemicals Codex* (1981) National Academy Press, Washington, D.C. pp. 492-493.

Needleman & Wunsch (1970), J. of Molecular Biology 48, 443-453.

Nelson and Long, Analytical Biochemistry (1989), 180, p. 147-151.

Nerland A H, Journal of Fish Diseases, vol. 19, No. 2, 1996, pp. 145-150.

Neugnot Virginie et al, European Journal of Biochemistry, 2002, vol. 269, pp. 1734-1745.

Newport, G., et al., "KEX2 Influences *Candida albicans* Proteinase Secretion and Hyphal Formation", The Journal of Biological Chemistry, 1997, vol. 272, No. 46, pp. 28954-28961.

Nicolas, Anne, et al., "Contribution of Cutinase Serine 42 Side Chain to the Stabilization of the Oxyanion Transition State", Biochemistry, vol. 35, pp. 398-410, 1996.

Nierle W et al, Fette Seifen Anstrichmittel (1981), vol. 83(10), p. 391-395.

Nierle, W., et al., "Versuche zur Verlangerung der Haltbarkeit von Dartoffelprodukten", Chem. Mikrobiol. Technol. Lebensm., 1975, vol. 3, pp. 172-175.

Nobutoshi M et al, Tetrahedron Letters (1991), vol. 31(1), p. 1331-4.

Ohm, J.B., et al., "Relationships of Free Lipids with Quality Factors in Hard Winter Wheat Flours", Cereal Chem., vol. 79, No. 2, pp. 274-278, 2002.

Ohta, S. et al., "Application of Enzymatic Modification of Phospholipids on Breadmaking", Abstract from AACC 68th Annual Meeting in Kansas City, MO, Oct. 30-Nov. 3, 1983, published in Cerial Foods World, p. 561.

Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.

Okiy D.A. (1977) Partial glycerides and palm oil Crystallisation, in Journal of Science and Food Agriculture 28:955.

Okiy D.A. (1978) Interaction of triglycerides and diglycerides of palm oil, in Oleagineux 33:625-628.

Okiy D.A., Wright, W.B., Berger, K.G. & Morton I.D. (1978), The physical properties of modified palm oil, in Journal of Science of Food and Agriculture 29:1061-1068.

Oluwatosin, Yemisi E., et al., "Phenotype: a Possible Role for the Kex2 Endoprotease in Vacuolar Acidification", Molecular and Cellular Biology, 1998, pp. 1534-1543.

Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.

Orberg, Marie-Louise, "Self-assembly Structures Formed by Wheat Polar Lipids and their Interaction with Lipases", Master of Scient Thesis, Apr. 2005.

Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.

Osman, Mohamed, et al., "Lipolytic activity of *Alternaria alternata* and *Fusarium oxysporum* and certain properties of their lipids", Microbios Letters, vol. 39, pp. 131-135, 1988.

Ostrovskaya L K et al, Dokl Akad Nauk SSSR, (vol. 186(4), p. 961-3) p. 59-61.

O'Sullivan et al, J Plant Physiol, vol. 313, (1987) p. 393-404.

Outtrup, Günther H., et al., "Properties and Application of a Thermostable Maltogenic Amylase Produced by a Strain of *Bacillus* Modified by Recombinant-DNA Techniques", Starch/Starke, vol. 36, No. 12, pp. 405-411.

Palomo, Jose M., et al., "Enzymatic production of (3S, 4R)-(-)-4-(4'-fluorophenyl)-6-oxo-piperidin-3-carboxylic acid using a commercial preparation of lipase A from *Candida antarctica*: the role of a contaminant esterase" Tetrahedron: Asymmetry, vol. 13, 2002, pp. 2653-2659.

Palomo, Jose M., et al., "Enzymatic resolution of (±)-glycidyl butyrate in aquenous media. Strong modulation of the properties of the lipase from *Rhizopus oryzae* via immobilization techniques", Tetrahedron: Asymmetry, vol. 15, 2004, pp. 1157-1161.

Palomo, Jose M., et al., "Modulation of the enantioselectivity of *Candida antarctica* B lipase via conformational engineering: kinetic resolution of (±)-α-hydroxy-phenylacetic acid derivatives", Tetrahedron: Asymmetry, vol. 13, 2002, pp. 1337-1345.

Pariza, Michael, et al., "Evaluating the safety of Microbiol Enzyme Preparations Used in Food Processing: Update for a New Century", Regulatory Toxicology and Pharmacology, vol. 33, pp. 173-186.

Patent Abstracts of Japan vol. 016, No. 528 (C-1001), Oct. 29, 1992 & JP 04 200339 A see abstract.

Patent Abstracts of Japan vol. 095, No. 001, Feb. 28, 1995 & JP 06 296467 A see abstract.

Peelman F, et al, Protein Science Mar. 1998; 7(3): 587-99.

Persson, Mattias, et al., "Enzymatic fatty acid exchange in digalactosyldiacylglycerol", Chemistry and Physics of Lipids, vol. 104, 2000, pp. 13-21.

Peters, G.H., et al., "Active Serine Involved in the Stabilization of the Active Site Loop in the *Humicola lanuginosa* Lipase", Biochemistry, 1998, vol. 37, pp. 12375-12383.

Peters, Günther H., et al., "Theoretical Investigation of the Dynamics of the Active Site Lid in *Rhizomucor miehei* Lipase", Biophysical Journal, vol. 71, 1996, pp. 119-129.

Plou et al, J. Biotechnology 92 (2002) 55-66.

Ponte J G, Cereal Chemistry (1969), vol. 46(3), p. 325-29.

Queener et al. (1994) Ann N Y Acad Sci. 721, 178-93.

Rambosek and Leach, CRC Crit. Rev. Biotechnol., 1987, 6:357-393.

Rapp, Peter; "Production, regulation, and some properties of lipase activity from *Fusarium oxysporum* f. sp. *vasinfectum*"; Enzyme and Microbial Technology(1995); vol. 17; pp. 832-838.
Reetz M.T., Jaeger K.E. Chem Phys Lipids. Jun. 1998; 93(1-2): 3-14.
Reetz Manfred T, Current Opinion in Chemical Biology, Apr. 2002, vol. 6, No. 2, pp. 145-150.
Reiser J et al. (1990) Adv Biochem Eng Biotechnol. 43, 75-102.
Richardson, Toby H., et al., "A Novel, High Performance Enzyme for Starch Liquefaction", The Journal of Biological Chemistry, vol. 277, No. 29, Issue of Jul. 19, pp. 25501-26507, 2002.
Roberts et al. (1992) Gene 122(1), 155-61.
Roberts, et al.; "Extracellular Lipase Production by Fungi from Sunflower Seed"; Mycologia(1987); vol. 79(2); pp. 265-273.
Roberts, Ian N., et al., Heterologous gene expression in *Aspergillus niger*: a glucoamylase-porcine pancreatic prophospholipase A2 fusion protein is secreted and processed to yield mature enzyme.
Robertson et al, Journal of Biological Chemistry, 1994, 2146-2150.
Rodrigues, et al.;"Short Communication: Bioseparations with Permeable Particles"; Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.;"CODEHOP (Consensus-Degenerate Hybrid Oligonucleotide Primer) PCR primer design"; Nucleic Acids Research(2003); vol. 31(13); pp. 3763-3766.
Rousseau, Derick, et al., "Tailoring the Textural Attributes of Butter Fat/Canola Oil Blends via *Rhizopus arrhizus* Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin Is A Lipid Acyl Hydrolase with a Ser-Asp Catalytic Dyad", Biochemistry, 2003, vol. 42, pp. 6696-6708.
Sahsah, Y., et al., "Enzymatic degradation of polar lipids in *Vigna unguiculata* leaves and influence of drought stress", Physiologia Plantarum, vol. 104, pp. 577-586, 1998.
Sahsah, Y., et al., "Purification and characterization of a soluble lipolytic acylhydrolase from Cowpea (*Vigna unguiculata* L.) leaves", Biochimica et Biophysica Acta, vol. 1215, pp. 66-73, 1994.
Sakai, Norio, et al., "Human glactocerebrosidase gene: promoter analysis of the 5'-flanking region and structural organization", Biochimica et Biophysica Acta, vol. 1395, pp. 62-67, 1998.
Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.
Sanchez et al., "Solution and Interface Aggregation States of *Crotalus atrox* Venom Phospholipase A2 by Two-Photon Excitation Fluorescence Correlation Spectroscopy", Biochemistry, 2001, vol. 40, pp. 6903-6911.
Saxena, et al.; "Purification Strategies for Microbial Lipases"; Journal of Microbilogical Methods (2003); pp. 1-18.
Scheib et al.; "Stereoselectivity of Mucorales lipases toward triradylglycerols—A simple solution to a complex problem"; Protein Science (1999); vol. 8; pp. 215-221.
Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.
Scopes, Robert K., "Section 8.4: Ultrafiltration" in *Protein Purification Principles and Practice, Third Edition* (1994) Springer-Verlag, New York, p. 267-9.
Shimada et al, J. of Bioscience and Bioengineering vol. 91, No. 6, 529-538 (2001).
Shimada et al, J. of Fermentation and Bioengineering vol. 75, No. 5, 349-352 (1993).
Shin, et al.; "Butyl-Toyopearl 650 as a New Hydrophobic Adsorbent for Water-Soluable Enzyme Proteins"; Analytical Biochemistry(1984); vol. 138; pp. 259-261.
Sias B et al, Biochemistry, (2004), vol. 43(31), p. 10138-48.
Siew W.L. & Ng W.L. (1999) Influence of diglycerides on crystalisation of palm oil, in Journal of Science of Food and Agriculture 79:722-726.
Siew W.L. & Ng W.L. (2000) Differential scanning thermograms of palm oil triglycerides in the presence of diglycerides, in Journal of Oil Palm Research 12:107.
Skovgaard, et al.;"Comparison of Intra- and extracellualr isozyme banding patterns of *Fusarium oxysporum*"; Mycol. Res. (1998); vol. 102(9); pp. 1077-1084.
Slotboom et al Chem. Phys. Lipids 4 (1970) 15-29.
Smith, Timothy L., et al., "The promoter of the glucoamylase-encoding gene of *Aspergillus niger* functions in *Ustilago maydis*", Gene. 88, 259-262, 1990.
Solares, Laura F., et al., "Enzymatic resolution of new carbonate intermediates for the synthesis of (S)-(+)-zopiclone", Tetrahedron: Asymmetry, vol. 13, 2002, pp. 2577-2582.
Sols and De Le Fuente, "On the substrate specificity of glucose oxidase", Biochem et Biophysica Acta (1957) 24:206-7.
Sonntag N.O.V. (1982a) Glycerolysis of Fats and methyl esters—status, review and critique, in Journal of American Oil Chemist Society 59:795-802A.
Soragni, Elisabetta, et al., "A nutrient-regulated, dual localization phospholipase A2 in the symbiotic fungus" The EMBO Journal, vol. 20, No. 18, pp. 5079-5090, 2001.
Spendler, et al., "Functionality and mechanism of a new 2nd generation lipase for baking industry"—Abstract 2001 AACC Annual Meeting; Symposia at Charlotte, NC. Oct. 14-18, 2001.
Spradlin J E, Biocatalysis in Agric. Technol., ACS Symposium, 389(3), 24-43 (1989).
Sreekrishna K et al (1988) J Basic Microbiol. 28(4), 265-78.
Stadler et al., "Understanding Lipase Action and Selectivity", CCACAA, vol. 68, No. 3, pp. 649-674, 1995.
Steinstraesser, et al., "Activity of Novispirin G10 against *Pseudomonas aeruginosa* In Vitro and in Infected Burns", Antimicrobial Agents and Chemotherapy, Jun. 2002, vol. 46, No. 6, pp. 1837-1844.
Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.
Stemmer, Willem P.C.; "Rapid evolution of a protein in vitro by DNA shuffling"; Affymax Research Institute, Nature, vol. 370, Aug. 4, 1994.
Sternberg, M., "Purification of Industrial Enzymes with Polyacrylic Acids", Process Biochemistry, Sep. 1976.
Strickland, James A., et al., "Inhibition of Diabrotica Larval Growth by Patatin, the Lipid Acyl Hydrolase from Potato Tubers", Plant Physiol, vol. 109, pp. 667-674, 1995.
Sudbery et al (1988) Biochem Soc Trans. 16(6), 1081-3.
Sugatani, Junko, et al., "Studies of a Phospholipase B from *Penicillium notatum* Substrate Specificity and Properties of Active Site", Biochimica et Biophysica Acta, vol. 620, 1980, pp. 372-386.
Sugimoto et al., Agric. Biol. Chem. 47(6), 1201-1206 (1983).
Svendsen, A. "Engineered lipases for practical use", INFORM (1994) 5(5):619-623.
Svendsen, Allan, "Lipase protein engineering" Biochimica et Biophysica Acta, vol. 1543, 2000, pp. 223-238.
Svendsen, Allan, et al., "Biochemical properties of cloned lipases from the *Pseudomonas* family", Biochimica et Biophysica Acta, vol. 1259, 1995, pp. 9-17.
Sweigard, James A., et al., "Cloning and analysis of CUT1, a cutinase gene from *Magnaporthe grisea*", Mol. Gen. Genet., 232:174-182, 1992.
Swinkels et al (1993) Antonie van Leeuwenhoek 64, 187-201.
Sztajer H et al Acta Biotechnol, vol. 8, 1988, pp. 169-175.
Talker-Huiber, Cynthia Z., et al., "Esterase EstE from *Xanthomonas vesicatoria* (Xv_EstE) is an outer membrane protein capable of hydrolyzing long-chain polar esters", Appl. Microbiol Biotechnol, 61:479-487, 2003.
Terasaki, Masaru, et al., "Glycerolipid Acyl Hydrolase Activity in the Brown Alga *Cladosiphon okamuranus* Tokida", Biosci. Biotechnol. Biochem., vol. 67, No. 9, pp. 1986-1989, 2003.
Thornton et al 1988 Biochem. Et Biophys. Acta. 959, 153-159.
Tiss, Aly, et al., "Effects of Gum Arabic on Lipase Interfacial Binding and Activity", Analytical Biochemistry, vol. 294, pp. 36-43, 2001.
Toida J et al, Bioscience, Biotechnology, and Biochemistry, Jul. 1995, vol. 59, No. 7, pp. 1199-1203.

Tombs and Blake, Biochim. Biophys (1982) 700:81-89.
Topakas, E., et al. "Purification and characterization of a feruloyl esterase from *Fusarium oxysporum* catalyzing esterification of phenolic acids in ternary water—organic solvent mixtures", Journal of Biotechnology, vol. 102, 2003, pp. 33-44.
Torossian and Bell (Biotechnol. Appl. Biochem., 1991, 13:205-211.
Tsao et al. (1973) J Supramol Struct. 1(6), 490-7.
Tsychiya Atsushi, et al., "Cloning and nucleotide sequence of the mono- and diacylglycerol lipase gene (mdlB) of *Aspergillus oryzae*", FEMS Microbiology Letters, vol. 143, pp. 63-67, 1996.
Turnbull, K.M., et al., "Early expression of grain hardness in the developing wheat endosperm", Planta, 2003, vol. 216, pp. 699-706.
Turner, Nigel A., et al., "At what temperature can enzymes maintain their catalytic activity?", Enzyme and Microbial Technology, vol. 27, 2000, pp. 108-113.
Turner, Progress in Industrial Microbiology, Martinelli and Kinghorn (eds.), Elsevier, Amsterdam, 1994, 29:641-666.
Uppenberg, Jonas, et al., "Crystallographic and Molecular-Modeling Studies of Lipase B from *Candida antarctia* Reveal a Stereospecificity Pocket for Secondary alcohols", Biochemistry, 1995, vol. 34, pp. 16838-16851.
Uppenberg, Jonas, et al., "The Sequence, crystal structure determination and refinement of two crystal forms of lipase B from *Candida antarctica*", Structure 1994, vol. 2, No. 4.
Upton C et al TIBS Trends in Biochemical Sciences, Elsevier Publications (1995), vol. 20, pp. 178-179.
Uusitalo et al. (1991) J Biotechnol. 17(1), 35-49.
Uwajima T et al, Agricultural and Biological Chemistry, 43(12), pp. 2633-2634, 1979.
Uwajima T et al, Agricultural and Biological Chemistry, 44(9), pp. 2039-2045, 1980.
Uwajima T et al, Methods in Enzymology, 89(41), pp. 243-248.
Vaidehi, et al.; "Lipase Activity of Some Fungi Isolated from Groundnut"; Current Science (1984); vol. 53(23); p. 1253.
van Binsbergen, Jan, et al., "Substitution of PHE-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.
van Gemeren, I.A., et al., "Expression and Secretion of Defined Cutinase Variants by *Aspergillus awamori*" Applied and Environmental Microbiology, vol. 64, No. 8, pp. 2794-2799, Aug. 1998.
van Kampen, M.D., et al., "The phospholipase activity of *Staphylococcus hyicus* lipase strongly depends on a single Ser to Val mutation", Chemistry and Physics of Lipids, vol. 93, 1998, pp. 39-45.
Vaysse et al J. of Biotechnology 53 (1997) 41-46.
Vujaklija, Dušica, et al., "A novel streptomycete lipase: cloning, sequencing and high-level expression of the *Streptomyces rimosus* GDS (L)-lipase gene", Arch. Microbiol, vol. 178, pp. 124-130, 2002.
Wahnelt S.V., Meusel D, & Tülsner M, (1991) Zur kenntnis des diglyceride influsses auf das kristallisationsverhalten von Fetten, in Fat Science Technology 4:117-121.
Waninge, Rianne, et al., "Milk membrane lipid vesicle structures studied with Cryo-TEM", Colloids and Surfaces B: Biointerfaces 31 (2003), pp. 257-264.
Warmuth et al, 1992, Bio Forum 9, 282-283.
Watanabe et al. Bio sci Biochem 63(5) 820-826, 1999.
Watanabe, Yasuo et al., "Cloning and sequencing of phospholipase B gene from the yeast *Torulaspora delbrueckii*", FEMS Microbiology Letters, vol. 124, 1994, pp. 29-34.
Webb EC, Enzyme Nomenclature, 1992, p. 310.
Weber et al. J Agric Food Chem 1985, 33, 1093-1096.
Wen-Chen Suen et al., "Improved activity and thermostability of *Candida antarctica* lipase B by DNA family shuffling", Protein Engineering, Design & Selection, vol. 17, No. 2, pp. 133-140, 2004.
West S.; "Olive and Other Edible Oils"; Industrial Enzymology (1996); pp. 295-299.
Whitehead, Michael, et al., "Transformation of a nitrate reductase deficient mutant of *Penicillium chrysogenum* with the corresponding *Aspergillus niger* and *A. nidulans* niaD genes", Mol Gen Genet, 216: 408-411, 1989.

Wilhelm et al., "A Novel Lipolytic Enzyme Located in the Outer Membrane of *Pseudomonas aeruginosa*", Journal of Bacteriology, vol. 181, No. 22, Nov. 1999, pp. 6977-6986.
Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.
Witt, Wolfgang et al., "Secretion of Phospholipase B From *Saccharomyces cerevisiae*", Biochimica et Biophysica Acta, vol. 795, 1984, pp. 117-124.
Xu, Jun, et al., "Intron requirement for AFP gene expression in *Trichoderma viride*", Microbiology, 2003, vol. 149, pp. 3093-3097.
Yamaguchi et al, 1991, Gene 103:61-67.
Yamauchi, Asao et al., "Evolvability of random polypetides through functional selection within a small library", Protein Engineering, vol. 15, No. 7, pp. 619-626, 2002.
Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.
Zaks, Aleksey, et al., "Enzyme-catalyzed processes in organic solvents", Proc. Natl. Acad. Sci. USA, vol. 82, pp. 3192-3196, May 1985.
Zaks, Aleksey, et al., "The Effect of Water on Enzyme Action in Organic Media", The Journal of Biological Chemistry, vol. 263, No. 17, Issue of Jun. 15, pp. 8017-8021, 1988.
Zangenbert, Niels Honberg, et al., "A dynamic in vitro lipolysis model I. Controlling the rate of lipolysis by continuous addition of calcium", European Journal of Pharmaceutical Sciences, vol. 14, 2001, pp. 115-122.
Zangenbert, Niels Honberg, et al., "A dynamic in vitro lipolysis model II. Evaluation of the model", European Journal of Pharmaceutical Sciences, vol. 14, 2001, pp. 237-244.
Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.
Accession No., P10480 "Glycerophosphopholipid-cholesterol acyltransferase" created Jul. 1, 1989, availabel at www.ncbi.nlm.nih.gov/entrez.
Garcia et al., 1,2-Diacyl-*sn*-glycerol:Sterol Acyl Transferase from Spinach Leaves (*Spinacia olerecea* L.) Methods in Enzymology, 1981, vol. 71, p. 768-772.
Score Search Results Details for Application 11852274 and Search Result 20090123_133146_us-11-8.
Score Search Results Details for Application 11852274 and Search Result 20090116_120302_us-11-8.
Anna Maria V. Garzillo et al., Production, purification and characterization of glucose oxidase from *Penicillium variabile* P16[1], Biotechnol. Appl. Biochem. 22, 169-178 (1995).
Roberto A. Chica et al., "Semi-rational approaches to engineering enzyme activity: combining the benefits of directed evolution and rational design", Current Opinion in Biotechnology 2005, pp. 378-384.
Hajime Seino et al., "Enzymatic Synthesis of Carbohydrate Esters of Fatty Acid (1) Esterification of Sucrose, Glucose, Fructose and Sorbitol", vol. 61, No. 11 (Nov. 1984) pp. 1761-1765.
Delphine Briand[*a*] et al., "Substrate Specificity of the Lipase from *Candida parapsilosis*", Lipids, vol. 30, No. 8 (1995), pp. 747-754.
International Dairy Federation, Bulletin, Document 116, 1979, p. 5.
Andrzej Witkowski et al., "Conversion of a β-Ketoacyl Synthase to a Malonyl Decarboxylase by Replacement of the Active-Site Cysteine with Glutamine", Biochemistry 1999, 38, 11643-11650.
Jennifer L. Seffernick et al., "Melamine Deaminase and Atrazine Chlorohyrolase: 98 Percent Indentical but Functionally Different", Journal of Bacteriology, Apr. 2001, p. 2405-2410.
Stryer, L. 1981. Biochemistry, 2nd Ed. W.H. Freeman and Co. San Francisco, p. 16.
Buckley. Substrate specificity of bacterial glycerophospholipid: cholesterol acyltransferase. Biochemistry 1982, 21: 6699-6703.
Nerland A.H., "The Nucleotide Sequence of the Gene Encoding GCAT from *Aeromonas salmonicida* SSP. Salmonicida", Journal of Fish Diseases, 1996, vol. 19, No. 2, pp. 145-150, XP008049669.

Nerland A.H., "Glycerophospholipid-cholesterol acyltransferase precursor", SwissProt, Feb. 11, 2005, XP002318368.

Buckley J. Thomas, "Substrate specificity of bacterial glycerophospholipid" Cholesterol Acyltransferase, Biochemistry, 1982, vol. 21, pp. 6699-6703.

Sen, et al., Developments in Directed Evolution for Improving Enzyme Functions, Appl. Biochem. Biotechnol (2007) vol. 143, No. 3, p. 212-223.

Verenium Corporation leaflet Purifine Enzyme, "Convert Gums to Oils Significantly Increase oil Yields no increase in Free Fatty Acids", San Diego, Jan. 2008.

AOCS Introduction to the Processing of Fats and Oils, four modules on CD-ROM American Oil Chemists Society, 2003, pp. 111-16 —111-19.

Anguita et al., Appl. Environ. Microbiol., 1983, vol. 59, No. 8, pp. 2411-2417.

Sutrisno et al., Journal of Bioscience and Bioengineering, 2001vol. 91, No. 6, pp. 599-602.

Kalscheuer et al., Applied and Environmental Microbiology, 2004, vol. 70, No. 12, pp. 7119-7125.

Brunel et al., J. Biotechnology, Jul. 1, 2004, vol. 111, No. 1, pp. 41-50.

Figure 1

SEQ ID No. 1

```
  1 ivafGDSlTd geayygdsdg ggwgagladr Ltallrlrar prgvdvfnrg isGrtsdGrl
 61 ivDalvallF laqslglpnL pPYLsgdflr GANFAsagAt Ilptsgpfli QvqFkdfksq
121 vlelrqalgl lqellrllpv ldakspdlvt imiGtNDlit saffgpkste sdrnvsvpef
181 kdnlrqlikr Lrsnngarii vlitlvilnl gplGClPlkl alalassknv dasgclerln
241 eavadfneal relaiskled qlrkdglpdv kgadvpyvDl ysifqdldgi qnpsayvyGF
301 ettkaCCGyG gryNynrvCG naglcnvtak aCnpssylls flfwDgfHps ekGykavAea
361 l
```

Figure 2

SEQ ID No. 2

```
  1 mkkwfvcllg lvaltvqaad srpafsrivm fgdslsdtgk myskmrgylp ssppyyegrf
 61 sngpvwleql tnefpgltia neaeggptav aynkiswnpk yqvinnldye vtqflqkdsf
121 kpddlvilwv gandylaygw nteqdakrvr daisdaanrm vlngakeill fnlpdlgqnp
181 sarsqkvvea ashvsayhnq lllnlarqla ptgmvklfei dkqfaemlrd pqnfglsdqr
241 nacyggsyvw kpfasrsast dsqlsafnpq erlaiagnpl laqavaspma arsastlnce
301 gkmfwdqvhp ttvvhaalse paatfiesqy eflah
```

Figure 3

SEQ ID No. 3

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydggyvw kpfatrsvst drqlsafspq erlaiagnpl laqavaspma rrsasplnce
301 gkmfwdqvhp ttvvhaalse raatfietqy eflahg
```

Figure 4

SEQ ID No. 4

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

Figure 5

SEQ ID No. 5

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

Figure 6

SEQ ID No. 6

```
  1 mdyekfllfg dsitefafnt rpiedgkdqy algaalvney trkmdilqrg fkgytsrwal
 61 kilpeilkhe snivmatifl gandacsagp qsvplpefid nirqmvslmk syhirpiiig
121 pglvdrekwe kekseeialg yfrtnenfai ysdalaklan eekvpfvaln kafqqeggda
181 wqqlltdglh fsgkgykifh dellkvietf ypqyhpknmq yklkdwrdvl ddgsnims
```

Figure 7

```
Alignment of pfam00657.6 consensus sequence with P10480
                *->ivafGDSlTdg...............eayygdsdgggwgagladrL
                   iv+fGDSl+d+++  ++ ++  +++++++ +++s+g  w ++l + +
       P10480   28  IVMFGDSLSDTgkmyskmrgylpssppYYEGRFSNGPVWLEQLTNEF  74 tall..rlrarprgvdvfnrgisGrtsdGrlivDalvallFlaqslglpn
                   + l   +  ++++++++  +n+  +
       P10480   75  PGLTiaNEAEGGPTAVAYNKISWNPK-----------------------  100

LpPYLsgdflrGANFAsagAtIlptsgpfliQvqFkdfksqvlelrqalg
                                                                 ++ ++
       P10480  101  ------------------------------------------YQVINN  106 llqellrllpvldakspdlvtimiGtNDlitsaffgpkstesdrnvsvpe
                   l++e+ ++l +++ k+ dlv++++G+ND+        ++ ++ ++++++
       P10480  107  LDYEVTQFLQKDSFKPDDLVILWVGANDY--------LAYGWNTEQDAKR  148 fkdnlrqlikrLrsnngariivlitlvilnlgplGClPlklalalasskn
                   ++d ++++++r+   nga+       ++++nl+ 1G+ P+
       P10480  149  VRDAISDAANRMV-LNGAK-----EILLFNLPDLGQNPS----------- 181 vdasgclerlneavadfnealrelaiskledqlrkdglpdvkgadvpyvD
                   ++++ +e +  ++a++n++l +la     +ql+++g++++++++d ++++
       P10480  182  ARSQKVVEAASHVSAYHNQLLLNLA-----RQLAPTGMVKLFEIDKQFAE 226 lysifqdldgiqnpsayv.y....GFe.ttkaCCGyGgr.yNyn.rv.CG
                   +   +q+++ + + +a++++++   +++ +++a+++++++ +N+++r+ ++
       P10480  227  MLRDPQNFGLSDQRNACYgGsyvwKPFaSRSASTDSQLSaFNPQeRLaIA 276 nag.l.c.nvtakaC.npssyll.sflfwDgfHpsekGykavAeal<-*
                   +++  l  +  ++++a++  +s+ ++++++fwD++Hp+   ++a+  e
       P10480  277  GNPlLaQaVASPMAArSASTLNCeGKMFWDQVHPTTVVHAALSEPA     322

Alignment of pfam00657.6 consensus sequence with AAG09804
                *->ivafGDSlTdg...............eayygdsdgggwgagladrL
                   iv+fGDSl+d+++  ++ ++  +++++++ +++s+g  w ++l + +
      AAG09804   28  IVMFGDSLSDTgkmyskmrgylpssppYYEGRFSNGPVWLEQLTKQF  74 tallrlrarprgvdvfnrgisGrtsdGrlivDalvallFlaqslglpnLp
                                                   +g+++ n + +G+t
      AAG09804   75  ----------PGLTIANEAEGGAT-------------------------  88

PYLsgdflrGANFAsagAtIlptsgpfliQvqFkdfksqvlelrqa....
                                                        ++++ + ++++ +
      AAG09804   89  ---------------------------------AVAYNKISWNpkyq  102

..lgllqellrllpvldakspdlvtimiGtNDlitsaffgpkstesdrnv
                     ++l++e+ ++l +++ k+ dlv++++G+ND+        ++ ++ ++
      AAG09804  103  vyNNLDYEVTQFLQKDSFKPDDLVILWVGANDY--------LAYGWNTEQ 144 svpefkdnlrqlikrLrsnngariivlitlvilnlgplGClPlklalala
                   ++++++d ++++++r+   nga+        ++++nl+ 1G+ P+
      AAG09804  145  DAKRVRDAISDAANRMV-LNGAK-----QILLFNLPDLGQNPS------- 181 ssknvdasgclerlneavadfnealrelaiskledqlrkdglpdvkgadv
                         ++++ +e +  ++a++n++l +la     +ql+++g+++++++d
      AAG09804  182  ----ARSQKVVEAVSHVSAYHNKLLLNLA-----RQLAPTGMVKLFEIDK 222 pyvDlysifqdldgiqnpsayv.y....GFe.ttkaCCGyGgr.yNyn.r
                   +++++   +q+++ +  ++ +++++   +++ t++ +++ +++ + +++r
      AAG09804  223  QFAEMLRDPQNFGLSDVENPCYdGgyvwKPFaTRSVSTDRQLSaFSPQeR 272 v.CGnag.l.c.nvtakaC.npssyll.sflfwDgfHpsekGykavAeal
                   +  +++++ l  +  ++++a++  +s  ++++++fwD++Hp+    ++a+ e+
      AAG09804  273  LaIAGNPlLaQaVASPMARrSASPLNCeGKMFWDQVHPTTVVHAALSERA 322
                                                                  <-*
```

Figure 7 continued

```
AAG09804

Alignment of pfam00657.6 consensus sequence with NP_631558
                    *->ivafGDSlTdgeayygdsdgggwgagladrLtallrlrarprgvdvf
                       +va+GDS ++g         +g  +  +++L     + + + ++   +
NP_631558       42     YVALGDSYSAG---------SGVLPVDPANL----LCLRSTANYPHV  75 nrgisGrtsdGrlivD.a.l.vallPlaqslglpnLpPYLsgdflrGANP
                    +  ++G++        D + + +
NP_631558       76  IADTTGAR-----LTDvTcGaAQ-------------------------  93

AsagAtIlptsgpfliQvqFkdfksqvlelrqalgllqellrllpvldak
                                                  +++    ++ +  ++ +++
NP_631558       94  --------------------------TADPTRAQYPGVAPQLDALGT  114 spdlvtimiGtNDl................itsaffgpkstesdrnvsvp
                    + dlvt+ iG+ND ++  +   +  ++ +    ++  + +k   ++ + +++
NP_631558      115  GTDLVTLTIGGNDNstfinaitacgtagvlSGGKGSPCKDRHGTSFDDEI 164 efkdn..lrqlikrLrs.nngariivlitlvilnlg...........plG
                    e  +++ l++++  +r+++ +ar+ +l  ++i+++  +++   + +   G
NP_631558      165  EANTYpaLKEALLGVRArAPHARVAALGYPWITPATadpscflklplAAG 214

ClPlklalalassknvdasgclerlneavadfnealrelaiskledqlrk
                    P+                      l+ ++a   n  a+r   a
NP_631558      215  DVPY-------------------LRAIQAHLNDAVRRAA---------- 234 dglpdvkgadvpyvDlysifqdldgiqnpsayvyGFettkaCCGyGgryN
                     ++  +  +yvD+ ++
NP_631558      235  ------EETGATYVDFSGVSDG--------------------------- 250 ynrvCGnaglcnvtakaC.npssyll.sflfwDgf...HpsekGykavAe
                                      ++aC+ p +++ +    lf + + + Hp++ G +++Ae
NP_631558      251  -------------HDACeAPGTRWIePLLPGHSLvpvHPNALGERRMAE 286 al<-*
                    +
NP_631558      287  HT    288

Alignment of pfam00657.6 consensus sequence with CAC42140
                    *->ivafGDSlTdgeayygdsdgggwgagladrLtallrlrarprgvdvf
                       +va+GDS ++g         +g  +  +++L     + + + ++   +
CAC42140        42     YVALGDSYSAG---------SGVLPVDPANL----LCLRSTANYPHV  75 nrgisGrtsdGrlivD.a.l.vallPlaqslglpnLpPYLsgdflrGANP
                    +  ++G++        D + + +
CAC42140        76  IADTTGAR-----LTDvTcGaAQ-------------------------  93

AsagAtIlptsgpfliQvqFkdfksqvlelrqalgllqellrllpvldak
                                                  +++    ++ +  ++ +++
CAC42140        94  --------------------------TADPTRAQYPGVAPQLDALGT  114 spdlvtimiGtNDl................itsaffgpkstesdrnvsvp
                    + dlvt+ iG+ND ++  +   +  ++ +    ++  + +k   ++ + +++
CAC42140       115  GTDLVTLTIGGNDNstfinaitacgtagvlSGGKGSPCKDRHGTSFDDEI 164 efkdn..lrqlikrLrs.nngariivlitlvilnlg...........plG
                    e  +++ l++++  +r+++ +ar+ +l  ++i+++  +++   + +   G
CAC42140       165  EANTYpaLKEALLGVRArAPHARVAALGYPWITPATadpscflklplAAG 214

ClPlklalalassknvdasgclerlneavadfnealrelaiskledqlrk
                    P+                      l+ ++a   n  a+r   a
CAC42140       215  DVPY-------------------LRAIQAHLNDAVRRAA---------- 234 dglpdvkgadvpyvDlysifqdldgiqnpsayvyGFettkaCCGyGgryN
                     ++  +  +yvD+ ++
CAC42140       235  ------EETGATYVDFSGVSDG--------------------------- 250 ynrvCGnaglcnvtakaC.npssyll.sflfwDgf...HpsekGykavAe
                                      ++aC+ p +++ +    lf + + + Hp++ G +++Ae
CAC42140       251  -------------HDACeAPGTRWIePLLPGHSLvpvHPNALGERRMAE 286
```

Figure 7 continued

```
                      al<-*
                      +
CAC42140    287  HT   288

Alignment of pfam00657.6 consensus sequence with P41734
              *->ivafGDSlTdg....eayygdsdgggwgagladrLtallrlrarprg
                 ++fGDS+T+    +++ + +  d+   ga+l + +        +r+
P41734      6    PLLFGDSITEFafntRPIEDGKDQYALGAALVNEY---------TRK   43 vdvfnrgisGrtsdGrlivDalvallFlaqslglpnLpPYLsgdflrGAN
                 +d+  rg++G+t
P41734      44   MDILQRGFKGYT--------------------------------------   55

FAsagAtIlptsgpfliQvqPkdfksqvlelrqalglIqellrllpvlda
                                                  +r+al++l+e+l+     +
P41734      56   ---------------------SRWALKILPEILKH-----E            70 kspdlvtimiGtNDlitsaffgpkstesdrnvsvpefkdnlrqlikrLrs
                  +  + ti++G+ND+           ++ +++ v++pef+dn+rq+++++s
P41734      71   SNIVMATIFLGANDA---------CSAGPQSVPLPEFIDNIRQMVSLMKS   111 nngariivlitlvilnlgplGClPlklalalassknvdasgclerlneav
                 ++++ii++++lv    ++              ++ k ++ +  + r+ne +
P41734      112  YHIRPIIIGPGLVDREKW------------EKEKSEEIALGYFRTNENF   148 adfnealrelaiskledqlrkdglpdvkgadvpyvDlysifqdldgiqnp
                 a +   al +la              ++ +vp+v l+++fq+ +g++++
P41734      149  AIYSDALAKLA----------------NEEKVPFVALNKAFQQEGGDAWQ   182 sayvyGFettkaCCGyGgryNynrvCGnaglcnvtakaCnpssyllsflf
                 +                                                l+
P41734      183  Q-----------------------------------------------LL   185 wDgfHpsekGykavAeal<-*
                 Dg+H+s kGyk++++l
P41734      186  TDGLHPSGKGYKIFHDEL       203
```

Figure 8

```
A.sal   1    MKKWFVCLLGLIALTVQAADTRPAFSRIVMFGDSLSDTGKMYSKMRGYLPSSPPYYEGRF  60
                         +           +
A.hyd   1    MKKWFVCLLGLVALTVQAADSRPAFSRIVMFGDSLSDTGKMYSKMRGYLPSSPPYYEGRF  60

A. sal  61   SNGPVWLEQLTKQFPGLTIANEAEGGATAVAYNKISWNPKYQVINNLDYEVTQFLQKDSF  120
                          ++           +
A. hyd  61   SNGPVWLEQLTNEFPGLTIANEAEGGPTAVAYNKISWNPKYQVINNLDYEVTQFLQKDSF  120

A. sal  121  KPDDLVILWVGANDYLAYGWNTEQDAKRVRDAISDAANRMVLNGAKQILLFNLPDLGQNP  180
                                                            +
A. hyd  121  KPDDLVILWVGANDYLAYGWNTEQDAKRVRDAISDAANRMVLNGAKEILLFNLPDLGQNP  180

A. sal  181  SARSQKVVEAVSHVSAYHNKLLLNLARQLAPTGMVKLFEIDKQFAEMLRDPQNFGLSDVE  240
                       +       +                                         ++
A.hyd   181  SARSQKVVEAASHVSAYHNQLLLNLARQLAPTGMVKLFEIDKQFAEMLRDPQNFGLSDQR  240

A. sal  241  NPCYDGGYVWKPFATRSVSTDRQLSAFSPQERLAIAGNPLLAQAVASPMARRSASPLNCE  300
               + ++ +        + + +      +                    +    +
A. hyd  241  NACYGGSYVWKPFASRSASTDSQLSAFNPQERLAIAGNPLLAQAVASPMAARSASTLNCE  300

A. sal  301  GKMFWDQVHPTTVVHAALSERAATFIETQYEFLAH  335
                                  +      +
A. hyd  301  GKMFWDQVHPTTVVHAALSEPAATFIESQYEFLAH  335
```

Figure 9

```
  1  ATGAAAAAAT GGTTTGTGTG TTTATTGGGA TTGGTCGCGC TGACAGTTCA GGCAGCCGAC
 61  AGCCGTCCCG CCTTCTCCCG GATCGTGATG TTTGGCGACA GCCTCTCCGA TACCGGCAAG
121  ATGTACAGCA AGATGCGCGG TTACCTCCCC TCCAGCCCCC CCTACTATGA GGGCCGCTTC
181  TCCAACGGGC CGTCTGGCT  GGAGCAGCTG ACCAACGAGT TCCCGGGCCT GACCATAGCC
241  AACGAGGCGG AAGGCGGACC GACCGCCGTG GCTTACAACA AGATCTCCTG GAATCCCAAG
301  TATCAGGTCA TCAACAACCT GGACTACGAG GTCACCCAGT TCCTGCAAAA AGACAGCTTC
361  AAGCCGGACG ATCTGGTGAT CCTCTGGGTC GGCGCCAACG ACTATCTGGC CTATGGCTGG
421  AACACAGAGC AGGATGCCAA GCGGGTGCGC GACGCCATCA GCGATGCGGC CAACCGCATG
481  GTGCTGAACG GCGCCAAGGA GATACTGCTG TTCAACCTGC CGGATCTGGG CCAGAACCCC
541  TCGGCCCGCA GCCAGAAGGT GGTCGAGGCG CCAGCCATG  TCTCCGCCTA CCACAACCAG
601  CTGCTGCTGA ACCTGGCACG CCAGCTGGCT CCCACCGGCA TGGTGAAGCT GTTCGAGATC
661  GACAAGCAGT TTGCCGAGAT GCTGCGTGAT CCGCAGAACT TCGGCCTGAG CGACCAGAGG
721  AACGCCTGCT ACGGTGGCAG CTATGTATGG AAGCCGTTTG CCTCCCGCAG CGCCAGCACC
781  GACAGCCAGC TCTCCGCCTT CAACCCGCAG GAGCGCCTCG CCATCGCCGG CAACCCGCTG
841  CTGGCCCAGG CCGTCGCCAG CCCCATGGCT GCCCGCAGCG CCAGCACCCT CAACTGTGAG
901  GGCAAGATGT TCTGGGATCA GGTCCACCCC ACCACTGTCG TGCACGCCGC CCTGAGCGAG
961  CCCGCCGCCA CCTTCATCGA GAGCCAGTAC GAGTTCCTCG CCCAC
```

Figure 10

```
  1  ATGAAAAAAT GGTTTGTTTG TTTATTGGGG TTGATCGCGC TGACAGTTCA GGCAGCCGAC
 61  ACTCGCCCCG CCTTCTCCCG GATCGTGATG TTCGGCGACA GCCTCTCCGA TACCGGCAAA
121  ATGTACAGCA AGATGCGCGG TTACCTCCCC TCCAGCCCGC CCTACTATGA GGGCCGTTTC
181  TCCAACGGAC CCGTCTGGCT GGAGCAGCTG ACCAAGCAGT TCCCGGGTCT GACCATCGCC
241  AACGAAGCGG AAGGCGGTGC CACTGCCGTG GCTTACAACA AGATCTCCTG GAATCCCAAG
301  TATCAGGTCT ACAACAACCT GGACTACGAG GTCACCCAGT TCTTGCAGAA AGACAGCTTC
361  AAGCCGGACG ATCTGGTGAT CCTCTGGGTC GGTGCCAATG ACTATCTGGC ATATGGCTGG
421  AATACGGAGC AGGATGCCAA GCGAGTTCGC GATGCCATCA GCGATGCGGC CAACCGCATG
481  GTACTGAACG GTGCCAAGCA GATACTGCTG TTCAACCTGC CGGATCTGGG CCAGAACCCG
541  TCAGCCCGCA GTCAGAAGGT GGTCGAGGCG GTCAGCCATG TCTCCGCCTA TCACAACAAG
601  CTGCTGCTGA ACCTGGCACG CCAGCTGGCC CCCACCGGCA TGGTAAAGCT GTTCGAGATC
661  GACAAGCAAT TGCCGAGAT GCTGCGTGAT CCGCAGAACT TCGGCCTGAG CGACGTCGAG
721  AACCCCTGCT ACGACGGCGG CTATGTGTGG AAGCCGTTTG CCACCCGCAG CGTCAGCACC
781  GACGCCAGC TCTCCGCCTT CAGTCCGCAG GAACGCCTCG CCATCGCCGG CAACCCGCTG
841  CTGGCACAGG CCGTTGCCAG TCCTATGGCC CGCCGCAGCG CCAGCCCCCT CAACTGTGAG
901  GGCAAGATGT TCTGGGATCA GGTACACCCG ACCACTGTCG TGCACGCAGC CCTGAGCGAG
961  CGCGCCGCCA CCTTCATCGA GACCCAGTAC GAGTTCCTCG CCCACGGATG A
```

Figure 11

```
  1 ATGCCGAAGC CTGCCCTTCG CCGTGTCATG ACCGCGACAG TCGCCGCCGT CGGCACGCTC
 61 GCCCTCGGCC TCACCGACGC CACCGCCCAC GCCGCGCCCG CCCAGGCCAC TCCGACCCTG
121 GACTACGTCG CCCTCGGCGA CAGCTACAGC GCCGGCTCCG GCGTCCTGCC CGTCGACCCC
181 GCCAACCTGC TCTGTCTGCG CTCGACGGCC AACTACCCCC ACGTCATCGC GGACACGACG
241 GGCGCCCGCC TCACGGACGT CACCTGCGGC GCCGCGCAGA CCGCCGACTT CACGCGGGCC
301 CAGTACCCGG GCGTCGCACC CCAGTTGGAC GCGCTCGGCA CCGGCACGGA CCTGGTCACG
361 CTCACCATCG GCGGCAACGA CAACAGCACC TTCATCAACG CCATCACGGC CTGCGGCACG
421 GCGGGTGTCC TCAGCGGCGG CAAGGGCAGC CCCTGCAAGG ACAGGCACGG CACCTCCTTC
481 GACGACGAGA TCGAGGCCAA CACGTACCCC GCGCTCAAGG AGGCGCTGCT CGGCGTCCGC
541 GCCAGGGCTC CCCACGCCAG GGTGGCGGCT CTCGGCTACC CGTGGATCAC CCCGGCCACC
601 GCCGACCCGT CCTGCTTCCT GAAGCTCCCC CTCGCCGCCG GTGACGTGCC CTACCTGCGG
661 GCCATCCAGG CACACCTCAA CGACGCGGTC CGGCGGGCCG CCGAGGAGAC CGGAGCCACC
721 TACGTGGACT TCTCCGGGGT GTCCGACGGC CACGACGCCT GCGAGGCCCC CGGCACCCGC
781 TGGATCGAAC CGCTGCTCTT CGGGCACAGC CTCGTTCCCG TCCACCCCAA CGCCCTGGGC
841 GAGCGGCGCA TGGCCGAGCA CACGATGGAC GTCCTCGGCC TGGACTGA
```

Figure 12

```
  1  TCAGTCCAGG CCGAGGACGT CCATCGTGTG CTCGGCCATG CGCCGCTCGC CCAGGGCGTT
 61  GGGGTGGACG GGAACGAGGC TGTGCCCGAA GAGCAGCGGT TCGATCCAGC GGGTGCCGGG
121  GGCCTCGCAG GCGTCGTGGC CGTCGGACAC CCCGGAGAAG TCCACGTAGG TGGCTCCGGT
181  CTCCTCGGCG GCCCGCCGGA CCGCGTCGTT GAGGTGTGCC TGGATGGCCC GCAGGTAGGG
241  CACGTCACCG GCGGCGAGGG GGAGCTTCAG GAAGCAGGAC GGGTCGGCGG TGGCCGGGGT
301  GATCCACGGG TAGCCGAGAG CCGCCACCCT GGCGTGGGGA GCCCTGGCGC GGACGCCGAG
361  CAGCGCCTCC TTGAGCGCGG GGTACGTGTT GGCCTCGATC TCGTCGTCGA AGGAGGTGCC
421  GTGCCTGTCC TTGCAGGGGC TGCCCTTGCC GCCGCTGAGG ACACCCGCCG TGCCGCAGGC
481  CGTGATGGCG TTGATGAAGG TGCTGTTGTC GTTGCCGCCG ATGGTGAGCG TGACCAGGTC
541  CGTGCCGGTG CCGAGCGCGT CCAACTGGGG TGCGACGCCC GGGTACTGGG CCCGCGTGAA
601  GTCGGCGGTC TGCGCGGCGC CGCAGGTGAC GTCCGTGAGG CGGGCGCCCG TCGTGTCCGC
661  GATGACGTGG GGGTAGTTGG CCGTCGAGCG CAGACAGAGC AGGTTGGCGG GGTCGACGGG
721  CAGGACGCCG GAGCCGGCGC TGTAGCTGTC GCCGAGGGCG ACGTAGTCCA GGGTCGGAGT
781  GGCCTGGGCG GGCGCGGCGT GGGCGGTGGC GTCGGTGAGG CCGAGGGCGA GCGTGCCGAC
841  GGCGGCGACT GTCGCGGTCA TGACACGGCG AAGGGCAGGC TTCGGCAT
```

Figure 13

```
  1  ATGGATTACG AGAAGTTTCT GTTATTTGGG GATTCCATTA CTGAATTTGC TTTTAATACT
 61  AGGCCCATTG AAGATGGCAA AGATCAGTAT GCTCTTGGAG CCGCATTAGT CAACGAATAT
121  ACGAGAAAAA TGGATATTCT TCAAAGAGGG TTCAAAGGGT ACACTTCTAG ATGGGCGTTG
181  AAAATACTTC CTGAGATTTT AAAGCATGAA TCCAATATTG TCATGGCCAC AATATTTTTG
241  GGTGCCAACG ATGCATGCTC AGCAGGTCCC CAAAGTGTCC CCTCCCCGA ATTTATCGAT
301  AATATTCGTC AAATGGTATC TTTGATGAAG TCTTACCATA TCCGTCCTAT TATAATAGGA
361  CCGGGGCTAG TAGATAGAGA GAAGTGGGAA AAAGAAAAAT CTGAAGAAAT AGCTCTCGGA
421  TACTTCCGTA CCAACGAGAA CTTTGCCATT TATTCCGATG CCTTAGCAAA ACTAGCCAAT
481  GAGGAAAAAG TTCCCTTCGT GGCTTTGAAT AAGGCGTTTC AACAGGAAGG TGGTGATGCT
541  TGGCAACAAC TGCTAACAGA TGGACTGCAC TTTTCCGGAA AAGGGTACAA AATTTTTCAT
601  GACGAATTAT TGAAGGTCAT TGAGACATTC TACCCCCAAT ATCATCCCAA AAACATGCAG
661  TACAAACTGA AAGATTGGAG AGATGTGCTA GATGATGGAT CTAACATAAT GTCTTGA
```

Figure 14

(SEQ ID No. 12)

```
          10          20          30          40          50          60
          |           |           |           |           |           |
   MNLRQWMGAA  TAALALGLAA  CGGGGTDQSG  NPNVAKVQRM  VVFGDSLSDI  GTYTPVAQAV 70          80          90         100         110         120
          |           |           |           |           |           |
   GGGKFTTNPG  PIWAETVAAQ  LGVTLTPAVM  GYATSVQNCP  KAGCFDYAQG  GSRVTDPNGI 130         140         150         160         170         180
          |           |           |           |           |           |
   GHNGGAGALT  YPVQQQLANF  YAASNNTFNG  NNDVVFVLAG  SNDIFFWTTA  AATSGSGVTP 190         200         210         220         230         240
          |           |           |           |           |           |
   AIATAQVQQA  ATDLVGYVKD  MIAKGATQVY  VFNLPDSSLT  PDGVASGTTG  QALLHALVGT 250         260         270         280         290         300
          |           |           |           |           |           |
   FNTTLQSGLA  GTSARIIDFN  AQLTAAIQNG  ASFGFANTSA  RACDATKINA  LVPSAGGSSL 310         320         330         340
          |           |           |           |
   FCSANTLVAS  GADQSYLFAD  GVHPTTAGHR  LIASNVLARL  LADNVAH
```

Figure 15

(SEQ ID No. 13)

```
atgaacctgc gtcaatggat gggcgccgcc acggctgccc ttgccttggg cttggccgcg    60
tgcggggggcg gtgggaccga ccagagcggc aatcccaatg tcgccaaggt gcagcgcatg   120
gtggtgttcg gcgacagcct gagcgatatc ggcacctaca cccccgtcgc gcaggcggtg   180
ggcggcggca agttcaccac caacccgggc ccgatctggg ccgagaccgt ggccgcgcaa   240
ctgggcgtga cgctcacgcc ggcggtgatg ggctacgcca cctccgtgca gaattgcccc   300
aaggccggct gcttcgacta tgcgcagggc ggctcgcgcg tgaccgatcc gaacggcatc   360
ggccacaacg gcggcgcggg ggcgctgacc tacccggttc agcagcagct cgccaacttc   420
tacgcggcca gcaacaacac attcaacggc aataacgatg tcgtcttcgt gctggccggc   480
agcaacgaca ttttcttctg gaccactgcg gcggccacca gcggctccgg cgtgacgccc   540
gccattgcca cggcccaggt gcagcaggcc gcgacggacc tggtcggcta tgtcaaggac   600
atgatcgcca agggtgcgac gcaggtctac gtgttcaacc tgcccgacag cagcctgacg   660
ccggacggcg tggcaagcgg cacgaccggc caggcgctgc tgcacgcgct ggtgggcacg   720
ttcaacacga cgctgcaaag cgggctggcc ggcacctcgg cgcgcatcat cgacttcaac   780
gcacaactga ccgcggcgat ccagaatggc gcctcgttcg gcttcgccaa caccagcgcc   840
cgggcctgcg acgccaccaa gatcaatgcc ctggtgccga gcgccggcgg cagctcgctg   900
ttctgctcgg ccaacacgct ggtggcttcc ggtgcggacc agagctacct gttcgccgac   960
ggcgtgcacc cgaccacggc cggccatcgc ctgatcgcca gcaacgtgct ggcgcgcctg  1020
ctggcggata acgtcgcgca ctga                                         1044
```

Figure 16 (SEQ ID No. 20)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalragqal glrvpadpdq pwpplpprgt ldvrrddvhw areylvpwig rrlrgessgd
241 hvtakgtlsp daiktriaav a
```

Figure 17 (SEQ ID No. 21)

```
  1 gtgatcgggt cgtacgtggc ggtgggggac agcttcaccg agggcgtcgg cgaccccggc
 61 cccgacgggg cgttcgtcgg ctgggccgac cggctcgccg tactgctcgc ggaccggcgc
121 cccgagggcg acttcacgta cacgaacctc gccgtgcgcg gcaggctcct cgaccagatc
181 gtggcggaac aggtcccgcg ggtcgtcgga ctcgcgcccg acctcgtctc gttcgcggcg
241 ggcggcaacg acatcatccg gcccggcacc gatcccgacg aggtcgccga gcggttcgag
301 ctggcggtgg ccgcgctgac cgccgcggcc ggaaccgtcc tggtgaccac cgggttcgac
361 acccggggg tgcccgtcct caagcacctg cgcggcaaga tcgccacgta caacgggcac
421 gtccgcgcca tcgccgaccg ctacggctgc ccggtgctcg acctgtggtc gctgcggagc
481 gtccaggacc gcagggcgtg ggacgccgac cggctgcacc tgtcgccgga ggggcacacc
541 cgggtggcgc tgcgcgcggg gcaggccctg ggcctgcgcg tcccggccga ccctgaccag
601 ccctggccgc cctgccgcc gcgcggcacg ctcgacgtcc ggcgcgacga cgtgcactgg
661 gcgcgcgagt acctggtgcc gtggatcggg cgccggctgc ggggcgagtc gtcgggcgac
721 cacgtgacgg ccaaggggac gctgtcgccg gacgccatca agacgcggat cgccgcggtg
781 gcctga
```

Figure 18
(SEQ ID No. 22)

```
  1 mqtnpaytsl vavgdsfteg msdllpdgsy rgwadllatr maarspgfry anlavrgkli
 61 gqivdeqvdv aaamgadvit lvgglndtlr pkcdmarvrd lltqaverla phceqlvlmr
121 spgrqgpvle rfrprmealf aviddlagrh gavvvdlyga qsladprmwd vdrlhltaeg
181 hrrvaeavwq slghepedpe whapipatpp pgwvtrrtad vrfarqhllp wigrrltgrs
241 sgdglpakrp dllpyedpar
```

Figure 19 (SEQ ID No. 23)

```
  1 atgcagacga accccgcgta caccagtctc gtcgccgtcg gcgactcctt caccgagggc
 61 atgtcggacc tgctgcccga cggctcctac cgtggctggg ccgacctcct cgccacccgg
121 atggcggccc gctcccccgg cttccggtac gccaacctgg cggtgcgcgg gaagctgatc
181 ggacagatcg tcgacgagca ggtggacgtg gccgccgcca tgggagccga cgtgatcacg
241 ctggtcggcg ggctcaacga cacgctgcgg cccaagtgcg acatggcccg ggtgcgggac
301 ctgctgaccc aggccgtgga acggctcgcc ccgcactgcg agcagctggt gctgatgcgc
361 agtcccggtc gccagggtcc ggtgctggag cgcttccggc ccgcatgga ggccctgttc
421 gccgtgatcg acgacctggc cgggcggcac ggcgccgtgg tcgtcgacct gtacggggcc
481 cagtcgctgg ccgaccctcg gatgtgggac gtggaccggc tgcacctgac cgccgagggc
541 caccgccggg tgcggaggc ggtgtggcag tcgctcggcc acgagcccga ggaccccgag
601 tggcacgcgc cgatcccggc gacgccgccg ccggggtggg tgacgcgcag gaccgcggac
661 gtccggttcg cccggcagca cctgctgccc tggataggcc gcaggctgac cgggcgctcg
721 tccggggacg gcctgccggc caagcgcccg gacctgctgc cctacgagga ccccgcacgg
781 tga
```

Figure 20 (SEQ ID No. 24)

```
  1 mtrgrdggag apptkhrall aaivtlivai saaiyagasa ddgsrdhalq aggrlprgda
 61 apastgawvg awatapaaae pgtettglag rsvrnvvhts vggtgaritl snlygqsplt
121 vthasialaa gpdtaaaiad tmrrltfggs arviipaggq vmsdtarlai pyganvlvtt
181 yspipsgpvt yhpqarqtsy ladgdrtadv tavayttptp ywryltaldv lsheadgtvv
241 afgdsitdga rsqsdanhrw tdvlaarlhe aagdgrdtpr ysvvnegisg nrlltsrpgr
301 padnpsglsr fqrdvlertn vkavvvvlgv ndvlnspela drdailtglr tlvdraharg
361 lrvvgatitp fggyggytea retmrqevne eirsgrvfdt vvdfdkalrd pydprrmrsd
421 ydsgdhlhpg dkgyarmgav idlaalkgaa pvka
```

Figure 21 (SEQ ID No. 25)

```
   1 atgacccggg gtcgtgacgg gggtgcgggg gcgcccccca ccaagcaccg tgccctgctc
  61 gcggcgatcg tcaccctgat agtggcgatc tccgcggcca tatacgccgg agcgtccgcg
 121 gacgacggca gcagggacca cgcgctgcag gccggaggcc gtctcccacg aggagacgcc
 181 gcccccgcgt ccaccggtgc ctgggtgggc gcctgggcca ccgcaccggc cgcggccgag
 241 ccgggcaccg agacgaccgg cctggcgggc cgctccgtgc gcaacgtcgt gcacacctcg
 301 gtcggcggca ccggcgcgcg gatcaccctc tcgaacctgt acgggcagtc gccgctgacc
 361 gtcacacacg cctcgatcgc cctggccgcc gggcccgaca ccgccgccgc gatcgccgac
 421 accatgcgcc ggctcacctt cggcggcagc gcccgggtga tcatcccggc gggcggccag
 481 gtgatgagcg acaccgcccg cctcgccatc ccctacgggg cgaacgtcct ggtcaccacg
 541 tactccccca tcccgtccgg gccggtgacc taccatccgc aggcccggca gaccagctac
 601 ctggccgacg gcgaccgcac ggcggacgtc accgccgtcg cgtacaccac ccccacgccc
 661 tactggcgct acctgaccgc cctcgacgtg ctgagccacg aggccgacgg cacggtcgtg
 721 gcgttcggcg actccatcac cgacggccgc cgctcgcaga gcgacgccaa ccaccgctgg
 781 accgacgtcc tgccgcacg cctgcacgag gcggcgggcg acggccggga cacgccccgc
 841 tacagcgtcg tcaacgaggg catcagcggc aaccggctcc tgaccagcag gccggggcgg
 901 ccggccgaca cccgagcgg actgagccgg ttccagcggg acgtgctgga acgcaccaac
 961 gtcaaggccg tcgtcgtcgt cctcggcgtc aacgacgtcc tgaacagccc ggaactcgcc
1021 gaccgcgacg ccatcctgac cggcctgcgc accctcgtcg accgggcgca cgcccggga
1081 ctgcgggtcg tcggcgccac gatcacgccg ttcggcggct acggcggcta caccgaggcc
1141 cgcgagacga tgcggcagga ggtcaacgag gagatccgct ccggccgggt cttcgacacg
1201 gtcgtcgact tcgacaaggc cctgcgcgac ccgtacgacc cgcgccggat gcgctccgac
1261 tacgacagcg gcgaccacct gcaccccggc gacaaggggt acgcgcgcat gggcgcggtc
1321 atcgacctgg ccgcgctgaa gggcgcggcg ccggtcaagg cgtag
```

Figure 22 (SEQ ID No. 26)

```
  1 mtsmsrarva rriaagaayg gggiglagaa avglvvaevq larrrvgvgt ptrvpnaqgl
 61 yggtlptagd pplrlmmlgd staagqgvhr agqtpgalla sglaavaerp vrlgsvaqpg
121 acsddldrqv alvlaepdrv pdicvimvga ndvthrmpat rsvrhlssav rrlrtagaev
181 vvgtcpdlgt iervrqplrw larrasrqla aaqtigaveq ggrtvslgdl lgpefaqnpr
241 elfgpdnyhp saegyataam avlpsvcaal glwpadeehp dalrregflp varaaaeaas
301 eagtevaaam ptgprgpwal lkrrrrrrvs eaepsspsgv
```

Figure 23 (SEQ ID No. 27)

```
   1 atgacgagca tgtcgagggc gagggtggcg cggcggatcg cggccggcgc ggcgtacggc
  61 ggcggcggca tcggcctggc gggagcggcg gcggtcggtc tggtggtggc cgaggtgcag
 121 ctggccagac gcagggtggg ggtgggcacg ccgacccggg tgccgaacgc gcagggactg
 181 tacggcggca ccctgcccac ggccggcgac ccgccgctgc ggctgatgat gctgggcgac
 241 tccacggccg ccgggcaggg cgtgcaccgg gccgggcaga cgccgggcgc gctgctggcg
 301 tccgggctcg cggcggtggc ggagcggccg gtgcggctgg ggtcggtcgc ccagccgggg
 361 gcgtgctcgg acgacctgga ccggcaggtg gcgctggtgc tcgccgagcc ggaccgggtg
 421 cccgacatct gcgtgatcat ggtcggcgcc aacgacgtca cccaccggat gccggcgacc
 481 cgctcggtgc ggcacctgtc ctcggcggta cggcggctgc gcacggccgg tgcggaggtg
 541 gtggtcggca cctgtccgga cctgggcacg atcgagcggg tgcggcagcc gctgcgctgg
 601 ctggcccggc gggcctcacg gcagctcgcg gcggcacaga ccatcggcgc cgtcgagcag
 661 ggcgggcgca cggtgtcgct gggcgacctg ctgggtccgg agttcgcgca gaacccgcgg
 721 gagctcttcg gccccgacaa ctaccacccc tccgccgagg gtacgccac ggccgcgatg
 781 gcggtactgc cctcggtgtg cgccgcgctc ggcctgtggc cggccgacga ggagcacccg
 841 gacgcgctgc gccgcgaggg cttcctgccg gtggcgcgcg cggcggcgga ggcggcgtcc
 901 gaggcgggta cggaggtcgc cgccgccatg cctacggggc ctcgggggcc ctgggcgctg
 961 ctgaagcgcc ggagacggcg tcgggtgtcg gaggcggaac cgtccagccc gtccggcgtt
1021 tga
```

Figure 24 (SEQ ID No. 28)

```
  1 mgrgtdqrtr ygrrrarval aaltaavlgv gvagcdsvgg dspapsgsps krtrtapawd
 61 tspasvaavg dsitrgfdac avlsdcpevs watgssakvd slavrllgka daaehswnya
121 vtgarmadlt aqvtraaqre pelvavmaga ndacrsttsa mtpvadfraq feeamatlrk
181 klpkaqvyvs sipdlkrlws qgrtnplgkq vwklglcpsm lgdadsldsa atlrrntvrd
241 rvadynevlr evcakdrrcr sddgavhefr fgtdqlshwd wfhpsvdgqa rlaeiayrav
301 taknp
```

Figure 25 (SEQ ID No. 29)

```
  1 atgggtcgag ggacggacca gcggacgcgg tacggccgtc gccgggcgcg tgtcgcgctc
 61 gccgccctga ccgccgccgt cctgggcgtg ggcgtggcgg gctgcgactc cgtgggcggc
121 gactcacccg ctccttccgg cagcccgtcg aagcggacga ggacggcgcc cgcctgggac
181 accagcccgg cgtccgtcgc cgccgtgggc gactccatca cgcgcggctt cgacgcctgt
241 gcggtgctgt cggactgccc ggaggtgtcg tgggcgaccg gcagcagcgc gaaggtcgac
301 tcgctggccg tacggctgct ggggaaggcg gacgcggccc agcacagctg gaactacgcg
361 gtcaccgggg cccggatggc ggacctgacc gctcaggtga cgcgggcggc gcagcgcgag
421 ccggagctgg tggcggtgat ggccggggcg aacgacgcgt gccggtccac gacctcggcg
481 atgacgccgg tggcggactt ccgggcgcag ttcgaggagg cgatggccac cctgcgcaag
541 aagctcccca aggcgcaggt gtacgtgtcg agcatcccgg acctcaagcg gctctggtcc
601 cagggccgca ccaacccgct gggcaagcag gtgtggaagc tcggcctgtg cccgtcgatg
661 ctgggcgacg cggactccct ggactcggcg gcgaccctgc ggcgcaacac ggtgcgcgac
721 cgggtggcgg actacaacga ggtgctgcgg gaggtctgcg cgaaggaccg gcggtgccgc
781 agcgacgacg gcgcggtgca cgagttccgg ttcggcacgg accagttgag ccactgggac
841 tggttccacc cgagtgtgga cggccaggcc cggctggcgg agatcgccta ccgcgcggtc
901 accgcgaaga atccctga
```

Figure 26 (SEQ ID No. 30)

```
  1 mrlsrraata sallltpala lfgasaavsa priqatdyva lgdsyssgvg agsydsssgs
 61 ckrstksypa lwaashtgtr fnftacsgar tgdvlakqlt pvnsgtdlvs itiggndagf
121 adtmttcnlq gesaclaria karayiqqtl paqldqvyda idsrapaaqv vvlgyprfyk
181 lggscavgls eksraainaa addinavtak raadhgfafg dvnttfaghe lcsgapwlhs
241 vtlpvensyh ptangqskgy lpvlnsat
```

Figure 27 (SEQ ID No. 31)

```
   1 ttcatcacaa cgatgtcaca acaccggcca tccgggtcat ccctgatcgt gggaatgggt
  61 gacaagcctt cccgtgacga aagggtcctg ctacatcaga aatgacagaa atcctgctca
 121 gggaggttcc atgagactgt cccgacgcgc ggccacggcg tccgcgctcc tcctcacccc
 181 ggcgctcgcg ctcttcggcg cgagcgccgc cgtgtccgcg ccgcgaatcc aggccaccga
 241 ctacgtggcc ctcggcgact cctactcctc gggggtcggc gcgggcagct acgacagcag
 301 cagtggctcc tgtaagcgca gcaccaagtc ctaccoggcc ctgtgggccg cctcgcacac
 361 cggtacgcgg ttcaacttca ccgcctgttc gggcgcccgc acaggagacg tgctggccaa
 421 gcagctgacc ccggtcaact ccggcaccga cctggtcagc attaccatcg gcggcaacga
 481 cgcgggcttc gccgacacca tgaccacctg caacctccag ggcgagagcg cgtgcctggc
 541 gcggatcgcc aaggcgcgcg cctacatcca gcagacgctg cccgcccagc tggaccaggt
 601 ctacgacgcc atcgacagcc gggccccgc agcccaggtc gtcgtcctgg gctaccgcg
 661 cttctacaag ctgggcggca gctgcgccgt cggtctctcg gagaagtccc gcgcggccat
 721 caacgccgcc gccgacgaca tcaacgccgt caccgccaag cgcgccgcc accacggctt
 781 cgccttcggg gacgtcaaca cgaccttcgc cgggcacgag ctgtgctccg gcgcccctg
 841 gctgcacagc gtcacccttc ccgtggagaa ctcctaccac cccacggcca acggacagtc
 901 caagggctac ctgcccgtcc tgaactccgc cacctgatct cgcggctact ccgcccctga
 961 cgaagtcccg ccccgggcg gggcttcgcc gtaggtgcgc gtaccgccgt cgcccgtcgc
1021 gccggtggcc ccgccgtacg tgccgccgcc cccggacgcg gtcggttc
```

Figure 28 (SEQ ID No. 32)

```
  1  MKKWFVCLLG LVALTVQAAD SRPAFSRIVM FGDSLSDTGK MYSKMRGYLP
 51  SSPPYYEGRF SNGPVWLEQL TKQFPGLTIA NEAEGGATAV AYNKISWNPK
101  YQVINNLDYE VTQFLQKDSF KPDDLVILWV GANDYLAYGW NTEQDAKRVR
151  DAISDAANRM VLNGAKQILL FNLPDLGQNP SARSQKVVEA VSHVSAYHNQ
201  LLLNLARQLA PTGMVKLFEI DKQFAEMLRD PQNFGLSDVE NPCYDGGYVW
251  KPFATRSVST DRQLSAFSPQ ERLAIAGNPL LAQAVASPMA RRSASPLNCE
301  GKMFWDQVHP TTVVHAALSE RAATFIANQY EFLAH*
```

Figure 29 (SEQ ID No. 33)

```
   1  ATGAAAAAAT GGTTTGTGTG TTTATTGGGA TTGGTCGCGC TGACAGTTCA
      TACTTTTTTA CCAAACACAC AAATAACCCT AACCAGCGCG ACTGTCAAGT

51  GGCAGCCGAC AGTCGCCCCG CCTTTTCCCG GATCGTGATG TTCGGCGACA
      CCGTCGGCTG TCAGCGGGGC GGAAAAGGGC CTAGCACTAC AAGCCGCTGT

101  GCCTCTCCGA TACCGGCAAA ATGTACAGCA AGATGCGCGG TTACCTCCCC
      CGGAGAGGCT ATGGCCGTTT TACATGTCGT TCTACGCGCC AATGGAGGGG

151  TCCAGCCCGC CCTACTATGA GGGCCGTTTC TCCAACGGAC CCGTCTGGCT
      AGGTCGGGCG GGATGATACT CCCGGCAAAG AGGTTGCCTG GGCAGACCGA

201  GGAGCAGCTG ACCAAACAGT TCCCGGGTCT GACCATCGCC AACGAAGCGG
      CCTCGTCGAC TGGTTTGTCA AGGGCCCAGA CTGGTAGCGG TTGCTTCGCC

251  AAGGCGGTGC CACTGCCGTG GCTTACAACA AGATCTCCTG GAATCCCAAG
      TTCCGCCACG GTGACGGCAC CGAATGTTGT TCTAGAGGAC CTTAGGGTTC

301  TATCAGGTCA TCAACAACCT GGACTACGAG GTCACCCAGT TCTTGCAGAA
      ATAGTCCAGT AGTTGTTGGA CCTGATGCTC CAGTGGGTCA AGAACGTCTT

351  AGACAGCTTC AAGCCGGACG ATCTGGTGAT CCTCTGGGTC GGTGCCAATG
      TCTGTCGAAG TTCGGCCTGC TAGACCACTA GGAGACCCAG CCACGGTTAC

401  ACTATCTGGC CTATGGCTGG AACACGGAGC AGGATGCCAA GCGGGTTCGC
      TGATAGACCG GATACCGACC TTGTGCCTCG TCCTACGGTT CGCCCAAGCG

451  GATGCCATCA GCGATCGGC CAACCGCATG GTACTGAACG GTGCCAAGCA
      CTACGGTAGT CGCTACGCCG GTTGGCGTAC CATGACTTGC CACGGTTCGT

501  GATACTGCTG TTCAACCTGC CGGATCTGGG CCAGAACCCG TCAGCTCGCA
      CTATGACGAC AAGTTGGACG GCCTAGACCC GGTCTTGGGC AGTCGAGCGT

551  GTCAGAAGGT GGTCGAGGCG GTCAGCCATG TCTCCGCCTA TCACAACCAG
      CAGTCTTCCA CCAGCTCCGC CAGTCGGTAC AGAGGCGGAT AGTGTTGGTC

601  CTGCTGCTGA ACCTGGCACG CCAGCTGGCC CCCACCGGCA TGGTAAAGCT
      GACGACGACT TGGACCGTGC GGTCGACCGG GGGTGGCCGT ACCATTTCGA

651  GTTCGAGATC GACAAGCAAT TTGCCGAGAT GCTGCGTGAT CCGCAGAACT
      CAAGCTCTAG CTGTTCGTTA AACGGCTCTA CGACGCACTA GGCGTCTTGA

701  TCGGCCTGAG CGACGTCGAG AACCCCTGCT ACGACGGCGG CTATGTGTGG
      AGCCGGACTC GCTGCAGCTC TTGGGGACGA TGCTGCCGCC GATACACACC

751  AAGCCGTTTG CCACCCGCAG CGTCAGCACC GACCGCCAGC TCTCCGCCTT
      TTCGGCAAAC GGTGGGCGTC GCAGTCGTGG CTGGCGGTCG AGAGGCGGAA

801  CAGTCCGCAG GAACGCCTCG CCATCGCCGG CAACCCGCTG CTGGCACAGG
      GTCAGGCGTC CTTGCGGAGC GGTAGCGGCC GTTGGGCGAC GACCGTGTCC

851  CCGTTGCCAG TCCTATGGCC CGCCGCAGCG CCAGCCCCCT CAACTGTGAG
      GGCAACGGTC AGGATACCGG GCGGCGTCGC GGTCGGGGGA GTTGACACTC

901  GGCAAGATGT TCTGGGATCA GGTACACCCG ACCACTGTCG TGCACGCAGC
      CCGTTCTACA AGACCCTAGT CCATGTGGGC TGGTGACAGC ACGTGCGTCG

951  CCTGAGCGAG CGCGCCGCCA CCTTCATCGC GAACCAGTAC GAGTTCCTCG
      GGACTCGCTC GCGCGGCGGT GGAAGTAGCG CTTGGTCATG CTCAAGGAGC

1001  CCCAC TGA
      GGGTG ACT
```

Figure 30 (SEQ ID No. 34)

```
  1  MKKWFVCLLG  LIALTVQAAD  TRPAFSRIVM  FGDSLSDTGK  MYSKMRGYLP
 51  SSPPYYEGRF  SNGPVWLEQL  TKQFPGLTIA  NEAEGGATAV  AYNKISWNPK
101  YQVINNLDYE  VTQFLQKDSF  KPDDLVILWV  GANDYLAYGW  NTEQDAKRVR
151  DAISDAANRM  VLNGAKQILL  FNLPDLGQNP  SARSQKVVEA  VSHVSAYHNK
201  LLLNLARQLA  PTGMVKLFEI  DKQFAEMLRD  PQNFGLSDVE  NPCYDGGYVW
251  KPFATRSVST  DRQLSAFSPQ  ERLAIAGNPL  LAQAVASPMA  RRSASPLNCE
301  GKMFWDQVHP  TTVVHAALSE  RAATFIETQY  EFLAHG*
```

Figure 31 (SEQ ID No. 35)

```
   1 ATGAAAAAAT GGTTTGTTTG TTTATTGGGG TTGATCGCGC TGACAGTTCA
     TACTTTTTTA CCAAACAAAC AAATAACCCC AACTAGCGCG ACTGTCAAGT

51 GGCAGCCGAC ACTCGCCCCG CCTTCTCCCG GATCGTGATG TTCGGCGACA
     CCGTCGGCTG TGAGCGGGGC GGAAGAGGGC CTAGCACTAC AAGCCGCTGT

101 GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151 TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201 GGAGCAGCTG ACCAAGCAGT TCCCGGGTCT GACCATCGCC AACGAAGCGG
     CCTCGTCGAC TGGTTCGTCA AGGGCCCAGA CTGGTAGCGG TTGCTTCGCC

251 AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301 TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351 AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401 ACTATCTGGC ATATGGCTGG AATACGGAGC AGGATGCCAA GCGAGTTCGC
     TGATAGACCG TATACCGACC TTATGCCTCG TCCTACGGTT CGCTCAAGCG

451 GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501 GATACTGCTG TTCAACCTGC CGGATCTGGG CCAGAACCCG TCAGCCCGCA
     CTATGACGAC AAGTTGGACG GCCTAGACCC GGTCTTGGGC AGTCGGGCGT

551 GTCAGAAGGT GGTCGAGGCG GTCAGCCATG TCTCCGCCTA TCACAACAAG
     CAGTCTTCCA CCAGCTCCGC CAGTCGGTAC AGAGGCGGAT AGTGTTGTTC

601 CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651 GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701 TCGGCCTGAG CGACGTCGAG AACCCCTGCT ACGACGGCGG CTATGTGTGG
     AGCCGGACTC GCTGCAGCTC TTGGGGACGA TGCTGCCGCC GATACACACC

751 AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801 CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851 CCGTTGCCAG TCCTATGGCC CGCCGCAGCG CCAGCCCCCT CAACTGTGAG
     GGCAACGGTC AGGATACCGG GCGGCGTCGC GGTCGGGGGA GTTGACACTC

901 GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951 CCTGAGCGAG CGCGCCGCCA CCTTCATCGA GACCCAGTAC GAGTTCCTCG
     GGACTCGCTC GCGCGGCGGT GGAAGTAGCT CTGGGTCATG CTCAAGGAGC

1001 CCCACGGATG A
     GGGTGCCTAC T
```

Figure 32

```
              1         10        20        30        40        50
              |---------+---------+---------+---------+---------|
      satA        ADTRPAFSRIYMFGDSLSDTGKMYSKMRGYLPSSPPYYEGRFSN--G
      R.sol   QSGNPNYAKVQRMYVFGDSLSDIGT---------YTPYAQAYGGGKFTTNPG
    Consensus ...adnraafqRiYmFGDSLSDiGk.......YlPsaqaygeGrFsn..G 51        60        70        80        90        100
              |---------+---------+---------+---------+---------|
      satA    PVMLEQLTKQFPGLTIAMEAEGGATAVAYNKISMNPKYQVINNLDYEVTQ
      R.sol   PIMAETVAAQL-GVTLTPAVMGYATSVQNCPKAGCFDYAQGGSRVTDPNG
    Consensus P!MaEqlaaQl.GlTianaaeGgATaVannkiagnfdYaqgnnrdt#pnq 101       110       120       130       140       150
              |---------+---------+---------+---------+---------|
      satA    FLQKDSFKPDDLVILMVGANDYLAYG---MNTEQDAKRYRDAISDAANRMV
      R.sol   IGHNGGAGALTYPVQQQLANFYAASNNTFNGMNDVVFVLAGSNDIFFMTT
    Consensus igqndgagaddlp!qqqgANdYaAsn..fNg##DakrVraainDaanrmt 151       160       170       180       190       200
              |---------+---------+---------+---------+---------|
      satA    LNGAKQILLFNLPDLGQNPSARSQKVVEAVSHVSAYHNKL-LLNLARQLA
      R.sol   AAATSGSGVTPAIATAQVQQRATDLVGYVKDMIAKGATQVYVFNLPDSSL
    Consensus aaaakqiglfnaiala@nqqRas#lVgeakdh!aaganql.llNLarqla 201       210       220       230       240       250
              |---------+---------+---------+---------+---------|
      satA    PTGMVKLFEIDKQFAEMLRDPQNFGLSDVENPCYDGGYVMKPFATRSVST
      R.sol   TPDGVASGTTGQALLHALVGTFNTTLQSGLAGTSARIIDFNAQLTAAIQN
    Consensus ppdgValgeidqalaeaLrdpqNfgLqdgeagcsargidfnaqaTaa!qn 251       260       270       280       290       300
              |---------+---------+---------+---------+---------|
      satA    DRQLSAFSPQERLAIAG--NPLLAQAVASPM---ARRSASPLNCEGKMFW
      R.sol   GASFGFANTSARACDATKINALVPSAGGSSLFCSANTLVASGADQSYLFA
    Consensus daqlgaanpqaRaadAg..NaLlaqAgaSp$...Arrlaapgad#gk$Fa 301       310       320       330
              |---------+---------+---------|
      satA    DQVMPTTYVHAALSERAATFIETQYEFLAH
      R.sol   DGVMPTTAGHRLIASNVLARLLA--DNVAH
    Consensus DqVMPTTagHaaiaeraaariea..#nlAH
```

Figure 33

```
                        ▼
Pfam           *->ivafGDSltdggg...............ayygdsdgggwgagladrltsla..rlrargrgvdv
Sriml   38        YVALGDSYSSGVG.............agSYDSSSGSCKRSTKSYPALWAAS..------HTGTRF  81
Scoe1    5        YVAVGDSFTEG--................--VGDPGPDGAFVGWADRLAVLL..ADRRPEGDFTY  47
Scoe2   10        LVAVGDSFTEG--................--MSDLLPDGSYRGWADLLATRM...--AARSPGFRY  50
Scoe3  239        VVAFGDSITDG--............ARSQSDANHRWTDVLAARLHEAA..GDGRDTPRYSV 283
Scoe4   75        LMMLGDSTAAG--................------QGVHRAGQTPGALLASG..LAAVAERPVRL 113
Scoe5   66        VAAVGDSITRGFD.............acAVLSDCPEVSWATGSSAKVDSLAvrLLGKADAAEHS 116
Ahyd1   28        IVMFGDSLSDTGKmyskmrgylpssppyYEGRFSNGPVWLEQLTNEFPGLTiaNEAEGGPTAVA  91
Asal1   28        IVMFGDSLSDTGKmyskmrgylpssppyYEGRFSNGPVWLEQLTKQF----........-PGLTI  79
Ahyd2   40        IVMFGDSLSDTGKmyskmrgylpssppyYEGRFSNGPVWLEQLTKQFPGLTiaNEAEGGATAVA 103

Pfam           fnrgisGrtsdGrlvvDarlvatllFlaqflGlnlpPYLsgdflrGANFAsagAtIlgtslipflni
Sriml   82        NFTACSGAR-------------------------------------------------------  90
Scoe1   48        TNLAVRGRL-------------------------------------------------------  56
Scoe2   51        ANLAVRGKL-------------------------------------------------------  59
Scoe3  284        VNEGISGNR------------------------------------------------------- 292
Scoe4  114        GSVAQPGAC------------------------------------------------------- 122
Scoe5  117        WNYAVTGAR------------------------------------------------------- 125
Ahyd1   92        YNKISWNPK------------------------------------------------------- 100
Asal1   80        ANEAEGGAT-------------------------------------------------------  88
Ahyd2  104        YNKISWNPK------------------------------------------------------- 112

▼
Pfam           QvqFkdfkskvlelrqa......lgllqellrlvpvldakspdlvtimiGtNDl...itvakfgpks
Sriml   91        -------------------.......---TGDVLAKQLTPVNSGTDLVSITIGGNDAgfaDTMTTCNLQG 131
Scoe1   57        -------------------.......--LDQIVAEQVPRVVGLAPDLVSFAAGGNDI.........-I----  86
Scoe2   60        -------------------.......--IGQIVDEQVDVAAAMGADVITLVGGLNDT............--  88
Scoe3  293        -------LLTSRPGRPA......DNPSGLSRFQRDVLERTNVKAVVVVLGVNDV..----------- 333
Scoe4  123        -------------------........SDDLDRQVALVLAEPDRVPDICVIMVGANDV............. 153
Scoe5  126        -------------------.......---MADLTAQVTRAAQREPELVAVMAGANDA..--------CR 155
Ahyd1  101        -------------YQVI......NNLDYEVTQFLQKDSFKPDDLVILWVGANDY..---------LA 137
Asal1   89        -------AVAYNKISWNpkyqvyNNLDYEVTQFLQKDSFKPDDLVILWVGANDY...--------LA 137
Ahyd2  113        -------------YQVI......NNLDYEVTQFLQKDSFKPDDLVILWVGANDY...--------LA 149

Pfam           .......tksdrnvsvpefrdnlrklikrLrsangariiilitlvllnlpl..........plGCl
Sriml  132        esaclarIAKARAYIQQTLPAQLDQVYDAIDSRAPAA-----QVVVLGYP-.............----- 176
Scoe1   87        ........---RPGTDPDEVAERFELAVAALT-AAAGTVLVTTGFDTRGVP-................----- 125
Scoe2   89        .........---LRPKCDMARVRDLLTQAVERLAPHCEQLVLMRSP-...................----- 122
Scoe3  334        .......LNSPELADRDAILTGLRTLVDRAHARGLRVVGATITPFGGYGG-................----- 376
Scoe4  154        ........---THRMPATRSVRHLSSAVRRLR-TAGAEVVVGTCPDLGTIE-...................----- 192
Scoe5  156        .......STTSAMTPVADFRAQFEEAMATLR-KKLPKAQVYVSSIPDLKRLwsqgrtnplgkQVWKL 214
Ahyd1  138        .......YGWNTEQDAKRVRDAISDAANRMV-LNGAK-----EILLFNLP-................----- 174
Asal1  138        .......YGWNTEQDAKRVRDAISDAANRMV-LNGAK-----QILLFNLP-................----- 174
Ahyd2  150        .......YGWNTEQDAKRVRDAISDAANRMV-LNGAK-----QILLFNLP-................----- 186

Pfam           pq.klalalasssknvdatgclerlneavadynealrelaei.ek.l.q.aqlrkdglpdlkeanvpy
Sriml  177        --.RFYKLGGSCAVGLSEKSRAAINAAADDINAVTAKRA--.--.-.-.-.-----------ADHGFAF 219
Scoe1  126        --.----------------VLKHLRGKIATYNGHVRAIA--.--.-.-.-.-----------DRYGCPV 152
Scoe2  123        --..----------GRQGPVLERFRPRMEALFAVIDDLA--.--.-.-.-.-----------GRHGAVV 154
Scoe3  377        --.YTEARETMRQEVNEEIRSGRVFDTVVDFDKALRDPY--.--.-.-.-.------------------ 412
Scoe4  193        --.--------------------------RVRQPLRWLaRRaSrQlAAAQTIGAVEQGGRTVSL 227
Scoe5  215        GLcPSMLGDADSLDSAATLRRNTVRDRVADYNEVLREVC--.--.-.-.AkDRRCRSDDGAVHEFRFGT 273
Ahyd1  175        --.----DLGQNPSARSQKVVEAASHVSAYHNQLLLNLA--.--.-.-.-.RQLAPTGMVKLFEIDKQF 224
Asal1  175        --.----DLGQNPSARSQKVVEAVSHVSAYHNKLLLNLA--.--.-.-.-.RQLAPTGMVKLFEIDKQF 224
Ahyd2  187        --.----DLGQNPSARSQKVVEAVSHVSAYHNQLLLNLA--.--.-.-.-.RQLAPTGMVKLFEIDKQF 236

Pfam           VDlysifqdldgiqnpsayv.y....GFeet.kaCCGyGgr.yNyn.rv.CGnag.l.ck.vtakaC
Sriml  220        GDVNT----------------.----.-----.---------.-TFAgHElCSGAPwL.HS.VT---- 242
Scoe1  153        LDLWSLRSVQDRRA------------.---.--------.------.----.--.-------.------ 166
Scoe2  155        VDLYGAQSLADPRM------------.---.--------.------.----.--.-------.------ 168
Scoe3  413        -----------------------.-----.---------.----.--.-------.------ 413
Scoe4  228        GDLLGPEFAQNPREL-----------.---.--------.------.----.--.-------.------ 242
```

Figure 33 continued

```
Scoe5   274 DQL------------------.-...-----.----------.----.--.------.-.--.------ 276
Ahyd1   225 AEMLRDPQNFGLSDQRNACYgGgyvwKPFASrSASTDSQLSaFNPQeRLaIAGNPlLaQAvASPMAA 291
Asal1   225 AEMLRDPQNFGLSDVENPCYdGgyvwKPFATrSVSTDRQLSaFSPQeRLaIAGNPlLaQAvASPMAR 291
Ahyd2   237 AEMLRDPQNFGLSDVENPCYdGgyvwKPFATrSVSTDRQLSaFSPQeRLaIAGNPlLaQAvASPMAR 303

▼
Pfam        .dassyll.atlfwDgf.HpsekGykavAeal<-*
Sriml   243 .--------.--LPVENSyHPTANGQSKGYLPV       263
Scoe1   167 .--------.--WDADRL.HLSPEGHTRVALRA       186
Scoe2   169 .--------.--WDVDRL.HLTAEGHRRVAEAV       188
Scoe3   413 .-DPRRMRsDYDSGDHL.HPGDKGYARMGAVI        441
Scoe4   243 .--------.--FGPDNY.HPSAEGYATAAMAV       262
Scoe5   277 .--------.--SHWDWF.HPSVDGQARLAEIA       296
Ahyd1   292 rSASTLNCeGKMFWDQV.HPTTVVHAALSEPA        322
Asal1   292 rSASPLNCeGKMFWDQV.HPTTVVHAALSERA        322
Ahyd2   304 rSASPLNCeGKMFWDQV.HPTTVVHAALSERA        334
```

Figure 34

```
                                ▼
Pfam         *->ivafGDSltdggg..............ayygdsdgggwgagladrltsla..rlrargrgvdv
Sriml     38    YVALGDSYSSGVG.............agSYDSSSGSCKRSTKSYPALWAAS.------HTGTRF   81
Scoel      5    YVAVGDSFTEG--................--VGDPGPDGAFVGWADRLAVLL..ADRRPEGDFTY   47
Scoe2     10    LVAVGDSFTEG--................--MSDLLPDGSYRGWADLLATRM.---AARSPGFRY   50
Ahydl     28    IVMFGDSLSDTGKmyskmrgylpssppyYEGRFSNGPVWLEQLTNEFPGLTiaNEAEGGPTAVA   91
Asall     28    IVMFGDSLSDTGKmyskmrgylpssppyYEGRFSNGPVWLEQLTKQF-----.-------PGLTI   79
Ahyd2     40    IVMFGDSLSDTGKmyskmrgylpssppyYEGRFSNGPVWLEQLTKQFPGLTiaNEAEGGATAVA  103

Pfam         fnrgisGrtsdGrlvvDarlvatllFlaqflGlnlpPYLsgdflrGANFAsagAtIlgtslipflni
Sriml     82    NFTACSGAR----------------------------------------------------------   90
Scoel     48    TNLAVRGRL----------------------------------------------------------   56
Scoe2     51    ANLAVRGKL----------------------------------------------------------   59
Ahydl     92    YNKISWNPK----------------------------------------------------------  100
Asall     80    ANEAEGGAT----------------------------------------------------------   88
Ahyd2    104    YNKISWNPK----------------------------------------------------------  112

▼
Pfam         QvqFkdfkskvlelrqa......lgllqellrlvpvldakspdlvtimiGtNDl...itvakfgpks
Sriml     91    -------------------......---TGDVLAKQLTPVNSGTDLVSITIGGNDAgfaDTMTTCNLQG  131
Scoel     57    -------------------......--LDQIVAEQVPRVVGLAPDLVSFAAGGNDI.........I----   86
Scoe2     60    -------------------......--IGQIVDEQVDVAAAMGADVITLVGGLNDT..-----------   88
Ahydl    101    ------------YQVI......NNLDYEVTQFLQKDSFKPDDLVILWVGANDY...---------LA  137
Asall     89    -------AVAYNKISWNpkyqvyNNLDYEVTQFLQKDSFKPDDLVILWVGANDY...---------LA  137
Ahyd2    113    ------------YQVI......NNLDYEVTQFLQKDSFKPDDLVILWVGANDY...---------LA  149

Pfam         .......tksdrnvsvpefrdnlrklikrLrsangariiilitlvllnlplplGCl
Sriml    132    esaclarIAKARAYIQQTLPAQLDQVYDAIDSRAPAA-----QVVVLGYP------  176
Scoel     87    .........---RPGTDPDEVAERFELAVAALT-AAAGTVLVTTGFDTRGVP------  125
Scoe2     89    .........---------LRPKCDMARVRDLLTQAVERLAPHCEQLVLMRSP------  122
Ahydl    138    .......YGWNTEQDAKRVRDAISDAANRMV-LNGAK-----EILLFNLP------  174
Asall    138    .......YGWNTEQDAKRVRDAISDAANRMV-LNGAK-----QILLFNLP------  174
Ahyd2    150    .......YGWNTEQDAKRVRDAISDAANRMV-LNGAK-----QILLFNLP------  186

Pfam         pqklalalassknvdatgclerlneavadyneal relaeieklqaqlrkdglpdlkeanvpy
Sriml    177    --RFYKLGGSCAVGLSEKSRAAINAAADDINAVTAKRA---------------ADHGFAF  219
Scoel    126    ------------------VLKHLRGKIATYNGHVRAIA---------------DRYGCPV  152
Scoe2    123    -------------GRQGPVLERFRPRMEALFAVIDDLA---------------GRHGAVV  154
Ahydl    175    ------DLGQNPSARSQKVVEAASHVSAYHNQLLLNLA------RQLAPTGMVKLFEIDKQF  224
Asall    175    ------DLGQNPSARSQKVVEAVSHVSAYHNKLLLNLA------RQLAPTGMVKLFEIDKQF  224
Ahyd2    187    ------DLGQNPSARSQKVVEAVSHVSAYHNQLLLNLA------RQLAPTGMVKLFEIDKQF  236

Pfam         VDlysifqdldgiqnpsayv.y....GFeet.kaCCGyGgr.yNyn.rv.CGnag.l.ck.vtakaC
Sriml    220    GDVNT----------------...-----.---------.-TFAgHElCSGAPwL.HS.VT----  242
Scoel    153    LDLWSLRSVQDRRA-------.-----.----.---------.----.--.-----.---.------  166
Scoe2    155    VDLYGAQSLADPRM-------.-----.----.---------.----.---.-----.---.------  168
Ahydl    225    AEMLRDPQNFGLSDQRNACYgGsyvwKPFASrSASTDSQLSaFNPQeRLaIAGNPlLaQAvASPMAA  291
Asall    225    AEMLRDPQNFGLSDVENPCYdGgyvwKPFATrSVSTDRQLSaFSPQeRLaIAGNPlLaQAvASPMAR  291
Ahyd2    237    AEMLRDPQNFGLSDVENPCYdGgyvwKPFATrSVSTDRQLSaFSPQeRLaIAGNPlLaQAvASPMAR  303

▼
Pfam         .dassyll.atlfwDgf.HpsekGykavAeal<-*
Sriml    243    .--------.--LPVENSyHPTANGQSKGYLPV       263
Scoel    167    .--------.--WDADRL.HLSPEGHTRVALRA       186
Scoe2    169    .--------.--WDVDRL.HLTAEGHRRVAEAV       188
Ahydl    292    rSASTLNCeGKMFWDQV.HPTTVVHAALSEPA        322
Asall    292    rSASPLNCeGKMFWDQV.HPTTVVHAALSERA        322
Ahyd2    304    rSASPLNCeGKMFWDQV.HPTTVVHAALSERA        334
```

Figure 45

(SEQ ID No. 36)

```
  1  MFKFKKNFLV GLSAALMSIS LFSATASAAS ADSRPAFSRI VMFGDSLSDT
 51  GKMYSKMRGY LPSSPPYYEG RFSNGPVWLE QLTKQFPGLT IANEAEGGAT
101  AVAYNKISWN PKYQVINNLD YEVTQFLQKD SFKPDDLVIL WVGANDYLAY
151  GWNTEQDAKR VRDAISDAAN RMVLNGAKQI LLFNLPDLGQ NPSARSQKVV
201  EAVSHVSAYH NQLLLNLARQ LAPTGMVKLF EIDKQFAEML RDPQNFGLSD
251  VENPCYDGGY VWKPFATRSV STDRQLSAFS PQERLAIAGN PLLAQAVASP
301  MARRSASPLN CEGKMFWDQV HPTTVVHAAL SERAATFIAN QYEFLAH**
```

Figure 46 (SEQ ID No. 45)

```
   1 ATGTTTAAGT TTAAAAAGAA TTTCTTAGTT GGATTATCGG CAGCTTTAAT
     TACAAATTCA AATTTTTCTT AAAGAATCAA CCTAATAGCC GTCGAAATTA

51 GAGTATTAGC TTGTTTTCGG CAACCGCCTC TGCAGCTAGC GCCGACAGCC
     CTCATAATCG AACAAAAGCC GTTGGCGGAG ACGTCGATCG CGGCTGTCGG

101 GTCCCGCCTT TTCCCGGATC GTGATGTTCG GCGACAGCCT CTCCGATACC
     CAGGGCGGAA AAGGGCCTAG CACTACAAGC CGCTGTCGGA GAGGCTATGG

151 GGCAAAATGT ACAGCAAGAT GCGCGGTTAC CTCCCCTCCA GCCCGCCCTA
     CCGTTTTACA TGTCGTTCTA CGCGCCAATG GAGGGGAGGT CGGGCGGGAT

201 CTATGAGGGC CGTTTCTCCA ACGGACCCGT CTGGCTGGAG CAGCTGACCA
     GATACTCCCG GCAAAGAGGT TGCCTGGGCA GACCGACCTC GTCGACTGGT

251 AACAGTTCCC GGGTCTGACC ATCGCCAACG AAGCGGAAGG CGGTGCCACT
     TTGTCAAGGG CCCAGACTGG TAGCGGTTGC TTCGCCTTCC GCCACGGTGA

301 GCCGTGGCTT ACAACAAGAT CTCCTGGAAT CCCAAGTATC AGGTCATCAA
     CGGCACCGAA TGTTGTTCTA GAGGACCTTA GGGTTCATAG TCCAGTAGTT

351 CAACCTGGAC TACGAGGTCA CCCAGTTCTT GCAGAAAGAC AGCTTCAAGC
     GTTGGACCTG ATGCTCCAGT GGGTCAAGAA CGTCTTTCTG TCGAAGTTCG

401 CGGACGATCT GGTGATCCTC TGGGTCGGTG CCAATGACTA TCTGGCCTAT
     GCCTGCTAGA CCACTAGGAG ACCCAGCCAC GGTTACTGAT AGACCGGATA

451 GGCTGGAACA CGGAGCAGGA TGCCAAGCGG GTTCGCGATG CCATCAGCGA
     CCGACCTTGT GCCTCGTCCT ACGGTTCGCC CAAGCGCTAC GGTAGTCGCT

501 TGCGGCCAAC CGCATGGTAC TGAACGGTGC CAAGCAGATA CTGCTGTTCA
     ACGCCGGTTG GCGTACCATG ACTTGCCACG GTTCGTCTAT GACGACAAGT

551 ACCTGCCGGA TCTGGGCCAG AACCCGTCAG CTCGCAGTCA GAAGGTGGTC
     TGGACGGCCT AGACCCGGTC TTGGGCAGTC GAGCGTCAGT CTTCCACCAG

601 GAGGCGGTCA GCCATGTCTC CGCCTATCAC AACCAGCTGC TGCTGAACCT
     CTCCGCCAGT CGGTACAGAG GCGGATAGTG TTGGTCGACG ACGACTTGGA

651 GGCACGCCAG CTGGCCCCCA CCGGCATGGT AAAGCTGTTC GAGATCGACA
     CCGTGCGGTC GACCGGGGGT GGCCGTACCA TTTCGACAAG CTCTAGCTGT

701 AGCAATTTGC CGAGATGCTG CGTGATCCGC AGAACTTCGG CCTGAGCGAC
     TCGTTAAACG GCTCTACGAC GCACTAGGCG TCTTGAAGCC GGACTCGCTG

751 GTCGAGAACC CCTGCTACGA CGGCGGCTAT GTGTGGAAGC CGTTTGCCAC
     CAGCTCTTGG GGACGATGCT GCCGCCGATA CACACCTTCG GCAAACGGTG

801 CCGCAGCGTC AGCACCGACC GCCAGCTCTC CGCCTTCAGT CCGCAGGAAC
     GGCGTCGCAG TCGTGGCTGG CGGTCGAGAG GCGGAAGTCA GGCGTCCTTG

851 GCCTCGCCAT CGCCGGCAAC CCGCTGCTGG CACAGGCCGT TGCCAGTCCT
     CGGAGCGGTA GCGGCCGTTG GGCGACGACC GTGTCCGGCA ACGGTCAGGA

901 ATGGCCCGCC GCAGCGCCAG CCCCCTCAAC TGTGAGGGCA AGATGTTCTG
     TACCGGGCGG CGTCGCGGTC GGGGGAGTTG ACACTCCCGT TCTACAAGAC

951 GGATCAGGTA CACCCGACCA CTGTCGTGCA CGCAGCCCTG AGCGAGCGCG
     CCTAGTCCAT GTGGGCTGGT GACAGCACGT GCGTCGGGAC TCGCTCGCGC

1001 CCGCCACCTT CATCGCGAAC CAGTACGAGT TCCTCGCCCA CTGATGA
     GGCGGTGGAA GTAGCGCTTG GTCATGCTCA AGGAGCGGGT GACTACT
```

Figure 51

SEQ ID NO. 54:

ACAGGCCGATGCACGGAACCGTACCTTTCCGCAGTGAAGCGCTCTCCCCCCATCGTTCGC
CGGGACTTCATCCGCGATTTTGGCATGAACACTTCCTTCAACGCGCGTAGCTTGCTACAA
GTGCGGCAGCAGACCCGCTCGTTGGAGGCTCAGTGAGATTGACCCGATCCCTGTCGGCCG
CATCCGTCATCGTCTTCGCCCTGCTGCTCGCGCTGCTGGGCATCAGCCCGGCCCAGGCAG
CCGGCCCGGCCTATGTGGCCCTGGGGGATTCCTATTCCTCGGGCAACGGCGCCGGAAGTT
ACATCGATTCGAGCGGTGACTGTCACCGCAGCAACAACGCGTACCCCGCCCGCTGGGCGG
CGGCCAACGCACCGTCCTCCTTCACCTTCGCGGCCTGCTCGGGAGCGGTGACCACGGATG
TGATCAACAATCAGCTGGGCGCCCTCAACGCGTCCACCGGCCTGGTGAGCATCACCATCG
GCGGCAATGACGCGGGCTTCGCGGACGCGATGACCACCTGCGTCACCAGCTCGGACAGCA
CCTGCCTCAACCGGCTGGCCACCGCCACCAACTACATCAACACCACCCTGCTCGCCCGGC
TCGACGCGGTCTACAGCCAGATCAAGGCCCGTGCCCCCAACGCCCGCGTGGTCGTCCTCG
GCTACCCGCGCATGTACCTGGCCTCGAACCCCTGGTACTGCCTGGGCCTGAGCAACACCA
AGCGCGCGGCCATCAACACCACCGCCGACACCCTCAACTCGGTGATCTCCTCCCGGGCCA
CCGCCCACGGATTCCGATTCGGCGATGTCCGCCCGACCTTCAACAACCACGAACTGTTCT
TCGGCAACGACTGGCTGCACTCACTCACCCTGCCGGTGTGGGAGTCGTACCACCCCACCA
GCACGGGCCATCAGAGCGGCTATCTGCCGGTCCTCAACGCCAACAGCTCGACCTGATCAA
CGCACGGCCGTGCCCGCCCCGCGCGTCACGCTCGGCGCGGGCGCCGCAGCGCGTTGATCA
GCCCACAGTGCCGGTGACGGTCCCACCGTCACGGTCGAGGGTGTACGTCACGGTGGCGCC
GCTCCAGAAGTGGAACGTCAGCAGGACCGTGGAGCCGTCCCTGACCTCGTCGAAGAACTC
CGGGGTCAGCGTGATCACCCCTCCCCCGTAGCCGGGGGCGAAGGCGGCGCCGAACTCCTT
GTAGGACGTCCAGTCGTGCGGCCCGGCGTTGCCACCGTCCGCGTAGACCGCTTCCATGGT
CGCCAGCCGGTCCCCGCGGAACTCGGTGGGGATGTCCGTGCCCAAGGTGGTCCCGGTGGT
GTCCGAGAGCACCGGGGGCTCGTACCGGATGATGTGCAGATCCAAAGAATT

FIGURE 52

SEQ ID NO. 55:

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

SEQUENCE LISTING

<160> NUMBER OF SEQ ID NOS: 73

<210> SEQ ID NO 1
<211> LENGTH: 361
<212> TYPE: PRT
<213> ORGANISM: Artificial
<220> FEATURE:
<223> OTHER INFORMATION: pfam00567 consensus sequence

<400> SEQUENCE: 1

```
Ile Val Ala Phe Gly Asp Ser Leu Thr Asp Gly Glu Ala Tyr Tyr Gly
1               5                   10                  15

Asp Ser Asp Gly Gly Gly Trp Gly Ala Gly Leu Ala Asp Arg Leu Thr
            20                  25                  30

Ala Leu Leu Arg Leu Arg Ala Arg Pro Arg Gly Val Asp Val Phe Asn
        35                  40                  45

Arg Gly Ile Ser Gly Arg Thr Ser Asp Gly Arg Leu Ile Val Asp Ala
    50                  55                  60

Leu Val Ala Leu Leu Phe Leu Ala Gln Ser Leu Gly Leu Pro Asn Leu
65                  70                  75                  80

Pro Pro Tyr Leu Ser Gly Asp Phe Leu Arg Gly Ala Asn Phe Ala Ser
                85                  90                  95

Ala Gly Ala Thr Ile Leu Pro Thr Ser Gly Pro Phe Leu Ile Gln Val
            100                 105                 110

Gln Phe Lys Asp Phe Lys Ser Gln Val Leu Glu Leu Arg Gln Ala Leu
        115                 120                 125

Gly Leu Leu Gln Glu Leu Leu Arg Leu Leu Pro Val Leu Asp Ala Lys
    130                 135                 140

Ser Pro Asp Leu Val Thr Ile Met Ile Gly Thr Asn Asp Leu Ile Thr
145                 150                 155                 160

Ser Ala Phe Phe Gly Pro Lys Ser Thr Glu Ser Asp Arg Asn Val Ser
                165                 170                 175

Val Pro Glu Phe Lys Asp Asn Leu Arg Gln Leu Ile Lys Arg Leu Arg
            180                 185                 190

Ser Asn Asn Gly Ala Arg Ile Ile Val Leu Ile Thr Leu Val Ile Leu
        195                 200                 205

Asn Leu Gly Pro Leu Gly Cys Leu Pro Leu Lys Leu Ala Leu Ala Leu
    210                 215                 220

Ala Ser Ser Lys Asn Val Asp Ala Ser Gly Cys Leu Glu Arg Leu Asn
225                 230                 235                 240

Glu Ala Val Ala Asp Phe Asn Glu Ala Leu Arg Glu Leu Ala Ile Ser
                245                 250                 255

Lys Leu Glu Asp Gln Leu Arg Lys Asp Gly Leu Pro Asp Val Lys Gly
            260                 265                 270

Ala Asp Val Pro Tyr Val Asp Leu Tyr Ser Ile Phe Gln Asp Leu Asp
        275                 280                 285

Gly Ile Gln Asn Pro Ser Ala Tyr Val Tyr Gly Phe Glu Thr Thr Lys
    290                 295                 300

Ala Cys Cys Gly Tyr Gly Gly Arg Tyr Asn Tyr Asn Arg Val Cys Gly
305                 310                 315                 320

Asn Ala Gly Leu Cys Asn Val Thr Ala Lys Ala Cys Asn Pro Ser Ser
                325                 330                 335

Tyr Leu Leu Ser Phe Leu Phe Trp Asp Gly Phe His Pro Ser Glu Lys
            340                 345                 350
```

```
Gly Tyr Lys Ala Val Ala Glu Ala Leu
        355                 360

<210> SEQ ID NO 2
<211> LENGTH: 335
<212> TYPE: PRT
<213> ORGANISM: Aeromonas hydrophila

<400> SEQUENCE: 2

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Asn Glu Phe Pro Gly Leu Thr Ile Ala
65              70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
            180                 185                 190

His Val Ser Ala Tyr His Asn Gln Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
            260                 265                 270

Leu Ala Ile Ala Gly Asn Pro Leu Leu Ala Gln Ala Val Ala Ser Pro
        275                 280                 285

Met Ala Ala Arg Ser Ala Ser Thr Leu Asn Cys Glu Gly Lys Met Phe
    290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 3
<211> LENGTH: 336
<212> TYPE: PRT
```

<213> ORGANISM: Aeromonas salmonicida

<400> SEQUENCE: 3

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Tyr Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Lys Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 4
<211> LENGTH: 295
<212> TYPE: PRT
<213> ORGANISM: Streptomyces coelicolor

<400> SEQUENCE: 4

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala

```
                    20                  25                  30
Pro Ala Gln Ala Thr Pro Thr Leu Asp Tyr Val Ala Leu Gly Asp Ser
            35                  40                  45
Tyr Ser Ala Gly Ser Gly Val Leu Pro Val Asp Pro Ala Asn Leu Leu
        50                  55                  60
Cys Leu Arg Ser Thr Ala Asn Tyr Pro His Val Ile Ala Asp Thr Thr
65                  70                  75                  80
Gly Ala Arg Leu Thr Asp Val Thr Cys Gly Ala Ala Gln Thr Ala Asp
                85                  90                  95
Phe Thr Arg Ala Gln Tyr Pro Gly Val Ala Pro Gln Leu Asp Ala Leu
            100                 105                 110
Gly Thr Gly Thr Asp Leu Val Thr Leu Thr Ile Gly Gly Asn Asp Asn
        115                 120                 125
Ser Thr Phe Ile Asn Ala Ile Thr Ala Cys Gly Thr Ala Gly Val Leu
    130                 135                 140
Ser Gly Gly Lys Gly Ser Pro Cys Lys Asp Arg His Gly Thr Ser Phe
145                 150                 155                 160
Asp Asp Glu Ile Glu Ala Asn Thr Tyr Pro Ala Leu Lys Glu Ala Leu
                165                 170                 175
Leu Gly Val Arg Ala Arg Ala Pro His Ala Arg Val Ala Ala Leu Gly
            180                 185                 190
Tyr Pro Trp Ile Thr Pro Ala Thr Ala Asp Pro Ser Cys Phe Leu Lys
        195                 200                 205
Leu Pro Leu Ala Ala Gly Asp Val Pro Tyr Leu Arg Ala Ile Gln Ala
    210                 215                 220
His Leu Asn Asp Ala Val Arg Arg Ala Ala Glu Glu Thr Gly Ala Thr
225                 230                 235                 240
Tyr Val Asp Phe Ser Gly Val Ser Asp Gly His Asp Ala Cys Glu Ala
                245                 250                 255
Pro Gly Thr Arg Trp Ile Glu Pro Leu Phe Gly His Ser Leu Val
            260                 265                 270
Pro Val His Pro Asn Ala Leu Gly Glu Arg Arg Met Ala Glu His Thr
        275                 280                 285
Met Asp Val Leu Gly Leu Asp
    290                 295

<210> SEQ ID NO 5
<211> LENGTH: 295
<212> TYPE: PRT
<213> ORGANISM: Streptomyces coelicolor

<400> SEQUENCE: 5

Met Pro Lys Pro Ala Leu Arg Arg Val Met Thr Ala Thr Val Ala Ala
1               5                   10                  15
Val Gly Thr Leu Ala Leu Gly Leu Thr Asp Ala Thr Ala His Ala Ala
            20                  25                  30
Pro Ala Gln Ala Thr Pro Thr Leu Asp Tyr Val Ala Leu Gly Asp Ser
        35                  40                  45
Tyr Ser Ala Gly Ser Gly Val Leu Pro Val Asp Pro Ala Asn Leu Leu
    50                  55                  60
Cys Leu Arg Ser Thr Ala Asn Tyr Pro His Val Ile Ala Asp Thr Thr
65                  70                  75                  80
Gly Ala Arg Leu Thr Asp Val Thr Cys Gly Ala Ala Gln Thr Ala Asp
                85                  90                  95
```

```
Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
        130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
            195                 200                 205

Leu Pro Leu Ala Ala Gly Asp Val Pro Tyr Leu Arg Ala Ile Gln Ala
            210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
            275                 280                 285

Met Asp Val Leu Gly Leu Asp
    290                 295

<210> SEQ ID NO 6
<211> LENGTH: 238
<212> TYPE: PRT
<213> ORGANISM: Saccharomyces cerevisiae

<400> SEQUENCE: 6

Met Asp Tyr Glu Lys Phe Leu Leu Phe Gly Asp Ser Ile Thr Glu Phe
1               5                   10                  15

Ala Phe Asn Thr Arg Pro Ile Glu Asp Gly Lys Asp Gln Tyr Ala Leu
            20                  25                  30

Gly Ala Ala Leu Val Asn Glu Tyr Thr Arg Lys Met Asp Ile Leu Gln
        35                  40                  45

Arg Gly Phe Lys Gly Tyr Thr Ser Arg Trp Ala Leu Lys Ile Leu Pro
    50                  55                  60

Glu Ile Leu Lys His Glu Ser Asn Ile Val Met Ala Thr Ile Phe Leu
65                  70                  75                  80

Gly Ala Asn Asp Ala Cys Ser Ala Gly Pro Gln Ser Val Pro Leu Pro
                85                  90                  95

Glu Phe Ile Asp Asn Ile Arg Gln Met Val Ser Leu Met Lys Ser Tyr
            100                 105                 110

His Ile Arg Pro Ile Ile Gly Pro Gly Leu Val Asp Arg Glu Lys
            115                 120                 125

Trp Glu Lys Glu Lys Ser Glu Glu Ile Ala Leu Gly Tyr Phe Arg Thr
    130                 135                 140

Asn Glu Asn Phe Ala Ile Tyr Ser Asp Ala Leu Ala Lys Leu Ala Asn
145                 150                 155                 160

Glu Glu Lys Val Pro Phe Val Ala Leu Asn Lys Ala Phe Gln Gln Glu
                165                 170                 175
```

Gly Gly Asp Ala Trp Gln Gln Leu Leu Thr Asp Gly Leu His Phe Ser
            180                 185                 190

Gly Lys Gly Tyr Lys Ile Phe His Asp Glu Leu Leu Lys Val Ile Glu
        195                 200                 205

Thr Phe Tyr Pro Gln Tyr His Pro Lys Asn Met Gln Tyr Lys Leu Lys
        210                 215                 220

Asp Trp Arg Asp Val Leu Asp Asp Gly Ser Asn Ile Met Ser
225                 230                 235

<210> SEQ ID NO 7
<211> LENGTH: 1005
<212> TYPE: DNA
<213> ORGANISM: Aeromonas hydrophila

<400> SEQUENCE: 7

| | | | | | |
|---|---|---|---|---|---|
| atgaaaaaat | ggtttgtgtg | tttattggga | ttggtcgcgc | tgacagttca | ggcagccgac | 60 |
| agccgtcccg | ccttctcccg | gatcgtgatg | tttggcgaca | gcctctccga | taccggcaag | 120 |
| atgtacagca | agatgcgcgg | ttacctcccc | tccagccccc | cctactatga | gggccgcttc | 180 |
| tccaacgggc | ccgtctggct | ggagcagctg | accaacgagt | tcccgggcct | gaccatagcc | 240 |
| aacgaggcgg | aaggcggacc | gaccgccgtg | gcttacaaca | agatctcctg | gaatcccaag | 300 |
| tatcaggtca | tcaacaacct | ggactacgag | gtcacccagt | tcctgcaaaa | agacagcttc | 360 |
| aagccggacg | atctggtgat | cctctgggtc | ggcgccaacg | actatctggc | ctatggctgg | 420 |
| aacacagagc | aggatgccaa | gcgggtgcgc | gacgccatca | gcgatgcggc | caaccgcatg | 480 |
| gtgctgaacg | cgccaaggga | gatactgctg | ttcaacctgc | cggatctggg | ccagaaccc | 540 |
| tcggcccgca | gccagaaggt | ggtcgaggcg | ccagccatg | tctccgccta | ccacaaccag | 600 |
| ctgctgctga | acctggcacg | ccagctggct | cccaccggca | tggtgaagct | gttcgagatc | 660 |
| gacaagcagt | ttgccgagat | gctgcgtgat | ccgcagaact | tcggcctgag | cgaccagagg | 720 |
| aacgcctgct | acggtggcag | ctatgtatgg | aagccgtttg | cctcccgcag | cgccagcacc | 780 |
| gacagccagc | tctccgcctt | caacccgcag | gagcgcctcg | ccatcgccgg | caaccccgctg | 840 |
| ctggcccagg | ccgtcgccag | ccccatggct | gcccgcagcg | ccagcaccct | caactgtgag | 900 |
| ggcaagatgt | tctgggatca | ggtccacccc | accactgtcg | tgcacgccgc | cctgagcgag | 960 |
| cccgccgcca | ccttcatcga | gagccagtac | gagttcctcg | cccac | | 1005 |

<210> SEQ ID NO 8
<211> LENGTH: 1011
<212> TYPE: DNA
<213> ORGANISM: Aeromonas salmonicida

<400> SEQUENCE: 8

| | | | | | |
|---|---|---|---|---|---|
| atgaaaaaat | ggtttgtttg | tttattgggg | ttgatcgcgc | tgacagttca | ggcagccgac | 60 |
| actcgccccg | ccttctcccg | gatcgtgatg | ttcggcgaca | gcctctccga | taccggcaaa | 120 |
| atgtacagca | agatgcgcgg | ttacctcccc | tccagcccgc | cctactatga | gggccgtttc | 180 |
| tccaacggac | ccgtctggct | ggagcagctg | accaagcagt | tcccgggtct | gaccatcgcc | 240 |
| aacgaagcgg | aaggcggtgc | cactgccgtg | gcttacaaca | agatctcctg | gaatcccaag | 300 |
| tatcaggtct | acaacaacct | ggactacgag | gtcacccagt | tcttgcagaa | agacagcttc | 360 |
| aagccggacg | atctggtgat | cctctgggtc | ggtgccaatg | actatctggc | atatggctgg | 420 |
| aatacggagc | aggatgccaa | gcgagttcgc | gatgccatca | gcgatgcggc | caaccgcatg | 480 |

-continued

| | |
|---|---|
| gtactgaacg gtgccaagca gatactgctg ttcaacctgc cggatctggg ccagaacccg | 540 |
| tcagcccgca gtcagaaggt ggtcgaggcg gtcagccatg tctccgccta tcacaacaag | 600 |
| ctgctgctga acctggcacg ccagctggcc cccaccggca tggtaaagct gttcgagatc | 660 |
| gacaagcaat tgccgagat gctgcgtgat ccgcagaact tcggcctgag cgacgtcgag | 720 |
| aaccccctgct acgacggcgg ctatgtgtgg aagccgtttg ccacccgcag cgtcagcacc | 780 |
| gaccgccagc tctccgcctt cagtccgcag gaacgcctcg ccatcgccgg caacccgctg | 840 |
| ctggcacagg ccgttgccag tcctatggcc cgccgcagcg ccagcccct caactgtgag | 900 |
| ggcaagatgt tctgggatca ggtacacccg accactgtcg tgcacgcagc cctgagcgag | 960 |
| cgcgccgcca ccttcatcga gacccagtac gagttcctcg cccacggatg a | 1011 |

<210> SEQ ID NO 9
<211> LENGTH: 888
<212> TYPE: DNA
<213> ORGANISM: Streptomyces coelicolor

<400> SEQUENCE: 9

| | |
|---|---|
| atgccgaagc ctgcccttcg ccgtgtcatg accgcgacag tcgccgccgt cggcacgctc | 60 |
| gccctcggcc tcaccgacgc caccgcccac gccgcgcccg cccaggccac tccgaccctg | 120 |
| gactacgtcg ccctcggcga cagctacagc gccggctccg cgtcctgcc cgtcgacccc | 180 |
| gccaacctgc tctgtctgcg ctcgacggcc aactaccccc acgtcatcgc ggacacgacg | 240 |
| ggcgcccgcc tcacggacgt cacctgcggc gccgcgcaga ccgccgactt cacgcgggcc | 300 |
| cagtacccgg gcgtcgcacc ccagttggac gcgctcggca ccggcacgga cctggtcacg | 360 |
| ctcaccatcg gcggcaacga caacagcacc ttcatcaacg ccatcacggc ctgcggcacg | 420 |
| gcgggtgtcc tcagcggcgg caagggcagc ccctgcaagg acaggcacgg cacctccttc | 480 |
| gacgacgaga tcgaggccaa cacgtacccc gcgctcaagg aggcgctgct cggcgtccgc | 540 |
| gccagggctc cccacgccag ggtggcggct ctcggctacc cgtggatcac cccggccacc | 600 |
| gccgacccgt cctgcttcct gaagctcccc ctcgccgccg gtgacgtgcc ctacctgcgg | 660 |
| gccatccagg cacacctcaa cgacgcggtc cggcgggccc ccgaggagac cggagccacc | 720 |
| tacgtggact tctccggggt gtccgacggc cacgacgcct gcgaggcccc cggcacccgc | 780 |
| tggatcgaac cgctgctctt cgggcacagc ctcgttcccg tccaccccaa cgccctgggc | 840 |
| gagcggcgca tggccgagca cacgatggac gtcctcggcc tggactga | 888 |

<210> SEQ ID NO 10
<211> LENGTH: 888
<212> TYPE: DNA
<213> ORGANISM: Streptomyces coelicolor

<400> SEQUENCE: 10

| | |
|---|---|
| tcagtccagg ccgaggacgt ccatcgtgtg ctcggccatg cgccgctcgc ccagggcgtt | 60 |
| ggggtggacg ggaacgaggc tgtgcccgaa gagcagcggt tcgatccagc gggtgccggg | 120 |
| ggcctcgcag gcgtcgtggc cgtcggacac cccggagaag tccacgtagg tggctccggt | 180 |
| ctcctcggcg gccgccgga ccgcgtcgtt gaggtgtgcc tggatggccc gcaggtaggg | 240 |
| cacgtcaccg gcggcgaggg ggagcttcag gaagcaggac gggtcggcgg tggccggggt | 300 |
| gatccacggg tagccgagag ccgccaccct ggcgtgggga gccctggcgc ggacgccgag | 360 |
| cagcgcctcc ttgagcgcgg ggtacgtgtt ggcctcgatc tcgtcgtcga aggaggtgcc | 420 |
| gtgcctgtcc ttgcaggggc tgcccttgcc gccgctgagg acacccgccg tgccgcaggc | 480 |

-continued

```
cgtgatggcg ttgatgaagg tgctgttgtc gttgccgccg atggtgagcg tgaccaggtc    540
cgtgccggtg ccgagcgcgt ccaactgggg tgcgacgccc gggtactggg cccgcgtgaa    600
gtcggcggtc tgcgcggcgc cgcaggtgac gtccgtgagg cgggcgcccg tcgtgtccgc    660
gatgacgtgg gggtagttgg ccgtcgagcg cagacagagc aggttggcgg ggtcgacggg    720
caggacgccg gagccggcgc tgtagctgtc gccgagggcg acgtagtcca gggtcggagt    780
ggcctgggcg gcgcggcgt gggcggtggc gtcggtgagg ccgagggcga gcgtgccgac    840
ggcggcgact gtcgcggtca tgacacggcg aagggcaggc ttcggcat    888
```

<210> SEQ ID NO 11
<211> LENGTH: 717
<212> TYPE: DNA
<213> ORGANISM: Saccharomyces cerevisiae

<400> SEQUENCE: 11

```
atggattacg agaagtttct gttatttggg gattccatta ctgaatttgc ttttaatact     60
aggcccattg aagatggcaa agatcagtat gctcttggag ccgcattagt caacgaatat    120
acgagaaaaa tggatattct tcaaagaggg ttcaaagggt cacttctag atgggcgttg     180 aaaatacttc ctgagatttt aaagcatgaa tccaatattg tcatggccac aatattttg     240 ggtgccaacg atgcatgctc agcaggtccc caaagtgtcc ccctccccga atttatcgat    300
aatattcgtc aaatggtatc tttgatgaag tcttaccata tccgtcctat tataatagga    360
ccggggctag tagatagaga gaagtgggaa aaagaaaaat ctgaagaaat agctctcgga    420
tacttccgta ccaacgagaa ctttgccatt tattccgatg ccttagcaaa actagccaat    480
gaggaaaaag ttcccttcgt ggctttgaat aaggcgtttc aacaggaagg tggtgatgct    540
tggcaacaac tgctaacaga tggactgcac ttttccggaa aagggtacaa aattttttcat    600 gacgaattat tgaaggtcat tgagacattc tacccccaat atcatcccaa aaacatgcag    660
tacaaactga agattggag agatgtgcta atgatggat ctaacataat gtcttga         717
```

<210> SEQ ID NO 12
<211> LENGTH: 347
<212> TYPE: PRT
<213> ORGANISM: Ralstonia spp

<400> SEQUENCE: 12

```
Met Asn Leu Arg Gln Trp Met Gly Ala Ala Thr Ala Ala Leu Ala Leu
1               5                   10                  15

Gly Leu Ala Ala Cys Gly Gly Gly Thr Asp Gln Ser Gly Asn Pro
            20                  25                  30

Asn Val Ala Lys Val Gln Arg Met Val Val Phe Gly Asp Ser Leu Ser
        35                  40                  45

Asp Ile Gly Thr Tyr Thr Pro Val Ala Gln Ala Val Gly Gly Gly Lys
    50                  55                  60

Phe Thr Thr Asn Pro Gly Pro Ile Trp Ala Glu Thr Val Ala Ala Gln
65                  70                  75                  80

Leu Gly Val Thr Leu Thr Pro Ala Val Met Gly Tyr Ala Thr Ser Val
                85                  90                  95

Gln Asn Cys Pro Lys Ala Gly Cys Phe Asp Tyr Ala Gln Gly Gly Ser
            100                 105                 110

Arg Val Thr Asp Pro Asn Gly Ile Gly His Asn Gly Gly Ala Gly Ala
        115                 120                 125
```

```
Leu Thr Tyr Pro Val Gln Gln Leu Ala Asn Phe Tyr Ala Ala Ser
    130                 135                 140

Asn Asn Thr Phe Asn Gly Asn Asn Asp Val Val Phe Val Leu Ala Gly
145                 150                 155                 160

Ser Asn Asp Ile Phe Phe Trp Thr Thr Ala Ala Ala Thr Ser Gly Ser
                165                 170                 175

Gly Val Thr Pro Ala Ile Ala Thr Ala Gln Val Gln Gln Ala Ala Thr
                180                 185                 190

Asp Leu Val Gly Tyr Val Lys Asp Met Ile Ala Lys Gly Ala Thr Gln
            195                 200                 205

Val Tyr Val Phe Asn Leu Pro Asp Ser Ser Leu Thr Pro Asp Gly Val
    210                 215                 220

Ala Ser Gly Thr Thr Gly Gln Ala Leu Leu His Ala Leu Val Gly Thr
225                 230                 235                 240

Phe Asn Thr Thr Leu Gln Ser Gly Leu Ala Gly Thr Ser Ala Arg Ile
                245                 250                 255

Ile Asp Phe Asn Ala Gln Leu Thr Ala Ala Ile Gln Asn Gly Ala Ser
                260                 265                 270

Phe Gly Phe Ala Asn Thr Ser Ala Arg Ala Cys Asp Ala Thr Lys Ile
            275                 280                 285

Asn Ala Leu Val Pro Ser Ala Gly Gly Ser Ser Leu Phe Cys Ser Ala
290                 295                 300

Asn Thr Leu Val Ala Ser Gly Ala Asp Gln Ser Tyr Leu Phe Ala Asp
305                 310                 315                 320

Gly Val His Pro Thr Thr Ala Gly His Arg Leu Ile Ala Ser Asn Val
                325                 330                 335

Leu Ala Arg Leu Leu Ala Asp Asn Val Ala His
            340                 345

<210> SEQ ID NO 13
<211> LENGTH: 1044
<212> TYPE: DNA
<213> ORGANISM: Ralstonia spp

<400> SEQUENCE: 13
atgaacctgc gtcaatggat gggcgccgcc acggctgccc ttgccttggg cttggccgcg    60
tgcgggggcg gtgggaccga ccagagcggc aatcccaatg tcgccaaggt gcagcgcatg   120
gtggtgttcg cgacagcct gagcgatatc ggcacctaca ccccgtcgc gcaggcggtg    180 ggcggcggca agttcaccac caacccgggc ccgatctggg ccgagaccgt ggccgcgcaa   240
ctgggcgtga cgctcacgcc ggcggtgatg ggctacgcca cctccgtgca gaattgcccc   300
aaggccggct gcttcgacta tgcgcagggc ggctcgcgcg tgaccgatcc gaacggcatc   360
ggccacaacg gcggcgcggg ggcgctgacc tacccggttc agcagcagct cgccaacttc   420
tacgcggcca gcaacaacac attcaacggc aataacgatg tcgtcttcgt gctggccggc   480
agcaacgaca tttctcttctg gaccactgcg gcggccacca gcggctccgg cgtgacgccc   540
gccattgcca cggcccaggt gcagcaggcc gcgacggacc tggtcggcta tgtcaaggac   600
atgatcgcca agggtgcgac gcaggtctac gtgttcaacc tgcccgacag cagcctgacg   660
ccggacggcg tggcaagcgg cacgaccggc caggcgctgc tgcacgcgct ggtgggcacg   720
ttcaacacga cgctgcaaag cgggctggcc ggcacctcgg cgcgcatcat cgacttcaac   780
gcacaactga ccgcggcgat ccagaatggg gcctcgttcg gcttcgccaa caccagcgcc   840
cgggcctgcg acgccaccaa gatcaatgcc ctggtgccga cgccggcgg cagctcgctg   900
```

```
ttctgctcgg ccaacacgct ggtggcttcc ggtgcggacc agagctacct gttcgccgac    960
ggcgtgcacc cgaccacggc cggccatcgc ctgatcgcca gcaacgtgct ggcgcgcctg   1020
ctggcggata acgtcgcgca ctga                                          1044
```

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 261
<212> TYPE: PRT
<213> ORGANISM: Artificial
<220> FEATURE:
<223> OTHER INFORMATION: conserved hypothetical protein Streptomyces
      coelicolor

<400> SEQUENCE: 20

```
Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Ala Gly Thr
```

-continued

```
              100                 105                 110
Val Leu Val Thr Thr Gly Phe Asp Thr Arg Gly Val Pro Val Leu Lys
        115                 120                 125

His Leu Arg Gly Lys Ile Ala Thr Tyr Asn Gly His Val Arg Ala Ile
    130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Pro Leu Pro Pro Arg
        195                 200                 205

Gly Thr Leu Asp Val Arg Arg Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260
```

<210> SEQ ID NO 21
<211> LENGTH: 786
<212> TYPE: DNA
<213> ORGANISM: Streptomyces coelicolor

<400> SEQUENCE: 21

```
gtgatcgggt cgtacgtggc ggtgggggac agcttcaccg agggcgtcgg cgaccccggc      60
cccgacgggg cgttcgtcgg ctgggccgac cggctcgccg tactgctcgc ggaccggcgc     120
cccgagggcg acttcacgta cacgaacctc gccgtgcgcg gcaggctcct cgaccagatc     180
gtggcggaac aggtcccgcg ggtcgtcgga ctcgcgcccg acctcgtctc gttcgcggcg     240
ggcggcaacg acatcatccg gcccggcacc gatcccgacg aggtcgccga gcggttcgag     300
ctggcggtgg ccgcgctgac cgccgcggcc ggaaccgtcc tggtgaccac cgggttcgac     360
acccgggggg tgcccgtcct caagcacctg cgcggcaaga tcgccacgta caacgggcac     420
gtccgcgcca tcgccgaccg ctacggctgc ccggtgctcg acctgtggtc gctgcggagc     480
gtccaggacc gcagggcgtg ggacgccgac cggctgcacc tgtcgccgga ggggcacacc     540
cgggtggcgc tgcgcgcggg gcaggccctg ggcctgcgcg tcccggccga ccctgaccag     600
ccctggccgc ccctgccgcc gcgcggcacg ctcgacgtcc ggcgcgacga cgtgcactgg     660
gcgcgcgagt acctggtgcc gtggatcggg cgccggctgc ggggcgagtc gtcgggcgac     720
cacgtgacgg ccaaggggac gctgtcgccg gacgccatca agacgcggat cgccgcggtg     780
gcctga                                                                786
```

<210> SEQ ID NO 22
<211> LENGTH: 260
<212> TYPE: PRT
<213> ORGANISM: Streptomyces coelicolor

<400> SEQUENCE: 22

```
Met Gln Thr Asn Pro Ala Tyr Thr Ser Leu Val Ala Val Gly Asp Ser
1               5                   10                  15
```

```
Phe Thr Glu Gly Met Ser Asp Leu Leu Pro Asp Gly Ser Tyr Arg Gly
             20                  25                  30

Trp Ala Asp Leu Leu Ala Thr Arg Met Ala Ala Arg Ser Pro Gly Phe
         35                  40                  45

Arg Tyr Ala Asn Leu Ala Val Arg Gly Lys Leu Ile Gly Gln Ile Val
 50                  55                  60

Asp Glu Gln Val Asp Val Ala Ala Met Gly Ala Asp Val Ile Thr
 65                  70                  75                  80

Leu Val Gly Gly Leu Asn Asp Thr Leu Arg Pro Lys Cys Asp Met Ala
                 85                  90                  95

Arg Val Arg Asp Leu Leu Thr Gln Ala Val Glu Arg Leu Ala Pro His
            100                 105                 110

Cys Glu Gln Leu Val Leu Met Arg Ser Pro Gly Arg Gln Gly Pro Val
            115                 120                 125

Leu Glu Arg Phe Arg Pro Arg Met Glu Ala Leu Phe Ala Val Ile Asp
130                 135                 140

Asp Leu Ala Gly Arg His Gly Ala Val Val Asp Leu Tyr Gly Ala
145                 150                 155                 160

Gln Ser Leu Ala Asp Pro Arg Met Trp Asp Val Asp Arg Leu His Leu
                165                 170                 175

Thr Ala Glu Gly His Arg Arg Val Ala Glu Ala Val Trp Gln Ser Leu
            180                 185                 190

Gly His Glu Pro Glu Asp Pro Glu Trp His Ala Pro Ile Pro Ala Thr
        195                 200                 205

Pro Pro Pro Gly Trp Val Thr Arg Thr Ala Asp Val Arg Phe Ala
210                 215                 220

Arg Gln His Leu Leu Pro Trp Ile Gly Arg Arg Leu Thr Gly Arg Ser
225                 230                 235                 240

Ser Gly Asp Gly Leu Pro Ala Lys Arg Pro Asp Leu Leu Pro Tyr Glu
                245                 250                 255

Asp Pro Ala Arg
            260

<210> SEQ ID NO 23
<211> LENGTH: 783
<212> TYPE: DNA
<213> ORGANISM: Streptomyces coelicolor

<400> SEQUENCE: 23
atgcagacga accccgcgta caccagtctc gtcgccgtcg gcgactcctt caccgagggc     60
atgtcggacc tgctgcccga cggctcctac cgtggctggg ccgacctcct cgccacccgg    120
atggcggccc gctcccccgg cttccggtac gccaacctgg cggtgcgcgg aagctgatc    180 ggacagatcg tcgacgagca ggtggacgtg gccgccgcca tgggagccga cgtgatcacg    240
ctggtcggcg ggctcaacga cacgctgcgc ccaagtgcg acatggcccg gtgcgggac    300 ctgctgaccc aggccgtgga acggctcgcc ccgcactgcg agcagctggt gctgatgcgc    360
agtcccggtc gccagggtcc ggtgctggag cgcttccggc ccgcatgga ggccctgttc    420 gccgtgatcg acgacctggc cggcggcac ggcgccgtgg tcgtcgacct gtacggggcc    480
cagtcgctgg ccgaccctcg gatgtgggac gtggaccggc tgcacctgac cgccgagggc    540
caccgccggg tcgcggaggc ggtgtggcag tcgctcggcc acgagcccga ggaccccgag    600
tggcacgcgc cgatccccgg cacgccgccg ccggggtggg tgacgcgcag gaccgcggac    660
gtccggttcg cccggcagca cctgctgccc tggataggcc gcaggctgac cgggcgctcg    720
```

```
tccggggacg gcctgccggc caagcgcccg gacctgctgc cctacgagga ccccgcacgg    780
tga                                                                 783
```

<210> SEQ ID NO 24
<211> LENGTH: 454
<212> TYPE: PRT
<213> ORGANISM: Streptomyces coelicolor

<400> SEQUENCE: 24

```
Met Thr Arg Gly Arg Asp Gly Gly Ala Gly Pro Pro Thr Lys His
1               5                   10                  15

Arg Ala Leu Leu Ala Ala Ile Val Thr Leu Ile Val Ala Ile Ser Ala
            20                  25                  30

Ala Ile Tyr Ala Gly Ala Ser Ala Asp Asp Gly Ser Arg Asp His Ala
        35                  40                  45

Leu Gln Ala Gly Gly Arg Leu Pro Arg Gly Asp Ala Ala Pro Ala Ser
    50                  55                  60

Thr Gly Ala Trp Val Gly Ala Trp Ala Thr Ala Pro Ala Ala Glu
65                  70                  75                  80

Pro Gly Thr Glu Thr Thr Gly Leu Ala Gly Arg Ser Val Arg Asn Val
            85                  90                  95

Val His Thr Ser Val Gly Gly Thr Gly Ala Arg Ile Thr Leu Ser Asn
        100                 105                 110

Leu Tyr Gly Gln Ser Pro Leu Thr Val Thr His Ala Ser Ile Ala Leu
    115                 120                 125

Ala Ala Gly Pro Asp Thr Ala Ala Ile Ala Asp Thr Met Arg Arg
130                 135                 140

Leu Thr Phe Gly Gly Ser Ala Arg Val Ile Ile Pro Ala Gly Gly Gln
145                 150                 155                 160

Val Met Ser Asp Thr Ala Arg Leu Ala Ile Pro Tyr Gly Ala Asn Val
            165                 170                 175

Leu Val Thr Thr Tyr Ser Pro Ile Pro Ser Gly Pro Val Thr Tyr His
        180                 185                 190

Pro Gln Ala Arg Gln Thr Ser Tyr Leu Ala Asp Gly Asp Arg Thr Ala
    195                 200                 205

Asp Val Thr Ala Val Ala Tyr Thr Thr Pro Thr Pro Tyr Trp Arg Tyr
210                 215                 220

Leu Thr Ala Leu Asp Val Leu Ser His Glu Ala Asp Gly Thr Val Val
225                 230                 235                 240

Ala Phe Gly Asp Ser Ile Thr Asp Gly Ala Arg Ser Gln Ser Asp Ala
            245                 250                 255

Asn His Arg Trp Thr Asp Val Leu Ala Ala Arg Leu His Glu Ala Ala
        260                 265                 270

Gly Asp Gly Arg Asp Thr Pro Arg Tyr Ser Val Val Asn Glu Gly Ile
    275                 280                 285

Ser Gly Asn Arg Leu Leu Thr Ser Arg Pro Gly Arg Pro Ala Asp Asn
290                 295                 300

Pro Ser Gly Leu Ser Arg Phe Gln Arg Asp Val Leu Glu Arg Thr Asn
305                 310                 315                 320

Val Lys Ala Val Val Val Leu Gly Val Asn Asp Val Leu Asn Ser
            325                 330                 335

Pro Glu Leu Ala Asp Arg Asp Ala Ile Leu Thr Gly Leu Arg Thr Leu
        340                 345                 350
```

```
Val Asp Arg Ala His Ala Arg Gly Leu Arg Val Val Gly Ala Thr Ile
        355                 360                 365

Thr Pro Phe Gly Gly Tyr Gly Tyr Thr Glu Ala Arg Glu Thr Met
    370                 375                 380

Arg Gln Glu Val Asn Glu Glu Ile Arg Ser Gly Arg Val Phe Asp Thr
385                 390                 395                 400

Val Val Asp Phe Asp Lys Ala Leu Arg Asp Pro Tyr Asp Pro Arg Arg
                405                 410                 415

Met Arg Ser Asp Tyr Asp Ser Gly Asp His Leu His Pro Gly Asp Lys
            420                 425                 430

Gly Tyr Ala Arg Met Gly Ala Val Ile Asp Leu Ala Ala Leu Lys Gly
        435                 440                 445

Ala Ala Pro Val Lys Ala
        450
```

<210> SEQ ID NO 25
<211> LENGTH: 1365
<212> TYPE: DNA
<213> ORGANISM: Streptomyces coelicolor

<400> SEQUENCE: 25

```
atgacccggg gtcgtgacgg gggtgcgggg gcgcccccca ccaagcaccg tgccctgctc      60
gcggcgatcg tcaccctgat agtggcgatc tccgcggcca tatacgccgg agcgtccgcg     120
gacgacggca gcagggacca cgcgctgcag gccggaggcc gtctcccacg aggagacgcc     180
gcccccgcgt ccaccggtgc ctgggtgggc gcctgggcca ccgcaccggc cgcggccgag     240
ccgggcaccg agacgaccgg cctggcgggc cgctccgtgc gcaacgtcgt gcacacctcg     300
gtcggcggca ccggcgcgcg gatcaccctc tcgaacctgt acgggcagtc gccgctgacc     360
gtcacacacg cctcgatcgc cctggccgcc gggcccgaca ccgccgccgc gatcgccgac     420
accatgcgcc ggctcacctt cggcggcagc gcccgggtga tcatcccggc gggcggccag     480
gtgatgagcg acaccgcccg cctcgccatc ccctacgggg cgaacgtcct ggtcaccacg     540
tactccccca tcccgtccgg gccggtgacc taccatccgc aggcccggca gaccagctac     600
ctggccgacg gcgaccgcac ggcggacgtc accgccgtcg cgtacaccac ccccacgccc     660
tactggcgct acctgaccgc cctcgacgtg ctgagccacg aggccgacgg cacggtcgtg     720
gcgttcggcg actccatcac cgacggcgcc cgctcgcaga gcgacgccaa ccaccgctgg     780
accgacgtcc tcgccgcacg cctgcacgag gcggcgggcg acggccggga cacgccccgc     840
tacagcgtcg tcaacgaggg catcagcggc aaccggctcc tgaccagcag gccggggcgg     900
ccggccgaca cccgagcgg actgagccgg ttccagcggg acgtgctgga acgcaccaac     960
gtcaaggccg tcgtcgtcgt cctcggcgtc aacgacgtcc tgaacagccc ggaactcgcc    1020
gaccgcgacg ccatcctgac cggcctgcgc accctcgtcg accgggcgca cgccggga     1080 ctgcgggtcg tcggcgccac gatcacgccg ttcgcggct acgcggcta caccgaggcc    1140 cgcgagacga tgcggcagga ggtcaacgag gagatccgct ccggccgggt cttcgacacg    1200
gtcgtcgact tcgacaaggc cctgcgcgac ccgtacgacc cgcgccggat cgctccgac    1260 tacgacagcg gcgaccacct gcaccccggc gacaagggt acgcgcgcat gggcgcggtc    1320
atcgacctgg ccgcgctgaa gggcgcggcg ccggtcaagg cgtag                   1365
```

<210> SEQ ID NO 26
<211> LENGTH: 340
<212> TYPE: PRT

<213> ORGANISM: Streptomyces coelicolor

<400> SEQUENCE: 26

| | | | | | | | | | | | | | | | |
|---|---|---|---|---|---|---|---|---|---|---|---|---|---|---|---|
| Met | Thr | Ser | Met | Ser | Arg | Ala | Arg | Val | Ala | Arg | Arg | Ile | Ala | Ala | Gly |
| 1 | | | | 5 | | | | | 10 | | | | | 15 | |
| Ala | Ala | Tyr | Gly | Gly | Gly | Ile | Gly | Leu | Ala | Gly | Ala | Ala | Ala | Val | |
| | | | 20 | | | | 25 | | | | | 30 | | | |
| Gly | Leu | Val | Val | Ala | Glu | Val | Gln | Leu | Ala | Arg | Arg | Val | Gly | Val | |
| | | | 35 | | | | 40 | | | | | 45 | | | |
| Gly | Thr | Pro | Thr | Arg | Val | Pro | Asn | Ala | Gln | Gly | Leu | Tyr | Gly | Gly | Thr |
| | 50 | | | | | 55 | | | | | 60 | | | | |
| Leu | Pro | Thr | Ala | Gly | Asp | Pro | Pro | Leu | Arg | Leu | Met | Met | Leu | Gly | Asp |
| 65 | | | | | 70 | | | | | 75 | | | | | 80 |
| Ser | Thr | Ala | Ala | Gly | Gln | Gly | Val | His | Arg | Ala | Gly | Gln | Thr | Pro | Gly |
| | | | | 85 | | | | | 90 | | | | | 95 | |
| Ala | Leu | Leu | Ala | Ser | Gly | Leu | Ala | Ala | Val | Ala | Glu | Arg | Pro | Val | Arg |
| | | | 100 | | | | | 105 | | | | | 110 | | |
| Leu | Gly | Ser | Val | Ala | Gln | Pro | Gly | Ala | Cys | Ser | Asp | Asp | Leu | Asp | Arg |
| | | | 115 | | | | | 120 | | | | | 125 | | |
| Gln | Val | Ala | Leu | Val | Leu | Ala | Glu | Pro | Asp | Arg | Val | Pro | Asp | Ile | Cys |
| | 130 | | | | | 135 | | | | | 140 | | | | |
| Val | Ile | Met | Val | Gly | Ala | Asn | Asp | Val | Thr | His | Arg | Met | Pro | Ala | Thr |
| 145 | | | | | 150 | | | | | 155 | | | | | 160 |
| Arg | Ser | Val | Arg | His | Leu | Ser | Ser | Ala | Val | Arg | Arg | Leu | Arg | Thr | Ala |
| | | | | 165 | | | | | 170 | | | | | 175 | |
| Gly | Ala | Glu | Val | Val | Val | Gly | Thr | Cys | Pro | Asp | Leu | Gly | Thr | Ile | Glu |
| | | | 180 | | | | | 185 | | | | | 190 | | |
| Arg | Val | Arg | Gln | Pro | Leu | Arg | Trp | Leu | Ala | Arg | Arg | Ala | Ser | Arg | Gln |
| | | | 195 | | | | | 200 | | | | | 205 | | |
| Leu | Ala | Ala | Ala | Gln | Thr | Ile | Gly | Ala | Val | Glu | Gln | Gly | Gly | Arg | Thr |
| | 210 | | | | | 215 | | | | | 220 | | | | |
| Val | Ser | Leu | Gly | Asp | Leu | Leu | Gly | Pro | Glu | Phe | Ala | Gln | Asn | Pro | Arg |
| 225 | | | | | 230 | | | | | 235 | | | | | 240 |
| Glu | Leu | Phe | Gly | Pro | Asp | Asn | Tyr | His | Pro | Ser | Ala | Glu | Gly | Tyr | Ala |
| | | | | 245 | | | | | 250 | | | | | 255 | |
| Thr | Ala | Ala | Met | Ala | Val | Leu | Pro | Ser | Val | Cys | Ala | Ala | Leu | Gly | Leu |
| | | | 260 | | | | | 265 | | | | | 270 | | |
| Trp | Pro | Ala | Asp | Glu | Glu | His | Pro | Asp | Ala | Leu | Arg | Arg | Glu | Gly | Phe |
| | | | 275 | | | | | 280 | | | | | 285 | | |
| Leu | Pro | Val | Ala | Arg | Ala | Ala | Ala | Glu | Ala | Ala | Ser | Glu | Ala | Gly | Thr |
| | 290 | | | | | 295 | | | | | 300 | | | | |
| Glu | Val | Ala | Ala | Ala | Met | Pro | Thr | Gly | Pro | Arg | Gly | Pro | Trp | Ala | Leu |
| 305 | | | | | 310 | | | | | 315 | | | | | 320 |
| Leu | Lys | Arg | Arg | Arg | Arg | Arg | Val | Ser | Glu | Ala | Glu | Pro | Ser | Ser | |
| | | | | 325 | | | | | 330 | | | | | 335 | |
| Pro | Ser | Gly | Val | | | | | | | | | | | | |
| | | | 340 | | | | | | | | | | | | |

<210> SEQ ID NO 27
<211> LENGTH: 1023
<212> TYPE: DNA
<213> ORGANISM: Streptomyces coelicolor

<400> SEQUENCE: 27
atgacgagca tgtcgagggc gagggtggcg cggcggatcg cggccggcgc ggcgtacggc    60

```
ggcggcggca tcggcctggc gggagcggcg gcggtcggtc tggtggtggc cgaggtgcag    120
ctggccagac gcagggtggg ggtgggcacg ccgacccggg tgccgaacgc gcagggactg    180 tacgcggca ccctgcccac ggccggcgac ccgccgctgc ggctgatgat gctgggcgac     240
tccacggccg ccgggcaggg cgtgcaccgg gccgggcaga cgccgggcgc gctgctggcg    300
tccgggctcg cggcggtggc ggagcggccg gtgcggctgg ggtcggtcgc ccagccgggg    360
gcgtgctcgg acgacctgga ccggcaggtg cgctggtgc tcgccgagcc ggaccgggtg     420
cccgacatct gcgtgatcat ggtcggcgcc aacgacgtca cccaccggat gccggcgacc    480
cgctcggtgc ggcacctgtc ctcggcggta cggcggctgc gcacggccgg tgcggaggtg    540
gtggtcggca cctgtccgga cctgggcacg atcgagcggg tgcggcagcc gctgcgctgg    600
ctggcccggc gggcctcacg gcagctcgcg gcggcacaga ccatcggcgc cgtcgagcag    660
ggcgggcgca cggtgtcgct gggcgacctg ctgggtccgg agttcgcgca gaacccgcgg    720
gagctcttcg gccccgacaa ctaccacccc tccgccgagg ggtacgccac ggccgcgatg    780
gcggtactgc cctcggtgtg cgccgcgctc ggcctgtggc cggccgacga ggagcacccg    840
gacgcgctgc gccgcgaggg cttcctgccg gtggcgcgcg cggcggcgga ggcggcgtcc    900
gaggcgggta cggaggtcgc cgccgccatg cctacgggc ctcggggggcc ctgggcgctg     960 ctgaagcgcc ggagacggcg tcgggtgtcg gaggcggaac cgtccagccc gtccggcgtt   1020
tga                                                                 1023
```

<210> SEQ ID NO 28
<211> LENGTH: 305
<212> TYPE: PRT
<213> ORGANISM: Streptomyces coelicolor

<400> SEQUENCE: 28

```
Met Gly Arg Gly Thr Asp Gln Arg Thr Arg Tyr Gly Arg Arg Arg Ala
1               5                   10                  15

Arg Val Ala Leu Ala Ala Leu Thr Ala Ala Val Leu Gly Val Gly Val
            20                  25                  30

Ala Gly Cys Asp Ser Val Gly Asp Ser Pro Ala Pro Ser Gly Ser
        35                  40                  45

Pro Ser Lys Arg Thr Arg Thr Ala Pro Ala Trp Asp Thr Ser Pro Ala
    50                  55                  60

Ser Val Ala Ala Val Gly Asp Ser Ile Thr Arg Gly Phe Asp Ala Cys
65                  70                  75                  80

Ala Val Leu Ser Asp Cys Pro Glu Val Ser Trp Ala Thr Gly Ser Ser
                85                  90                  95

Ala Lys Val Asp Ser Leu Ala Val Arg Leu Leu Gly Lys Ala Asp Ala
            100                 105                 110

Ala Glu His Ser Trp Asn Tyr Ala Val Thr Gly Ala Arg Met Ala Asp
        115                 120                 125

Leu Thr Ala Gln Val Thr Arg Ala Ala Gln Arg Glu Pro Glu Leu Val
    130                 135                 140

Ala Val Met Ala Gly Ala Asn Asp Ala Cys Arg Ser Thr Thr Ser Ala
145                 150                 155                 160

Met Thr Pro Val Ala Asp Phe Arg Ala Gln Phe Glu Glu Ala Met Ala
                165                 170                 175

Thr Leu Arg Lys Lys Leu Pro Lys Ala Gln Val Tyr Val Ser Ser Ile
            180                 185                 190
```

```
Pro Asp Leu Lys Arg Leu Trp Ser Gln Gly Arg Thr Asn Pro Leu Gly
        195                 200                 205

Lys Gln Val Trp Lys Leu Gly Leu Cys Pro Ser Met Leu Gly Asp Ala
    210                 215                 220

Asp Ser Leu Asp Ser Ala Ala Thr Leu Arg Arg Asn Thr Val Arg Asp
225                 230                 235                 240

Arg Val Ala Asp Tyr Asn Glu Val Leu Arg Glu Val Cys Ala Lys Asp
                245                 250                 255

Arg Arg Cys Arg Ser Asp Asp Gly Ala Val His Glu Phe Arg Phe Gly
            260                 265                 270

Thr Asp Gln Leu Ser His Trp Asp Trp Phe His Pro Ser Val Asp Gly
        275                 280                 285

Gln Ala Arg Leu Ala Glu Ile Ala Tyr Arg Ala Val Thr Ala Lys Asn
    290                 295                 300

Pro
305

<210> SEQ ID NO 29
<211> LENGTH: 918
<212> TYPE: DNA
<213> ORGANISM: Streptomyces coelicolor

<400> SEQUENCE: 29
atgggtcgag ggacggacca gcggacgcgg tacggccgtc gccgggcgcg tgtcgcgctc     60
gccgccctga ccgccgccgt cctgggcgtg ggcgtggcgg gctgcgactc cgtgggcggc    120
gactcacccg ctccttccgg cagcccgtcg aagcggacga ggacggcgcc cgcctgggac    180
accagcccgg cgtccgtcgc cgccgtgggc gactccatca cgcgcggctt cgacgcctgt    240
gcggtgctgt cggactgccc ggaggtgtcg tgggcgaccg gcagcagcgc gaaggtcgac    300
tcgctggccg tacggctgct ggggaaggcg gacgcggccg agcacagctg gaactacgcg    360
gtcaccgggg cccggatggc ggacctgacc gctcaggtga cgcgggcggc gcagcgcgag    420
ccggagctgg tggcggtgat ggccggggcg aacgacgcgt gccggtccac gacctcggcg    480
atgacgccgg tggcggactt ccgggcgcag ttcgaggagc gatgccacc ctgcgcaag     540 aagctccca ggcgcaggt gtacgtgtcg agcatcccgg acctcaagcg gctctggtcc    600
cagggccgca ccaacccgct gggcaagcag gtgtggaagc tcggcctgtg cccgtcgatg    660
ctgggcgacg cggactccct ggactcggcg gcgaccctgc ggcgcaacac ggtgcgcgac    720
cgggtggcgg actacaacga ggtgctgcgg gaggtctgcg cgaaggaccg gcggtgccgc    780
agcgacgacg gcgcggtgca cgagttccgg ttcggcacgg accagttgag ccactgggac    840
tggttccacc cgagtgtgga cggccaggcc cggctggcgg agatcgccta ccgcgcggtc    900
accgcgaaga atccctga                                                   918

<210> SEQ ID NO 30
<211> LENGTH: 268
<212> TYPE: PRT
<213> ORGANISM: Streptomyces rimosus

<400> SEQUENCE: 30

Met Arg Leu Ser Arg Arg Ala Ala Thr Ala Ser Ala Leu Leu Leu Thr
1               5                   10                  15

Pro Ala Leu Ala Leu Phe Gly Ala Ser Ala Val Ser Ala Pro Arg
            20                  25                  30

Ile Gln Ala Thr Asp Tyr Val Ala Leu Gly Asp Ser Tyr Ser Ser Gly
```

```
                    35                  40                  45
Val Gly Ala Gly Ser Tyr Asp Ser Ser Gly Ser Cys Lys Arg Ser
 50                  55                  60

Thr Lys Ser Tyr Pro Ala Leu Trp Ala Ala Ser His Thr Gly Thr Arg
 65                  70                  75                  80

Phe Asn Phe Thr Ala Cys Ser Gly Ala Arg Thr Gly Asp Val Leu Ala
                 85                  90                  95

Lys Gln Leu Thr Pro Val Asn Ser Gly Thr Asp Leu Val Ser Ile Thr
                100                 105                 110

Ile Gly Gly Asn Asp Ala Gly Phe Ala Asp Thr Met Thr Thr Cys Asn
                115                 120                 125

Leu Gln Gly Glu Ser Ala Cys Leu Ala Arg Ile Ala Lys Ala Arg Ala
130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Val Leu Gly Tyr Pro
                165                 170                 175

Arg Phe Tyr Lys Leu Gly Gly Ser Cys Ala Val Gly Leu Ser Glu Lys
                180                 185                 190

Ser Arg Ala Ala Ile Asn Ala Ala Asp Asp Ile Asn Ala Val Thr
                195                 200                 205

Ala Lys Arg Ala Ala Asp His Gly Phe Ala Phe Gly Asp Val Asn Thr
210                 215                 220

Thr Phe Ala Gly His Glu Leu Cys Ser Gly Ala Pro Trp Leu His Ser
225                 230                 235                 240

Val Thr Leu Pro Val Glu Asn Ser Tyr His Pro Thr Ala Asn Gly Gln
                245                 250                 255

Ser Lys Gly Tyr Leu Pro Val Leu Asn Ser Ala Thr
                260                 265

<210> SEQ ID NO 31
<211> LENGTH: 1068
<212> TYPE: DNA
<213> ORGANISM: Streptomyces rimosus

<400> SEQUENCE: 31
ttcatcacaa cgatgtcaca acaccggcca tccgggtcat ccctgatcgt gggaatgggt     60
gacaagcctt cccgtgacga aagggtcctg ctacatcaga atgacagaa atcctgctca    120 gggaggttcc atgagactgt cccgacgcgc ggccacggcg tccgcgctcc tcctcacccc    180
ggcgctcgcg ctcttcggcg cgagcgccgc cgtgtccgcg ccgcgaatcc aggccaccga    240
ctacgtggcc ctcggcgact cctactcctc ggggtcggc gcgggcagct acgacagcag    300
cagtggctcc tgtaagcgca gcaccaagtc ctacccggcc ctgtgggccg cctcgcacac    360
cggtacgcgg ttcaacttca ccgcctgttc gggcgcccgc acaggagacg tgctggccaa    420
gcagctgacc ccggtcaact ccggcaccga cctggtcagc attaccatcg gcggcaacga    480
cgcgggcttc gccgacacca tgaccacctg caacctccag ggcgagagcg cgtgcctggc    540
gcggatcgcc aaggcgcgcg cctacatcca gcagacgctg cccgcccagc tggaccaggt    600
ctacgacgcc atcgacagcc gggccccgc agcccaggtc gtcgtcctgg gctaccgcg    660 cttctacaag ctgggcggca gctgcgccgt cggtctctcg gagaagtccc gcgcggccat    720
caacgccgcc gccgacgaca tcaacgccgt caccgccaag cgcgccgccg accacggctt    780
cgccttcggg gacgtcaaca cgaccttcgc cgggcacgag ctgtgctccg cgcccctg    840
```

```
gctgcacagc gtcacccttc ccgtggagaa ctcctaccac cccacggcca acggacagtc    900
caagggctac ctgcccgtcc tgaactccgc cacctgatct cgcggctact ccgcccctga    960
cgaagtcccg cccccgggcg gggcttcgcc gtaggtgcgc gtaccgccgt cgcccgtcgc   1020
gccggtggcc ccgccgtacg tgccgccgcc cccggacgcg gtcggttc               1068
```

<210> SEQ ID NO 32
<211> LENGTH: 335
<212> TYPE: PRT
<213> ORGANISM: Aeromonas hydrophila

<400> SEQUENCE: 32

```
Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Gln Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Ala Asn Gln Tyr Glu Phe Leu Ala His
                325                 330                 335
```

<210> SEQ ID NO 33
<211> LENGTH: 1008
<212> TYPE: DNA
<213> ORGANISM: Aeromonas hydrophila

<400> SEQUENCE: 33

```
atgaaaaaat ggtttgtgtg tttattggga ttggtcgcgc tgacagttca ggcagccgac      60
agtcgccccg ccttttcccg gatcgtgatg ttcggcgaca gcctctccga taccggcaaa     120
atgtacagca gatgcgcggt tacctcccc tccagcccgc cctactatga gggccgtttc     180
tccaacggac ccgtctggct ggagcagctg accaaacagt tcccgggtct gaccatcgcc     240
aacgaagcgg aaggcggtgc cactgccgtg gcttacaaca agatctcctg gaatcccaag     300
tatcaggtca tcaacaacct ggactacgag gtcacccagt tcttgcagaa agacagcttc     360
aagccggacg atctggtgat cctctgggtc ggtgccaatg actatctggc ctatggctgg     420
aacacggagc aggatgccaa gcgggttcgc gatgccatca gcgatgcggc caaccgcatg     480
gtactgaacg gtgccaagca gatactgctg ttcaacctgc cggatctggg ccagaacccg     540
tcagctcgca gtcagaaggt ggtcgaggcg gtcagccatg tctccgccta tcacaaccag     600
ctgctgctga acctggcacg ccagctggcc cccaccggca tggtaaagct gttcgagatc     660
gacaagcaat ttgccgagat gctgcgtgat ccgcagaact tcggcctgag cgacgtcgag     720
aaccccctgct acgacggcgg ctatgtgtgg aagccgtttg ccacccgcag cgtcagcacc     780
gaccgccagc tctccgcctt cagtccgcag gaacgcctcg ccatcgccgg caacccgctg     840
ctggcacagg ccgttgccag tcctatggcc cgccgcagcg ccagcccct caactgtgag     900
ggcaagatgt tctgggatca ggtacacccg accactgtcg tgcacgcagc cctgagcgag     960
cgcgccgcca ccttcatcgc gaaccagtac gagttcctcg cccactga                 1008
```

<210> SEQ ID NO 34
<211> LENGTH: 336
<212> TYPE: PRT
<213> ORGANISM: Aeromonas salmonicida subsp. Salmonicida

<400> SEQUENCE: 34

```
Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
```

```
                145                 150                 155                 160

Val Leu Asn Gly Ala Lys Gln Ile Leu Leu Phe Asn Leu Pro Asp Leu
                    165                 170                 175

Gly Gln Asn Pro Ser Ala Arg Ser Gln Lys Val Val Glu Ala Val Ser
                    180                 185                 190

His Val Ser Ala Tyr His Asn Lys Leu Leu Leu Asn Leu Ala Arg Gln
                    195                 200                 205

Leu Ala Pro Thr Gly Met Val Lys Leu Phe Glu Ile Asp Lys Gln Phe
                    210                 215                 220

Ala Glu Met Leu Arg Asp Pro Gln Asn Phe Gly Leu Ser Asp Val Glu
    225                 230                 235                 240

Asn Pro Cys Tyr Asp Gly Gly Tyr Val Trp Lys Pro Phe Ala Thr Arg
                    245                 250                 255

Ser Val Ser Thr Asp Arg Gln Leu Ser Ala Phe Ser Pro Gln Glu Arg
                    260                 265                 270

Leu Ala Ile Ala Gly Asn Pro Leu Ala Gln Ala Val Ala Ser Pro
                    275                 280                 285

Met Ala Arg Arg Ser Ala Ser Pro Leu Asn Cys Glu Gly Lys Met Phe
                    290                 295                 300

Trp Asp Gln Val His Pro Thr Thr Val Val His Ala Ala Leu Ser Glu
    305                 310                 315                 320

Arg Ala Ala Thr Phe Ile Glu Thr Gln Tyr Glu Phe Leu Ala His Gly
                    325                 330                 335

<210> SEQ ID NO 35
<211> LENGTH: 1011
<212> TYPE: DNA
<213> ORGANISM: Aeromonas salmonicida subsp. Salmonicida

<400> SEQUENCE: 35
atgaaaaaat ggtttgtttg tttattgggg ttgatcgcgc tgacagttca ggcagccgac      60
actcgccccg ccttctcccg gatcgtgatg ttcggcgaca gcctctccga taccggcaaa     120
atgtacagca gatgcgcggg ttacctcccc tccagcccgc cctactatga gggccgtttc     180
tccaacggac ccgtctggct ggagcagctg accaagcagt tcccgggtct gaccatcgcc     240
aacgaagcgg aaggcggtgc cactgccgtg gcttacaaca gatctcctg  gaatcccaag     300 tatcaggtca tcaacaacct ggactacgag gtcacccagt tcttgcagaa agacagcttc     360
aagccggaca tctggtgat  cctctgggtc ggtgccaatg actatctggc atatggctgg     420
aatacggagc aggatgccaa gcgagttcgc gatgccatca gcgatgcggc caaccgcatg     480
gtactgaacg gtgccaagca gatactgctg ttcaacctgc cggatctggg ccagaacccg     540
tcagcccgca gtcagaaggt ggtcgaggcg gtcagccatg tctccgccta tcacaacaag     600
ctgctgctga acctggcacg ccagctggcc ccaccggca  tggtaaagct gttcgagatc     660
gacaagcaat ttgccgagat gctgcgtgat ccgcagaact tcggcctgag cgacgtcgag     720 aaccctgct  acgacggcgg ctatgtgtgg aagccgtttg ccaccgcag  cgtcagcacc     780 gaccgccagc tctccgcctt cagtccgcag gaacgcctcg ccatcgccgg caaccgctg      840 ctggcacagg ccgttgccag tcctatggcc cgccgcagcg ccagccccct caactgtgag     900
ggcaagatgt tctgggatca ggtacacccg accactgtcg tgcacgcagc cctgagcgag     960
cgcgccgcca ccttcatcga gacccagtac gagttcctcg cccacggatg a             1011

<210> SEQ ID NO 36
```

<211> LENGTH: 347
<212> TYPE: PRT
<213> ORGANISM: Artificial
<220> FEATURE:
<223> OTHER INFORMATION: fusion construct

<400> SEQUENCE: 36

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Ala Asp
            20                  25                  30

Ser Arg Pro Ala Phe Ser Arg Ile Val Met Phe Gly Asp Ser Leu Ser
        35                  40                  45

Asp Thr Gly Lys Met Tyr Ser Lys Met Arg Gly Tyr Leu Pro Ser Ser
    50                  55                  60

Pro Pro Tyr Tyr Glu Gly Arg Phe Ser Asn Gly Pro Val Trp Leu Glu
65                  70                  75                  80

Gln Leu Thr Lys Gln Phe Pro Gly Leu Thr Ile Ala Asn Glu Ala Glu
                85                  90                  95

Gly Gly Ala Thr Ala Val Ala Tyr Asn Lys Ile Ser Trp Asn Pro Lys
            100                 105                 110

Tyr Gln Val Ile Asn Asn Leu Asp Tyr Glu Val Thr Gln Phe Leu Gln
        115                 120                 125

Lys Asp Ser Phe Lys Pro Asp Asp Leu Val Ile Leu Trp Val Gly Ala
    130                 135                 140

Asn Asp Tyr Leu Ala Tyr Gly Trp Asn Thr Glu Gln Asp Ala Lys Arg
145                 150                 155                 160

Val Arg Asp Ala Ile Ser Asp Ala Ala Asn Arg Met Val Leu Asn Gly
                165                 170                 175

Ala Lys Gln Ile Leu Leu Phe Asn Leu Pro Asp Leu Gly Gln Asn Pro
            180                 185                 190

Ser Ala Arg Ser Gln Lys Val Val Glu Ala Val Ser His Val Ser Ala
        195                 200                 205

Tyr His Asn Gln Leu Leu Leu Asn Leu Ala Arg Gln Leu Ala Pro Thr
    210                 215                 220

Gly Met Val Lys Leu Phe Glu Ile Asp Lys Gln Phe Ala Glu Met Leu
225                 230                 235                 240

Arg Asp Pro Gln Asn Phe Gly Leu Ser Asp Val Glu Asn Pro Cys Tyr
                245                 250                 255

Asp Gly Gly Tyr Val Trp Lys Pro Phe Ala Thr Arg Ser Val Ser Thr
            260                 265                 270

Asp Arg Gln Leu Ser Ala Phe Ser Pro Gln Glu Arg Leu Ala Ile Ala
        275                 280                 285

Gly Asn Pro Leu Leu Ala Gln Ala Val Ala Ser Pro Met Ala Arg Arg
    290                 295                 300

Ser Ala Ser Pro Leu Asn Cys Glu Gly Lys Met Phe Trp Asp Gln Val
305                 310                 315                 320

His Pro Thr Thr Val Val His Ala Ala Leu Ser Glu Arg Ala Ala Thr
                325                 330                 335

Phe Ile Ala Asn Gln Tyr Glu Phe Leu Ala His
            340                 345

<210> SEQ ID NO 37
<211> LENGTH: 27
<212> TYPE: DNA
<213> ORGANISM: Artificial

```
<220> FEATURE:
<223> OTHER INFORMATION: Primer asls950new

<400> SEQUENCE: 37
gtgatggtgg gcgaggaact cgtactg                                           27

<210> SEQ ID NO 38
<211> LENGTH: 35
<212> TYPE: DNA
<213> ORGANISM: Artificial
<220> FEATURE:
<223> OTHER INFORMATION: Primer 1USNEW

<400> SEQUENCE: 38
agcatatgaa aaatggttt gtttgtttat tgggg                                   35

<210> SEQ ID NO 39
<211> LENGTH: 39
<212> TYPE: DNA
<213> ORGANISM: Artificial
<220> FEATURE:
<223> OTHER INFORMATION: Primer AHLS1001

<400> SEQUENCE: 39
ttggatccga attcatcaat ggtgatggtg atggtgggc                              39

<210> SEQ ID NO 40
<211> LENGTH: 18
<212> TYPE: DNA
<213> ORGANISM: Artificial
<220> FEATURE:
<223> OTHER INFORMATION: T7 promoter primer

<400> SEQUENCE: 40
taatacgact cactatag                                                     18

<210> SEQ ID NO 41
<211> LENGTH: 18
<212> TYPE: DNA
<213> ORGANISM: Artificial
<220> FEATURE:
<223> OTHER INFORMATION: T7 terminator primer

<400> SEQUENCE: 41
ctagttattg ctcagcgg                                                     18

<210> SEQ ID NO 42
<211> LENGTH: 41
<212> TYPE: DNA
<213> ORGANISM: Artificial
<220> FEATURE:
<223> OTHER INFORMATION: Primer AHUS1

<400> SEQUENCE: 42
gtcatatgaa aaatggttt gtgtgtttat tgggattggt c                            41

<210> SEQ ID NO 43
<211> LENGTH: 30
<212> TYPE: DNA
<213> ORGANISM: Artificial
<220> FEATURE:
<223> OTHER INFORMATION: Primer ahls950

<400> SEQUENCE: 43
atggtgatgg tgggcgagga actcgtactg                                        30
```

<210> SEQ ID NO 44
<211> LENGTH: 41
<212> TYPE: DNA
<213> ORGANISM: Artificial
<220> FEATURE:
<223> OTHER INFORMATION: Primer AHUS1

<400> SEQUENCE: 44
gtcatatgaa aaatggttt gtgtgtttat tgggattggt c					41

<210> SEQ ID NO 45
<211> LENGTH: 2094
<212> TYPE: DNA
<213> ORGANISM: Aeromonas hydrophila

<400> SEQUENCE: 45

| | |
|---|---|
| atgtttaagt ttaaaaagaa tttcttagtt ggattatcgg cagctttaat tacaaattca | 60 |
| aatttttctt aaagaatcaa cctaatagcc gtcgaaatta gagtattagc ttgttttcgg | 120 |
| caaccgcctc tgcagctagc gccgacagcc ctcataatcg aacaaaagcc gttggcggag | 180 |
| acgtcgatcg cggctgtcgg gtcccgcctt ttcccggatc gtgatgttcg gcgacagcct | 240 |
| ctccgatacc cagggcggaa aagggcctag cactacaagc cgctgtcgga gaggctatgg | 300 |
| ggcaaaatgt acagcaagat gcgcggttac ctccctcca gccgccta ccgttttaca | 360 |
| tgtcgttcta cgcgccaatg gaggggaggt cgggcgggat ctatgagggc cgtttctcca | 420 |
| acggacccgt ctggctggag cagctgacca gatactcccg gcaaagaggt tgcctgggca | 480 |
| gaccgacctc gtcgactggt aacagttccc gggtctgacc atcgccaacg aagcggaagg | 540 |
| cggtgccact ttgtcaaggg cccagactgg tagcggttgc ttcgccttcc gccacggtga | 600 |
| gccgtggctt acaacaagat ctcctggaat cccaagtatc aggtcatcaa cggcaccgaa | 660 |
| tgttgttcta gaggacctta gggttcatag tccagtagtt caacctggac tacgaggtca | 720 |
| cccagttctt gcagaaagac agcttcaagc gttggacctg atgctccagt gggtcaagaa | 780 |
| cgtctttctg tcgaagttcg cggacgatct ggtgatcctc tgggtcggtg ccaatgacta | 840 |
| tctggcctat gcctgctaga ccactaggag acccagccac ggttactgat agaccggata | 900 |
| ggctggaaca cggagcagga tgccaagcgg gttcgcgatg ccatcagcga ccgaccttgt | 960 |
| gcctcgtcct acggttcgcc caagcgctac ggtagtcgct tgcggccaac cgcatggtac | 1020 |
| tgaacggtgc caagcagata ctgctgttca cgccggttg gcgtaccatg acttgccacg | 1080 |
| gttcgtctat gacgacaagt acctgccgga tctgggccag aacccgtcag ctcgcagtca | 1140 |
| gaaggtggtc tggacggcct agacccggtc ttgggcagtc gagcgtcagt cttccaccag | 1200 |
| gaggcggtca gccatgtctc cgcctatcac aaccagctgc tgctgaacct ctccgccagt | 1260 |
| cggtacagag gcggatagtg ttggtcgacg acgacttgga ggcacgccag ctggccccca | 1320 |
| ccggcatggt aaagctgttc gagatcgaca ccgtgcggtc gaccggggt ggccgtacca | 1380 |
| tttcgacaag ctctagctgt agcaatttgc cgagatgctg cgtgatccgc agaacttcgg | 1440 |
| cctgagcgac tcgttaaacg gctctacgac gcactaggcg tcttgaagcc ggactcgctg | 1500 |
| gtcgagaacc cctgctacga cggcggctat gtgtggaagc cgtttgccac cagctcttgg | 1560 |
| ggacgatgct gccgccgata cacccttcg gcaaacggtg ccgcagcgtc agcaccgacc | 1620 |
| gccagctctc cgccttcagt ccgcaggaac ggcgtcgcag tcgtggctgg cggtcgagag | 1680 |
| gcggaagtca ggcgtccttg gcctcgccat gccggcaac ccgctgctgg cacaggccgt | 1740 |
| tgccagtcct cggagcggta gcggccgttg ggcgacgacc gtgtccggca acggtcagga | 1800 |

```
atggcccgcc gcagcgccag ccccctcaac tgtgagggca agatgttctg taccgggcgg    1860
cgtcgcggtc gggggagttg acactcccgt tctacaagac ggatcaggta cacccgacca    1920
ctgtcgtgca cgcagccctg agcgagcgcg cctagtccat gtgggctggt gacagcacgt    1980
gcgtcgggac tcgctcgcgc ccgccacctt catcgcgaac cagtacgagt tcctcgccca    2040
ctgatgaggc ggtggaagta gcgcttggtc atgctcaagg agcgggtgac tact          2094
```

<210> SEQ ID NO 46
<211> LENGTH: 26
<212> TYPE: DNA
<213> ORGANISM: Artificial
<220> FEATURE:
<223> OTHER INFORMATION: Primer usAHncol

<400> SEQUENCE: 46
atgccatggc cgacagccgt cccgcc                                          26

<210> SEQ ID NO 47
<211> LENGTH: 27
<212> TYPE: DNA
<213> ORGANISM: Artificial
<220> FEATURE:
<223> OTHER INFORMATION: Primer lsAH

<400> SEQUENCE: 47
ttggatccga attcatcaat ggtgatg                                         27

<210> SEQ ID NO 48
<211> LENGTH: 26
<212> TYPE: DNA
<213> ORGANISM: Artificial
<220> FEATURE:
<223> OTHER INFORMATION: Primer US-AhnheI

<400> SEQUENCE: 48
ttgctagcgc cgacagccgt cccgcc                                          26

<210> SEQ ID NO 49
<211> LENGTH: 27
<212> TYPE: DNA
<213> ORGANISM: Artificial
<220> FEATURE:
<223> OTHER INFORMATION: Primer lsAH

<400> SEQUENCE: 49
ttggatccga attcatcaat ggtgatg                                         27

<210> SEQ ID NO 50
<211> LENGTH: 26
<212> TYPE: DNA
<213> ORGANISM: Artificial
<220> FEATURE:
<223> OTHER INFORMATION: Primer US-Asncol

<400> SEQUENCE: 50
ttgccatggc cgacactcgc cccgcc                                          26

<210> SEQ ID NO 51
<211> LENGTH: 27
<212> TYPE: DNA
<213> ORGANISM: Artificial
<220> FEATURE:
<223> OTHER INFORMATION: Primer lsAH

<400> SEQUENCE: 51
ttggatccga attcatcaat ggtgatg                                    27

<210> SEQ ID NO 52
<211> LENGTH: 26
<212> TYPE: DNA
<213> ORGANISM: Artificial
<220> FEATURE:
<223> OTHER INFORMATION: Primer US-ASnhe1

<400> SEQUENCE: 52
ttgctagcgc cgacactcgc cccgcc                                     26

<210> SEQ ID NO 53
<211> LENGTH: 27
<212> TYPE: DNA
<213> ORGANISM: Artificial
<220> FEATURE:
<223> OTHER INFORMATION: Primer lsAH

<400> SEQUENCE: 53
ttggatccga attcatcaat ggtgatg                                    27

<210> SEQ ID NO 54
<211> LENGTH: 1371
<212> TYPE: DNA
<213> ORGANISM: Streptomyces spp

<400> SEQUENCE: 54
acaggccgat gcacggaacc gtacctttcc gcagtgaagc gctctccccc catcgttcgc    60
cgggacttca tccgcgattt tggcatgaac acttccttca acgcgcgtag cttgctacaa   120
gtgcggcagc agacccgctc gttggaggct cagtgagatt gacccgatcc ctgtcggccg   180
catccgtcat cgtcttcgcc ctgctgctcg cgctgctggg catcagcccg gcccaggcag   240
ccggcccggc ctatgtggcc tgggggatt cctattcctc gggcaacggc gccggaagtt   300
acatcgattc gagcggtgac tgtcaccgca gcaacaacgc gtaccccgcc cgctgggcgg   360
cggccaacgc accgtcctcc ttcaccttcg cggcctgctc gggagcggtg accacggatg   420
tgatcaacaa tcagctgggc gccctcaacg cgtccaccgg cctggtgagc atcaccatcg   480
gcggcaatga cgcgggcttc gcggacgcga tgaccacctg cgtcaccagc tcggacagca   540
cctgcctcaa ccggctggcc accgccacca actacatcaa caccaccctg ctcgcccggc   600
tcgacgcggt ctacagccag atcaaggccc gtgcccccaa cgcccgcgtg tcgtcctcg    660
gctaccgcg catgtacctg gcctcgaacc cctggtactg cctgggcctg agcaacacca   720
agcgcgcggc catcaacacc accgccgaca ccctcaactc ggtgatctcc tcccgggcca   780
ccgcccacgg attccgattc ggcgatgtcc gcccgacctt caacaaccac gaactgttct   840
tcggcaacga ctggctgcac tcactcaccc tgccggtgtg ggagtcgtac caccccacca   900
gcacgggcca tcagagcggc tatctgccgg tcctcaacgc caacagctcg acctgatcaa   960
cgcacggccg tgcccgcccc gcgcgtcacg ctcggcgcgg gcgccgcagc gcgttgatca  1020
gcccacagtg ccggtgacgg tcccaccgtc acggtcgagg gtgtacgtca cggtggcgcc  1080
gctccagaag tggaacgtca gcaggaccgt ggagccgtcc ctgacctcgt cgaagaactc  1140
cggggtcagc gtgatcaccc ctccccgta gccggggcg aaggcggcgc cgaactcctt   1200
gtaggacgtc cagtcgtgcg gcccggcgtt gccaccgtcc gctagaccg cttccatggt   1260
cgccagccgg tccccgcgga actcggtggg gatgtccgtg cccaaggtgg tcccggtggt  1320

```
gtccgagagc accgggggct cgtaccggat gatgtgcaga tccaaagaat t          1371
```

<210> SEQ ID NO 55
<211> LENGTH: 267
<212> TYPE: PRT
<213> ORGANISM: Streptomyces spp

<400> SEQUENCE: 55

```
Met Arg Leu Thr Arg Ser Leu Ser Ala Ala Ser Val Ile Val Phe Ala
1               5                   10                  15
Leu Leu Leu Ala Leu Leu Gly Ile Ser Pro Ala Gln Ala Ala Gly Pro
            20                  25                  30
Ala Tyr Val Ala Leu Gly Asp Ser Tyr Ser Ser Gly Asn Gly Ala Gly
        35                  40                  45
Ser Tyr Ile Asp Ser Ser Gly Asp Cys His Arg Ser Asn Asn Ala Tyr
    50                  55                  60
Pro Ala Arg Trp Ala Ala Ala Asn Ala Pro Ser Ser Phe Thr Phe Ala
65                  70                  75                  80
Ala Cys Ser Gly Ala Val Thr Thr Asp Val Ile Asn Asn Gln Leu Gly
                85                  90                  95
Ala Leu Asn Ala Ser Thr Gly Leu Val Ser Ile Thr Ile Gly Gly Asn
            100                 105                 110
Asp Ala Gly Phe Ala Asp Ala Met Thr Thr Cys Val Thr Ser Ser Asp
        115                 120                 125
Ser Thr Cys Leu Asn Arg Leu Ala Thr Ala Thr Asn Tyr Ile Asn Thr
    130                 135                 140
Thr Leu Leu Ala Arg Leu Asp Ala Val Tyr Ser Gln Ile Lys Ala Arg
145                 150                 155                 160
Ala Pro Asn Ala Arg Val Val Val Leu Gly Tyr Pro Arg Met Tyr Leu
                165                 170                 175
Ala Ser Asn Pro Trp Tyr Cys Leu Gly Leu Ser Asn Thr Lys Arg Ala
            180                 185                 190
Ala Ile Asn Thr Thr Ala Asp Thr Leu Asn Ser Val Ile Ser Ser Arg
        195                 200                 205
Ala Thr Ala His Gly Phe Arg Phe Gly Asp Val Arg Pro Thr Phe Asn
    210                 215                 220
Asn His Glu Leu Phe Phe Gly Asn Asp Trp Leu His Ser Leu Thr Leu
225                 230                 235                 240
Pro Val Trp Glu Ser Tyr His Pro Thr Ser Thr Gly His Gln Ser Gly
                245                 250                 255
Tyr Leu Pro Val Leu Asn Ala Asn Ser Ser Thr
            260                 265
```

<210> SEQ ID NO 56
<211> LENGTH: 35
<212> TYPE: DNA
<213> ORGANISM: Artificial
<220> FEATURE:
<223> OTHER INFORMATION: Primer 1USNEW

<400> SEQUENCE: 56

```
agcatatgaa aaaatggttt gtttgtttat tgggg                            35
```

<210> SEQ ID NO 57
<211> LENGTH: 39
<212> TYPE: DNA
<213> ORGANISM: Artificial

<220> FEATURE:
<223> OTHER INFORMATION: Primer AHLS1001

<400> SEQUENCE: 57
ttggatccga attcatcaat ggtgatggtg atggtgggc                          39

<210> SEQ ID NO 58
<211> LENGTH: 548
<212> TYPE: PRT
<213> ORGANISM: Thermobifida fusca

<400> SEQUENCE: 58

```
Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
            20                  25                  30

His Glu Thr Arg Pro Leu Arg Gly Arg Cys Gly Cys Gly Glu Arg Arg
        35                  40                  45

Val Pro Pro Leu Thr Leu Pro Gly Asp Gly Val Leu Cys Thr Thr Ser
    50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
            100                 105                 110

Phe Glu Val Cys Arg Arg Asp Thr Pro Gly Leu Ser Arg Thr Arg Asn
        115                 120                 125

Gly Asp Ser Pro Pro Phe Arg Ala Gly Trp Ser Leu Pro Pro Lys
    130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Leu Phe Leu Gly
            180                 185                 190

Ile Pro Ala Leu Val Leu Val Thr Ala Leu Thr Leu Val Leu Ala Val
        195                 200                 205

Pro Thr Gly Arg Glu Thr Leu Trp Arg Met Trp Cys Glu Ala Thr Gln
    210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
            260                 265                 270

Asp Tyr Tyr Pro Gly Thr Ala Val Lys Gly Gly Cys Trp Arg Ser Ala
        275                 280                 285

Asn Ala Tyr Pro Glu Leu Val Ala Glu Ala Tyr Asp Phe Ala Gly His
    290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                325                 330                 335

Ser Leu Val Thr Ile Gly Ile Gly Gly Asn Asp Leu Gly Phe Ser Thr
```

```
                340             345             350
Val Leu Lys Thr Cys Met Val Arg Val Pro Leu Leu Asp Ser Lys Ala
            355                 360                 365

Cys Thr Asp Gln Glu Asp Ala Ile Arg Lys Arg Met Ala Lys Phe Glu
        370                 375                 380

Thr Thr Phe Glu Glu Leu Ile Ser Glu Val Arg Thr Arg Ala Pro Asp
385                 390                 395                 400

Ala Arg Ile Leu Val Val Gly Tyr Pro Arg Ile Phe Pro Glu Glu Pro
                405                 410                 415

Thr Gly Ala Tyr Tyr Thr Leu Thr Ala Ser Asn Gln Arg Trp Leu Asn
            420                 425                 430

Glu Thr Ile Gln Glu Phe Asn Gln Leu Ala Glu Ala Val Ala Val
        435                 440                 445

His Asp Glu Glu Ile Ala Ala Ser Gly Gly Val Gly Ser Val Glu Phe
        450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                485                 490                 495

Val Asp Arg Ser Thr Phe His Pro Asn Ala Ala Gly His Arg Ala Val
            500                 505                 510

Gly Glu Arg Val Ile Glu Gln Ile Glu Thr Gly Pro Gly Arg Pro Leu
        515                 520                 525

Tyr Ala Thr Phe Ala Val Val Ala Gly Ala Thr Val Asp Thr Leu Ala
        530                 535                 540

Gly Glu Val Gly
545

<210> SEQ ID NO 59
<211> LENGTH: 3000
<212> TYPE: DNA
<213> ORGANISM: Thermobifida fusca

<400> SEQUENCE: 59
ggtggtgaac cagaacaccc ggtcgtcggc gtgggcgtcc aggtgcaggt gcaggttctt        60
caactgctcc agcaggatgc cgccgtggcc gtgcacgatg ccttgggca ggcctgtggt        120 ccccgacgag tacagcaccc atagcggatg gtcgaacggc agcggggtga actccagttc       180
cgcgccttcg cccgcggctt cgaactccgc ccaggacagg gtgtcggcga cagggccgca       240
gcccaggtac ggcaggacga cggtgtgctg caggctgggc atgccgtcgc gcagggcttt       300
gagcacgtca cggcggtcga agtccttacc gccgtagcgg tagccgtcca cggccagcag       360
cactttcggt tcgatctgcg cgaaccggtc gaggacgctg cgcaccccga gtcggggga       420 acaggacgac caggtcgcac cgatcgcggc gcaggcgagg aatgcggccg tcgcctcggc       480
gatgttcggc aggtaggcca cgacccggtc gccggggccc accccgaggc tgcggagggc       540
cgcagcgatc gcggcggtgc gggtccgcag ttctccccag gtccactcgg tcaacgccg       600 gagttcggac gcgtgccgga tcgccacggc tgatgggtca cggtcgcgga agatgtgctc       660
ggcgtagttg agggtggcgc cggggaacca gacggcgccg gcatggcgt cggaggcgag       720 cactgtggtg tacggggtgg cggcgcgcac ccggtagtac tcccagatcg cggaccagaa       780
tccttcgagg tcggttaccg accagcgcca cagtgcctcg tagtccggtg cgtcccacacc      840 gcggtgctcc cgcaccccagc gggtgaacgc ggtgaggttg cgcgcgttctt tgcgctcctc    900
```

```
gtcgggactc cacaggatcg gcggctgcgg cttgagtgtc atgaaacgcg accccttcgt      960
ggacggtgcg gatgcggtga gcgtcggtg  cctcccctaa cgctcccggg tgacggagtg     1020
ttgtgcacca catctagcac gcgggacgcg gaaaccgtat ggagaaaaca cctacaaccc     1080
cggccggacg gtgggtttcg gccacactta ggggtcgggt gcctgcttgc cgggcagggc     1140
agtcccgggg tgctgtggtg cgggcggag  ggctgtcgct tcgaggtgtg ccggcgggac     1200
actccgggcc tcagccgtac ccgcaacggg gacagttctc ctcccttccg ggctggatgg     1260
tcccttcccc cgaaatgcgg cgagatctcc cagtcagccc ggaaaacacc cgctgtgccc     1320
aggtactctt tgcttcgaac agacaggccg gacggtccac ggggaggtt  tgtgggcagc     1380 ggaccacgtg cggcgaccag acgacggttg ttcctcggta tccccgctct tgtacttgtg     1440
acagcgctca cgctggtctt ggctgtcccg acggggcgcg agacgctgtg gcgcatgtgg     1500
tgtgaggcca cccaggactg gtgcctgggg gtgccggtcg actcccgcgg acagcctgcg     1560
gaggacggca gtttctgct  gctttctccg gtccaggcag cgacctgggg gaactattac     1620
gcgctcgggg attcgtactc ttcggggac  ggggcccgcg actactatcc cggcaccgcg     1680
gtgaagggcg gttgctggcg gtccgctaac gcctatccgg agctggtcgc cgaagcctac     1740
gacttcgccg gacacttgtc gttcctggcc tgcagcggcc agcgcggcta cgccatgctt     1800
gacgctatcg acgaggtcgg ctcgcagctg gactggaact cccctcacac gtcgctggtg     1860
acgatcggga tcggcggcaa cgatctgggg ttctccacgg ttttgaagac ctgcatggtg     1920
cgggtgccgc tgctggacag caaggcgtgc acggaccagg aggacgctat ccgcaagcgg     1980
atggcgaaat tcgagacgac gtttgaagag ctcatcagcg aagtgcgcac ccgcgcgccg     2040
gacgcccgga tccttgtcgt gggctacccc cggattttc  cggaggaacc gaccggcgcc     2100
tactacacgc tgaccgcgag caaccagcgg tggctcaacg aaaccattca ggagttcaac     2160
cagcagctcg ccgaggctgt cgcggtccac gacgaggaga ttgccgcgtc gggcggggtg     2220
ggcagcgtgg agttcgtgga cgtctaccac gcgttggacg gccacgagat cggctcggac     2280
gagccgtggg tgaacggggt gcagttgcgg gacctcgcca ccggggtgac tgtggaccgc     2340
agtaccttcc accccaacgc cgctgggcac cgggcggtcg gtgagcgggt catcgagcag     2400
atcgaaaccg gcccgggccg tccgctctat gccactttcg cggtggtggc ggggcgacc      2460 gtggacactc tcgcgggcga ggtggggtga cccggcttac cgtccggccc gcaggtctgc     2520
gagcactgcg gcgatctggt ccactgccca gtgcagttcg tcttcggtga tgaccagcgg     2580
cggggagagc cggatcgttg agccgtgcgt gtctttgacg agcacacccc gctgcaggag     2640
ccgttcgcac agttctcttc cggtggccag agtcgggtcg acgtcgatcc cagcccacag     2700
gccgatgctg cgggccgcga ccacgccgtt gccgaccagt tggtcgaggc gggcgcgcag     2760 cacggggggcg agggcgcgga catggtccag gtaagggccg tcgcggacga ggctcaccac     2820
ggcagtgccg accgcgcagg cgagggcgtt gccgccgaag gtgctgccgt gctggccggg     2880
gcggatcacg tcgaagactt ccgcgtcgcc taccgccgcc gccacgggca ggatgccgcc     2940
gcccagcgct tgccgaaca  ggtagatatc ggcgtcgact ccgctgtggt cgcaggcccg     3000
```

<210> SEQ ID NO 60
<211> LENGTH: 372
<212> TYPE: PRT
<213> ORGANISM: Thermobifida fusca

<400> SEQUENCE: 60

Val Gly Ser Gly Pro Arg Ala Ala Thr Arg Arg Arg Leu Phe Leu Gly

```
  1               5                  10                 15
Ile Pro Ala Leu Val Leu Val Thr Ala Leu Thr Leu Val Leu Ala Val
                20                 25                 30

Pro Thr Gly Arg Glu Thr Leu Trp Arg Met Trp Cys Glu Ala Thr Gln
                35                 40                 45

Asp Trp Cys Leu Gly Val Pro Val Asp Ser Arg Gly Gln Pro Ala Glu
 50                 55                 60

Asp Gly Glu Phe Leu Leu Leu Ser Pro Val Gln Ala Ala Thr Trp Gly
 65                 70                 75                 80

Asn Tyr Tyr Ala Leu Gly Asp Ser Tyr Ser Gly Asp Gly Ala Arg
                85                 90                 95

Asp Tyr Tyr Pro Gly Thr Ala Val Lys Gly Gly Cys Trp Arg Ser Ala
                100                105                110

Asn Ala Tyr Pro Glu Leu Val Ala Glu Ala Tyr Asp Phe Ala Gly His
                115                120                125

Leu Ser Phe Leu Ala Cys Ser Gly Gln Arg Gly Tyr Ala Met Leu Asp
                130                135                140

Ala Ile Asp Glu Val Gly Ser Gln Leu Asp Trp Asn Ser Pro His Thr
145                 150                155                160

Ser Leu Val Thr Ile Gly Ile Gly Gly Asn Asp Leu Gly Phe Ser Thr
                165                170                175

Val Leu Lys Thr Cys Met Val Arg Val Pro Leu Leu Asp Ser Lys Ala
                180                185                190

Cys Thr Asp Gln Glu Asp Ala Ile Arg Lys Arg Met Ala Lys Phe Glu
                195                200                205

Thr Thr Phe Glu Glu Leu Ile Ser Glu Val Arg Thr Arg Ala Pro Asp
                210                215                220

Ala Arg Ile Leu Val Val Gly Tyr Pro Arg Ile Phe Pro Glu Glu Pro
225                 230                235                240

Thr Gly Ala Tyr Tyr Thr Leu Thr Ala Ser Asn Gln Arg Trp Leu Asn
                245                250                255

Glu Thr Ile Gln Glu Phe Asn Gln Gln Leu Ala Glu Ala Val Ala Val
                260                265                270

His Asp Glu Glu Ile Ala Ala Ser Gly Gly Val Gly Ser Val Glu Phe
                275                280                285

Val Asp Val Tyr His Ala Leu Asp Gly His Glu Ile Gly Ser Asp Glu
                290                295                300

Pro Trp Val Asn Gly Val Gln Leu Arg Asp Leu Ala Thr Gly Val Thr
305                 310                315                320

Val Asp Arg Ser Thr Phe His Pro Asn Ala Ala Gly His Arg Ala Val
                325                330                335

Gly Glu Arg Val Ile Glu Gln Ile Glu Thr Gly Pro Gly Arg Pro Leu
                340                345                350

Tyr Ala Thr Phe Ala Val Val Ala Gly Ala Thr Val Asp Thr Leu Ala
                355                360                365

Gly Glu Val Gly
                370

<210> SEQ ID NO 61
<211> LENGTH: 300
<212> TYPE: PRT
<213> ORGANISM: Corynebacterium efficiens

<400> SEQUENCE: 61
```

```
Met Arg Thr Thr Val Ile Ala Ala Ser Ala Leu Leu Leu Ala Gly
1               5                   10                  15

Cys Ala Asp Gly Ala Arg Glu Glu Thr Ala Gly Ala Pro Pro Gly Glu
                20                  25                  30

Ser Ser Gly Gly Ile Arg Glu Glu Gly Ala Glu Ala Ser Thr Ser Ile
            35                  40                  45

Thr Asp Val Tyr Ile Ala Leu Gly Asp Ser Tyr Ala Ala Met Gly Gly
    50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
            100                 105                 110

Thr Leu Pro Ala Gln Val Asp Ala Leu Thr Glu Asp Thr Thr Leu Val
    115                 120                 125

Thr Leu Ser Ile Gly Gly Asn Asp Leu Gly Phe Gly Glu Val Ala Gly
130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
            180                 185                 190

Val Val Val Thr Gly Tyr Leu Pro Leu Val Ser Ala Gly Asp Cys Pro
    195                 200                 205

Glu Leu Gly Asp Val Ser Glu Ala Asp Arg Arg Trp Ala Val Glu Leu
210                 215                 220

Thr Gly Gln Ile Asn Glu Thr Val Arg Glu Ala Ala Glu Arg His Asp
225                 230                 235                 240

Ala Leu Phe Val Leu Pro Asp Ala Asp Glu His Thr Ser Cys Ala
                245                 250                 255

Pro Pro Gln Gln Arg Trp Ala Asp Ile Gln Gly Gln Thr Asp Ala
            260                 265                 270

Tyr Pro Leu His Pro Thr Ser Ala Gly His Glu Ala Met Ala Ala Ala
    275                 280                 285

Val Arg Asp Ala Leu Gly Leu Glu Pro Val Gln Pro
290                 295                 300

<210> SEQ ID NO 62
<211> LENGTH: 3000
<212> TYPE: DNA
<213> ORGANISM: Corynebacterium efficiens

<400> SEQUENCE: 62
ttctggggtg ttatggggtt gttatcggct cgtcctgggt ggatcccgcc aggtggggta    60
ttcacggggg acttttgtgt ccaacagccg agaatgagtg ccctgagcgg tgggaatgag   120
gtgggcgggg ctgtgtcgcc atgagggggc ggcgggctct gtggtgcccc gcgaccccg   180 gccccggtga gcggtgaatg aaatccggct gtaatcagca tcccgtgccc acccgtcgg   240 ggaggtcagc gcccggagtg tctacgcagt cggatcctct cggactcggc catgctgtcg   300
gcagcatcgc gctcccgggt cttggcgtcc ctcggctgtt ctgcctgctg tccctggaag   360
gcgaaatgat caccggggag tgatacaccg gtggtctcat cccggatgcc cacttcggcg   420
```

```
ccatccggca attcgggcag ctccgggtgg aagtaggtgg catccgatgc gtcggtgacg        480
ccatagtggg cgaagatctc atcctgctcg agggtgctca ggccactctc cggatcgata        540
tcggggcgt  ccttgatggc gtccttgctg aaaccgaggt gcagcttgtg ggcttccaat        600
ttcgcaccac ggagcgggac gaggctggaa tgacggccga agagcccgtg gtggacctca        660
acgaaggtgg gtagtcccgt gtcatcattg aggaacacgc cctccaccgc acccagcttg        720
tggccggagt tgtcgtaggc gctggcatcc agaagggaaa cgatctcata tttgtcggtg        780
tgctcagaca tgatcttcct ttgctgtcgg tgtctggtac taccacggta gggctgaatg        840
caactgttat ttttctgtta ttttaggaat tggtccatat cccacaggct ggctgtggtc        900
aaatcgtcat caagtaatcc ctgtcacaca aatgggtgg tgggagccct ggtcgcggtt         960
ccgtggagg cgccgtgccc cgcaggatcg tcggcatcgg cggatctggc cggtaccccg        1020
cggtgaataa aatcattctg taaccttcat cacggttggt tttaggtatc cgccccttc        1080
gtcctgaccc cgtccccggc gcgcgggagc ccgcggttg cggtagacag gggagacgtg        1140
gacaccatga ggacaacggt catcgcagca agcgcattac tccttctcgc cggatgcgcg        1200
gatgggccc gggaggagac cgccggtgca ccgccgggtg agtcctccgg ggcatccgg         1260
gaggagggg cggaggcgtc gacaagcatc accgacgtct acatcgccct cggggattcc        1320
tatgcggcga tgggcgggcg ggatcagccg ttacggggtg agccgttctg cctgcgctcg        1380
tccggtaatt acccggaact cctccacgca gaggtcaccg atctcacctg ccaggggcg        1440
gtgaccgggg atctgctcga acccaggacg ctggggggagc gcacgctgcc ggcgcaggtg        1500
gatgcgctga cggaggacac caccctggtc accctctcca tcggggcaa tgacctcgga        1560
ttcggggagg tggcgggatg catccgggaa cggatcgccg gggagaacgc tgatgattgc        1620
gtggacctgc tgggggaaac catcggggag cagctcgatc agcttccccc gcagctggac        1680
cgcgtgcacg aggctatccg ggaccgcgcc gggacgcgc aggttgtggt caccggttac        1740
ctgccgctcg tgtctgccgg ggactgcccc gaactgggggg atgtctccga ggcggatcgt        1800
cgttgggcgg ttgagctgac cgggcagatc aacgagaccg tgcgcgaggc ggccgaacga        1860
cacgatgccc tctttgtcct gcccgacgat gccgatgagc acaccagttg tgcaccccca        1920
cagcagcgct gggcggatat ccagggccaa cagaccgatg cctatccgct gcacccgacc        1980
tccgccggcc atgaggcgat ggccgccgcc gtccgggacg cgctgggcct ggaaccggtc        2040
cagccgtagc gccgggcgcg cgcttgtcga cgaccaaccc atgccaggct gcagtcacat        2100
ccgcacatag cgcgcgcggg cgatggagta cgcaccatag aggatgagcc cgatgccgac        2160
gatgatgagc agcacactgc cgaagggttg ttccccgagg gtgcgcagag ccgagtccag        2220
acctgcggcc tgctccggat catgggccca accggcgatg acgatcaaca cccccaggat        2280
cccgaaggcg ataccacggg cgacataacc ggctgttccg gtgatgatga tcgcggtccc        2340
gacctgccct gaccccgcac ccgcctccag atcctcccgg aaatcccggg tggccccctt        2400
ccagaggttg tagacacccg cccccagtac caccagcccg gcgaccacaa ccagcaccac        2460
accccagggt tgggatagga cggtggcggt gacatcggtg gcggtctccc catcggaggt        2520
gctgccgccc cgggcgaagg tggaggtggt caccgccagg gagaagtaga ccatggccat        2580
gaccgccccc ttggccctt ccttgaggtc ctcgcccgcc agcagctggc tcaattgcca         2640
gagtcccagg gccgccaggg cgatgacggc aacccacagg aggaactgcc cacccggagc        2700
ctccgcgatg gtggccaggg cacctgaatt cgaggcctca tcacccgaac cgccggatcc        2760
agtggcgatg cgcaccgcga tccacccgat gaggatgtgc agtatgccca ggacaatgaa        2820
```

```
accacctctg gccagggtgg tcagcgcggg gtggtcctcg gcctggtcgg cagcccgttc     2880
gatcgtccgt ttcgcggatc tggtgtcgcc cttatccata gctcccattg aaccgccttg     2940
aggggtgggc ggccactgtc agggcggatt gtgatctgaa ctgtgatgtt ccatcaaccc     3000
```

<210> SEQ ID NO 63
<211> LENGTH: 284
<212> TYPE: PRT
<213> ORGANISM: Novosphingobium aromaticivorans

<400> SEQUENCE: 63

```
Met Gly Gln Val Lys Leu Phe Ala Arg Arg Cys Ala Pro Val Leu Leu
1               5                   10                  15

Ala Leu Ala Gly Leu Ala Pro Ala Ala Thr Val Ala Arg Glu Ala Pro
            20                  25                  30

Leu Ala Glu Gly Ala Arg Tyr Val Ala Leu Gly Ser Ser Phe Ala Ala
        35                  40                  45

Gly Pro Gly Val Gly Pro Asn Ala Pro Gly Ser Pro Glu Arg Cys Gly
    50                  55                  60

Arg Gly Thr Leu Asn Tyr Pro His Leu Leu Ala Glu Ala Leu Lys Leu
65                  70                  75                  80

Asp Leu Val Asp Ala Thr Cys Ser Gly Ala Thr Thr His Val Leu
                85                  90                  95

Gly Pro Trp Asn Glu Val Pro Pro Gln Ile Asp Ser Val Asn Gly Asp
            100                 105                 110

Thr Arg Leu Val Thr Leu Thr Ile Gly Gly Asn Asp Val Ser Phe Val
        115                 120                 125

Gly Asn Ile Phe Ala Ala Ala Cys Glu Lys Met Ala Ser Pro Asp Pro
    130                 135                 140

Arg Cys Gly Lys Trp Arg Glu Ile Thr Glu Glu Trp Gln Ala Asp
145                 150                 155                 160

Glu Glu Arg Met Arg Ser Ile Val Arg Gln Ile His Ala Arg Ala Pro
                165                 170                 175

Leu Ala Arg Val Val Val Val Asp Tyr Ile Thr Val Leu Pro Pro Ser
            180                 185                 190

Gly Thr Cys Ala Ala Met Ala Ile Ser Pro Asp Arg Leu Ala Gln Ser
        195                 200                 205

Arg Ser Ala Ala Lys Arg Leu Ala Arg Ile Thr Ala Arg Val Ala Arg
    210                 215                 220

Glu Glu Gly Ala Ser Leu Leu Lys Phe Ser His Ile Ser Arg Arg His
225                 230                 235                 240

His Pro Cys Ser Ala Lys Pro Trp Ser Asn Gly Leu Ser Ala Pro Ala
                245                 250                 255

Asp Asp Gly Ile Pro Val His Pro Asn Arg Leu Gly His Ala Glu Ala
            260                 265                 270

Ala Ala Ala Leu Val Lys Leu Val Lys Leu Met Lys
        275                 280
```

<210> SEQ ID NO 64
<211> LENGTH: 1500
<212> TYPE: DNA
<213> ORGANISM: Novosphingobium aromaticivorans

<400> SEQUENCE: 64

```
tgccggaact caagcggcgt ctagccgaac tcatgcccga aagcgcgtgg cactatcccg     60
```

```
aagaccaggt ctcggacgcc agcgagcgcc tgatggccgc cgaaatcacg cgcgaacagc    120
tctaccgcca gctccacgac gagctgccct atgacagtac cgtacgtccc gagaagtacc    180
tccatcgcaa ggacggttcg atcgagatcc accagcagat cgtgattgcc cgcgagacac    240
agcgtccgat cgtgctgggc aagggtggcg cgaagatcaa ggcgatcgga gaggccgcac    300
gcaaggaact ttcgcaattg ctcgacacca aggtgcacct gttcctgcat gtgaaggtcg    360
acgagcgctg ggccgacgcc aaggaaatct acgaggaaat cggcctcgaa tgggtcaagt    420
gaagctcttc gcgcgccgct gcgccccagt acttctcgcc cttgccgggc tggctccggc    480
ggctacggtc gcgcgggaag caccgctggc cgaaggcgcg cgttacgttg cgctgggaag    540
ctccttcgcc gcaggtccgg gcgtgggccc caacgcgccc ggatcgcccg aacgctgcgg    600
ccggggcacg ctcaactacc cgcacctgct cgccgaggcg ctcaagctcg atctcgtcga    660
tgcgacctgc agcggcgcga cgacccacca cgtgctgggc ccctggaacg aggttccccc    720
tcagatcgac agcgtgaatg cgacacccg cctcgtcacc ctgaccatcg gcggaaacga    780
tgtgtcgttc gtcggcaaca tcttcgccgc cgcttgcgag aagatggcgt cgcccgatcc    840
gcgctgcggc aagtggcggg agatcaccga ggaagagtgg caggccgacg aggagcggat    900
gcgctccatc gtacgccaga tccacgcccg cgcgcctctc gcccgggtgg tggtggtcga    960
ttacatcacg gtcctgccgc catcaggcac ttgcgctgcc atggcgattt cgccggaccg   1020
gctggcccag agccgcagcg ccgcgaaacg gcttgcccgg attaccgcac gggtcgcgcg   1080
agaagagggt gcatcgctgc tcaagttctc gcatatctcg cgccggcacc atccatgctc   1140
tgccaagccc tggagcaacg gcctttccgc cccggccgac gacggcatcc cggtccatcc   1200
gaaccggctc ggacatgctg aagcggcagc ggcgctggtc aagcttgtga aattgatgaa   1260
gtagctactg cactgatttc aaatagtatt gcctgtcagc tttccagccc ggattgttgc   1320
agcgcaacag aaacttgtcc gtaatggatt gatggtttat gtcgctcgca aattgccgtc   1380
gaagggaacg ggcgcgtcgc tcgttaacgt cctgggtgca gcagtgacgg agcgcgtgga   1440
tgagtgatac tggcggtgtc atcggtgtac gcgccgccat tcccatgcct gtacgcgccg   1500
```

<210> SEQ ID NO 65
<211> LENGTH: 268
<212> TYPE: PRT
<213> ORGANISM: Streptomyces coelicolor

<400> SEQUENCE: 65

```
Met Arg Arg Phe Arg Leu Val Gly Phe Leu Ser Ser Leu Val Leu Ala
1               5                   10                  15

Ala Gly Ala Ala Leu Thr Gly Ala Ala Thr Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala His Ser Pro Ser Thr
65                  70                  75                  80

Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
        115                 120                 125
```

```
Leu Gln Ser Glu Ser Ser Cys Leu Ser Arg Ile Ala Thr Ala Glu Ala
    130                 135                 140
Tyr Val Asp Ser Thr Leu Pro Gly Lys Leu Asp Gly Val Tyr Ser Ala
145                 150                 155                 160
Ile Ser Asp Lys Ala Pro Asn Ala His Val Val Ile Gly Tyr Pro
                165                 170                 175
Arg Phe Tyr Lys Leu Gly Thr Cys Ile Gly Leu Ser Glu Thr Lys
                180                 185                 190
Arg Thr Ala Ile Asn Lys Ala Ser Asp His Leu Asn Thr Val Leu Ala
                195                 200                 205
Gln Arg Ala Ala Ala His Gly Phe Thr Phe Gly Asp Val Arg Thr Thr
    210                 215                 220
Phe Thr Gly His Glu Leu Cys Ser Gly Ser Pro Trp Leu His Ser Val
225                 230                 235                 240
Asn Trp Leu Asn Ile Gly Glu Ser Tyr His Pro Thr Ala Ala Gly Gln
                245                 250                 255
Ser Gly Gly Tyr Leu Pro Val Leu Asn Gly Ala Ala
                260                 265
```

<210> SEQ ID NO 66
<211> LENGTH: 2000
<212> TYPE: DNA
<213> ORGANISM: Streptomyces coelicolor

<400> SEQUENCE: 66

```
cccggcggcc cgtgcaggag cagcagccgg cccgcgatgt cctcgggcgt cgtcttcatc      60
aggccgtcca tcgcgtcggc gaccggcgcc gtgtagttgg cccggacctc gtcccaggtg     120
cccgcggcga tctggcgggt ggtgcggtgc gggccgcgcc gaggggagac gtaccagaag     180
cccatcgtca cgttctccgg ctgcggttcg ggctcgtccg ccgctccgtc cgtcgcctcg     240
ccgagcacct tctcggcgag gtcggcgctg gtcgccgtca ccgtgacgtc ggcgccccgg     300
ctccagcgcg agatcagcag cgtccagccg tcgccctccg ccagcgtcgc gctgcggtcg     360
tcgtcgcggg cgatccgcag cacgcgcgcg ccgggcggca gcagcgtggc gccggaccgt     420
acgcggtcga tgttcgccgc gtgcgagtac ggctgctcac ccgtggcgaa acggccgagg     480
aacagcgcgt cgacgacgtc ggacggggag tcgctgtcgt ccacgttgag ccggatcggc     540
agggcttcgt gcgggttcac ggacatgtcg ccatgatcgg gcaccggcc gccgcgtgca     600
cccgctttcc cgggcacgca cgacagggggc tttctcgccg tcttccgtcc gaacttgaac     660
gagtgtcagc catttcttgg catggacact tccagtcaac gcgcgtagct gctaccacgg     720
ttgtggcagc aatcctgcta agggaggttc catgagacgt ttccgacttg tcggcttcct     780
gagttcgctc gtcctcgccc ccggcgccgc cctcaccggg gcagcgaccg cccaggcggc     840
ccaacccgcc gccgccgacg gctatgtggc cctcggcgac tcctactcct ccggggtcgg     900
agcgggcagc tacatcagct cgagcggcga ctgcaagcgc agcacgaagg cccatcccta     960
cctgtgggcg gccgcccact cgccctccac gttcgacttc accgcctgtt ccggcgcccg    1020
tacgggtgat gttctctccg gacagctcgg cccgctcagc tccggcaccg gcctcgtctc    1080
gatcagcatc ggcggcaacg acgccggttt cgccgacacc atgacgacct gtgtgctcca    1140
gtccgagagc tcctgcctgt cgcggatcgc caccgccgag gcgtacgtcg actcgacgct    1200
gcccggcaag ctcgacggcg tctactcggc aatcagcgac aaggcgccga acgcccacgt    1260
cgtcgtcatc ggctacccgc gcttctacaa gctcggcacc acctgcatcg gcctgtccga    1320
```

```
gaccaagcgg acggcgatca acaaggcctc cgaccacctc aacaccgtcc tcgcccagcg   1380
cgccgccgcc cacggcttca ccttcggcga cgtacgcacc accttcaccg gccacgagct   1440
gtgctccggc agcccctggc tgcacagcgt caactggctg aacatcggcg agtcgtacca   1500
ccccaccgcg gccggccagt ccggtggcta cctgccggtc ctcaacggcg ccgcctgacc   1560
tcaggcggaa ggagaagaag aaggagcgga gggagacgag gagtgggagg ccccgcccga   1620
cggggtcccc gtccccgtct ccgtctccgt cccggtcccg caagtcaccg agaacgccac   1680
cgcgtcggac gtggcccgca ccggactccg cacctccacg cgcacggcac tctcgaacgc   1740
gccggtgtcg tcgtgcgtcg tcaccaccac gccgtcctgg cgcgagcgct cgccgcccga   1800
cgggaaggac agcgtccgcc accccggatc ggagaccgac ccgtccgcgg tcacccaccg   1860
gtagccgacc tccgcgggca gccgcccgac cgtgaacgtc gccgtgaacg cgggtgcccg   1920
gtcgtgcggc ggcggacagg cccccgagta gtgggtgcgc gagcccacca cggtcacctc   1980
caccgactgc gctgcggggc                                               2000
```

<210> SEQ ID NO 67
<211> LENGTH: 269
<212> TYPE: PRT
<213> ORGANISM: Streptomyces avermitilis

<400> SEQUENCE: 67

```
Met Arg Arg Ser Arg Ile Thr Ala Tyr Val Thr Ser Leu Leu Leu Ala
1               5                   10                  15

Val Gly Cys Ala Leu Thr Gly Ala Ala Thr Ala Gln Ala Ser Pro Ala
            20                  25                  30

Ala Ala Ala Thr Gly Tyr Val Ala Leu Gly Asp Ser Tyr Ser Ser Gly
        35                  40                  45

Val Gly Ala Gly Ser Tyr Leu Ser Ser Ser Gly Asp Cys Lys Arg Ser
    50                  55                  60

Ser Lys Ala Tyr Pro Tyr Leu Trp Gln Ala Ala His Ser Pro Ser Ser
65                  70                  75                  80

Phe Ser Phe Met Ala Cys Ser Gly Ala Arg Thr Gly Asp Val Leu Ala
                85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
        115                 120                 125

Leu Gln Ser Asp Ser Ala Cys Leu Ser Arg Ile Asn Thr Ala Lys Ala
    130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
            180                 185                 190

Lys Arg Ser Ala Ile Asn Asp Ala Asp Tyr Leu Asn Ser Ala Ile
        195                 200                 205

Ala Lys Arg Ala Ala Asp His Gly Phe Thr Phe Gly Asp Val Lys Ser
    210                 215                 220

Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
```

```
                    245                 250                 255
Gln Ser Gly Gly Tyr Leu Pro Val Met Asn Ser Val Ala
            260                 265

<210> SEQ ID NO 68
<211> LENGTH: 1980
<212> TYPE: DNA
<213> ORGANISM: Streptomyces avermitilis

<400> SEQUENCE: 68
ccaccgccgg gtcggcggcg agtctcctgg cctcggtcgc ggagaggttg gccgtgtagc      60
cgttcagcgc ggcgccgaac gtcttcttca ccgtgccgcc gtactcgttg atcaggccct     120
tgcccttgct cgacgcggcc ttgaagccgg tgcccttctt gagcgtgacg atgtagctgc     180
ccttgatcgc ggtgggggag ccggcggcga gcaccgtgcc ctcgccgggg gtggcctggg     240
cgggcagtgc ggtgaatccg cccacgaggg cgccggtcgc cacggcggtt atcgcggcga     300
tccggatctt cttgctacgc agctgtgcca tacgagggag tcctcctctg ggcagcggcg     360
cgcctgggtg gggcgcacgg ctgtgggggg tgcgcgcgtc atcacgcaca cggccctgga     420
gcgtcgtgtt ccgccctggg ttgagtaaag cctcggccat ctacggggt ggctcaaggg     480 agttgagacc ctgtcatgag tctgacatga gcacgcaatc aacggggccg tgagcacccc     540
ggggcgaccc cggaaagtgc cgagaagtct tggcatggac acttcctgtc aacacgcgta     600
gctggtacga cggttacggc agagatcctg ctaaagggag gttccatgag acgttcccga     660
attacggcat acgtgacctc actcctcctc gccgtcggct gcgccctcac cggggcagcg     720
acggcgcagg cgtccccagc cgccgcggcc acgggctatg tggccctcgg cgactcgtac     780
tcgtccggtg tcggcgccgg cagctacctc agctccagcg gcgactgcaa gcgcagttcg     840
aaggcctatc cgtacctctg gcaggccgcg cattcaccct cgtcgttcag tttcatggct     900
tgctcgggcg ctcgtacggg tgatgtcctg gccaatcagc tcggcaccct gaactcgtcc     960
accggcctgg tctccctcac catcggaggc aacgacgcgg gcttctccga cgtcatgacg    1020
acctgtgtgc tccagtccga cagcgcctgc ctctcccgca tcaacacggc gaaggcgtac    1080
gtcgactcca ccctgcccgg ccaactcgac agcgtgtaca cggcgatcag cacgaaggcc    1140
ccgtcggccc atgtggccgt gctgggctac ccccgcttct acaaactggg cggctcctgc    1200
ctcgcgggcc tctcggagac caagcggtcc gccatcaacg acgcggccga ctatctgaac    1260
agcgccatcg ccaagcgcgc cgccgaccac ggcttcacct cggcgacgt caagagcacc    1320 ttcaccggcc atgagatctg ctccagcagc acctggctgc acagtctcga cctgctgaac    1380
atcggccagt cctaccaccc gaccgcggcc ggccagtccg gcggctatct gccggtcatg    1440
aacagcgtgg cctgagctcc cacggcctga attttaagg cctgaatttt taaggcgaag    1500
gtgaaccgga agcggaggcc ccgtccgtcg gggtctccgt cgcacaggtc accgagaacg    1560
gcacggagtt ggacgtcgtg cgcaccgggt cgcgcacctc gacggcgatc tcgttcgaga    1620
tcgttccgct cgtgtcgtac gtggtgacga cacctgcttc tgctgggtc tttccgccgc    1680 tcgccgggaa ggacagcgtc ttccagcccg gatccgggac ctcgcccttc ttggtcaccc    1740
agcggtactc cacctcgacc ggcacccggc ccaccgtgaa ggtcgccgtg aacgtgggcg    1800
cctgggcggt gggcggcggg caggcaccgg agtagtcggg gtgcacgccg gtgaccgtca    1860
ccttcacgga ctgggccggc ggggtcgtcg taccgccgcc gccaccgccg cctcccggag    1920
tggagcccga gctgtggtcg cccccgccgt cggcgttgtc gtcctcgggg gttttcgaac    1980
```

<210> SEQ ID NO 69
<211> LENGTH: 1371
<212> TYPE: DNA
<213> ORGANISM: Streptomyces spp

<400> SEQUENCE: 69

```
acaggccgat gcacggaacc gtacctttcc gcagtgaagc gctctccccc catcgttcgc    60
cgggacttca tccgcgattt tggcatgaac acttccttca acgcgcgtag cttgctacaa   120
gtgcggcagc agacccgctc gttggaggct cagtgagatt gacccgatcc ctgtcggccg   180
catccgtcat cgtcttcgcc ctgctgctcg cgctgctggg catcagcccg gcccaggcag   240
ccggcccggc ctatgtggcc ctgggggatt cctattcctc gggcaacggc gccggaagtt   300
acatcgattc gagcggtgac tgtcaccgca gcaacaacgc gtaccccgcc cgctgggcgg   360
cggccaacgc accgtcctcc ttcaccttcg cggcctgctc gggagcggtg accacggatg   420
tgatcaacaa tcagctgggc ccctcaacga cgtccaccgg cctggtgagc atcaccatcg   480
gcggcaatga cgcgggcttc gcggacgcga tgaccacctg cgtcaccagc tcggacagca   540
cctgcctcaa ccgctggcc accgccacca actacatcaa caccaccctg ctcgcccggc   600
tcgacgcggt ctacagccag atcaaggccc gtgcccccaa cgcccgcgtg gtcgtcctcg   660
gctaccgcg catgtacctg gcctcgaacc cctggtactg cctgggcctg agcaacacca   720
agcgcgcggc catcaacacc accgccgaca ccctcaactc ggtgatctcc tcccgggcca   780
ccgcccacgg attccgattc ggcgatgtcc gcccgaccct caacaaccac gaactgttct   840
tcggcaacga ctggctgcac tcactcaccc tgccggtgtg ggagtcgtac caccccacca   900
gcacgggcca tcagagcggc tatctgccgg tcctcaacgc caacagctcg acctgatcaa   960
cgcacggccg tgcccgcccc gcgcgtcacg ctcggcgcgg gcgccgcagc gcgttgatca  1020
gcccacagtg ccggtgacgg tcccaccgtc acggtcgagg gtgtacgtca cggtggcgcc  1080
gctccagaag tggaacgtca gcaggaccgt ggagccgtcc ctgacctcgt cgaagaactc  1140
cggggtcagc gtgatcaccc ctcccccgta gccgggggcg aaggcggcgc cgaactcctt  1200
gtaggacgtc cagtcgtgcg gcccggcgtt gccaccgtcc gcgtagaccg cttccatggt  1260
cgccagccgg tccccgcgga actcggtggg gatgtccgtg cccaaggtgg tcccggtggt  1320
gtccgagagc accgggggct cgtaccggat gatgtgcaga tccaaagaat t            1371
```

<210> SEQ ID NO 70
<211> LENGTH: 267
<212> TYPE: PRT
<213> ORGANISM: Streptomyces spp

<400> SEQUENCE: 70

```
Met Arg Leu Thr Arg Ser Leu Ser Ala Ala Ser Val Ile Val Phe Ala
1               5                  10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95
```

```
Ala Leu Asn Ala Ser Thr Gly Leu Val Ser Ile Thr Ile Gly Gly Asn
                100                 105                 110

Asp Ala Gly Phe Ala Asp Ala Met Thr Thr Cys Val Thr Ser Ser Asp
            115                 120                 125

Ser Thr Cys Leu Asn Arg Leu Ala Thr Ala Thr Asn Tyr Ile Asn Thr
        130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
    210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
                260                 265

<210> SEQ ID NO 71
<211> LENGTH: 8
<212> TYPE: PRT
<213> ORGANISM: Artificial
<220> FEATURE:
<223> OTHER INFORMATION: Block 1 - GDSX block
<220> FEATURE:
<221> NAME/KEY: VARIANT
<222> LOCATION: (1)..(4)
<223> OTHER INFORMATION: Xaa is a hydrophobic residue selected from Met,
      Ile, Leu, Val, Ala, Gly, Cys, His, Lys, Trp, Tyr or Phe
<220> FEATURE:
<221> NAME/KEY: VARIANT
<222> LOCATION: (8)..(8)
<223> OTHER INFORMATION: Xaa is a hydrophobic residue selected from Met,
      Ile, Leu, Val, Ala, Gly, Cys, His, Lys, Trp, Tyr or Phe

<400> SEQUENCE: 71

Xaa Xaa Xaa Xaa Gly Asp Ser Xaa
1               5

<210> SEQ ID NO 72
<211> LENGTH: 6
<212> TYPE: PRT
<213> ORGANISM: Artificial
<220> FEATURE:
<223> OTHER INFORMATION: Block 2 - GANDY block
<220> FEATURE:
<221> NAME/KEY: VARIANT
<222> LOCATION: (1)..(1)
<223> OTHER INFORMATION: Xaa is a hydrophobic residue selected from Met,
      Ile, Leu, Val, Ala, Gly, Cys, His, Lys, Trp, Tyr or Phe
<220> FEATURE:
<221> NAME/KEY: VARIANT
<222> LOCATION: (3)..(3)
<223> OTHER INFORMATION: Xaa is a hydrophobic residue selected from Met,
      Ile, Leu, Val, Ala, Gly, Cys, His, Lys, Trp, Tyr or Phe
<220> FEATURE:
<221> NAME/KEY: VARIANT
<222> LOCATION: (6)..(6)
<223> OTHER INFORMATION: Xaa is a hydrophobic residue selected from Met,
      Ile, Leu, Val, Ala, Gly, Cys, His, Lys, Trp, Tyr or Phe
```

```
<400> SEQUENCE: 72

Xaa Gly Xaa Asn Asp Xaa
1               5

<210> SEQ ID NO 73
<211> LENGTH: 4
<212> TYPE: PRT
<213> ORGANISM: Artificial
<220> FEATURE:
<223> OTHER INFORMATION: Sequence motif
<220> FEATURE:
<221> NAME/KEY: VARIANT
<222> LOCATION: (4)..(4)
<223> OTHER INFORMATION: Xaa may be one or more of the following amino
      acid residues Leu, Ala, Val, Ile, Phe, Tyr, His, Gln, Thr, Asn,
      Met or Ser.

<400> SEQUENCE: 73

Gly Asp Ser Xaa
1
```

US 7,718,408 B2

METHOD

REFERENCE TO RELATED APPLICATIONS

This application claims priority to International Patent Application No. PCT/IB04/000655 filed Jan. 15, 2004 and published as WO 2004/064537, which claims priority to Great Britain Patent Application No. GB 0330016.7 filed Dec. 24, 2003. This application also claims priority to Great Britain Patent Application No. GB 0416023.0 filed Jul. 16, 2004. Each of these applications, and each application and patent mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference.

Furthermore, all documents cited in this text, and all documents cited or referenced in documents cited in this text, and any manufacturer's instructions or catalogues for any products cited or mentioned in this text, are hereby incorporated herein by reference.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

FIELD OF INVENTION

The present invention relates to a novel method for the enzymatic removal and/or reduction of diglyceride (preferably 1,2-diacylglyceride) from an edible oil.

TECHNICAL BACKGROUND

Oils and fats consist of complex mixtures of triacylglycerols (TAGs), diacylglycerols (DAGs), free fatty acids and other minor components. The crystallisation of these mixtures depends on the characteristics of the TAGs (structure, chain length, saturation compared with unsaturation, and the like) and the interaction of these TAGs with each other. Regarding the presence of DAGs, previous studies have shown that they have significant effect on the physical properties of oils and fats. These vary from rate of crystallisation, polymorphism changes, melting point, crystal size and habits (Siew, 2001).

In most oils that are extracted from oilseeds, the effect of DAGs is less pronounced, as DAGs are only present in small quantities. In primarily palm oil and olive oil, which are oils containing high natural amounts of DAGs, however, the quality of these oils suffers if DAGs are present therein.

Palm oil obtained from oil palm (*Elaeis guineensis*) is commercially important edible oil. Palm oil has been a prominent fat and oil resource for the food industry due to several advantageous properties, such as high productivity, low price, high thermal and oxidative stability and plasticity at room temperature. In addition, compared with other vegetable oils, palm oil is a rich source of the anti-oxidant vitamin E.

A typical chemical composition of refined palm oil is about 93% triglycerides, 6% diglycerides and 1% monoglycerides (MAGs) (Okiy, 1977).

When palm oil crystallizes, a complex 3-dimensional network of the present components is formed. In the theory it is described that the bigger the diversity of the building blocks (TAGs, DAGs and MAGs) in the network, the more complicated the network will be and the slower the crystallization will happen (Jacobsberg & Ho, 1976). This theory was confirmed by Drozdowski (1994). Furthermore, his studies showed that the more the fatty acid composition variation in the triacylglycerol molecule, the more difficult was the transition between the different crystal phases.

As previously mentioned, a high content of diglycerides in palm oil affects its crystallization properties (Okiy et al., 1978, Okiy, 1978).

The presence of diglycerides in such oils is disadvantageous. In particular, diglycerides in edible oils (in particular palm oil) can lead to a low quality oil.

The problems relating to the diglyceride content in palm oil and other edible oils and fat have been the subject of many studies and different solutions to attempt to overcome the problem of too much diglyceride can be found in the literature.

The Japanese enzyme producer Amano on their home page (Amano Enzyme Inc., 2004), recommend an enzymatic process to remove diglyceride in fats and oils. This process is based on the use of an enzyme LIPASE G "AMANO" 50 which is able to degrade diglycerides to free fatty acids and glycerol. This enzyme is a diglyceride (DAG) and/or monoglyceride (MAG) hydrolyzing. The free fatty acids produced are removed by vacuum distillation or fractional crystallisation.

EP 0 558 112 describes a process for the enzymatic hydrolysis of residual diglycerides in triglyceride preparations in emulsions. The process is based on the hydrolysis of diglyceride with Lipase G from Amano, Japan (supra). The process was enhanced by making the enzymatic reaction in an emulsion for the degradation of diglyceride to fatty acids and glycerol. The water phase is separated after reaction and the enzyme is partly reused.

JP 62061590 teaches a hard butter containing low amounts of diglyceride, which is manufactured by treating oils or fats with a partially glyceride-specific enzyme (e.g., a lipase) in the presence of a catalytic amount of water and by a lipase that is a 1,3-specific enzyme in the presence of fatty acids, fatty acid esters, or other glyceride oils or fats. The product is hard butter especially suitable for use as a cacao butter substitute. Thus, lipase G and *Rhizopus deremer* lipase (1,3-specific enzyme) were mixed with diatomaceous earth and granulated. The granules was mixed with palm medium melting point fraction (5.7% diglyceride, acid value 0.25) and water (10% with regard to the partial glyceride-specific enzyme). The mixture was stirred at room temp. for 1 h, and the enzymes and water removed to give a hard butter containing 1.2% diglyceride (acid value 10.5).

The prior art thus teaches ways to reduce or remove the content of diglyceride in palm oil and other edible oils by enzymatic reactions. These processes rely on the hydrolysis of diglyceride with a specific diglyceride hydrolysing lipase during formation of free fatty acids and glycerol. The free fatty acids can then be removed by means of different processes like vacuum distillation or fractionation.

The disadvantage of using a specific diglyceride hydrolysing enzyme is the disadvantageous formation of free fatty acids. These free fatty acids have to be removed from the palm oil. Thus, the formation of free fatty acids is often considered as loss of product.

To overcome the problems with the removal of free fatty acid and the loss of product caused by the free fatty acid formation we have found a new method to overcome the problems with high diglyceride content in palm oil and other vegetable oils.

Enzymatic removal of diglycerides from palm oil has been taught by use of lipases, which are typically 1,3 specific triacylglycerol hydrolyzing enzymes (E.C. 3.1.1.3) (for example see JP 62061590 or EP 0 652 289). WO00/05396 teaches inter alia treatment of a food material which may comprise glycerol with a lipase to effect glycerolysis in a low water environment.

However, both 1,3 specific triacylglycerol hydrolyzing enzymes (lipases) and DAG/MAG hydrolyzing enzymes result in a significant increase in free fatty acid in the oil, and also result in the hydrolysis of monoglycerides.

However, in some vegetable oils for some applications for example it may be desirable to increase the monoglyceride content of the oil as this provides emulsifier functionality. Thus, in one aspect it is preferable to reduce diglyceride content without decreasing the monoglyceride content. In another aspects it may preferably to reduce both the diglyceride and monoglyceride content.

Lipase enzymes can also result in a detrimental increase in DAG due to the hydrolysis of triacylglycerol (TAG), the bulk lipid present in food oils.

SUMMARY OF THE INVENTION

It has been found that the use of lipid acyltransferases as defined herein, specifically diglyceride:glycerol acyltransferases, results in the selective reduction and/or removal of diglycerides (preferably 1,2-diglycerides) from edible oils.

The term "selective" as used herein means that in an edible oil environment the enzyme utilizes diglycerides (DAGs), preferably 1,2-diglycerides, as a substrate preferentially to either triacylglycerides (TAGs) or monoglycerides (MAGs). Thus, diglycerides can be removed and/or reduced from the edible oil whilst leaving the amount of triglyceride in the oil unchanged (or substantially unchanged). The amount of monoglycerides in the oil either remains unchanged (or substantially unchanged) or may increase. In some applications, the amount of monoglyceride in the oil may be reduced.

In one aspect of the present invention there is provided a method of reducing and/or removing diglyceride from a foodstuff, comprising a) admixing a foodstuff or a portion thereof with an acyl acceptor substrate and a diglyceride:glycerol acyltransferase, wherein the diglyceride:glycerol acyltransferase is characterized as an enzyme which in an edible oil can transfer an acyl group from a diglyceride to glycerol.

In a further aspect of the present invention there is provided a method of reducing and/or removing diglyceride from an edible oil, comprising a) admixing an edible oil with an acyl acceptor substrate and a diglyceride:glycerol acyltransferase, wherein the diglyceride:glycerol acyltransferase is characterized as an enzyme which in an edible oil can transfer an acyl group from a diglyceride to glycerol.

The present invention yet further provides the use of a diglyceride:glycerol acyltransferase characterized as an enzyme which in an edible oil can transfer an acyl group from a diglyceride to glycerol, in the manufacture of a foodstuff, for reducing and/or removing (preferably selectively reducing and/or removing) diglyceride from said foodstuff.

In another aspect the present invention provides the use of a diglyceride:glycerol acyltransferase characterized as an enzyme which in an edible oil can transfer an acyl group from a diglyceride to glycerol, in the manufacture of an edible oil, for reducing and/or removing (preferably selectively reducing and/or removing) diglyceride from said edible oil.

DETAILED DISCLOSURE OF INVENTION

The terms "lipid acyltransferase" and "diglyceride:glycerol acyltransferase" as used herein means an enzyme which has acyltransferase activity (generally classified as E.C. 2.3.1.x in accordance with the Enzyme Nomenclature Recommendations (1992) of the Nomenclature Committee of the International Union of Biochemistry and Molecular Biology), whereby the enzyme is capable of transferring an acyl group from a diglyceride to one or more acceptor substrates).

As well as having acyltransferase activity the enzyme may have lipase activity, e.g. phospholipase activity, (generally classified as E.C. 3.1.1.x).

The lipid acyltransferase in accordance with the present invention is a diglyceride:glycerol acyltransferase. These terms may be used interchangeably herein.

Preferably the diglyceride:glycerol acyltransferase according to the present invention is an acyltransferase which comprises the amino acid sequence motif GDSX, wherein X is one or more of the following amino acid residues L, A, V, I, F, Y, H, Q, T, N, M or S.

The edible oil used in a process or use according to the present invention may be in the form of a crude oil or may be a refined oil.

In one embodiment, preferably the amount of diglyceride is reduced rather than completely removed.

The term "reduced" as used herein means that the amount of diglyceride in an edible oil treated with the enzyme in accordance with the present invention is less than the amount of diglyceride in the edible oil before enzyme treatment.

Preferably, diglycerides are not completely removed from the edible oil.

In some applications, such as in margarines and/or shortening, the amount of diglycerides, particularly 1,2 diglycerides, should be reduced to a point where the crystallisation speed of the fat blend produces small beta-crystals. The amount of 1,2-diglyceride to the amount of total diglyceride in the palm oil depends on the age and storage conditions of the oil. For commercial oils the ratio of 1,3 diglyceride:1,2 diglyceride is 1.8:3.3. The removal of 1,2 diglycerides will have the most impact on the crystallisation properties.

As will be readily apparent to the skilled person the reduction in the amount of diglyceride can be controlled by the reaction time and temperature of the reaction. In a flow reactor with an immobilised enzyme the reaction may be controlled by the flow rate.

Preferably, the lipid acyltransferase for use in the methods and/or uses of the present invention is capable of transferring an acyl group from a diglyceride to an acyl acceptor, wherein the acyl acceptor is any compound comprising a hydroxy group (—OH).

Suitably, the term "diglyceride" as used herein means one or more of 1,2-diglyceride or 1,3-diglyceride. Preferably, the diglyceride is a 1,2-diglyceride.

The terms "diglyceride" and "diacylglycerol" are used herein interchangeably.

The term "diglyceride" does not encompass digalactosyldiglyceride (DGDG) and/or lecithin, e.g. phosphatidylcholine.

Preferably the acyl acceptor is one which is soluble in an edible oil.

Suitably, the acyl acceptor may be an alcohol such as for example ethanol or polyvalent alcohols, including glycerol and mixtures and derivatives thereof. Suitably, the acyl acceptor may be one or more of a sterol, a stanol, a hydroxy acid, sorbitol, sorbitan or other carbohydrate.

In one preferred embodiment the acyl acceptor is glycerol.

Thus, in one embodiment the present invention provides a method of reducing and/or removing diglyceride from an edible oil, comprising a) admixing an edible oil with both glycerol and a diglyceride:glycerol acyltransferase, wherein the diglyceride:glycerol acyltransferase is characterized as an enzyme which possesses acyl transferase activity and which comprises the amino acid sequence motif GDSX, wherein X is one or more of the following amino acid residues L, A, V, I, F, Y, H, Q, T, N, M or S.

Preferably, the acyl acceptor according to the present invention is not water.

Preferably the acyl acceptor is not a monoglyceride and/or a diglyceride.

Preferably, the lipid acyltransferase according to the present invention is capable of cleaving the acyl bond between a fatty acid residue(s) and a glycerol backbone of a lipid substrate, wherein preferably the lipid substrate is a diglyceride, preferably 1,2-diglyceride.

Preferably, the lipid acyltransferase according to the present invention does not act on triglycerides and/or monoglycerides. In other words, preferably the lipid acyltransferase is selective for diglycerides, preferably selective for 1,2-diglycerides. This lipid substrate may be referred to herein as the "lipid acyl donor".

Thus in accordance with the present invention, one or more of the following advantageous properties can be achieved: reduction in diglyceride content of an edible oil; a reduction in the diglyceride content of an edible oil without a reduction in the triglyceride content of the edible oil; a reduction in the diglyceride content of the edible oil without an increase in the monoglyceride content; a reduction in the diglyceride content of the edible oil with an increase in the monoglyceride content; a reduction of diglyceride and a reduction in monoglyceride content of an edible oil; a reduction in the diglyceride content of the edible oil without a significant increase in the fatty acid content in the edible oil.

Preferably, the lipid acyltransferase in accordance with the present invention performs an alcoholysis reaction (preferably glycerolysis) by transferring a fatty acid acyl group from the diglyceride (preferably the 1,2-DAG) to an alcohol (preferably glycerol) thereby producing two monoglyceride molecules, i.e. one from the diglyceride and one from the glycerol together with the accepted acyl group.

Preferably, X of the GDSX motif is L. Thus, preferably the enzyme according to the present invention comprises the amino acid sequence motif GSDL (SEQ ID NO: 71).

The GDSX motif is comprised of four conserved amino acids. Preferably, the serine within the motif is a catalytic serine of the lipid acyltransferase enzyme. Suitably, the serine of the GDSX motif may be in a position corresponding to Ser-16 in *Aeromonas hydrophila* lipolytic enzyme taught in Brumlik & Buckley (Journal of Bacteriology April 1996, Vol. 178, No. 7, p 2060-2064).

To determine if a protein has the GDSX motif according to the present invention, the sequence is preferably compared with the hidden markov model profiles (HMM profiles) of the pfam database.

Pfam is a database of protein domain families. Pfam contains curated multiple sequence alignments for each family as well as profile hidden Markov models (profile HMMs) for identifying these domains in new sequences. An introduction to Pfam can be found in Bateman A et al. (2002) Nucleic Acids Res. 30; 276-280. Hidden Markov models are used in a number of databases that aim at classifying proteins, for review see Bateman A and Haft DH (2002) Brief Bioinform 3; 236-245 (abstracts available from National Center for Biotechnology Information website maintained in conjunction with the National Library of Medicine and the National Institutes of Health).

For a detailed explanation of hidden Markov models and how they are applied in the Pfam database see Durbin R, Eddy S, and Krogh A (1998) Biological sequence analysis; probabilistic models of proteins and nucleic acids. Cambridge University Press, ISBN 0-521-62041-4. The Hammer software package can be obtained from Washington University, St Louis, USA.

Alternatively, the GDSX motif can be identified using the Hammer software package, the instructions are provided in Durbin R, Eddy S, and Krogh A (1998) Biological sequence analysis; probabilistic models of proteins and nucleic acids. Cambridge University Press, ISBN 0-521-62041-4 and the references therein, and the HMMER2 profile provided within this specification.

The PFAM database can be accessed, for example, through several websites maintained by the Sanger Institute (UK) in conjunction with Wellcome Trust Institute, the Institut National de la Recherche Agronomique, and the Center for Genomics and Bioinformatics of the Karolinska Institutet, among others.

The database offers a search facility where one can enter a protein sequence. Using the default parameters of the database the protein sequence will then be analysed for the presence of Pfam domains. The GDSX domain is an established domain in the database and as such its presence in any query sequence will be recognised. The database will return the alignment of the Pfam00657 consensus sequence to the query sequence.

A multiple alignment, including *Aeromonas salmonicida* or *Aeromonas hydrophila* can be obtained by:
  a) manual
    obtain an alignment of the protein of interest with the Pfam00657 consensus sequence and obtain an alignment of P10480 with the Pfam00657 consensus sequence following the procedure described above;
    or
  through the database
    After identification of the Pfam00657 consensus sequence the database offers the option to show an alignment of the query sequence to the seed alignment of the Pfam00657 consensus sequence. P10480 is part of this seed alignment and is indicated by GCAT_AERHY. Both the query sequence and P10480 will be displayed in the same window.

The *Aeromonas hydrophila* Reference Sequence:

The residues of *Aeromonas hydrophila* GDSX lipase are numbered in the NCBI file P10480, the numbers in this text refer to the numbers given in that file which in the present invention is used to determine specific amino acids residues which, in a preferred embodiment are present in the lipid acyltransferase enzymes of the invention.

The Pfam Alignment was Performed (FIGS. 33 and 34):

The following conserved residues can be recognised and in a preferable embodiment may be present in the enzymes for use in the compositions and methods of the invention;

```
Block 1 - GDSX block
hid hid hid hid Gly Asp Ser hid
 28  29  30  31  32  33  34  35

Block 2 - GANDY block
hid Gly hid Asn Asp hid
130 131 132 133 134 135

Block 3 - HPT block
His
309
```

Where 'hid' means a hydrophobic residue selected from Met, Ile, Leu, Val, Ala, Gly, Cys, His, Lys, Trp, Tyr, Phe.

Preferably the lipid acyltransferase enzyme for use in the compositions/methods of the invention can be aligned using the Pfam00657 consensus sequence.

Preferably, a positive match with the hidden markov model profile (HMM profile) of the Pfam00657 domain family indicates the presence of the GDSL (SEQ ID NO: 18) or GDSX domain according to the present invention.

Preferably when aligned with the Pfam00657 consensus sequence the lipid acyltransferase for use in the compositions/methods of the invention have at least one, preferably more than one, preferably more than two, of the following, a GDSx block, a GANDY block, a HPT block. Suitably, the lipid acyltransferase may have a GDSx block and a GANDY block. Alternatively, the enzyme may have a GDSx block and a HPT block. Preferably the enzyme comprises at least a GDSx block.

Preferably, when aligned with the Pfam00657 consensus sequence the enzyme for use in the compositions/methods of the invention have at least one, preferably more than one, preferably more than two, preferably more than three, preferably more than four, preferably more than five, preferably more than six, preferably more than seven, preferably more than eight, preferably more than nine, preferably more than ten, preferably more than eleven, preferably more than twelve, preferably more than thirteen, preferably more than fourteen, of the following amino acid residues when compared to the reference *A. hydrophilia* polypeptide sequence, namely SEQ ID No. 32: 28hid, 29hid, 30hid, 31hid, 32gly, 33Asp, 34Ser, 35hid, 130hid, 131Gly, 132Hid, 133Asn, 134Asp, 135hid, 309His.

The pfam00657 GDSX domain is a unique identifier which distinguishes proteins possessing this domain from other enzymes.

The pfam00657 consensus sequence is presented in FIG. 1 as SEQ ID No. 1. This is derived from the identification of the pfam family 00657, database version 6, which may also be referred to as pfam00657.6 herein.

The consensus sequence may be updated by using further releases of the pfam database.

For example, FIGS. 33 and 34 show the pfam alignment of family 00657, from database version 11, which may also be referred to as pfam00657.11 herein.

The presence of the GDSx, GANDY and HPT blocks are found in the pfam family 00657 from both releases of the database. Future releases of the pfam database can be used to identify the pfam family 00657.

Preferably, the lipid acyltransferase enzyme according to the present invention may be characterised using the following criteria:
(i) the enzyme possesses acyl transferase activity which may be defined as ester transfer activity whereby the acyl part of an original ester bond of a lipid acyl donor is transferred to acyl acceptor to form a new ester;
(ii) the enzyme comprises the amino acid sequence motif GDSX, wherein X is one or more of the following amino acid residues L, A, V, I, F, Y, H, Q, T, N, M or S;
(iii) the enzyme comprises His-309 or comprises a histidine residue at a position corresponding to His-309 in the *Aeromonas hydrophila* lipolytic enzyme shown in FIG. 2 (SEQ ID No. 2 or SEQ ID No. 32).

Preferably, the amino acid residue of the GDSX motif is L.

In SEQ ID No. 2 or SEQ ID No. 32 the first 18 amino acid residues form a signal sequence. His-309 of the full length sequence, that is the protein including the signal sequence, equates to His-291 of the mature part of the protein, i.e. the sequence without the signal sequence.

Preferably, the lipid acyltransferase enzyme according to the present invention comprises the following catalytic triad: Ser-34, Asp-134 and His-309 or comprises a serine residue, an aspartic acid residue and a histidine residue, respectively, at positions corresponding to Ser-34, Asp-134 and His-309 in the *Aeromonas hydrophila* lipolytic enzyme shown in FIG. 2 (SEQ ID No. 2) or FIG. 28 (SEQ ID No. 32). As stated above, in the sequence shown in SEQ ID No. 2 or SEQ ID No. 32 the first 18 amino acid residues form a signal sequence. Ser-34, Asp-134 and His-309 of the full length sequence, that is the protein including the signal sequence, equate to Ser-16, Asp-116 and His-291 of the mature part of the protein, i.e. the sequence without the signal sequence. In the pfam00657 consensus sequence, as given in FIG. 1 (SEQ ID No. 1) the active site residues correspond to Ser-7, Asp-157 and His-348.

Preferably, the lipid acyltransferase enzyme according to the present invention may be characterised using the following criteria:
(i) the enzyme possesses acyl transferase activity which may be defined as ester transfer activity whereby the acyl part of an original ester bond of a first lipid acyl donor is transferred to an acyl acceptor to form a new ester; and
(ii) the enzyme comprises at least Gly-32, Asp-33, Ser-34, Asp-134 and His-309 or comprises glycine, aspartic acid, serine, aspartic acid and histidine residues at positions corresponding to Gly-32, Asp-33, Ser-34, Asp-134 and His-309, respectively, in the *Aeromonas hydrophila* lipolytic enzyme shown in FIG. 2 (SEQ ID No. 2) or FIG. 28 (SEQ ID No. 32).

Suitably, the lipid acyltransferase enzyme according to the present invention may be obtainable, preferably obtained, from organisms from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

Suitably, the lipid acyltransferase enzyme according to the present invention may be obtainable, preferably obtained, from one or more of the following organisms: *Aeromonas hydrophila, Aeromonas salmonicida, Streptomyces coeli-* color, *Streptomyces rimosus, Mycobacterium, Streptococcus pyogenes, Lactococcus lactis, Streptococcus pyogenes, Streptococcus thermophilus, Lactobacillus helveticus, Desulfitobacterium dehalogenans, Bacillus* sp, *Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis* and *Candida parapsilosis*.

In one aspect, preferably the lipid acyltransferase enzyme according to the present invention is obtainable, preferably obtained, from one or more of *Aeromonas hydrophila* or *Aeromonas salmonicida*.

Suitably, the lipid acyltransferase enzyme according to the present invention comprises one or more of the following amino acid sequences:

(i) the amino acid sequence shown as SEQ ID No. 2 (see FIG. 2)
(ii) the amino acid sequence shown as SEQ ID No. 3 (see FIG. 3)
(iii) the amino acid sequence shown as SEQ ID No. 4 (see FIG. 4)
(iv) the amino acid sequence shown as SEQ ID No. 5 (see FIG. 5)
(v) the amino acid sequence shown as SEQ ID No. 6 (see FIG. 6)
(vi) the amino acid sequence shown as SEQ ID No. 12 (see FIG. 14)
(vii) the amino acid sequence shown as SEQ ID No. 20 (FIG. 16)
(viii) the amino acid sequence shown as SEQ ID No. 22 (FIG. 18)
(ix) the amino acid sequence shown as SEQ ID No. 24 (FIG. 20)
(x) the amino acid sequence shown as SEQ ID No. 26 (FIG. 22)
(xi) the amino acid sequence shown as SEQ ID No. 28 (FIG. 24)
(xii) the amino acid sequence shown as SEQ ID No. 30 (FIG. 26)
(xiii) the amino acid sequence shown as SEQ ID No. 32 (FIG. 28)
(xiv) the amino acid sequence shown as SEQ ID No. 34 (FIG. 30)
(xv) the amino acid sequence shown as SEQ ID No. 55 (FIG. 52)
(xvi) the amino acid sequence shown as SEQ ID No. 58
(xvii) the amino acid sequence shown as SEQ ID No. 60
(xviii) the amino acid sequence shown as SEQ ID No. 61
(xix) the amino acid sequence shown as SEQ ID No. 63
(xx) the amino acid sequence shown as SEQ ID No. 65
(xxi) the amino acid sequence shown as SEQ ID No. 67
(xxii) the amino acid sequence shown as SEQ ID No. 70 or
(xxiii) an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 55, SEQ ID No. 58, SEQ ID No. 60, SEQ ID No. 61, SEQ ID No. 63, SEQ ID No. 65, SEQ ID No. 67 or SEQ ID No. 70.

Suitably, the lipid acyltransferase enzyme according to the present invention comprises either the amino acid sequence shown as SEQ ID No. 2 or as SEQ ID No. 3 or SEQ ID No. 32 or SEQ ID No. 34 or comprises an amino acid sequence which has 75% or more, preferably 80% or more, preferably 85% or more, preferably 90% or more, preferably 95% or more, identity with the amino acid sequence shown as SEQ ID No. 2 or the amino acid sequence shown as SEQ ID No. 3 or the amino acid sequence shown as SEQ ID No. 32 or the amino acid sequence shown as SEQ ID No. 34.

For the purposes of the present invention, the degree of identity is based on the number of sequence elements which are the same. The degree of identity in accordance with the present invention may be suitably determined by means of computer programs known in the art, such as GAP provided in the GCG program package (Program Manual for the Wisconsin Package, Version 8, August 1994, Genetics Computer Group, 575 Science Drive, Madison, Wis., US53711) (Needleman & Wunsch (1970), J. of Molecular Biology 48, 443-45) using the following settings for polypeptide sequence comparison: GAP creation penalty of 3.0 and GAP extension penalty of 0.1.

Suitably the lipid acyltransferase enzyme according to the present invention comprises an amino acid sequence which has 80% or more, preferably 85% or more, more preferably 90% or more and even more preferably 95% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 55, SEQ ID No. 58, SEQ ID No. 60, SEQ ID No. 61, SEQ ID No. 63, SEQ ID No. 65, SEQ ID No. 67 or SEQ ID No. 70.

Suitably, the lipid acyltransferase enzyme according to the present invention comprises one or more of the following amino acid sequences:

(a) an amino acid sequence shown as amino acid residues 1-100 of SEQ ID No. 2 or SEQ ID No. 32;
(b) an amino acid sequence shown as amino acids residues 101-200 of SEQ ID No. 2 or SEQ ID No. 32;
(c) an amino acid sequence shown as amino acid residues 201-300 of SEQ ID No. 2 or SEQ ID No. 32; or
(d) an amino acid sequence which has 75% or more, preferably 85% or more, more preferably 90% or more, even more preferably 95% or more identity to any one of the amino acid sequences defined in (a)-(c) above.

Suitably, the lipid acyltransferase enzyme according to the present invention comprises one or more of the following amino acid sequences:

(a) an amino acid sequence shown as amino acid residues 28-39 of SEQ ID No. 2 or SEQ ID No. 32;
(b) an amino acid sequence shown as amino acids residues 77-88 of SEQ ID No. 2 or SEQ ID No. 32;
(c) an amino acid sequence shown as amino acid residues 126-136 of SEQ ID No. 2 or SEQ ID No. 32;
(d) an amino acid sequence shown as amino acid residues 163-175 of SEQ ID No. 2 or SEQ ID No. 32;
(e) an amino acid sequence shown as amino acid residues 304-311 of SEQ ID No. 2 or SEQ ID No. 32; or
(f) an amino acid sequence which has 75% or more, preferably 85% or more, more preferably 90% or more, even more preferably 95% or more identity to any one of the amino acid sequences defined in (a)-(e) above.

Suitably, the lipid acyltransferase enzyme according to the present invention may comprise an amino acid sequence produced by the expression or one or more of the following nucleotide sequences:

(a) the nucleotide sequence shown as SEQ ID No. 7 (see FIG. 9);
(b) the nucleotide sequence shown as SEQ ID No. 8 (see FIG. 10);

(c) the nucleotide sequence shown as SEQ ID No. 9 (see FIG. 11);
(d) the nucleotide sequence shown as SEQ ID No. 10 (see FIG. 12);
(e) the nucleotide sequence shown as SEQ ID No. 11 (see FIG. 13);
(f) the nucleotide sequence shown as SEQ ID No. 13 (see FIG. 15);
(g) the nucleotide sequence shown as SEQ ID No. 21 (see FIG. 17);
(h) the nucleotide sequence shown as SEQ ID No. 23 (see FIG. 19);
(i) the nucleotide sequence shown as SEQ ID No. 25 (see FIG. 21);
(j) the nucleotide sequence shown as SEQ ID No. 27 (see FIG. 23);
(k) the nucleotide sequence shown as SEQ ID No. 29 (see FIG. 25);
(l) the nucleotide sequence shown as SEQ ID No. 31 (see FIG. 27);
(m) the nucleotide sequence shown as SEQ ID No. 33 (see FIG. 29);
(n) the nucleotide sequence shown as SEQ ID No. 35 (see FIG. 31);
(O) the nucleotide sequence shown as SEQ ID No. 54 (FIG. 51);
(p) the nucleotide sequence shown as SEQ ID No. 59;
(q) the nucleotide sequence shown as SEQ ID No. 62;
(r) the nucleotide sequence shown as SEQ ID No. 64;
(s) the nucleotide sequence shown as SEQ ID No. 66;
(t) the nucleotide sequence shown as SEQ ID No. 68
(u) the nucleotide sequence shown as SEQ ID No. 69 or
(v) a nucleotide sequence which has 75% or more identity with any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 54, SEQ ID No. 59, SEQ ID No. 62, SEQ ID No. 64, SEQ ID No. 66, SEQ ID No. 68 or SEQ ID No. 69.

Suitably the nucleotide sequence may have 80% or more, preferably 85% or more, more preferably 90% or more and even more preferably 95% or more identity with any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33 or SEQ ID No. 35, SEQ ID No. 54, SEQ ID No. 59, SEQ ID No. 62, SEQ ID No. 64, SEQ ID No. 66, SEQ ID No. 68 or SEQ ID No. 69.

In one aspect, the lipid acyltransferase according to the present invention may be a lecithin:cholesterol acyltransferases (LCAT) or variant thereof (for example a variant made by molecular evolution).

Suitable LCATs are known in the art and may be obtainable from one or more of the following organisms for example: mammals, rat, mice, chickens, *Drosophila melanogaster*, plants, including *Arabidopsis* and *Oryza sativa*, nematodes, fungi and yeast.

In one embodiment the lipid acyltransferase enzyme according to the present invention may be the lipid acyltransferase obtainable, preferably obtained, from the *E. coli* strains TOP 10 harbouring pPet12aAhydro and pPet12aASalmo deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 22 Dec. 2003 under accession numbers NICMB 41204 and NCIMB 41205, respectively.

Preferably, when carrying out a method according to the present invention the product is produced without increasing or substantially increasing the free fatty acids in the foodstuff.

The term "transferase" as used herein is interchangeable with the term "lipid acyltransferase".

Suitably, the lipid acyltransferase as defined herein catalyses one or more of the following reactions: interesterification, transesterification, alcoholysis, hydrolysis.

The term "interesterification" refers to the enzymatic catalysed transfer of acyl groups between a lipid donor and lipid acceptor, wherein the lipid donor is not a free acyl group.

The term "transesterification" as used herein means the enzymatic catalysed transfer of an acyl group from a lipid donor (other than a free fatty acid) to an acyl acceptor (other than water).

As used herein, the term "alcoholysis" refers to the enzymatic cleavage of a covalent bond of an acid derivative by reaction with an alcohol ROH so that one of the products combines with the H of the alcohol and the other product combines with the OR group of the alcohol.

As used herein, the term "alcohol" refers to an alkyl compound containing a hydroxyl group.

As used herein, the term "hydrolysis" refers to the enzymatic catalysed transfer of an acyl group from a lipid to the OH group of a water molecule. Acyl transfer which results from hydrolysis requires the separation of the water molecule.

The term "without increasing or without substantially increasing the free fatty acids" as used herein means that preferably the lipid acyl transferase according to the present invention has 100% transferase activity (i.e. transfers 100% of the acyl groups from an acyl donor onto the acyl acceptor, with no hydrolytic activity) in an edible oil environment; however, the enzyme may transfer less than 100% of the acyl groups present in the lipid acyl donor to the acyl acceptor. In which case, preferably the acyltransferase activity accounts for at least 30%, more preferably at least 40%, more preferably at least 50%, more preferably at least 70%, more preferably at least 80%, more preferably at least 90% and more preferably at least 98% of the total enzyme activity. The % transferase activity (i.e. the transferase activity as a percentage of the total enzymatic activity) may be determined by the following protocol:

Protocol for the Determination of % Acyltransferase Activity:

An edible oil to which a lipid acyltransferase according to the present invention has been added may be extracted following the enzymatic reaction with $CHCl_3:CH_3OH$ 2:1 and the organic phase containing the lipid material is isolated and analysed by GLC according to the procedure detailed herein below. From the GLC analyses the amount of free fatty acids and diglycerides are determined. A control edible oil to which no enzyme according to the present invention has been added, is analysed in the same way.

Calculation:

From the results of the GLC analyses the increase in free fatty acids and the decrease in diglycerides can be calculated:

$\Delta$ % fatty acid=% Fatty acid(enzyme)−% fatty acid (control);

Mv Fa=average molecular weight of the fatty acids;

Δ % diglyceride=% Diglyceride(control)−% Diglyceride(enzyme);

Mv Di=average molecular weight of diglyceride;

The transferase activity is calculated as a percentage of the total enzymatic activity:

$$\% \text{ transferase activity} = \frac{((\Delta\%Di/(MvDi) - \Delta\%Fa/(MvFA)) \times 100}{\Delta\%Di/(MvDi) - \Delta\%Fa/(MvFa) + \Delta\%Fa/(MvFa)}$$

$$\% \text{ transferase activity} = \frac{((\Delta\%Di/(MvDi) - \Delta\%Fa/(MvFA)) \times 100}{\Delta\%Di/(MvDi)}$$

If the free fatty acids are increased in the edible oil they are preferably not increased substantially, i.e. to a significant degree. By this we mean, that the increase in free fatty acid does not adversely affect the quality of the edible oil.

In some aspects of the present invention, the term "without substantially increasing free fatty acids" as used herein means that the amount of free fatty acid in an edible oil treated with an lipid acyltransferase according to the present invention is less than the amount of free fatty acid produced in an edible oil or composition when an enzyme other than a lipid acyltransferase according to the present invention had been used, such as for example as compared with the amount of free fatty acid produced when a conventional lipase e.g. *Pseudomonas cepacia* lipase (Lipase PS, Amano Japan) or *Rhizopus oryzae* lipase (LipaseF, Amano Japan).

Suitably, any glycerol remaining in the edible oil after the reaction has taken place may be removed, e.g. by centrifugation or vacuum distillation.

Optionally, the enzyme may be removed from the edible oil after the enzymatic reaction has taken place. Alternatively, the enzyme may simply be deactivated and left in the edible oil. Suitably, the enzyme may be deactivated by heating for example.

In one embodiment the lipase acyl transferase for use in the methods of the present invention may be immobilised. When it is the case that the enzyme is immobilised an admixture comprising an acyl acceptor and the edible oil may be passed through a column for example comprising the immobilised enzyme. By immobilising the enzyme it is possible to easily reuse it.

Suitably the immobilised enzyme may be used in a flow reactor or in a batch reactor containing a reaction mixture which comprises an acyl acceptor and an edible oil as a two-phase system. The reaction mixture may be optionally stirred or sonicated. Once the reaction has reached equilibrium for example, the reaction mixture and the immobilised enzyme may be separated. Suitably, excess acyl acceptor (such as excess glycerol) may be removed after the reaction, e.g. by centrifugation or vacuum distillation.

Immobilised lipid acyl transferase can be prepared using immobilisation techniques known in the art. There are numerous methods of preparing immobilised enzymes, which will be apparent to a person skilled in the art (for example the techniques referred to in EP 0 746 608; or Balcao V. M., Paiva A. L., Malcata F. X., Enzyme Microb Technol. 1996 May 1; 18(6): 392-416; or Retz M. T., Jaeger K. E. Chem Phys Lipids. 1998 June; 93(1-2): 3-14; Bornscheuer U. T., Bessler C, Srinivas R, Krishna S. H. Trends Biotechnol. 2002 October; 20(10): 433-7; Plou et al, J. Biotechnology 92 (2002) 55-66; Warmuth et al., 1992. Bio Forum 9, 282-283; Ferrer et al., 2000. J. Chem. Technol. Biotechnol. 75, 1-8; or Christensen et al., 1998. Nachwachsende Rohstoff 10, 98-105; Petersen and Christenen, 2000, Applied Biocatalysis. Harwood Academic Publishers, Amsterdam. (each of which is incorporated herein by reference). Techniques which may be used herein include covalent coupling to Eupergit C, adsorption on polypropylene and silica-granulation for example.

Preferably, the edible oil is any edible oil containing a diglyceride, preferably a significant amount of diglyceride.

Preferably, the edible oil is one or more of the following oils: oils extracted from or derived from palm oil, palm olein, palm stearin, palm mid fraction or any palm oil fraction or olive oil.

More preferably, the edible oil is palm oil and/or palm olein and/or palm stearin.

With regard to the admixing of the edible oil, the acyl acceptor substrate and the lipid acyltransferase, as a person skilled in the art would readily appreciate this can be done in any combination and/or order. By way of example only, the acyl acceptor substrate may be admixed with the edible oil followed by addition of the lipid acyltransferase. Alternatively, the edible oil may be admixed with the lipid acyltransferase followed by addition of the acyl acceptor substrate. Alternatively, the lipid acyltransferase and acyl acceptor substrate may be admixed followed by admixing of the enzyme/substrate mixture with the edible oil. Alternatively, of course, all three substances (namely the edible oil, the acyl acceptor substrate and the lipid acyltransferase) may be admixed simultaneously.

Preferably the method is carried out at a temperature above the melting point of the edible oil.

Suitably the method may be carried out at a temperature of between 30-50° C., preferably between 35-45° C., preferably between 40-45° C.

Although water may be added to the oil prior or during the method of the present invention, in a most preferable embodiment no water is added. If water is present in the edible oil, preferably there is less than 10% water present, more preferably less than 7.5%, less than 5%, less than 1%, less than 0.5%, less than 0.4%, less than 0.3%, less than 0.2% or less than 0.1% water present. Suitably, between 0.1. and 1% water may be present in the edible oil.

In one embodiment the edible oil used in a process according to the present invention may be supplemented with one or more acyl donors and/or may be supplemented with one or more acyl acceptors and/or may be supplemented with both one or more acyl acceptors and one or more acyl donors. By "supplemented with" means that either the acyl donor and/or the acyl acceptor is not naturally present in the edible oil and is added at the same time, immediately after and/or immediately before bringing the edible into contact with the lipid acyltransferase in accordance with the present invention.

Suitably, the supplementary acyl donor may be other than a DAG. Suitably the supplemental acyl donor may be for example a phospholipid (e.g. lecithin).

Suitably, the supplementary acyl acceptor may be glycerol. Suitably, however it may be an acyl acceptor other than glycerol, for example a plant sterol and/or plant stanol for instance. Suitably, the supplementary acyl acceptor may be a combination of glycerol and one or more further acyl acceptors.

The use of an oil supplemented with a phospholipid allows for an additional emulsifier (lyso-phospholipid) to be produced in the oil. The use of an oil supplemented with a plant sterol and/or plant stanol allows for a plant sterol ester and/or a plant stanol ester to be produced in the edible both. Both plant sterol esters and plant stanol esters have been reported to have blood serum cholesterol reducing effects when incorporated into the diet.

Enzymatic interesterification using immobilised lipases, such as Lipozyme® TL IM, a 1,3 specific lipase (Novozymes, Denmark), is used to reduce the amount of trans fatty acids in oils for dietary use and/or for modifying the melting characteristics of edible oils and fats.

During interesterification, one or two of the polyunsaturated fatty acids in the triglycerides of the food oil can be replaced with a fatty acid from another oil low in trans fatty acids, such as palm oil. This transfer of fatty acids from palm oil allows the modification of the melting point of the food oil without introduction of the trans fatty acids. The immobilisation of lipases is described in U.S. Pat. No. 5,776,741, U.S. Pat. No. 4,798,793 and U.S. Pat. No. 5,156,963. U.S. Pat. No. 6,284,501 describes the interesterification of phospholipids.

An immobilised transferase can be produced using the same technology as used for lipases.

In one embodiment, the lipid acyl transferase as described herein can be used in combination with a interesterification lipase. The lipase interesterification and the acyl transferase steps are preferably carried out separately.

In a further aspect, the lipid acyl transferase as described herein can be used in combination with conventional crystallisation inhibitors.

In a further aspect, the present invention provides a method of improving the crystallization properties in a foodstuff comprising an edible oil, comprising admixing an edible oil with an acyl acceptor substrate and a diglyceride:glycerol acyltransferase as described herein and optionally a further crystallization inhibitor.

The present invention yet further provides the use of a diglyceride:glycerol acyltransferase as described herein in the manufacture of a foodstuff comprising an edible oil for improving the crystallization properties of said foodstuff.

In another aspect, the present invention provides the use of a diglyceride:glycerol acyltransferase as described herein in combination with a further crystallization inhibitor in the manufacture of a foodstuff comprising an edible oil for improving the crystallization properties of said foodstuff.

The further crystallization inhibitor may be any conventional crystallization inhibitor such as one or more of sorbitan tristearates, lecithins, PGE or polysorbates for example.

Advantages

In the present invention by use of the method taught herein, and in particular by selection of the enzymes taught herein for use in the claimed method, for removing or reducing diglyceride from or in an edible oil, a selective reduction in diglyceride over mono- and di-glyceride can be effected, without a decrease in triglycerides and/or a significant increase in free fatty acids (FFAs).

The fact that the present inventive method can be carried out without substantially increasing free fatty acid content of the edible oil overcomes the problem of loss of product.

If a crude palm oil is treated with a conventional lipase it is necessary to remove the free fatty acid during the oil refining, but if a refined palm oil is treated with the lipid acyltransferase according to the present invention (thus negating the need to treat the crude palm oil with a conventional lipase) it is not necessary to remove the fatty acids because the content of free fatty acid does not increase substantially.

In addition or alternatively, the present invention results in the removal and/or reduction of diglycerides from or in an edible oil, with no significant decrease in monoglyceride levels.

In addition or alternatively, the present invention results in the removal and/or reduction of diglycerides from or in an edible oil, whilst increasing monoglyceride levels in the edible oil. This contrasts prior art enzymes which utilise monoglyceride as a substrate and therefore reduce the amount of monoglyceride in the edible oil.

Commercial Relevance of Removing/Reducing Diglyceride in Palm Oil

Diglycerides Retard the Crystallisation in Palm Based Margarines and Shortenings For many years, we have seen a steady increase in the growth of palm oil consumption, partially because of localised availability, partially because of economics, and primarily because of performance. Presence of Palm oil in Margarine/shortening type products is found to enhance the β quality of an oil blend. However, the use of palm oil was previously restricted to the use of palm stearine, and palm olein, with some use of palm kernels and its fractions. Today, this is more diverse, because of confectionery and food processors wanting very specific melting profiles.

With customers trying to increase the use of palm oil in formulations, the industry is seeing more crystallization issues than ever before. Where it is necessary to add "pro-crystal" promoters to initiate crystallization in low trans or no-trans formulations thereby preventing or delaying post crystal formation before point of use. Also increased interest in anti-crystallisers, such as Sorbitan Tristearates, lecithins, PGE, Polysorbates, which will slow, delay post-crystal growth has been seen. This is a symptom of high diglyceride presence.

The commercial benefits of the present invention may be one or more of the following:

a) reduces the need to add additional monoglyceride to the edible oil during processing and/or later during use. Monoglyceride is a widely used emulsifier in food systems.

b) decreases in diglyceride from about 6-8% to about 4-5%, and even more.

c) increases the flexibility on plant (factory) capacity—hence reduction in production overheads.

d) allows for major decreases in post-crystallisation issues.

e) in some formulations, it would be possible to remove some fully saturated oil triglycerides, because we reduce the need for crystal promotion. In this regard manufacturers conventionally add fully saturated triglycerides to formulations in order to "promote" crystal formation and overcome undesirable delayed crystal formation in the product post-sale. Such crystal formation is a symptom of having a significant amount of palm oil or its components in a formulation, which would contain concentrations of diglycerides sufficient to delay crystal growth to the desired crystal type (i.e. preferably beta-prime in the case of margarines and shortenings) during manufacture. However, by use of palm oil treated in accordance with the present invention, the diglyceride content is sufficiently reduced within a given blend or formulation to that the need for additional fully saturated triglyceride addition to aid crystal development becomes less important.

f) allows greater diversification towards palm based blends, with increased liquid oil costs, and without major process changes.

g) allows for replacement of anti-crystallisers and/or partial replacement of anti-crystallisers.

B Trans Fatty Acid

Today, we see legislation and public opinion against the use of trans acids in food products (Fødevareministeriet, Denmark 2003). So, this has led to performance problems. Manufacturers where possible may wish to switch to palm based solutions because of the high levels of C:16:0 and C:18:0 isomers found within this oil type. The result is that we are beginning to see increased consumption of palm in economies that previously did not use palm.

C Crystallisation Inhibition of Diglycerides in Confectionery Products

Cocoa Butter Equivalents (CBEs) are formulated from speciality fats such as fractionated palm oil, in particular palm mid fractions (PMF), fractionated shea fat as well as many other exotic fats. For cost reasons it is favourable to include as much as possible PMF in the CBE. In fact many CBEs may only contain palm fractions. The most delicate aspect of chocolate manufacture is the crystallisation of the fat. Diglycerides will have a negative impact on the crystallisation, for example demoulding can be a serious problem (Siew, 2001).

D Crystal Quality

Triglyceride quality greatly affects performance, and this is evident, from examples of a typical trans acid containing oil formula for standard 82% fat table margarine, against trans free version containing a typical interesterified palm stearine fraction and palm kernel as hard stock, both having similar SFC profile. Reduced speed and quality of crystallization can result in a symptom known as "oiling out." In turn this calls for the need of crystal promoters, such as hard MAGs. Further, delay in crystal stabilized crystal formation leads to symptom known as "sandiness" whereby transformation of desired crystal type eventually reverts to the more stable Beta form, and so gives sandy texture. This symptom is particular problem for Industrial type products.

Some Uses

Fat Modification

During the chemical production of fats for use in high fat solid food products such as margarines, spreads, confectionery/chocolate's, trans fatty acids are introduced into the food oil during a process of hydrogenation (hardening). This allows for the modification of the melting temperature of the food oil to ensure a suitable consistency of the final food product, e.g. a table margarine, which is solid but spreadable at room temperature, or a chocolate which is solid during storage, but melts in the mouth.

However, chemical production uses large quantities of solvents such as hexane which are considered hazardous to the environment and health and requires complete removal of the solvent prior to use of the modified oil/fat as a food ingredient.

In many countries the use of partial hydrogenation for food production is being limited by legislation and regulatory controls, and many major food producers are now switching to alternative low-trans alternatives.

The oil prepared by the process of the invention can be used as an ingredient for margarine and/or spreads.

Cocoa Butter Replacements/Equivalents

Cocoa butter contains a unique composition which provides a solid confectionery which melts in the mouth. In order to substitute cocoa butter using cheaper alternatives, plant oils have been hydrogenated to produce trans fatty acids, thereby raising the melting point of the food oil to provide a similar solid confectionery which melts at body temperature. Such modified plant oils are known as cocoa butter equivalents (CBEs) or, in the case where the modified fats enhance the characteristics of the chocolate product, cocoa butter replacements (CBRs). One major problem with CBEs and CBRs is that the hydrogenation of plant oils produces trans fats which are considered to be detrimental to health and temperature. This has lead to the use of low trans plant oils, or fractions thereof, which have a higher melting temperature. Palm oil and palm oil fractions are considered advantageous in this respect as a major component low in trans CBRs/CBEs.

Cocoa butter replacement (CBR) fats are used to provide preferable characteristics to chocolate products such as non-tempering, reduced post hardening, stability, bloom resistant. It is particularly desirable to use non-lauric/non-trans fats such as palm oil. The crystallisation properties of the fats used in CBRs play a key role in ensuring a suitable balance between the product melting in the mouth whilst retaining the above preferable characteristics. The use of low-trans fats, such as palm oil, in CBR blends is particularly desirable for health reasons. The use of palm oil in CBRs is described in EP0293194.

The oil prepared in accordance with a process of the present invention can be used as an ingredient for chocolate, for example within a fat blend as a cocoa butter replacement and/or equivalent.

Sequences of Some Diglyceride:Glycerol Acyltransferase Enzymes For Use in Accordance with the Present Invention Suitable diglyceride:glycerol acyltransferase enzymes for use in accordance with the present invention and/or in the methods of the present invention may comprise any one of the following amino acid sequences and/or be encoded by the following nucleotide sequences:

```
Termobifida\fusca GDSx 548 aa

SEQ ID No. 58
ZP 00058717
      1 mlphpagerg evgaffallv gtpqdrrlrl echetrplrg rcgcgerrvp pltlpgdgvl 61 cttsstrdae tvwrkhlqpr pdggfrphlg vgcllagqgs pgvlwcgreg crfevcrrdt 121 pglsrtrngd ssppfragws lppkcgeisq sarktpavpr ysllrtdrpd gprgrfvgsg 181 praatrrrlf lgipalvlvt altlvlavpt gretlwrmwc eatqdwclgv pvdsrgqpae 241 dgeflllspv qaatwgnyya lgdsyssgdg ardyypgtav kggcwrsana ypelvaeayd 301 faghlsflac sgqrgyamld aidevgsqld wnsphtslvt igiggndlgf stvlktcmvr 361 vplldskact dqedairkrm akfettfeel isevrtrapd arilvvgypr ifpeeptgay 421 ytltasnqrw lnetiqefnq qlaeavavhd eeiaasggvg svefvdvyha ldgheigsde
```

-continued 481 pwvngvqlrd latgvtvdrs tfhpnaaghr avgervieqi etgpgrplya tfavvagatv 541 dtlagevg SEQ ID No. 59
nt 1 ggtggtgaac cagaacaccc ggtcgtcggc gtgggcgtcc aggtgcaggt gcaggttctt 61 caactgctcc agcaggatgc cgccgtggcc gtgcacgatg ccttgggca ggcctgtggt 121 ccccgacgag tacagcaccc atagcggatg gtcgaacggc agcggggtga actccagttc 181 cgcgccttcg cccgcggctt cgaactccgc ccaggacagg gtgtcggcga cagggccgca 241 gcccaggtac ggcaggacga cggtgtgctg caggctgggc atgccgtcgc gcagggcttt 301 gagcacgtca cggcggtcga agtccttacc gccgtagcgg tagccgtcca cggccagcag 361 cactttcggt tcgatctgcg cgaaccggtc gaggacgctg cgcaccccga agtcggggga 421 acaggacgac caggtcgcac cgatcgcggc gcaggcgagg aatgcggccg tcgcctcggc 481 gatgttcggc aggtaggcca cgacccggtc gccggggccc accccgaggc tgcggagggc 541 cgcagcgatc gcggcggtgc gggtccgcag ttctccccag gtccactcgg tcaacggccg 601 gagttcggac gcgtgccgga tcgccacggc tgatgggtca cggtcgcgga agatgtgctc 661 ggcgtagttg agggtggcgc cggggaacca gacggcgccg gcatggcgt cggaggcgag 721 cactgtggtg tacggggtgg cggcgcgcac ccgtagtac tcccagatcg cggaccagaa 781 tccttcgagg tcggttaccg accagcgcca cagtgcctcg tagtccggtg cgtccacacc 841 gcggtgctcc cgcacccagc gggtgaacgc ggtgaggttg gcgcgttctt tgcgctcctc 901 gtcgggactc cacaggatcg gcggctgcgg cttgagtgtc atgaaacgcg accccttcgt 961 ggacggtgcg gatgcggtga gcgtcgggtg cctcccctaa cgctccccgg tgacggagtg 1021 ttgtgcacca catctagcac gcgggacgcg gaaaccgtat ggagaaaaca cctacaaccc 1081 cggccggacg gtgggtttcg gccacactta gggtcgggt gcctgcttgc cgggcagggc 1141 agtcccgggg tgctgtggtg cgggcggag ggctgtcgct tcgaggtgtg ccggcgggac 1201 actccgggcc tcagccgtac ccgcaacggg gacagttctc ctcccttccg ggctggatgg 1261 tccccttcccc cgaaatgcgg cgagatctcc cagtcagccc ggaaaacacc cgctgtgccc 1321 aggtactctt tgcttcgaac agacaggccg gacggtccac gggggaggtt tgtgggcagc 1381 ggaccacgtg cggcgaccag acgacggttg ttcctcggta tccccgctct tgtacttgtg 1441 acagcgctca cgctggtctt ggctgtcccg acggggcgcg agacgctgtg cgcatgtgg 1501 tgtgaggcca cccaggactg gtgcctgggg gtgccggtcg actcccgcgg acagcctgcg 1561 gaggacggcg agtttctgct gctttctccg gtccaggcag cgacctgggg gaactattac 1621 gcgctcgggg attcgtactc ttcgggggac ggggcccgcg actactatcc cggcaccgcg 1681 gtgaagggcg gttgctggcg gtccgctaac gcctatccgg agctggtcgc gaagcctac 1741 gacttcgccg gacacttgtc gttcctggcc tgcagcggcc agcgcggcta cgccatgctt 1801 gacgctatcg acgaggtcgg ctcgcagctg gactggaact cccctcacac gtcgctggtg 1861 acgatcggga tcggcggcaa cgatctgggg ttctccacgg ttttgaagac ctgcatggtg 1921 cgggtgccgc tgctggacag caaggcgtgc acgaccagg aggacgctat ccgcaagcgg 1981 atggcgaaat tcgagacgac gtttgaagag ctcatcagcg aagtgcgcac ccgcgcgccg 2041 gacgcccgga tccttgtcgt gggctacccc cggattttc cggaggaacc gaccggcgcc 2101 tactacacgc tgaccgcgag caaccagcgg tggctcaacg aaaccattca ggagttcaac 2161 cagcagctcg ccgaggctgt cgcggtccac gacgaggaga ttgccgcgtc gggcgggtg -continued

```
2221 ggcagcgtgg agttcgtgga cgtctaccac gcgttggacg gccacgagat cggctcggac 2281 gagccgtggg tgaacggggt gcagttgcgg gacctcgcca ccggggtgac tgtggaccgc 2341 agtaccttcc accccaacgc cgctgggcac cgggcggtcg gtgagcgggt catcgagcag 2401 atcgaaaccg gcccgggccg tccgctctat gccactttcg cggtggtggc ggggcgacc 2461 gtggacactc tcgcgggcga ggtggggtga cccggcttac cgtccggccc gcaggtctgc 2521 gagcactgcg gcgatctggt ccactgccca gtgcagttcg tcttcggtga tgaccagcgg 2581 cggggagagc cggatcgttg agccgtgcgt gtctttgacg agcacacccc gctgcaggag 2641 ccgttcgcac agttctcttc cggtggccag agtcgggtcg acgtcgatcc cagcccacag 2701 gccgatgctg cgggccgcga ccacgccgtt gccgaccagt tggtcgaggc gggcgcgcag 2761 cacggggcg agggcgcgga catggtccag gtaagggccg tcgcggacga ggctcaccac 2821 ggcagtgccg accgcgcagg cgagggcgtt gccgccgaag gtgctgccgt gctggccggg 2881 gcggatcacg tcgaagactt ccgcgtcgcc taccgccgcc gccacgggca ggatgccgcc 2941 gcccagcgct tgccgaaca ggtagatatc ggcgtcgact ccgctgtggt cgcaggcccg
//
```

Termobifida\fusca\- GDSx

SEQ ID No. 60

```
   1 vgsgpraatr rrlflgipal vlvtaltlvl avptgretlw rmwceatqdw clgvpvdsrg 61 qpaedgefll lspvqaatwg nyyalgdsys sgdgardyyp gtavkggcwr sanaypelva 121 eaydfaghls flacsgqrgy amldaidevg sqldwnspht slvtigiggn dlgfstvlkt 181 cmvrvpllds kactdqedai rkrmakfett feelisevrt rapdarilvv gyprifpeep 241 tgayytltas nqrwlnetiq efnqqlaeav avhdeeiaas ggvgsvefvd vyhaldghei 301 gsdepwvngv qlrdlatgvt vdrstfhpna aghravgerv ieqietgpgr plyatfavva 361 gatvdtlage vg
```

Corynebacterium\efficiens\GDSx 300 aa

SEQ ID No. 61

```
   1 mrttviaasa llllagcadg areetagapp gessggiree gaeastsitd vyialgdsya 61 amggrdqplr gepfclrssg nypellhaev tdltcqgavt gdlleprtlg ertlpaqvda 121 ltedttlvtl siggndlgfg evagcireri agenaddcvd llgetigeql dqlppqldrv 181 heairdragd aqvvvtgylp lvsagdcpel gdvseadrrw aveltgqine tvreaaerhd 241 alfvlpddad ehtscappqq rwadiqgqqt dayplhptsa gheamaaavr dalglepvqp
//
```

SEQ ID No. 62
nt

```
   1 ttctggggtg ttatgggggtt gttatcggct cgtcctgggt ggatcccgcc aggtggggta 61 ttcacggggg acttttgtgt ccaacagccg agaatgagtg ccctgagcgg tgggaatgag 121 gtgggcgggg ctgtgtcgcc atgaggggc ggcgggctct gtggtgcccc gcgacccccg 181 gccccggtga gcggtgaatg aaatccggct gtaatcagca tcccgtgccc accccgtcgg 241 ggaggtcagc gcccggagtg tctacgcagt cggatcctct cggactcggc catgctgtcg 301 gcagcatcgc gctcccgggt cttggcgtcc ctcggctgtt ctgcctgctg tccctggaag 361 gcgaaatgat caccggggag tgatacaccg gtgtctcat cccggatgcc cacttcggcg 421 ccatccggca attcgggcag ctccgggtgg aagtaggtgg catccgatgc gtcggtgacg 481 ccatagtggg cgaagatctc atcctgctcg agggtgctca ggccactctc cggatcgata
```

-continued

```
 541 tcgggggcgt ccttgatggc gtccttgctg aaaccgaggt gcagcttgtg ggcttccaat
 601 ttcgcaccac ggagcgggac gaggctggaa tgacgccga agagcccgtg gtggacctca
 661 acgaaggtgg gtagtccgt gtcatcattg aggaacacgc cctccaccgc acccagcttg
 721 tggccggagt tgtcgtaggc gctggcatcc agaagggaaa cgatctcata tttgtcggtg
 781 tgctcagaca tgatcttcct ttgctgtcgg tgtctggtac taccacggta gggctgaatg
 841 caactgttat ttttctgtta ttttaggaat tggtccatat cccacaggct ggctgtggtc
 901 aaatcgtcat caagtaatcc ctgtcacaca aaatgggtgg tgggagccct ggtcgcggtt
 961 ccgtgggagg cgccgtgccc cgcaggatcg tcggcatcgg cggatctggc cggtaccccg
1021 cggtgaataa aatcattctg taaccttcat cacggttggt tttaggtatc cgccccttc
1081 gtcctgaccc cgtccccggc gcgcgggagc ccgcgggttg cggtagacag gggagacgtg
1141 gacaccatga ggacaacggt catcgcagca agcgcattac tccttctcgc cggatgcgcg
1201 gatggggccc gggaggagac cgccggtgca ccgccgggtg agtcctccgg gggcatccgg
1261 gaggaggggg cggaggcgtc gacaagcatc accgacgtct acatcgccct cggggattcc
1321 tatgcggcga tgggcgggcg ggatcagccg ttacggggtg agccgttctg cctgcgctcg
1381 tccggtaatt acccggaact cctccacgca gaggtcaccg atctcacctg ccaggggggcg
1441 gtgaccgggg atctgctcga acccaggacg ctggggagc gcacgctgcc ggcgcaggtg
1501 gatgcgctga cggaggacac cacccctggtc accctctcca tcgggggcaa tgacctcgga
1561 ttcggggagg tggcgggatg catccgggaa cggatcgccg gggagaacgc tgatgattgc
1621 gtggacctgc tggggggaaac catcgggggag cagctcgatc agcttccccc gcagctggac
1681 cgcgtgcacg aggctatccg ggaccgcgcc ggggacgcgc aggttgtggt caccggttac
1741 ctgccgctcg tgtctgccgg ggactgcccc gaactggggg atgtctccga ggcggatcgt
1801 cgttgggcgg ttgagctgac cgggcagatc aacgagaccg tgcgcgaggc ggccgaacga
1861 cacgatgccc tctttgtcct gcccgacgat gccgatgagc acaccagttg tgcaccccca
1921 cagcagcgct gggcggatat ccagggccaa cagaccgatg cctatccgct gcacccgacc
1981 tccgccggcc atgaggcgat ggccgccgcc gtccgggacg cgctgggcct ggaaccggtc
2041 cagccgtagc gccgggcgcg cgcttgtcga cgaccaaccc atgccaggct gcagtcacat
2101 ccgcacatag cgcgcgcggg cgatggagta cgcaccatag aggatgagcc gatgccgac
2161 gatgatgagc agcacactgc cgaagggttg ttccccgagg gtgcgcagag ccgagtccag
2221 acctgcggcc tgctccggat catgggccca accggcgatg acgatcaaca cccccaggat
2281 cccgaaggcg ataccacggg cgacataacc ggctgttccg gtgatgatga tcgcggtccc
2341 gacctgccct gaccccgcac ccgcctccag atcctcccgg aaatcccggg tggcccctt
2401 ccagaggttg tagacacccg ccccagtac caccagcccg gcgaccacaa ccagcaccac
2461 accccagggt tgggatagga cggtggcggt gacatcggtg gcggtctccc catcggaggt
2521 gctgccgccc cgggcgaagg tggaggtggt caccgccagg agaagtaga ccatggccat
2581 gaccgccccc ttggcccttt ccttgaggtc ctcgcccgcc agcagctggc tcaattgcca
2641 gagtcccagg gccgccaggg cgatgacggc aacccacagg aggaactgcc cacccggagc
2701 ctccgcgatg gtggccaggg cacctgaatt cgaggcctca tcacccgaac cgccggatcc
2761 agtggcgatg cgcaccgcga tccacccgat gaggatgtgc agtatgccca ggacaatgaa
2821 accacctctg gccagggtgg tcagcgcggg gtggtcctcg gcctggtcgg cagcccgttc
```

-continued

```
    2881 gatcgtccgt tcgcggatc tggtgtcgcc cttatccata gctcccattg aaccgccttg
    2941 aggggtgggc ggccactgtc agggcggatt gtgatctgaa ctgtgatgtt ccatcaaccc
//
```

*Novosphingobium\aromaticivorans\GDSx 284 aa*

SEQ ID No. 63
ZP 00094165

```
      1 mgqvklfarr capvllalag lapaatvare aplaegaryv algssfaagp gvgpnapgsp
     61 ercgrgtlny phllaealkl dlvdatcsga tthhvlgpwn evppqidsvn gdtrlvtlti
    121 ggndvsfvgn ifaaacekma spdprcgkwr eiteeewqad eermrsivrq iharaplarv
    181 vvvdyitvlp psgtcaamai spdrlaqsrs aakrlarita rvareegasl lkfshisrrh
    241 hpcsakpwsn glsapaddgi pvhpnrlgha eaaaalvklv klmk
//
```

SEQ ID No. 64

```
      1 tgccggaact caagcggcgt ctagccgaac tcatgcccga aagcgcgtgg cactatcccg
     61 aagaccaggt ctcggacgcc agcgagcgcc tgatggccgc cgaaatcacg cgcgaacagc
    121 tctaccgcca gctccacgac gagctgccct atgacagtac cgtacgtccc gagaagtacc
    181 tccatcgcaa ggacggttcg atcgagatcc accagcagat cgtgattgcc cgcgagacac
    241 agcgtccgat cgtgctgggc aagggtggcg cgaagatcaa ggcgatcgga gaggccgcac
    301 gcaaggaact tcgcaattg ctcgacacca aggtgcacct gttcctgcat gtgaaggtcg
    361 acgagcgctg ggccgacgcc aaggaaatct acgaggaaat cggcctcgaa tgggtcaagt
    421 gaagctcttc gcgcgccgct gcgcccagt acttctcgcc cttgccgggc tggctccggc
    481 ggctacggtc gcgcgggaag caccgctggc cgaaggcgcg cgttacgttg cgctgggaag
    541 ctccttcgcc gcaggtccgg gcgtggggcc caacgcgccc ggatcgcccg aacgctgcgg
    601 ccggggcacg ctcaactacc cgcacctgct cgccgaggcg ctcaagctcg atctcgtcga
    661 tgcgacctgc agcggcgcga cgacccacca cgtgctgggc ccctggaacg aggttccccc
    721 tcagatcgac agcgtgaatg gcgacacccg cctcgtcacc ctgaccatcg gcggaaacga
    781 tgtgtcgttc gtcggcaaca tcttcgccgc cgcttgcgag aagatggcgt cgcccgatcc
    841 gcgctgcggc aagtggcggg agatcaccga ggaagagtgg caggccgacg aggagcggat
    901 gcgctccatc gtacgccaga tccacgcccg cgcgcctctc gcccgggtgg tggtggtcga
    961 ttacatcacg gtcctgccgc catcaggcac ttgcgctgcc atggcgattt cgccggaccg
   1021 gctggcccag agccgcagcg ccgcgaaacg gcttgcccgg attaccgcac gggtcgcgcg
   1081 agaagagggt gcatcgctgc tcaagttctc gcatatctcg cgccggcacc atccatgctc
   1141 tgccaagccc tggagcaacg gcctttccgc cccggccgac gacggcatcc cggtccatcc
   1201 gaaccggctc ggacatgctg aagcggcagg ggcgctggtc aagcttgtga aattgatgaa
   1261 gtagctactg cactgatttc aaatagtatt gcctgtcagc tttccagccc ggattgttgc
   1321 agcgcaacag aaacttgtcc gtaatggatt gatggttat gtcgctcgca aattgccgtc
   1381 gaagggaacg ggcgcgtcgc tcgttaacgt cctgggtgca gcagtgacgg agcgcgtgga
   1441 tgagtgatac tggcggtgtc atcggtgtac gcgccgccat tcccatgcct gtacgcgccg
//
```

*S. coelicolor\GDSx 268 aa*

-continued

SEQ ID No. 65
NP 625998.
```
     1 mrrfrlvgfl sslvlaagaa ltgaataqaa qpaaadgyva lgdsyssgvg agsyisssgd
    61 ckrstkahpy lwaaahspst fdftacsgar tgdvlsgqlg plssgtglvs isiggndagf
   121 adtmttcvlq sessclsria taeayvdstl pgkldgvysa isdkapnahv vvigyprfyk
   181 lgttciglse tkrtainkas dhlntvlaqr aaahgftfgd vrttftghel csgspwlhsv
   241 nwlnigesyh ptaagqsggy lpvlngaa
//
```

SEQ ID No. 66
```
     1 cccggcggcc cgtgcaggag cagcagccgg cccgcgatgt cctcgggcgt cgtcttcatc
    61 aggccgtcca tcgcgtcggc gaccggcgcc gtgtagttgg cccggacctc gtcccaggtg
   121 cccgcggcga tctggcgggt ggtgcggtgc gggccgcgcc gagggagac gtaccagaag
   181 cccatcgtca cgttctccgg ctgcggttcg ggctcgtccg ccgctccgtc cgtcgcctcg
   241 ccgagcacct tctcggcgag gtcggcgctg gtcgccgtca ccgtgacgtc ggcgccccgg
   301 ctccagcgcg agatcagcag cgtccagccg tcgccctccg ccagcgtcgc gctgcggtcg
   361 tcgtcgcggg cgatccgcag cacgcgcgcg ccgggcggca gcagcgtggc gccggaccgt
   421 acgcggtcga tgttcgccgc gtgcgagtac ggctgctcac ccgtggcgaa acgccgagg
   481 aacagcgcgt cgacgacgtc ggacggggag tcgctgtcgt ccacgttgag ccggatcggc
   541 agggcttcgt gcgggttcac ggacatgtcg ccatgatcgg caccccggcc gccgcgtgca
   601 cccgctttcc cggcacgca cgacagggc tttctcgccg tcttccgtcc gaacttgaac
   661 gagtgtcagc catttcttgg catggacact tccagtcaac gcgcgtagct gctaccacgg
   721 ttgtggcagc aatcctgcta agggaggttc catgagacgt ttccgacttg tcggcttcct
   781 gagttcgctc gtcctcgccg ccggcgccgc cctcaccggg gcagcgaccg cccaggcggc
   841 ccaacccgcc gccgccgacg gctatgtggc cctcggcgac tcctactcct ccggggtcgg
   901 agcgggcagc tacatcagct cgagcggcga ctgcaagcgc agcacgaagg cccatcccta
   961 cctgtgggcg gccgcccact cgccctccac gttcgacttc accgcctgtt ccggcgcccg
  1021 tacgggtgat gttctctccg gacagctcgg cccgctcagc tccggcaccg gcctcgtctc
  1081 gatcagcatc ggcggcaacg acgccggttt cgccgacacc atgacgacct gtgtgctcca
  1141 gtccgagagc tcctgcctgt cgcggatcgc caccgccgag cgtacgtcg actcgacgct
  1201 gccccggcaag ctcgacgcg tctactcgga aatcagcgac aaggcgccga acgcccacgt
  1261 cgtcgtcatc ggctacccgc gcttctacaa gctcggcacc acctgcatcg gcctgtccga
  1321 gaccaagcgg acggcgatca acaaggcctc cgaccacctc aacaccgtcc tcgcccagcg
  1381 cgccgccgcc cacggcttca ccttcggcga cgtacgcacc accttcaccg gccacgagct
  1441 gtgctccggc agcccctggc tgcacagcgt caactggctg aacatcggcg agtcgtacca
  1501 ccccaccgcg gccggccagt ccggtggcta cctgccggtc ctcaacggcg ccgcctgacc
  1561 tcaggcggaa ggagaagaag aaggagcgga gggagacgag gagtgggagg ccccgcccga
  1621 cggggtcccc gtccccgtct ccgtctccgt cccggtcccg caagtcaccg agaacgccac
  1681 cgcgtcggac gtggcccgca ccggactccg cacctccacg cgcacggcac tctcgaacgc
  1741 gccggtgtcg tcgtgcgtcg tcaccaccac gccgtcctgg cgcgagcgct cgccgcccga
  1801 cgggaaggac agcgtccgcc acccggatc ggagaccgac ccgtccgcgg tcacccaccg
  1861 gtagccgacc tccgcgggca gccgcccgac cgtgaacgtc gccgtgaacg cgggtgcccg
```

-continued

```
1921 gtcgtgcggc ggcggacagg ccccgagta gtgggtgcgc gagcccacca cggtcacctc
1981 caccgactgc gctgcgggc
```

//

S. avermitilis\GDSx 269 aa

SEQ ID No. 67
NP 827753.

```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
```

//

SEQ ID No. 68

```
   1 ccaccgccgg gtcggcggcg agtctcctgg cctcggtcgc ggagaggttg gccgtgtagc
  61 cgttcagcgc ggcgccgaac gtcttcttca ccgtgccgcc gtactcgttg atcaggccct
 121 tgcccttgct cgacgcggcc ttgaagccgg tgcccttctt gagcgtgacg atgtagctgc
 181 ccttgatcgc ggtgggggag ccggcggcga gcaccgtgcc ctcggccggg gtggcctggg
 241 cgggcagtgc ggtgaatccg cccacgaggg cgccggtcgc cacggcggtt atcgcggcga
 301 tccggatctt cttgctacgc agctgtgcca tacgagggag tcctcctctg ggcagcggcg
 361 cgcctgggtg gggcgcacgg ctgtgggggg tgcgcgcgtc atcacgcaca cggccctgga
 421 gcgtcgtgtt ccgccctggg ttgagtaaag cctcggccat ctacggggt ggctcaaggg
 481 agttgagacc ctgtcatgag tctgacatga gcacgcaatc aacggggccg tgagcacccc
 541 ggggcgaccc cggaaagtgc cgagaagtct tggcatggac acttcctgtc aacacgcgta
 601 gctggtacga cggttacggc agagatcctg ctaaaggag gttccatgag acgttcccga
 661 attacggcat acgtgacctc actcctcctc gccgtcggct cgccctcac cggggcagcg
 721 acggcgcagg cgtccccagc cgccgcggcc acgggctatg tggccctcgg cgactcgtac
 781 tcgtccggtg tcggcgccgg cagctacctc agctccagcg gcgactgcaa gcgcagttcg
 841 aaggcctatc cgtacctctg caggccgcg cattcaccct cgtcgttcag tttcatggct
 901 tgctcgggcg ctcgtacggg tgatgtcctg gccaatcagc tcggcaccct gaactcgtcc
 961 accggcctgg tctccctcac catcggaggc aacgacgcgg gcttctccga cgtcatgacg
1021 acctgtgtgc tccagtccga cagcgcctgc ctctcccgca tcaacacggc gaaggcgtac
1081 gtcgactcca ccctgcccgg ccaactcgac agcgtgtaca cggcgatcag cacgaaggcc
1141 ccgtcggccc atgtggccgt gctgggctac ccccgcttct acaaactggg cggctcctgc
1201 ctcgcgggcc tctcggagac caagcggtcc gccatcaacg acgcggccga ctatctgaac
1261 agcgccatcg ccaagcgcgc cgccgaccac ggcttcacct cggcgacgt caagagcacc
1321 ttcaccggcc atgagatctg ctccagcagc acctggctgc acagtctcga cctgctgaac
1381 atcggccagt cctaccacc gaccgcggg ggccagtccg gcggctatct gccggtcatg
1441 aacagcgtgg cctgagctcc cacggcctga ttttttaagg cctgaatttt taaggcgaag
1501 gtgaaccgga agcggaggcc ccgtccgtcg gggtctccgt cgcacaggtc accgagaacg
1561 gcacggagtt ggacgtcgtg cgcaccgggt cgcgcacctc gacggcgatc tcgttcgaga
1621 tcgttccgct cgtgtcgtac gtggtgacga cacctgctt ctgctgggtc tttccgccgc
1681 tcgccgggaa ggacagcgtc ttccagcccg gatccgggac ctcgcccttc ttggtcaccc
```

-continued

```
1741 agcggtactc cacctcgacc ggcacccggc ccaccgtgaa ggtcgccgtg aacgtgggcg 1801 cctgggcggt gggcggcggg caggcaccgg agtagtcggt gtgcacgccg tgaccgtca 1861 ccttcacgga ctgggccggc ggggtcgtcg taccgccgcc gccaccgccg cctcccggag 1921 tggagcccga gctgtggtcg ccccgccgt cggcgttgtc gtcctcgggg gttttcgaac
```
//

*Streptomyces* diglyceride:glycerol acyltransferase

SEQ ID No. 69
ACAGGCCGATGCACGGAACCGTACCTTTCCGCAGTGAAGCGCTCTCCCCCCATCGTTCGC

CGGGACTTCATCCGCGATTTTGGCATGAACACTTCCTTCAACGCGCGTAGCTTGCTACAA

GTGCGGCAGCAGACCCGCTCGTTGGAGGCTCAGTGAGATTGACCCGATCCCTGTCGGCCG

CATCCGTCATCGTCTTCGCCCTGCTGCTCGCGCTGCTGGGCATCAGCCCGGCCCAGGCAG

CCGGCCCGGCCTATGTGGCCCTGGGGGATTCCTATTCCTCGGGCAACGGCGCCGGAAGTT

ACATCGATTCGAGCGGTGACTGTCACCGCAGCAACAACGCGTACCCCGCCCGCTGGGCGG

CGGCCAACGCACCGTCCTCCTTCACCTTCGCGGCCTGCTCGGGAGCGGTGACCACGGATG

TGATCAACAATCAGCTGGGCGCCCTCAACGCGTCCACCGGCCTGGTGAGCATCACCATCG

GCGGCAATGACGCGGGCTTCGCGGACGCGATGACCACCTGCGTCACCAGCTCGGACAGCA

CCTGCCTCAACCGGCTGGCCACCGCCACCAACTACATCAACACCACCCTGCTCGCCCGGC

TCGACGCGGTCTACAGCCAGATCAAGGCCCGTGCCCCCAACGCCCGCGTGGTCGTCCTCG

GCTACCCGCGCATGTACCTGGCCTCGAACCCCTGGTACTGCCTGGGCCTGAGCAACACCA

AGCGCGCGGCCATCAACACCACCGCCGACACCCTCAACTCGGTGATCTCCTCCCGGGCCA

CCGCCCACGGATTCCGATTCGGCGATGTCCGCCCGACCTTCAACAACCACGAACTGTTCT

TCGGCAACGACTGGCTGCACTCACTCACCCTGCCGGTGTGGGAGTCGTACCACCCCACCA

GCACGGGCCATCAGAGCGGCTATCTGCCGGTCCTCAACGCCAACAGCTCGACCTGATCAA

CGCACGGCCGTGCCCGCCCCGCGCGTCACGCTCGGCGCGGGCGCCGCAGCGCGTTGATCA

GCCCACAGTGCCGGTGACGGTCCCACCGTCACGGTCGAGGGTGTACGTCACGGTGGCGCC

GCTCCAGAAGTGGAACGTCAGCAGGACCGTGGAGCCGTCCCTGACCTCGTCGAAGAACTC

CGGGGTCAGCGTGATCACCCCTCCCCCGTAGCCGGGGGCGAAGGCGGCGCCGAACTCCTT

GTAGGACGTCCAGTCGTGCGGCCCGGCGTTGCCACCGTCCGCGTAGACCGCTTCCATGGT

CGCCAGCCGGTCCCCGCGGAACTCGGTGGGGATGTCCGTGCCCAAGGTGGTCCCGGTGGT

GTCCGAGAGCACCGGGGGCTCGTACCGGATGATGTGCAGATCCAAAGAATT

*Streptomyces* diglyceride:glycerol acyltransferase

SEQ ID No. 70
MRLTRSLSAASVIVFALLLALLGISPAQAAGPAYVALGDSYSSGNGAGSYIDSSGDCHRSN

NAYPARWAAANAPSSFTFAACSGAVTTDVINNQLGALNASTGLVSITIGGNDAGFADAMTT

CVTSSDSTCLNRLATATNYINTTLLARLDAVYSQIKARAPNARVVVLGYPRMYLASNPWYC

LGLSNTKRAAINTTADTLNSVISSRATAHGFRFGDVRPTFNNHELFFGNDWLHSLTLPVWE

SYHPTSTGHQSGYLPVLNANSST

Identification of a Diglyceride:Glycerol Acyltransferase According To the Present Invention Assay for Enzymatic Reduction of Diglyceride in Palm Oil.

1 gram of palm oil containing 7% diglyceride is scaled in a glass with lid.

50 mg glycerol and 10 µl enzyme solution is added. The reaction mixture is agitated with a magnetic stirrer in a heating chamber at 40° C. for 20 hours. The enzyme reaction is stopped by heating to 100° C. for 10 minutes. A reference sample added 10 µl water instead of enzyme solution is treated in the same way. The samples are analysed by GLC according to standard procedures (see hereinbelow) and the amount of fatty acids, monoglyceride and diglyceride are calculated.

Calculation:

From the results of the GLC analyses the increase in free fatty acids and the decrease in diglycerides can be calculated:

$\Delta$ % fatty acid=% Fatty acid(enzyme)–% fatty acid (control);

Mv Fa=average molecular weight of the fatty acids;

$\Delta$ % diglyceride=% Diglyceride(control)–% Diglyceride(enzyme);

Mv Di=average molecular weight of diglyceride;

The transferase activity is calculated as a percentage of the total enzymatic activity:

$$\% \text{ transferase activity} = \frac{((\Delta\%Di/(MvDi) - \Delta\%Fa/(MvFA)) \times 100}{\Delta\%Di/(MvDi)}$$

GLC Analysis

Perkin Elmer Autosystem 9000 Capillary Gas Chromatograph equipped with WCOT fused silica column 12.5 m×0.25 mm ID×0.1µ film thickness 5% phenyl-methyl-silicone (CP Sil 8 CB from Chrompack).

Carrier gas: Helium.

Injector. PSSI cold split injection (initial temp 50° C. heated to 385° C.), volume 1.0 µl Detector FID: 395° C.

| Oven program: | 1 | 2 | 3 |
|---|---|---|---|
| Oven temperature, ° C. | 90 | 280 | 350 |
| Isothermal, time, min. | 1 | 0 | 10 |
| Temperature rate, ° C./min. |  | 15 | 4 |

Sample preparation: 30 mg of sample was dissolved in 9 ml Heptane:Pyridin, 2:1 containing internal standard heptadecane, 0.5 mg/ml. 300 µl sample solution was transferred to a crimp vial, 300 µl MSTFA (N-Methyl-N-trimethylsilyl-trifluoraceamid) was added and reacted for 20 minutes at 60° C.

Isolated

In one aspect, preferably the polypeptide or protein for use in the present invention is in an isolated form. The term "isolated" means that the sequence is at least substantially free from at least one other component with which the sequence is naturally associated in nature and as found in nature.

Purified

In one aspect, preferably the polypeptide or protein for use in the present invention is in a purified form. The term "purified" means that the sequence is in a relatively pure state— e.g. at least about 51% pure, or at least about 75%, or at least about 80%, or at least about 90%, or at least about 95% pure or at least about 98% pure.

Cloning a Nucleotide Sequence Encoding a Polypeptide According to The Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labelled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers N H et al (1980) Nuc Acids Res Symp Ser 215-23 and Horn T et al (1980) Nuc Acids Res Symp Ser 225-232).

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characterisitics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate.

As will be apparent to a person skilled in the art, using molecular evolution tools an enzyme may be altered to improve the functionality of the enzyme.

Suitably, the lipid acyltransferase used in the invention may be a variant, i.e. may contain at least one amino acid substitution, deletion or addition, when compared to a parental enzyme. Variant enzymes retain at least 20%, 30%, 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipid acyltransferase enzyme retains or incorporates at least one or more of the pfam00657 consensus sequence amino acid residues found in the GDSx, GANDY and HPT blocks.

Enzymes, such as lipases with no or low lipid acyltransferase activity in an aqueous environment may be mutated using molecular evolution tools to introduce or enhance the transferase activity, thereby producing a lipid acyltransferase enzyme with significant transferase activity suitable for use in the compositions and methods of the present invention.

Suitably, the lipid acyltransferase for use in the invention may be a variant with enhanced enzyme activity on polar lipids, preferably phospholipids and/or glycolipids when compared to the parent enzyme. Preferably, such variants also have low or no activity on lyso polar lipids. The enhanced activity on polar lipids, phospholipids and/or glycolipids may be the result of hydrolysis and/or transferase activity or a combination of both.

Variant lipid acyltransferases for use in the invention may have decreased activity on triglycerides, and/or monoglycerides and/or diglycerides compared with the parent enzyme.

Suitably the variant enzyme may have no activity on triglycerides and/or monoglycerides and/or diglycerides.

Alternatively, the variant enzyme for use in the invention may have increased activity on triglycerides, and/or may also have increased activity on one or more of the following, polar lipids, phospholipids, lecithin, phosphatidylcholine, glycolipids, digalactosyl monoglyceride, monogalactosyl monoglyceride.

Variants of lipid acyltransferases are known, and one or more of such variants may be suitable for use in the methods and uses according to the present invention and/or in the enzyme compositions according to the present invention. By way of example only, variants of lipid acyltransferases are described in the following references may be used in accordance with the present invention: Hilton & Buckley J. Biol. Chem. 1991 Jan. 15: 266 (2): 997-1000; Robertson et al J. Biol. Chem. 1994 Jan. 21; 269(3): 2146-50; Brumlik et al J. Bacteriol 1996 April; 178 (7): 2060-4; Peelman et al Protein Sci. 1998 March; 7(3): 587-99.

Amino Acid Sequences

The present invention also encompasses amino acid sequences of polypeptides having the specific properties as defined herein.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen.

135 µl of water and 5 µg of endoproteinase Lys-C in 5 µl of water may be added to the above reaction mixture and the digestion may be carried out at 37° C. under nitrogen for 24 hours.

The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software that can perform sequence comparisons include, but are not limited to, the BLAST package (see Ausubel et al 1999 Short Protocols in Molecular Biology, 4$^{th}$ Ed—Chapter 18), FASTA (Altschul et al 1990 J. Mol. Biol. 403-410) and the GENEWORKS suite of comparison tools. Both BLAST and FASTA are available for offline and online searching (see Ausubel et al 1999, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses sequences that are complementary to sequences that are capable of hybridising under high stringency conditions or intermediate stringency conditions to nucleotide sequences encoding polypeptides having the specific properties as defined herein.

More preferably, the present invention encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated in the genome of the organism. The term "incorporated" preferably covers stable incorporation into the genome.

The nucleotide sequence of the present invention or coding for a polypeptide having the specific properties as defined herein may be present in a vector, in which the nucleotide sequence is operably linked to regulatory sequences such that the regulatory sequences are capable of providing the expression of the nucleotide sequence by a suitable host organism, i.e. the vector is an expression vector.

The vectors of the present invention may be transformed into a suitable host cell as described below to provide for expression of a polypeptide having the specific properties as defined herein.

The choice of vector, e.g. plasmid, cosmid, virus or phage vector, will often depend on the host cell into which it is to be introduced.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

Thus, in a further embodiment, the invention provides a method of making nucleotide sequences of the present invention or nucleotide sequences encoding polypeptides having the specific properties as defined herein by introducing a nucleotide sequence into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, a nucleotide sequence for use in the present invention or a nucleotide sequence encoding a polypeptide having the specific properties as defined herein may be operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of heterologous regulatory regions, e.g. promoter, secretion leader and terminator regions.

Preferably, the nucleotide sequence of the present invention may be operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Host Cells

The term "host cell"—in relation to the present invention includes any cell that comprises either a nucleotide sequence encoding a polypeptide having the specific properties as defined herein or an expression vector as described above and which is used in the recombinant production of a polypeptide having the specific properties as defined herein.

Thus, a further embodiment of the present invention provides host cells transformed or transfected with a nucleotide sequence of the present invention or a nucleotide sequence that expresses a polypeptide having the specific properties as defined herein. The cells will be chosen to be compatible with the said vector and may for example be prokaryotic (for example bacterial), fungal, yeast or plant cells. Preferably, the host cells are not human cells.

Examples of suitable bacterial host organisms are gram negative bacterium or gram positive bacteria.

Depending on the nature of the nucleotide sequence encoding a polypeptide having the specific properties as defined herein, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells, such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

Organism

The term "organism" in relation to the present invention includes any organism that could comprise a nucleotide sequence according to the present invention or a nucleotide sequence encoding for a polypeptide having the specific properties as defined herein and/or products obtained therefrom.

Suitable organisms may include a prokaryote, fungus, yeast or a plant.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42: 205-225) and Christou (Agro-Food-Industry Hi-Tech Mar./Apr. 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus:* 50 years on. Progress in industrial microbiology vol 29. Elsevier Amsterdam 1994. pp. 641-666).

Gene expression in filamentous fungi has been reviewed in Punt et al. (2002) Trends Biotechnol 2002 May; 20(5): 200-6, Archer & Peberdy Crit Rev Biotechnol (1997) 17(4): 273-306.

Transformed Yeast

In another embodiment, the transgenic organism can be a yeast.

A review of the principles of heterologous gene expression in yeast are provided in, for example, *Methods Mol Biol* (1995), 49: 341-54, and *Curr Opin Biotechnol* (1997) October; 8(5): 554-60.

In this regard, yeast—such as the species *Saccharomyces cerevisi* or *Pichia pastoris* (see FEMS Microbiol Rev (2000 24(1): 45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

A suitable yeast host organism can be selected from the biotechnologically relevant yeasts species such as, but not limited to, yeast species selected from *Pichia* spp., *Hansenula* spp., *Kluyveromyces, Yarrowinia* spp., *Saccharomyces* spp., including *S. cerevisiae*, or *Schizosaccharomyce* spp. including *Schizosaccharomyce pombe*.

A strain of the methylotrophic yeast species *Pichia pastoris* may be used as the host organism.

In one embodiment, the host organism may be a *Hansenula* species, such as *H. polymorpha* (as described in WO01/39544).

Transformed Plants/Plant Cells

A host organism suitable for the present invention may be a plant. A review of the general techniques may be found in articles by Potrykus (*Annu Rev Plant Physiol Plant Mol Biol* [1991] 42: 205-225) and Christou (Agro-Food-Industry Hi-Tech Mar./Apr. 1994 17-27), or in WO01/16308. The transgenic plant may produce enhanced levels of phytosterol esters and phytostanol esters, for example.

Therefore the present invention also relates to a method for the production of a transgenic plant with enhanced levels of phytosterol esters and phytostanol esters, comprising the steps of transforming a plant cell with a lipid acyltransferase as defined herein (in particular with an expression vector or construct comprising a lipid acyltransferase as defined herein), and growing a plant from the transformed plant cell.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the α-factor gene (yeasts e.g. *Saccharomyces, Kluyveromyces* and *Hansenula*) or the α-amylase gene (*Bacillus*).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; US-A-3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

Fusion Proteins

A polypeptide having the specific properties as defined herein may be produced as a fusion protein, for example to aid in extraction and purification thereof. Examples of fusion protein partners include glutathione-S-transferase (GST), 6×His (SEQ ID NO: 19), GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. Coli* have been reviewed in Curr. Opin. Biotechnol. (1995) 6(5): 501-6.

In another embodiment of the invention, the amino acid sequence of a polypeptide having the specific properties as defined herein may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

The invention will now be described, by way of example only, with reference to the following Figures and Examples.

FIG. 1 shows a pfam00657 consensus sequence from database version 6 (SEQ ID No. 1);

FIG. 2 shows an amino acid sequence (SEQ ID No. 2) obtained from the organism *Aeromonas hydrophila* (P10480; GI:121051);

FIG. 3 shows an amino acid sequence (SEQ ID No. 3) obtained from the organism *Aeromonas salmonicida* (AAG098404; GI:9964017);

FIG. 4 shows an amino acid sequence (SEQ ID No. 4) obtained from the organism *Streptomyces coelicolor* A3(2) (Genbank accession number NP_631558);

FIG. 5 shows an amino acid sequence (SEQ ID No. 5) obtained from the organism *Streptomyces coelicolor* A3(2) (Genbank accession number: CAC42140);

FIG. 6 shows an amino acid sequence (SEQ ID No. 6) obtained from the organism *Saccharomyces cerevisiae* (Genbank accession number P41734);

Figure 35:
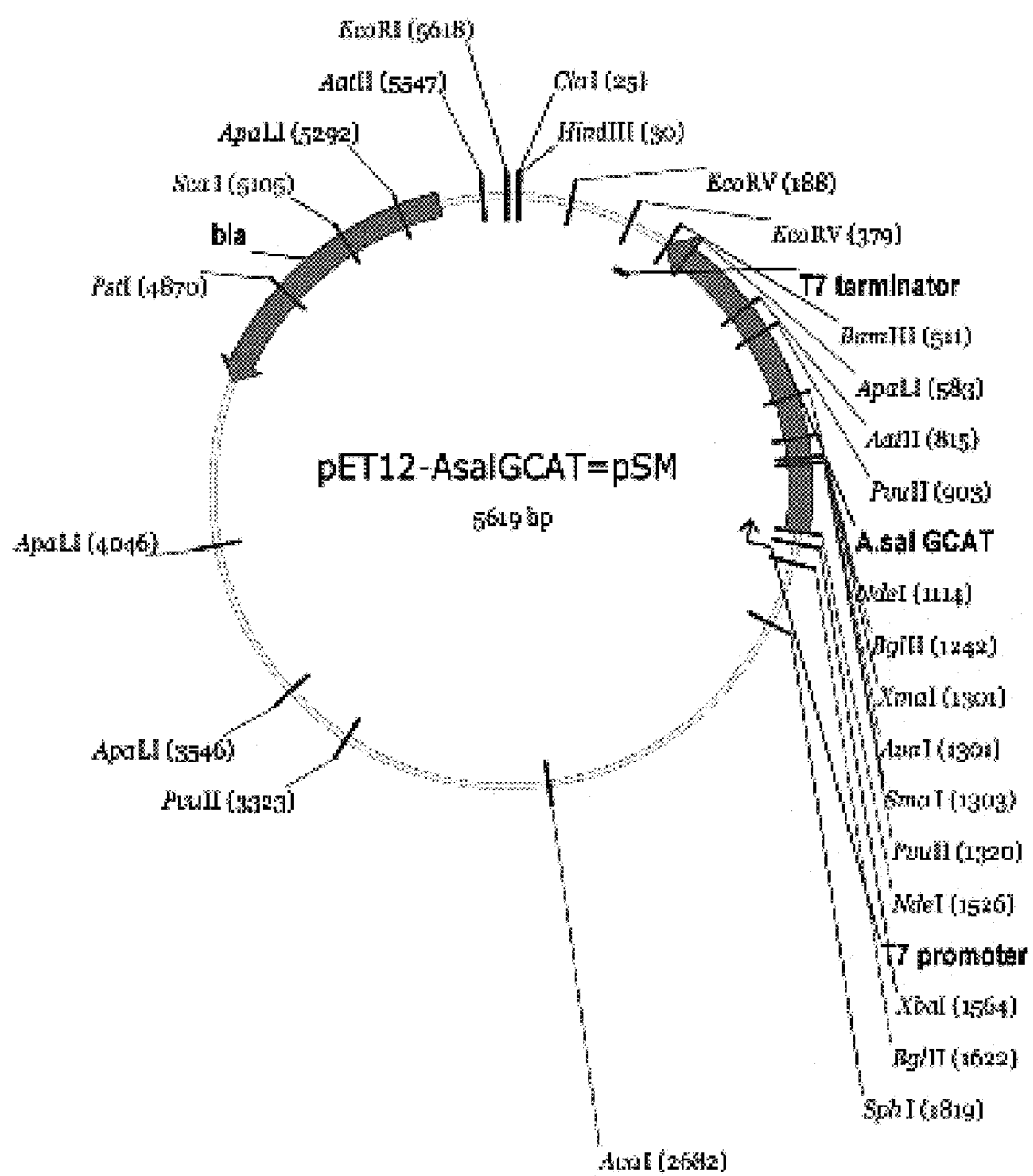

FIG. 7 shows an alignment of selected sequences (residues 28-322 of SEQ ID NO: 2, residues 28-322 of SEQ ID NO: 3, residues 42-288 of SEQ ID NO: 4, residues 42-288 of SEQ ID NO: 5, and residues 6-203 of SEQ ID NO: 6) to pfam00657 consensus sequence (SEQ ID NO: 1);

FIG. 8 shows a pairwise alignment of residues 1-335 of SEQ ID No. 3 with SEQ ID No. 2 showing 93% amino acid sequence identity. The signal sequence is underlined. + denotes differences. The GDSX motif containing the active site serine 16, and the active sites aspartic acid 116 and histidine 291 are highlighted (see shaded regions). Numbers after the amino acid is minus the signal sequence;

FIG. 9 shows a nucleotide sequence (SEQ ID No. 7) encoding a lipid acyl transferase according to the present invention obtained from the organism *Aeromonas hydrophila*;

FIG. 10 shows a nucleotide sequence (SEQ ID No. 8) encoding a lipid acyl transferase according to the present invention obtained from the organism *Aeromonas salmonicida*;

FIG. 11 shows a nucleotide sequence (SEQ ID No. 9) encoding a lipid acyl transferase according to the present invention obtained from the organism *Streptomyces coelicolor* A3(2) (Genbank accession number NC_003888.1: 8327480 . . . 8328367);

FIG. 12 shows a nucleotide sequence (SEQ ID No. 10) encoding a lipid acyl transferase according to the present invention obtained from the organism *Streptomyces coelicolor* A3(2) (Genbank accession number AL939131.1: 265480 . . . 266367);

FIG. 13 shows a nucleotide sequence (SEQ ID No. 11) encoding a lipid acyl transferase according to the present invention obtained from the organism *Saccharomyces cerevisiae* (Genbank accession number Z75034);

FIG. 14 shows an amino acid sequence (SEQ ID No. 12) obtained from the organism *Ralstonia* (Genbank accession number: AL646052);

FIG. 15 shows a nucleotide sequence (SEQ ID No. 13) encoding a lipid acyl transferase according to the present invention obtained from the organism *Ralstonia*;

FIG. 16 shows SEQ ID No. 20. Scoe1 NCBI protein accession code CAB39707.1 GI:4539178 conserved hypothetical protein [*Streptomyces coelicolor* A3(2)];

FIG. 17 shows a nucleotide sequence shown as SEQ ID No. 21 encoding NCBI protein accession code CAB39707.1 GI:4539178 conserved hypothetical protein [*Streptomyces coelicolor* A3(2)];

FIG. 18 shows an amino acid shown as SEQ ID No. 22. Scoe2 NCBI protein accession code CAC01477.1 GI:9716139 conserved hypothetical protein [*Streptomyces coelicolor* A3(2)];

FIG. 19 shows a nucleotide sequence shown as SEQ ID No. 23 encoding Scoe2 NCBI protein accession code CAC01477.1 GI:9716139 conserved hypothetical protein [*Streptomyces coelicolor* A3(2)];

FIG. 20 shows an amino acid sequence (SEQ ID No. 24) Scoe3 NCBI protein accession code CAB88833.1 GI:7635996 putative secreted protein. [*Streptomyces coelicolor* A3(2)];

FIG. 21 shows a nucleotide sequence shown as SEQ ID No. 25 encoding Scoe3 NCBI protein accession code CAB88833.1 GI:7635996 putative secreted protein. [*Streptomyces coelicolor* A3(2)];

FIG. 22 shows an amino acid sequence (SEQ ID No. 26) Scoe4 NCBI protein accession code CAB89450.1 GI:7672261 putative secreted protein. [*Streptomyces coelicolor* A3(2)];

FIG. 23 shows an nucleotide sequence shown as SEQ ID No. 27 encoding Scoe4 NCBI protein accession code CAB89450.1 GI:7672261 putative secreted protein. [*Streptomyces coelicolor* A3(2)];

FIG. 24 shows an amino acid sequence (SEQ ID No. 28) Scoe5 NCBI protein accession code CAB62724.1 GI:6562793 putative lipoprotein [*Streptomyces coelicolor* A3(2)];

FIG. 25 shows a nucleotide sequence shown as SEQ ID No. 29, encoding Scoe5 NCBI protein accession code CAB62724.1 GI:6562793 putative lipoprotein [*Streptomyces coelicolor* A3(2)];

FIG. 26 shows an amino acid sequence (SEQ ID No.30) Srim1 NCBI protein accession code AAK84028.1 GI:15082088 GDSL-lipase [Streptomyces rimosus] (GDSL peptide disclosed as SEQ ID NO: 18);

FIG. 27 shows a nucleotide sequence shown as SEQ ID No. 31 encoding Srim1 NCBI protein accession code AAK84028.1 GI: 15082088 GDSL-lipase [Streptomyces rimosus] (GDSL peptide disclosed as SEQ ID NO: 18);

FIG. 28 shows an amino acid sequence (SEQ ID No. 32) A lipid acyl transferase from *Aeromonas hydrophila* (ATCC # 7965);

FIG. 29 shows a nucleotide sequence (SEQ ID No. 33) encoding a lipid acyltransferase from *Aeromonas hydrophila* (ATCC #7965);

FIG. 30 shows an amino acid sequence (SEQ ID No. 34) of a lipid acyltransferase from *Aeromonas salmonicida* subsp. *Salmonicida* (ATCC#14174);

FIG. 31 shows a nucleotide sequence (SEQ ID No 35) encoding a lipid acyltransferase from *Aeromonas salmonicida* subsp. *Salmonicida* (ATCC#14174);

FIG. 32 shows that homologues of the Aeromonas genes can be identified using the basic local alignment search tool service at the National Center for Biotechnology Information, NIH, MD, USA and the completed genome databases. The GDSX motif was used in the database search and a number of sequences/genes potentially encoding enzymes with lipolytic activity were identified. Genes were identified from the genus *Streptomyces, Xanthomonas* and *Ralstonia*. As an example below, the *Raistonia solanacearum* (residues 28-347 of SEQ ID NO: 12) was aligned to the *Aeromonas salmonicida* (satA) gene (SEQ ID NO: 14). Pairwise alignment showed 23% identity. The active site serine is present at the amino terminus and the catalytic residues histidine and aspartic acid can be identified;

FIG. 33 shows the Pfam00657.11 [family 00657, database version 11] consensus sequence (SEQ ID NO: 15) (hereafter called Pfam consensus) and the alignment of various sequences (residues 38-263 of SEQ ID NO: 30, residues 5-186 of SEQ ID NO: 20, residues 10-188 of SEQ ID NO: 22, residues 239-441 of SEQ ID NO: 24, residues 75-262 of SEQ ID NO: 26, residues 66-296 of SEQ ID NO: 28, residues 28-322 of SEQ ID NO: 2, residues 28-322 of SEQ ID NO: 3, and residues 28-322 of SEQ ID NO: 32, respectively in order of appearance) to the Pfam consensus sequence. The arrows indicate the active site residues, the underlined boxes indicate three of the homology boxes indicated by [Upton C and Buckley JT (1995) Trends Biochem Sci 20; 179-179]. Capital letters in the Pfam consensus indicate conserved residues in many family members. The—symbol indicates a position where the hidden Markov model of the Pfam consensus expected to find a residue but did not, so a gap is inserted. The . symbol indicates a residue without a corresponding residue in the Pfam consensus. The sequences are the amino acid sequences listed in FIGS. 16, 18, 20, 22, 24, 26, 28 and 30.

FIG. 34 shows the Pfam00657. 11 [family 00657, database version 11] consensus sequence (SEQ ID NO: 15) (hereafter called Pfam consensus) and the alignment of various sequences (residues 38-263 of SEQ ID NO: 30, residues 5-186 of SEQ ID NO: 20, residues 10-188 of SEQ ID NO: 22, residues 239-441 of SEQ ID NO: 24, residues 75-262 of SEQ ID NO: 26, residues 66-296 of SEQ ID NO: 28, residues 28-322 of SEQ ID NO: 2, residues 28-322 of SEQ ID NO: 3, and residues 28-322 of SEQ ID NO: 32, respectively in order of appearance) to the Pfam consensus sequence. The arrows indicate the active site residues, the underlined boxes indicate three of the homology boxes indicated by [Upton C and Buckley JT (1995) Trends Biochem Sci 20; 179-179]. Capital letters in the Pfam consensus indicate conserved residues in many family members. The—symbol indicates a position where the hidden Markov model of the Pfam consensus expected to find a residue but did not, so a gap is inserted. The . symbol indicates a residue without a corresponding residue in the Pfam consensus. The sequences are the amino acid sequences listed in FIGS. 2, 16, 18, 20, 26, 28 and 30. All these proteins were found to be active against lipid substrates.

Figure 36:
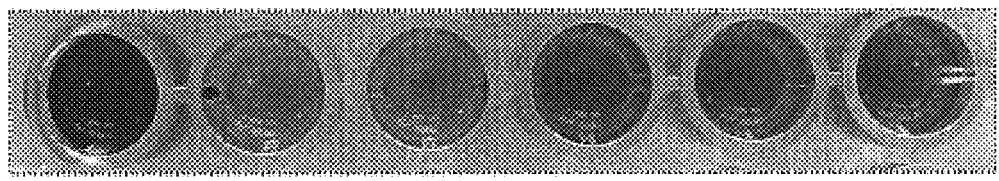
Figure 37:
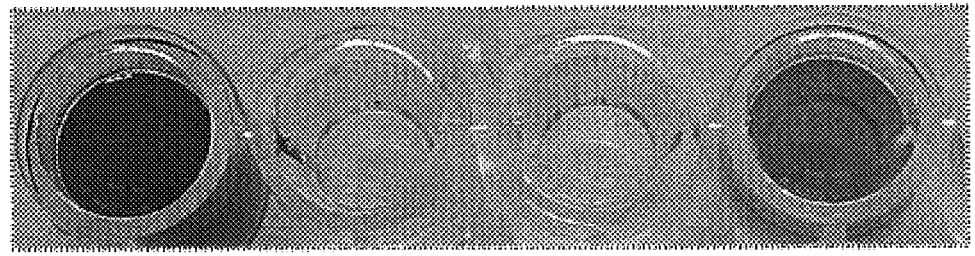
Figure 38:
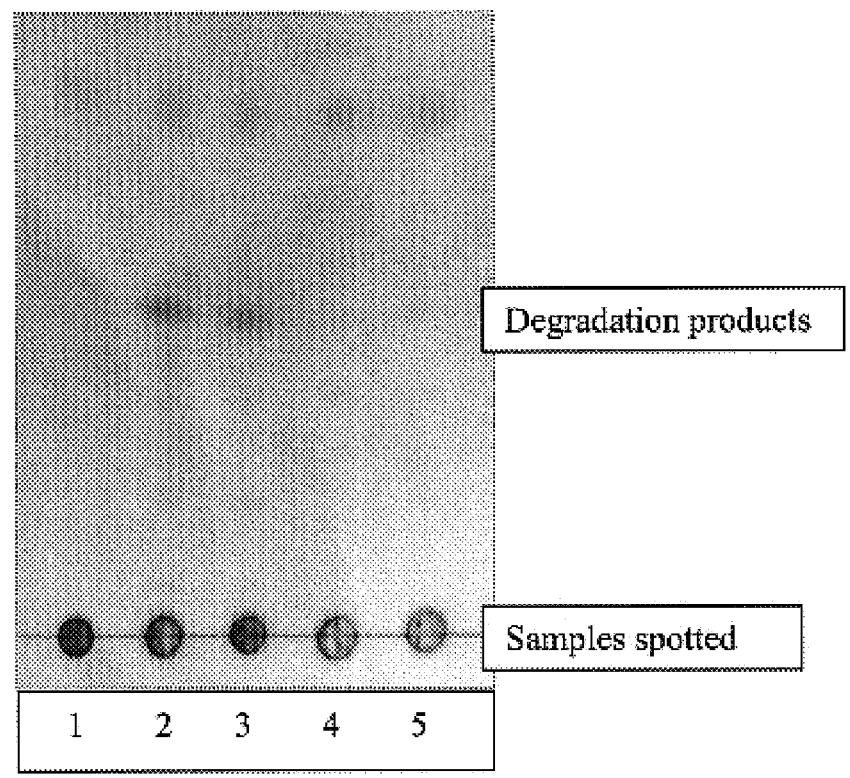
Figure 39:
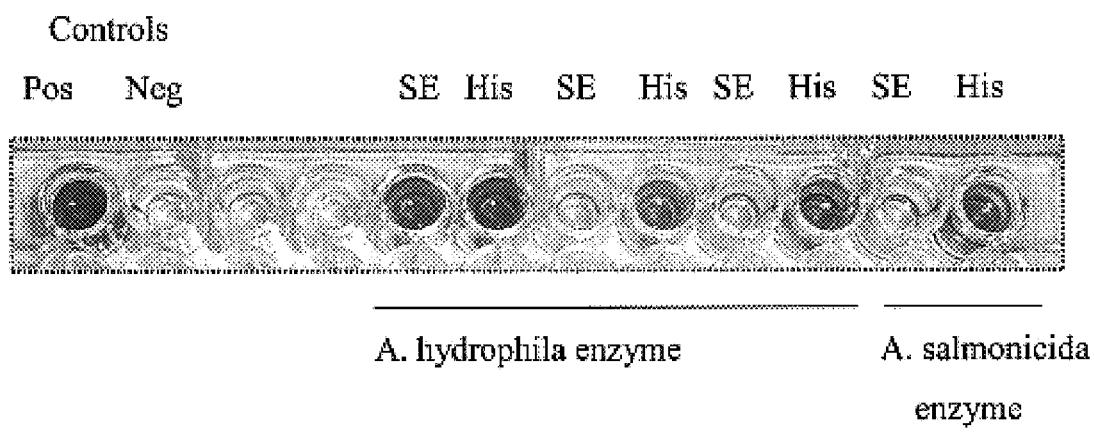
Figure 40:
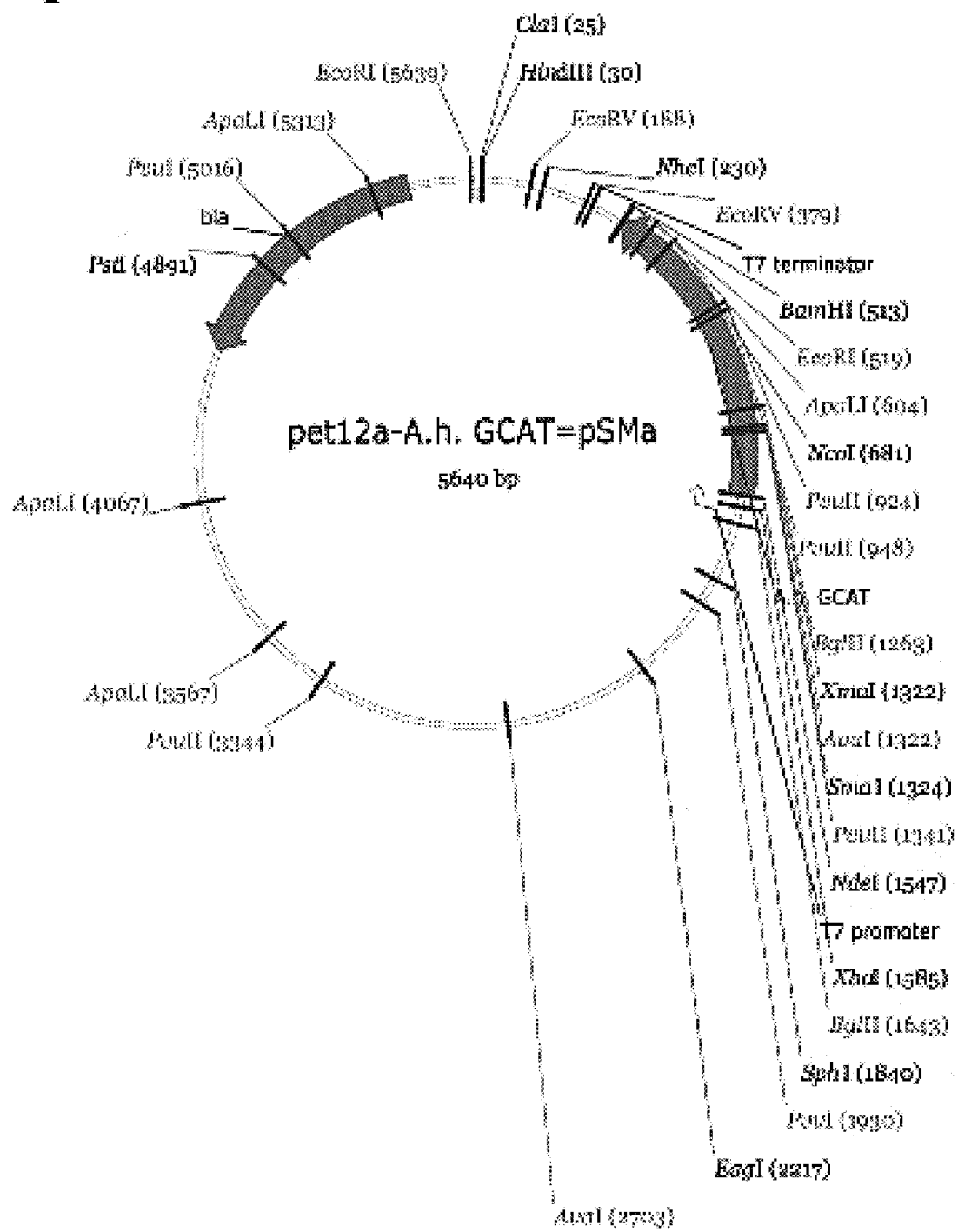
Figure 41:
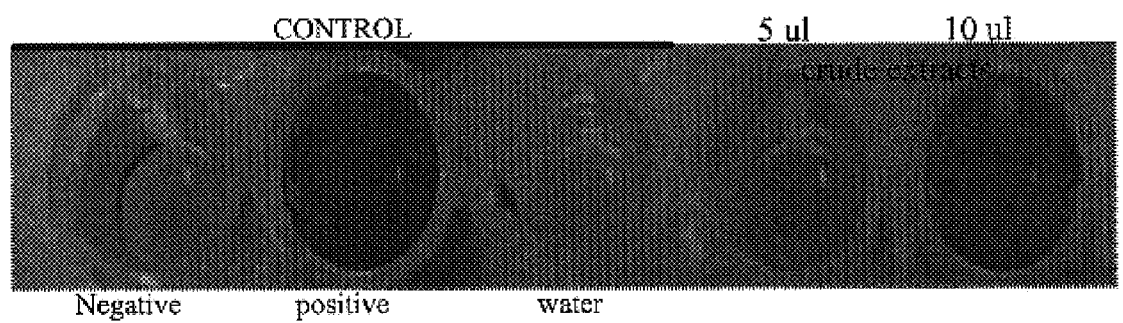
Figure 42:
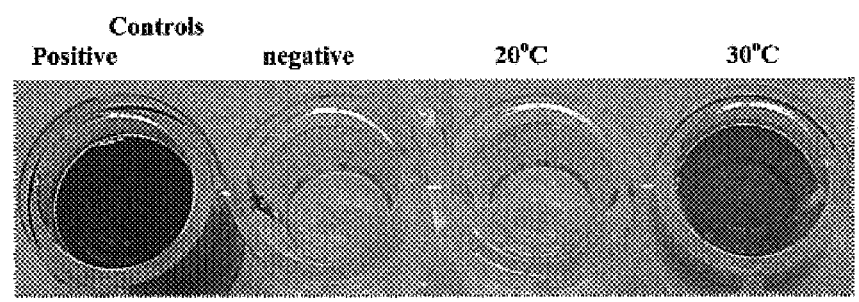
Figure 43:
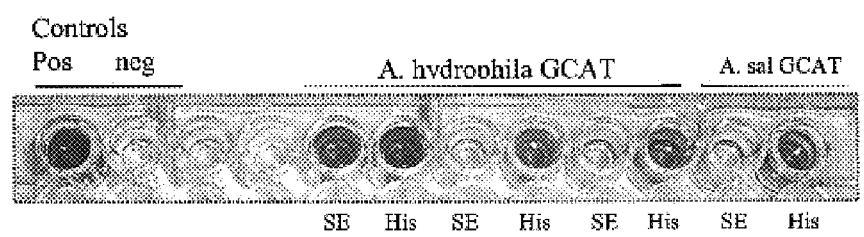
Figure 44:
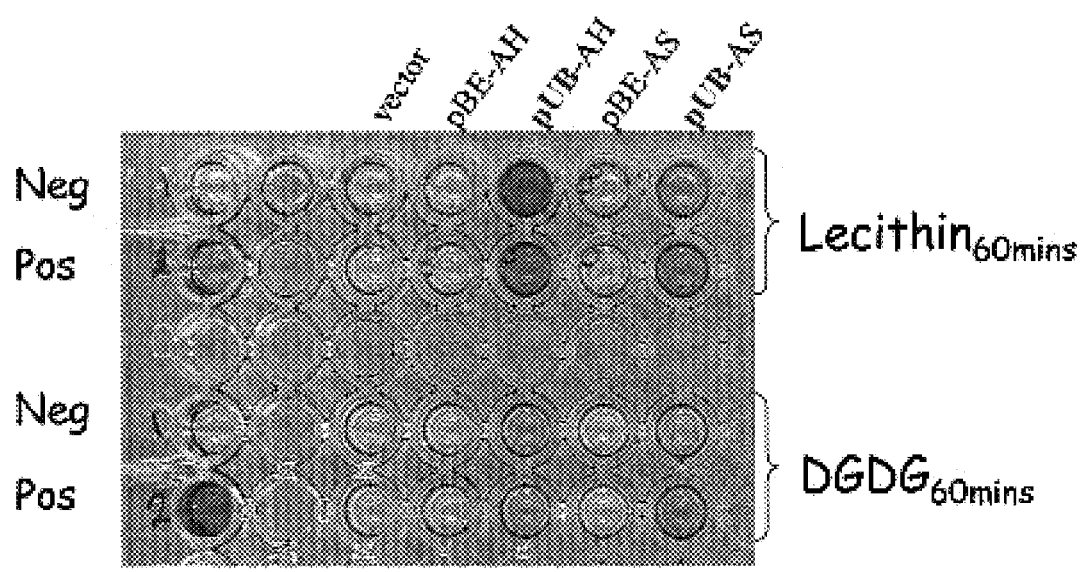

FIG. 35 shows a expression vector pet12-AsalGCAT=pSM containing the C-terminal His-tagged *Aeromonas salmonicida* lipid acyltransferase gene;

FIG. 36 shows the results of testing cell extracts in a NEFA Kit Assay, which depicts the activity of a recombinant, *A. salmonicida* lipid acyltransferase, towards lecithin. The wells from left to right indicate: a positive control, a negative control (i.e. extracts from empty plasmid) and samples collected after 0, 1, 2 and 3 hours cultivation after IPTG induction;

FIG. 37 shows growth optimisation of BL21(DE3)pLysS harboring the expression vector pet12-AsalGCAT=pSM showing cultivation at 30° C. resulted in the production of enzyme with high activity towards lecithin. Cell extracts were tested for phospholipase activity using the NEFA kit assay. Wells from left to right: positive control; negative control; 20° C.; 30° C.;

FIG. 38 shows crude cell extracts from BL21(DE3)pLysS expressing active lipid acyltransferase incubated with the substrate lecithin and reaction mixture was analyzed using thin layer chromatography showing the presence of degradation products. Lanes: 1. No enzyme; 2. +A.sal −10 ul 37° C.; 3. +A. sal −20 ul 37° C.; 4. +A.sal −10 ul 24° C.; 5. +A. sal −20 u 24° C.;

FIG. 39 shows partial purification of the *Aeromonas salmonicida* Acyl Transferase showing the phospholipase activity associated with purified His-tag protein. SE=Sonicated extracts, His=Purified with Ni-NTA spin-kit from Qiagen;

FIG. 40 shows the expression vector pet12-A.h. GCAT=pSMa containing the C-terminal His-tagged *Aeromonas hydrophila* Glycerolipid Acyl Transferase (GCAT) gene was used to transform *E. coli* strain BL21(DE3)pLysS;

FIG. 41 shows the activity of the crude extracts (5 & 10 ul) containing the recombinant *Aeromonas hydrophila* GCAT enzyme was tested towards lecithin using Non-Esterified Fatty Acid (NEFA) kit (Roche, Switzerland), showing the presence of active enzyme towards the phospholipid, lecithin;

FIG. 42 shows growth optimisation of BL21(DE3)pLysS harboring the expression vector pet12-AsalGCAT=pSM showing cultivation at 30° C. resulted in the production of enzyme with high activity towards lecithin. Cell extracts were tested for phospholipase activity using the NEFA kit assay;

FIG. 43 shows the partial purification of the *Aeromonas hydrophila* & *A. salmonicida* Acyl Transferases showing the phospholipase activity associated with purified His-tag protein. SE=Sonicated extracts, His=Purified with Ni-NTA spin-kit from Qiagen);

FIG. 44 shows the expression of the *Aeromonas* genes in *Bacillus subtilis* 163 showing the production of secreted enzyme with activity towards both lecithin and DGDG. pUB-AH=construct containing the *A. hydrophila* gene and pUB-AS, construct with the *A. salmonicida* gene, Culture filtrate was incubated with the substrates for 60 minutes.

Figure 47:
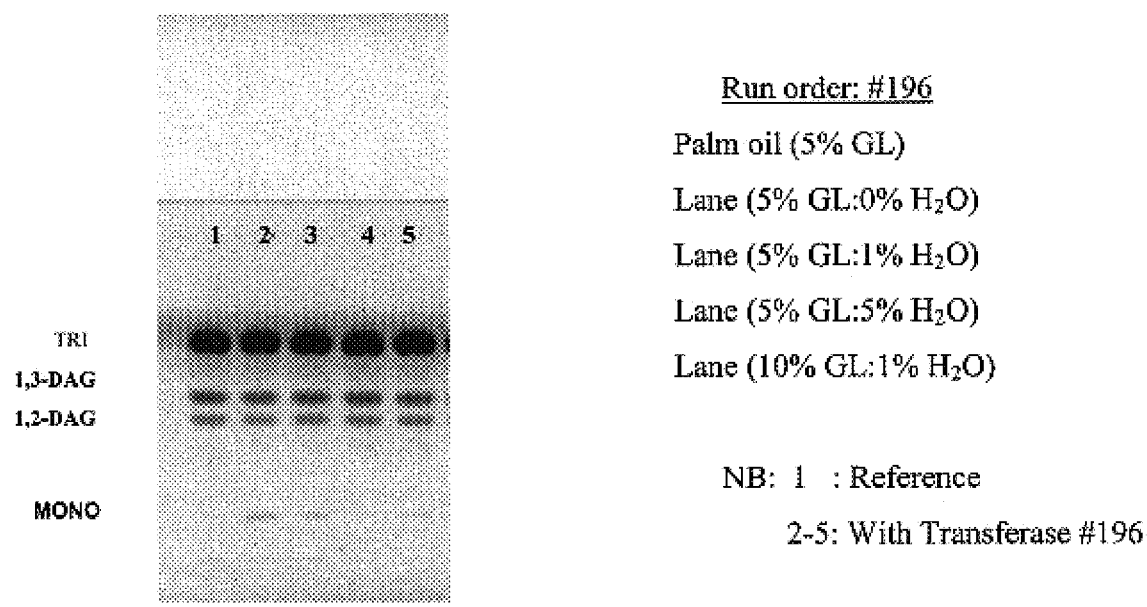
Figure 48:
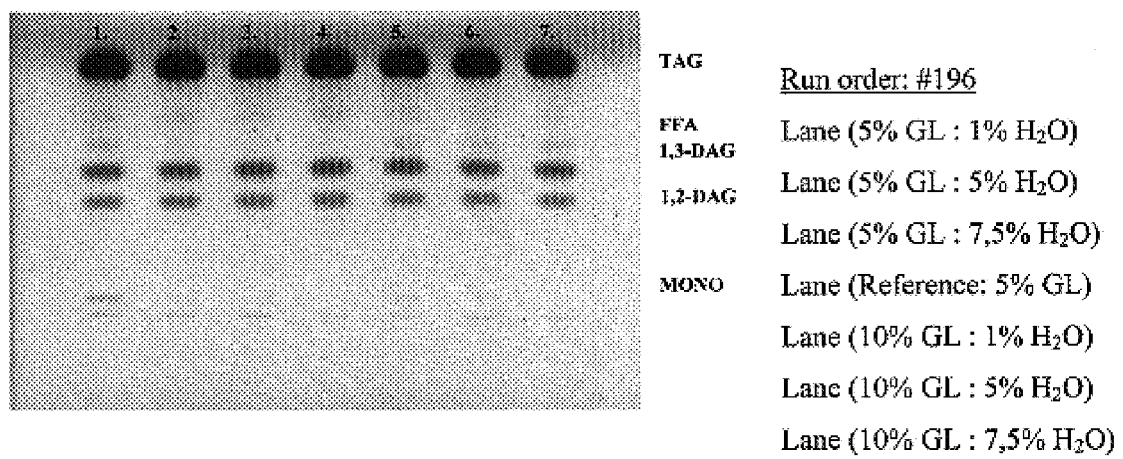
Figure 49:
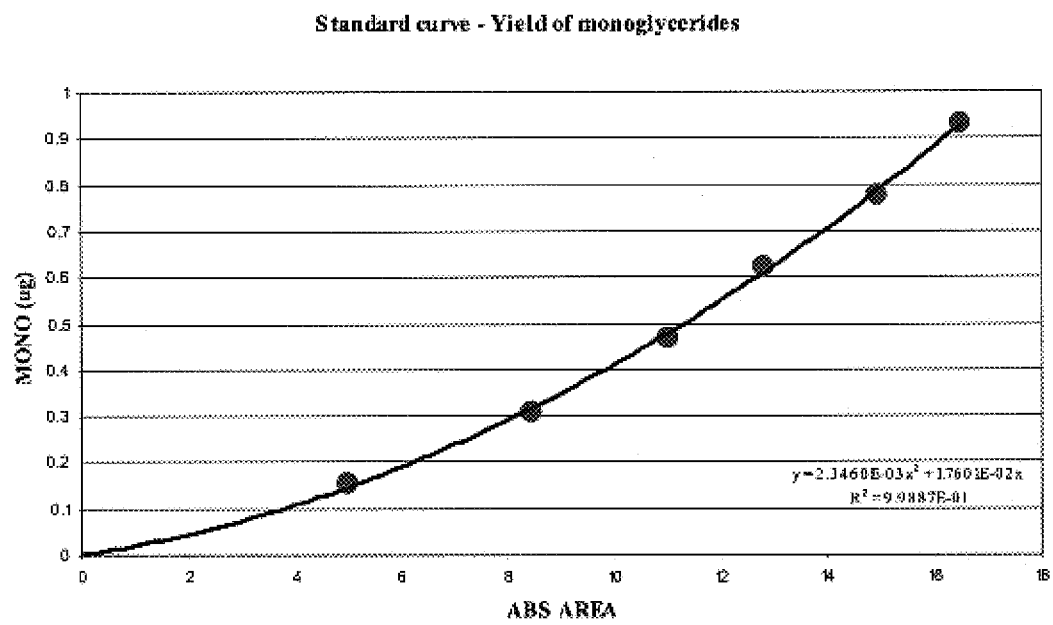
Figure 50:
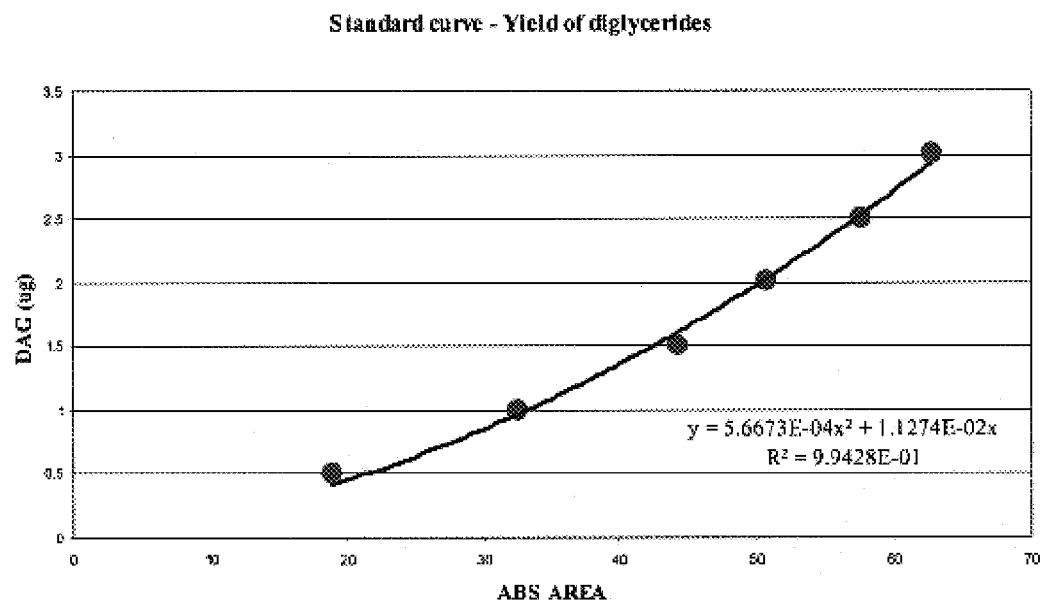

FIG. 45 shows an amino acid sequence (SEQ ID No. 36) of the fusion construct used for mutagenesis of the *Aeromonas hydrophila* lipid acyltransferase gene in Example 17. The underlined amino acids is a xylanase signal peptide;

FIG. 46 shows a nucleotide sequence (SEQ ID No. 45) encoding an enzyme from *Aeromonas hydrophila* including a xylanase signal peptide;

FIG. 47 shows the result of the HPTLC analysis in Experiment I;

FIG. 48 shows the result of the HPTLC analysis in Experiment II;

FIG. 49 shows a calibration curve for monoglyceride standard solutions;

FIG. 50 shows a calibration curve for diglyceride standard solutions.

FIG. 51 shows a nucleotide sequence encoding a lipid acyltransferase enzyme according to the present invention from *Streptomyces* (SEQ ID No. 54);

FIG. 52 shows a polypeptide sequence of a lipid acyltransferase enzyme according to the present invention from *Streptomyces* (SEQ ID No. 55);

EXAMPLES

For the avoidance of doubt, the following abbreviations may be used herein:
MONO=monoglyceride
MAG=monoacylglycerol=monoglyceride
MAG and MONO are interchangeable herein.
DAG=diacylglycerol
FFA=free fatty acid Example 1

The Cloning, Sequencing and Heterologous Expression of a Transferase from *Aeromonas salmonicida* Subsp. *Salmonicida*

Strains used:

*Aeromonas salmonicida* subsp. *Salmonicida* (ATCC 14174) was obtained from ATCC and grown overnight at 30° C. in Luria-Bertani medium (LB). The cells were centrifuged and genomic DNA was isolated using the procedures for genomic DNA isolation from Qiagen Ltd. Genomic DNA buffer set (cat. 19060), protease K (cat. 19131) and RNAse A (cat. 19101) were all obtained from Qiagen Ltd. (Boundary court Gatwick Court, West Sussex, RH10 2AX).

Host bacterial strain BL21(DE3)pLysS (Novagen) was used for production of the recombinant *Aeromonas* enzymes. Competent cells of BL21(DE3)pLysS were used as host for transformation with the expression vector pet12-AsalGCAT=pSM. Transformants containing the appropriate plasmid were grown at 37° C. in LB agar medium containing 100-ug ampicillin/ml.

Construction of Expression Vector pet12-AsalGCAT-pSM:

For all DNA amplifications of the transferase genes from *Aeromonas*, genomic DNA (0.2-1 ul) was used as template and pfu DNA polymerase (2.5 units) was used with 10 ul of 10×pfu buffer, 1 ul each primer (50 pmol/ul), 200 uM dNTP in a total reaction volume of 100 ul. PCR reactions were performed in a programmable thermal cycler using the following conditions: 95° C. for 30 seconds, 30 cycles of 95° C. for 30 seconds, 60° C. for 1 minute and 68° C. for 2 minutes. An additional extension of 5 minutes at 72° C. was applied.

The PCR amplification of the transferase gene from *A. salmonicida* was carried in 2 separate PCR reactions. PCR reaction 1 was performed using primer pairs, as1USNEW (5'AGCATATGAAAA AATGGTTTGT TTGTTTATTG GGG 3' [SEQ ID No. 56]) and as1s950new (5' GTG ATG GTG GGC GAG GAA CTC GTA CTG3' [SEQ ID No. 37]). A second PCR reaction was performed to incorporate a C-terminal Histidine tag using the PCR product from the first reaction and the primers: as1USNEW(5'AGCATATGAAAA AATGGTTTGT TTGTTTATTG GGG 3' [SEQ ID No. 38]) and AHLS1001 (5'TTGGATCC GAATTCAT CAATG GTG ATG GTG ATG GTG GGC3' [SEQ ID No. 39]). The PCR product from the second reaction was purified and digested with restriction enzymes Nde1 and BamHI. 2 ug of pET 12a vector DNA was also digested with restriction enzymes Nde1 and BamHI and treated with phosphatase. The restriction enzyme-treated pet12a and PCR product from reaction 2 were purified and ligated using the Rapid Ligation Kit (Roche, Switzerland). The ligation mix was used to transform *E. coli* TOP10 cells. Transformants were plated on LB agar medium containing 100 ug/ml ampicillin.

The T7 promoter primer (5'TAATACGACTCACTATAG3' [SEQ ID No. 40]) and the T7 terminator primer (5'CTAGT-TATTGCTCAGCGG3' [SEQ ID No. 41]) were used to verify the sequences and the orientation of the cloned transferase genes in pET12a vector. DNA sequencing was performed using ABI Prism® BigDye™ Terminators Cycle sequencing kit with 500 ng plasmid DNA as template and 3.2 pmol T7 promoter and terminator primers.

The construct shown in FIG. 35 was used to transform competent bacterial host strain BL21(DE3)pLysS (Novagen) and ampicillin resistant transformants were picked and used for expression analysis.

Expression of the Recombinant *Aeromonas salmonicida* Lipid Acyltransferase

Quantification of enzyme activity towards lecithin was determined on cell extracts using Non-Esterified Fatty Acid (NEFA) kit (Roche, Switzerland).

In FIG. 36, BL21(DE3)pLysS harboring the expression vector pet12-AsalGCAT=pSM was grown in LB medium+ 100 ug/ml ampicillin and incubated with shaking at 37° C. until $OD_{600}$=0.6 to 1.0 is reached. The cultures are then induced using IPTG (0.4 mM) and incubation was continued for the next 3 hours. Samples where taken at 0 hour, 1, 2, and 3 hours after IPTG induction. Enzyme Activity was tested using the NEFA kit and lecithin as substrate.

Growth Optimisation for the Production of More Active Enzymes

BL21(DE3)pLysS harboring the expression vector pet12-AsalGCAT=pSM was grown in LB medium+100 ug/ml ampicillin and incubated with shaking at different growth temperatures (37° C., 30° C., & 20° C.). The optimal condition for the production of active lipid acyltransferase enzyme was when cultures are grown at 30° C. as shown in FIG. 37.

Partial Purification of Recombinant *Aeromonas salmonicida* Transferase

Strain BL21(DE3)pLysS harboring the expression vector pet12-AsalGCAT=pSM was grown at 37° C. & crude cell extracts were prepared by sonication. The recombinant enzyme was further purified from the sonicated crude cell extracts using the Ni-NTA spin kit from Qiagen. Phospholipase activity using the NEFA kit & Lecithin as substrate. Crude cell extracts from BL21(DE3)pLysS expressing active transferase incubated with the substrate lecithin and reaction mixture was analysed using thin layer chromatography showing the presence of degradation products (see FIG. 38).

Partial Purification of recombinant *Aeromonas salmonicidae* transferase. Strain BL21(DE3)pLysS harbouring the expression vector pet12-AsalGCAT=pSM was grown at 37° C. and crude cell extracts were prepared by sonication. The recombinant enzyme ware further purified from the sonicated crude cell extract using the Ni-NTA spin kit from Qiagen. Phospholipase activity using the NEFA kit and lecithin as substrate was tested (see FIG. 39).

Example 2

Cloning and Expression of *Aeromonas hydrophila* Transferase in *E. coli*

*Aeromonas hydrophila* (ATCC # 7965) was obtained from ATCC and grown overnight at 30° C. in Luria-Bertani medium (LB). The cells were centrifuged and genomic DNA was isolated using the procedures for genomic DNA isolation from Qiagen Ltd. Genomic DNA buffer set (cat. 19060), protease K (cat. 19131) and RNAse A (cat. 19101) were all obtained from Qiagen Ltd. (Boundary court Gatwick Court, West Sussex, RH10 2AX).

Host bacterial strain BL21(DE3)pLysS (Novagen) was used for production of the recombinant *Aeromonas* enzymes. Competent cells of BL21(DE3)pLysS were used as host for transformation with the expression vector pet12a-A.h.GCAT=pSMa. Transformants containing the appropriate plasmid were grown at 37° C. in LB agar medium containing 100-ug ampicillin/ml.

Construction of Expression Vector pet12a-A.h.GCAT-pSMa:

For all DNA amplifications of the transferase gene from *Aeromonas*, genomic DNA (0.2-1 ul) was used as template and pfu DNA polymerase (2.5 units) was used with 10 ul of 10×pfu buffer, 1 ul each primer (50 pmol/ul), 200 uMdNTP in a total reaction volume of 100 ul. PCR reactions were performed in a programmable thermal cycler using the following conditions: 95° C. for 30 seconds, 30 cycles of 95° C. for 30 seconds, 60° C. for 1 minute and 68° C. for 2 minutes. An additional extension of 5 minutes at 72° C. was applied.

The PCR amplification of the transferase gene from *A. hydrophila* (ATCC # 7965) was carried out in 2 separate PCR reactions.

PCR reaction 1 was performed using primer pairs, AHUS1 (5'GTCATATGAAAAAATGGTTTGTGTGTT-TATTGGGATTGGTC3', SEQ ID No. 42) and ahls950 (5'ATGGTGATGGTGGGCGAGGAACTCGTACTG3', SEQ ID No. 43).

A second PCR reaction was performed to incorporate a C-terminal Histidine tag using the PCR product from the first reaction and the primer pairs:

AHUS1(5'GTCATATGAAAAAATGGTTTGTGTGTT-TATTGGG ATTGGTC3'SEQ ID No. 44,) And AHLS1001 (5'TTGGATCCGAATTCATCAATGGTGATGGTGATGG TGGGC3'SEQ ID No. 57).

The PCR product from the second reaction was purified and digested with restriction enzymes Nde1 and BamHI. 2 ug of pET 12a vector DNA was also digested with restriction enzymes Nde1 and BamHI and treated with phosphatase. The restriction enzyme-treated pet12a and PCR product from reaction 2 were purified and ligated using the Rapid Ligation Kit (Roche, Switzerland). The ligation mix was used to transform *E. coli* TOP10 cells. Transformants were plated on LB agar medium containing 100 ug/ml ampicillin.

The T7promoter primer (5'TAATACGACTCACTATAG3') (SEQ ID NO: 16) and the T7terminator primer (5'CTAGT-TATTGCTCAGCGG3') (SEQ ID NO: 17) were used to verify the sequences and the orientation of the cloned GCAT genes in pET 12a vector. DNA sequencing was performed using ABI Prism® BigDye™ Terminators Cycle sequencing kit with 500 ng plasmid DNA as template and 3.2 pmol T7 promoter and terminator primers.

The construct shown in FIG. 40 was used to transform competent bacterial host strain BL21 (DE3)pLysS (Novagen) and ampicillin resistant transformants were picked and used for expression analysis.

Expression of the *Aeromonas hydrophila* Transferase in BL21 (DE3)pLysS

The *E. coli* strain BL21(DE3)pLysS harboring the expression vector pet12a-A.h.GCAT=pSMa was grown in LB medium+100 ug/ml ampicillin and incubated with shaking at 37° C. until $OD_{600}$=0.6 to 1.0 is reached. The cultures are then induced using IPTG (0.4 mM) and incubation was continued for the next 3 hours. Samples where taken at 0 hour, 1, 2, and 3 hours after IPTG induction. Enzyme Activity was tested using the NEFA kit and lecithin as substrate (FIG. 41).

Growth Optimisation for the Production of More Active Enzymes

BL21(DE3)pLysS harboring the expression vector pet12a-A.h.GCAT=pSMa was grown in LB medium+100 ug/ml ampicillin and incubated with shaking at different growth temperatures (37° C., 30° C., & 20° C.). The optimal condition for the production of active GCAT enzyme was when cultures are grown at 30° C. as shown in FIG. 42.

Partial Purification of Recombinant *A. hydrophila* Transferase (GCAT)

Strain BL21(DE3)pLysS harboring the expression vector pet12a-A.h.GCAT=pSMa was grown at 37° C. & crude cell extracts were prepared by sonication. The recombinant enzyme was further purified from the sonicated crude cell extracts using the Ni-NTA spin kit from Qiagen. Phospholipase activity assay using the NEFA kit & Lecithin as substrate. (FIG. 43).

EXAMPLE 3

Expression of *Aeromonas* transferases in *Bacillus subtilis* 163

Plasmid Construction

Two different *Bacillus subtilis* expression vectors (pUB 110 & pBE5) were used for the heterologous expression of the *Aeromonas* genes in *Bacillus subtilis*. The pUB 110 vector contains the alpha amylase promoter while the pBE vector has the P32 promoter as the regulatory region for the expression of the fused *Aeromonas* genes. In pUB110, the first amino acid of the mature GCAT genes of *Aeromonas* were fused in frame with the last amino acid of the xylanase signal peptide sequence from *Bacillus subtilis* via the restriction site Nhe1, creating an additional 2 amino acids in front of the mature proteins. pBE5 contains the cgtase signal sequence fusion at the Nco1 site for secretion of the recombinant proteins into the culture filtrate.

PCR reactions were carried out to obtain the *Aeromonas* genes fuse in frame to the signal sequences of the pUB 110 and the pBE5 vectors. PCRs were performed using the following primer pairs for *A. hydrophila* gene:

PCR reaction 1: usAHncol (5'ATGCCATGGCCGA-CAGCCGTCCCGCC3', SEQ ID No. 46) and IsAH (5'TTG-GATCCGAATTCATCAATGGTGATG3', SEQ ID No. 47)

PCR reaction 2: US-AhnheI (5'TTGCTAGCGCCGA-CAGCCGTCCCGCC3', SEQ ID No. 48.) and IsAH (5'TTG-GATCCGAATTCATCAATGGTGATG3, SEQ ID No. 49)

PCRs were performed using the following primer pairs for *A. salmonicida* gene:

PCR reaction 3: US-Asncol (5'TTGCCATGGCCGA-CACTCGCCCCGCC3', SEQ ID No. 50) and lsAH (5'TTG-GATCCGAATTCATCAATGGTGATG3', SEQ ID No. 51)

PCR reaction 4: US-ASnhel (5'TTGCTAGCGCCGA-CACTCGCCCCGCC3', SEQ ID No. 52) and lsAH (5'TTG-GATCCGAATTCATCAATGGTGATG3', SEQ ID No. 53).

All the PCR products were cloned into PCR blunt II (TOPO vector) and sequenced with reverse & forward sequencing primers.

Clones from PCR reactions 1 & 3 were cut with Nco1 & Bam HI and used as inserts for ligation to the pBE5 vector cut with Nco1/BamH1/phosphatase. Clones from PCR reactions 2 & 4 were cut with Nhe1 & Bam H1 and used as inserts for ligation to the pUB vector that was cut with Nhe1/BamH1/phosphatase.

Expression of the *Aeromonas* transferase genes in *Bacillus subtilis* and characterization of the enzyme activity.

The acyl transferases from the two *Aeromonas* species have been successfully expressed in *E. coli* (results above). The *Bacillus* pUB110 & pBE5 gene fusion constructs were used to transform *Bacillus subtilis* and transformants were selected by plating on kanamycin plates. The kanamycin resistant transformants isolated and grown in 2xYT are capable of heterologous expression of the *Aeromonas* genes in *Bacillus*. The culture filtrates have digalactosyldiacylglycerol (DGDG) galactolipase activity, in addition to having both acyl transferase and phospholipase activities. The activity towards digalactosvldiacylgycerol (DGDG) was measured after 60 minutes of incubation of culture supernatant with the substrate. DGDG from wheat flour (obtainable form Sigma) as well as the activity towards lecithin as shown in FIG. 44. *Bacillus* produced the enzyme after overnight (20-24 hours) to 48 hours of cultivation in the culture medium as a secreted protein. In some instances, the expression of the *Aeromonas* genes has been shown to interfere with cell viability and growth in *Bacillus* & *E. coli*, it is therefore necessary to carefully select expression strains and optimise the growth conditions to ensure expression. For example, several *Bacillus* host strains (B.s 163, DB104 and OS 21) were transformed with the expression vectors for growth comparison. B.s163 is transformable with the 2 *Aeromonas* genes and is capable of expressing active protein. DB104 is transformable with all the constructs but is only able to express *A. salmonicida* transferase.

EXAMPLE 4

Fermentation and Purification of *Aeromonas* Lipid Acyltransferases Produced in *E. coli*

E. coli Fermentations:

Microorganisms

Two strains of *Eschericia coli*, one containing an *Aeromonas hydrophila* (Example 2) lipid acyltransferase and two containing *Aeromonas salmonicida* lipid acyltransferases, (Example 1) were used in this study.

The *E. coli* strain containing the *A. hydrophila* gene was named DIDK0124, and the *E. coli* strain containing the *A. salmonicida* gene was named DIDK0125. The fermentation with DIDK0124 was named HYDRO0303 and the fermentation with DIDK0125 was named SAL0302. The purified protein from HYDRO025 was named REF#138. The purified protein from HYDRO0303 was named REF#135.

Growth Media and Culture Conditions

LB-Agar

The LB agar plates used for maintaining the strains contained: 10 g/L tryptone, 5 g/L yeast extract, 5 g/L NaCl, 15 g/L agar, 100 mg/L ampicillin and 35 mg/L chloramphenicol. The agar plates were incubated at 30° C.

Lb Shake Flask

The LB medium (50 mL pr shake flask) used for production of inoculum material for the bioreactor cultivations contained: 10 g/L tryptone, 5 g/L yeast extract, 5 g/L NaCl, 100 mg/L ampicillin and 35 mg/L chloramphenicol. The shake flasks were inoculated from the LB agar plates, and incubated at 30° C. and 200 rpm.

Bioreactor Cultivation

The bioreactor cultivations were carried out in 6 L in-house built bioreactors filled with 4 L medium containing: 10 g/L tryptone, 5 g/L yeast extract, 5 g/L NaCl, 8 g/L $KH_2PO_4$, 0.9 g/L $MgSO_4$, $7H_2O$, 40 g/L glucose monohydrate, 0.4 mL/ADD APT® Foamstop Sin 260 (ADD APT Chemicals AG, Helmond, The Netherlands), 10 mg/L $(NH_4)_2Fe(SO_4)_2 \cdot 6H_2O$, 0.7 mg/L $CuSO_4.5H_2O$, 3 mg/L $ZnSO_4.7H_2O$, 3 mg/L $MnSO_4.H_2O$, 10 mg/L EDTA, 0.1 mg/L $NiSO_4.6H_2O$, 0.1 mg/L $CoCl_2$, 0.1 mg/L $H_3BO_4$, 0.1 mg/L KI, 0.1 mg/L $Na_2MoO_4.2H_2O$, 1 g/L ampicillin and 35 mg/L chloramphenicol.

The bioreactors were inoculated with an amount of LB culture ensuring end of growth after approximately 20 hours of cultivation (calculated from the maximum specific growth rate of 0.6 h$^{-1}$, the $OD_{600}$ of the LB shake flask and the final $OD_{600}$ in the bioreactor of approximately 20).

SAL0302 was inoculated with 10 mL of LB culture, and HYDRO0303 was inoculated with 4 mL of LB culture.

The bioreactors were operated at the following conditions: temperature 30° C., stirring 800-1000 rpm (depending on experiment), aeration 5 L/min, pH 6.9, pH control 8.75% (w/v) $NH_3$-water and 2 M $H_2SO_4$. Induction was achieved by addition of isopropyl β-D-thiogalactoside to a final concentration of 0.6 mM, when 0.4 moles (HYDRO0303) and 0.7 moles $CO_2$ was produced respectively.

Harvest

The following procedure was used for harvest and homogenisation of the biomass:
1) The fermentation broth from the fermentations was centrifuged at 5000×g and 4° C. for 10 minutes, and the supernatant was discharged. The biomass was stored at −20° C. until use. The biomass was thawed and resuspended in 500 mL of 20 mM $NaH_2PO_4$, pH 7.4, 500 mM NaCl, 10 mM Imidazole and Complete (EDTA-free) protease inhibitor (Roche, Germany).
2) The suspended biomass was homogenized at 2 kbar and 4° C. in a cell disrupter from Constant Systems Ltd (Warwick, UK).
3) The cell debris was removed by centrifugation at 10.000×g and 4° C. for 30 minutes followed by collection of the supernatant.
4) The supernatant was clarified further by centrifugation at 13.700×g and 4° C. for 60 minutes, followed by collection of the supernatant.
5) The supernatant was filtered through 0.2 μm Vacu Cap filters (Pall Life Sciences, UK) and the filtrate was collected for immediate chromatographic purification.

Chromatographic Purification of the Transferases

A column (2.5×10 cm) was packed with 50 ml of Chelating Sepharose ff. gel and charged with Ni-sulphate (according to the method described by manufacturer, Amersham Biosciences). The column was equilibrated with 200 ml of 20 mM $NaH_2PO_4$, pH 7.4, 500 mM NaCl, 10 mM Imidazole. 400 ml of crude was applied to the column at a flow rate of 5 ml/min. The column was then washed with 20 mM $NaH_2PO_4$, pH 7.4, 500 mM NaCl, 10 mM Imidazole until the $UV_{280}$ reached the base line. The GCAT was then eluted with 40 ml of 20 mM $NaH_2PO_4$, pH 7.4, 500 mM NaCl and 500 mM Imidazole.

EXAMPLE 5

Fermentation and Purification of *Aeromonas* Lipid Acyltransferases Produced in *Bacillus subtilis*

Fermentations
BAC0318-19, BAC0323-24

Microorganism

The microorganisms used in this study originate from transformation of a *Bacillus subtilis* host strain, #163 with a plasmid containing the gene encoding the *Aeromonas salmonicida* transferase inserted in the vector pUB110OIS. The expression of the gene is controlled by an alpha-amylase promoter, and the secretion of the transferase is mediated by the *B. subtilis* xylanase signal sequence (Example 3). The strains were named DIDK0138 (fermentation BAC0318-19) and DIDK0153 (fermentation BAC0323-24).

Growth Media and Culture Conditions

Pre Culture Medium

A shake flask (500 mL total volume, with baffles) was added 100 mL of a medium containing:

| | |
|---|---|
| NaCl | 5 g/L |
| $K_2HPO_4$ | 10 g/L |
| Soy flour | 20 g/L |
| Yeast extract, BioSpringer 106 | 20 g/L |
| Antifoam, SIN260 | 5 mL/L | pH was adjusted to 7.0 before autoclaving.

After autoclaving 6 mL 50% (w/w) Nutriose were added pr flask. Kanamycin was added at a concentration of 50 mg/L after autoclaving.

Inoculation

A pre culture shake flask was inoculated with frozen culture directly from a 25% (w/v) glycerol stock. The shake flask was incubated at 33° C. and 175 rpm for approximately 16 hours, whereupon 50 mL was used to inoculate the fermentor.

Fermentations

The fermentations were carried out in 6 L in house built fermentors.

The batch medium (3 L) contained:

| | |
|---|---|
| Corn steep liquor (50% dw) | 40 g/L |
| Yeast extract BioSpringer 153 (50% dw) | 10 g/L |
| NaCl | 5 g/L |
| $CaCl_2, 2H_2O$ | 0.25 g/L |
| $Mn(NO_3)_2, H_2O$ | 0.2 g/L |
| Antifoam SIN260 | 1 mL/L |
| Kanamycin (filter sterilised to the fermentor after autoclaving | 50 mg/L |

The feed contained:

| | |
|---|---|
| Glucose monohydrate | 540 g/kg |
| $MgSO_4, 7H_2O$ | 4.8 g/kg |
| Antofoam SIN260 | 4 mL/kg |
| Yeast extract, BioSpringer 153 (50% dw) | 150 g/kg (autoclaved separately) |

The feed in fermentation BAC0318 and BAC0323 was started based on the accumulated $CO_2$, according to the equations below:

Feed-flow[g/h]=0, $AcCO_2$<0.15

Feed-flow[g/h]=2.85+t·1.54, $AcCO_2 \geq 0.15$ and t<12

Feed-flow[g/h]=21.3, t>12 t: time (hours) from the point when the accumulated $CO_2$ ($AcCO_2$) reached 0.15 moles.

The feed in fermentation BAC0319 and BAC0324 was started based on the accumulated $CO_2$, according to the equations below:

Feed—flow[g/h]=0, AcCO$_2$<0.15

Feed—flow[g/h]=2.0+t·1.08, AcCO$_2$≧0.15 and t<12

Feed—flow[g/h]=15, t>12 t: time (hours) from the point when the accumulated CO$_2$ (AcCO$_2$) reached 0.15 moles.

The pH was controlled at 7.0 by adding 12.5% (w/v) NH$_3$-water or 2 M phosphoric acid.

The aeration was 3 L/min corresponding to 1 vvm.

The temperature was 33° C.

The fermentor was equipped with two 8 cm Ø Rushton impellers placed with a distance of 10 cm.

Harvest

The biomass was removed by centrifugation at 16,000×g for 10 minutes at room temperature. The supernatant was filter sterilized, and the filtrate was used for purification and application tests.

EXAMPLE 6

Enzymatic Removal of DAGs in Palm Oil Catalysed by a Lipid Acyltransferase from *Aeromonas salmonicidae*

SUMMARY

The enzymatic glycerolysis experiments were initiated by the addition of the glycerol/transferase solution to the reactor containing palm oil and glycerol/water in varying concentrations. All the reactions were conducted at 43° C., using magnetic stirring for 24 hours. After reaction, the samples were analyzed using HPTLC and in some experiments the result was confirmed by GC analysis. The conducted trials showed that there was a good correlation between the water concentration and levels of DAGs and MAGs, respectively: the lowest water concentrations tested gave the highest MAG level and the lowest DAG level.

Based on the trials, it can be concluded that it was possible to reduce the amount of DAGs in palm oil by a transferase-catalysed reaction where the enzyme used DAGs as donor molecules and glycerol as acceptor molecule—in a glycerolysis reaction in which monoglycerides were synthesized. This was in contrast to the glycerolysis reaction with conventional triglyceride hydrolyzing lipases where the amount of DAG increases.

Furthermore, it can be concluded that the water concentration has a significant impact on the synthesized yield of monoglycerides and amount of DAG. The following correlation was found: Low water concentration (<1%) and 5% glycerol gives increased MAG yield and decreased concentration of DAGs. The obtained results also show that primarily 1,2 isomer of diglyceride tend to be reduced.

It is known that diglycerides, especially 1,2 isomers delay the crystallization of fat. This effect causes post-crystallization of fat products like margarine and shortenings, which favors formation of large crystals (sandiness). In certain fat blends it was observed that diglycerides improve the stability of β' crystals. A reduction but not a complete removal of diglycerides in palm oil would therefore be preferable. It can thus be concluded that a reduction of diglyceride will result in a better and more uniform oil quality; a fact, which must not be underestimated.

Introduction

Problems concerning diglycerides depend to some extent on type of product, e.g. whether it is in margarine and shortenings. Thus, depending on the product the presence of diglycerides both have negative and positive effects. For margarine production, only fat product of a required crystal structure can be used in order to obtain proper consistency and plasticity. The β'-crystal form is the most required structure, showing small crystals and a high ability for maintaining the liquid fraction. The most stable crystal form (β-form) is undesirable, as having big crystals causes grained structure of the margarine. According to Hernquist & Anjou (1993) and Wahnelt et al. (1991) the presence of diglycerides in fat retard the transition from β' to β-crystal. But as diglycerides retard the transition from β' to β, they also retard the transition from α form to β' form (Walnet et al., 1991). For this reason it can be defined that the presence of diglycerides retards the whole crystallization process. Slow crystallization has a crucial impact on margarine application. The effect of retarding crystallization in margarine blends containing a high portion of palm oil is that after conventional processing the product may be somewhat soft, causing packing difficulties, and subsequent crystallization may lead to a firmer texture than desired (Berger, 1990). In spite of advantages and disadvantages, it may be important to find the right balance between reduced and total removal of diglycerides.

It has surprisingly been found that it is possible to reduce the amount of diglyceride in palm oil by enzymatic glycerolysis of palm oil using a lipid acyltransferase, for example the GDSx lipid acyl transferase from *Aeromonas salmonicida*. In this process the enzyme is added to palm oil together with small amount of glycerol and the enzyme catalyses the following reaction:

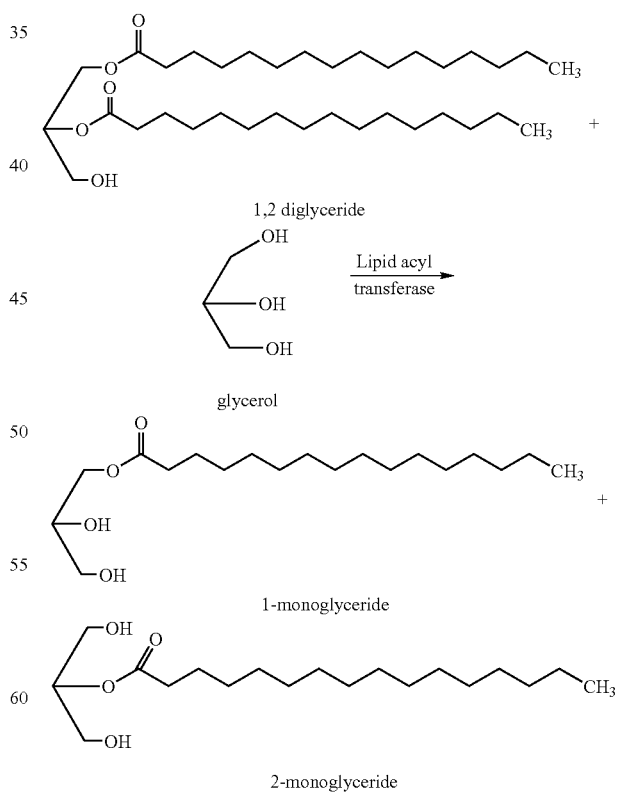

The enzyme according to the present invention may also catalyse the following reaction:

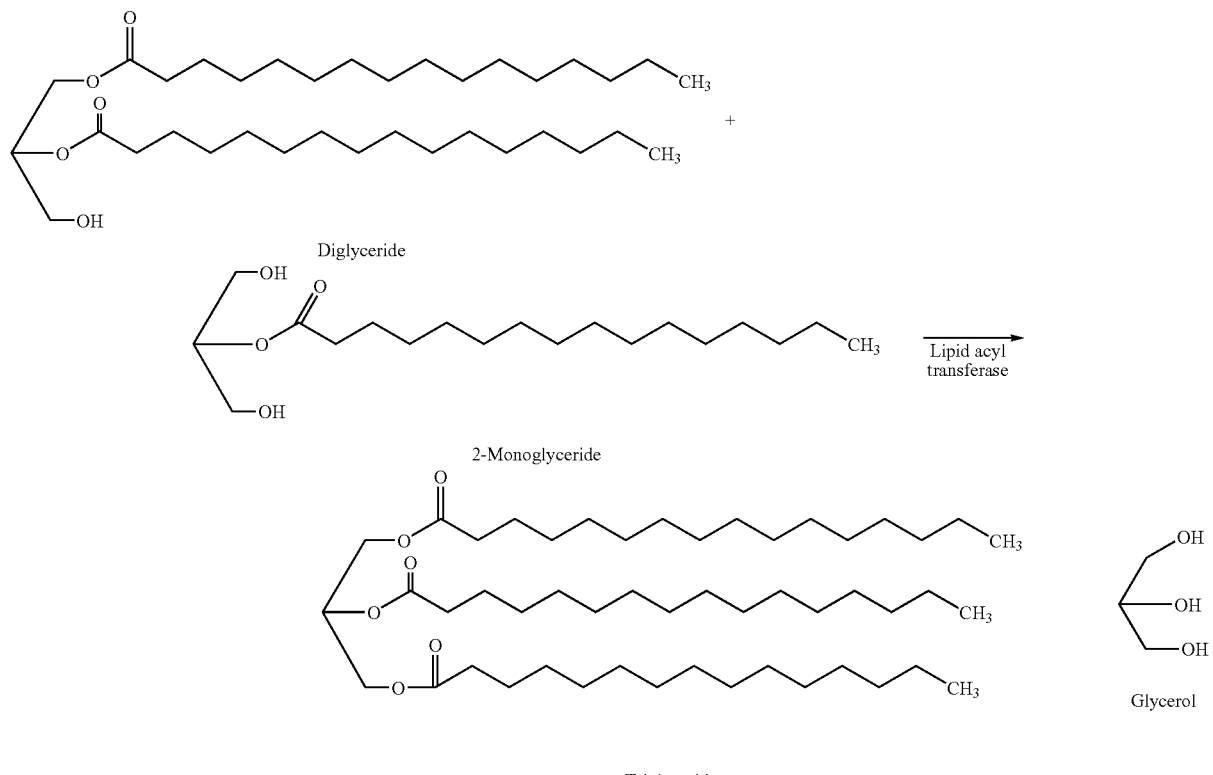

After the reaction the surplus glycerol can, if deemed necessary, easily be separated from the reaction mixture by centrifugation or other processes.

The advantage of this process is that the amount of diglyceride (preferably 1,2 diglyceride) is reduced by a glycerolysis reaction catalysed by an enzyme which is specific for diglyceride without using the triglyceride as donor for the transferase reaction.

The reaction products monoglycerides do not have to be removed from the reaction mixture, but can advantageously be used as an efficient emulsifier for the production of food products like margarine and shortening. The process thus solves two problems. First of all the amount of diglyceride is reduced and preferable 1,2 diglyceride is removed, which has a negative impact on the crystallisation properties of the triglycerides. Secondly the reaction product monoglyceride can be used as an efficient emulsifier in the production of food products like margarine and shortening.

In one embodiment, it is preferably to remove the monoglycerides produced (if any) by the transferase reaction.

Suitably, if the transferase reaction has been carried out in the crude palm oil, the monoglyceride and/or glycerol and/or residues of water (if any) may be removed by a deodorisation process during the edible oil refining process.

Another very interesting advantage of the use of the lipid acyl transferase is that this enzyme is less dependent of the water content in the reaction mixture and because this enzyme is a transferase low or no hydrolytic activity takes place which means that the amount of free fatty acids do not increase significantly.

It is well known the water content in glycerolysis reactions are very important when lipopytic enzymes like lipases are use in this process (Kristensen, 2004). Even small amount of water, which is necessary for most lipolytic reactions will cause the formation of significant amount of free fatty acids. This problem can be overcome by using the lipid acyl transferase in the glycerolysis reaction.

Another aspect is that lipases known in the art to catalyse glycerolysis reaction, mainly uses triglyceride as donor during formation of diglyceride instead of reducing the amount of diglyceride.

Materials:

Palm oil: Palmotex, Aarhus United, Denmark
Glycerol: J. T. Baker, (7044)
DIMODAN® P: Danisco A/S, Denmark
Enzyme: Lipid acyltransferase GCAT from *Aeromonas salmonicida* expressed in *B. subtilis* and fermented in lab scale (Transferase #196).

Methods

Lyophilization of Enzyme

The enzymes were desalted (PD-10 Desalting columns, Amersham Biosciences) before lyophilization. The desalted enzyme were mixed with glycerol (Enzyme:Glycerol ratio 3,5:1). The sample was lyophilised and added 10% water. The sample contained approximately 20 U (phospholipase units) per gram.

Determination of Phospholipase Activity (Phospholipase Activity Assay):

Substrate 0.6% L-α Phosphatidylcholine 95% Plant (Avanti # 441601), 0.4% Triton-X 100 (Sigma X-100) and 5 mM $CaCl_2$ was dissolved in 0.05M HEPES buffer pH 7.

Assay Procedure:

400 μL substrate was added to an 1.5 mL Eppendorf tube and placed in an Eppendorf Thermomixer at 37° C. for 5 minutes. At time t=0 min, 50 μL enzyme solution was added. Also a blank with water instead of enzyme was analyzed. The sample was mixed at 10*100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity PLU-7 at pH 7 was calculated as micromole fatty acid produced per minute under assay conditions Enzyme Reaction Palm oil was reacted with the glycerol-enzyme solution according to the following recipes in Table 1 and Table 2

TABLE 1

| | Experiment I | | | |
|---|---|---|---|---|
| Enz. no. | Transferase #196 | | | |
| Sample no. | 1 | 2 | 3 | 4 |
| Gl (%) | 5 | 5 | 5 | 10 |
| Water (%) | 0 | 1 | 5 | 1 |
| Oil phase (%) | 95 | 94 | 90 | 89 |
| Water in the reaction mixture | 0.5 | 1.5 | 5.5 | 1.5 |

TABLE 2

| | Experiment II | | | | | |
|---|---|---|---|---|---|---|
| Enz. No. | Transferase #196 | | | | | |
| Sample no. | 1 | 2 | 3 | 4 | 5 | 6 |
| Gl (%) | 5 | 5 | 5 | 10 | 10 | 10 |
| Water (%) | 1 | 5 | 7.5 | 1 | 5 | 7.5 |
| Oil phase (%) | 94 | 90 | 87.5 | 89 | 85 | 82.5 |
| Water in the reaction mixture | 1 | 5 | 7.5 | 1 | 5 | 7.5 |

The palm oil was scaled in a 20 ml Wheaton glass and the glycerol/enzyme and optional water was added. The sample was placed in heating block (Multitherm HP 15 Stheating block heated with differential stirring (15 wells) controlled by a VARIOMAG—Thermomodul 40 ST thermostat) and reacted under the following conditions:

| Reaction temperature | 43° C. |
|---|---|
| Magnetic Stirring | 650 rpm |
| Reaction time | 20 hours |

The enzyme in the reaction mixture was inactivated at 97.5° C. in 10 min. After reaction the sample were homogenized (Ultra Turrax) for 20 sec. and a homogeneous sample was taken out for further analysis.

HPTLC

Applicator: LINOMAT 5, CAMAG applicator.
HPTLC plate: 10×10 cm (Merck no. 1.05633)

The plate was activated before use by-drying in an oven at 180° C. for 20-30 minutes.

Application: 2.0 μl of a 2.0% solution of reacted palm oil dissolved in Chloroform:Methanol (2:1) was applied to the HPTLC plate using LINOMAT 5 applicator.

Running-buffer: P-ether:MTBE:Acetic acid (50:50:1)
Application/Elution time: 8 minutes.
Developing fluid: 6% Cupriacetate in 16% $H_3PO_4$ After elution the plate was dried in an oven at 180° C. for 10 minutes, cooled and immersed in the developing fluid and then dried additional in 20 minutes at 180° C. The plate was evaluated visually and scanned (ScanWizard 5) directly.

In Experiment II the components are quantified by Adobe photoshop 6.0 and the amount of MAG and DAG was calculated from calibrations curves of DAG and MAG standard solutions (see FIGS. 49 & 50).

Gas Chromatography

Perkin Elmer 8420 Capillary Gas Chromatography equipped with WCOT fused silica column 12.5 m×0.25 mm ID×0.1 μm 5% phenyl-methyl-silicone (CP Sil 8 CB from Crompack).

Carrier: Helium.
Injection: 1.5 μl with split.
Detector: FID. 385° C.

| Oven program | 1 | 2 | 3 | 4 |
|---|---|---|---|---|
| Oven temperature, ° C. | 80 | 200 | 240 | 360 |
| Isothermal, time, min. | 2 | 0 | 0 | 10 |
| Temperature rate, ° C./min. | 20 | 10 | 12 | |

Sample preparation: 50 mg lipid was dissolved in 12 ml heptane:pyridine (2:1) containing an internal standard heptadecane, 2 mg/ml. 500 μl of the sample was transferred to a crimp vial. 100 μl MSTFA (N-Methyl-N-trimethylsilyl-trifluoracetamid) was added and the reaction was incubated for 15 minutes at 60° C.

Calculation: Response factors for mono-di-triglycerides, free fatty acids were determined from reference mixtures of these components. Based on these response factors the lipids in the samples were calculated.

Results

Experiment I:

The aim of this experiment was to examine the impact of a diglyceride:glycerol acyltransferase from *Aeromonas salmonicida* on DAGs in palm oil by glycerolysis reaction. It is known that a GCAT is able to transfer fatty acid from lecithin the cholesterol during formation of cholesterolester and lysolecithin. In this study we have investigated the possibility of the enzyme to use DAGs as donor and glycerol as acceptor in order to reduce the amount of DAGs in palm oil and produce monoglyceride.

It is well known in the literature to use enzyme like lipases to catalyze glycerolysis reactions. In these reactions triglycerides is the main substrate and mono-and diglycerides are the reactions products. In these processes the amount of diglycerides increases significantly and the amount of diglycerides produced is on level or high than the amount of monoglyceride produced (Kristensen, 2004).

Four different sample compositions were tested and compared to a reference of palm oil mixed with 5% glycerol but without enzyme and treated in the same way as the samples. FIG. 47 shows the result of the HPTLC analysis of the sample from table 1.

The results obtained from the HPTLC analysis shows that the amount of DAGs varies according to the reaction conditions (referring to ratio between GL:H$_2$O). Equal to all the reactions was that the 1,3-isomers of diglyceride were in higher portion than the 1,2-(2,3-) isomers of diglyceride. This observation can be confirmed by theory, which says that the ratio of 1,3-isomer to 1,2-(2,3-) isomer in crude palm oil is 7:3 (Siew & Ng, 1999; Timms, 2004). Furthermore, analyzing the result, the HPTLC plate shows that the transferease successfully reduces the amount of DAGs. The reduction can to some extent correlate to the amount of synthesized MONO.

If we compare the 1,2 isomer with the 1,3 isomer DAGs in FIG. 1 it appears that the 1,2 DAGs are primarily reduced by the enzyme-catalyzed reaction. This is in agreement with the transferease has a preferred specificity for fatty acids in sn2-position.

In experiments conducted different water concentrations in range of 0.5-5.5% were used. It appears from the result that the water concentration has a significant impact on the synthesized amount of MONO combined to the reduced amount of DAGs. In this instance transferase #196 shows that if the system contains low water concentration increased concentration of MONO is formed and corresponding decreased amount of DAG is observed. The experiment also investigates whether the amount of glycerol has an effect on the equilibrium in the system (Lane 5: 10% GL: 1% H$_2$O). Transferease #196 shows that higher concentration of glycerol—also meaning double dosage of enzyme activity—dose not result in higher MONO concentration.

Preferably the present invention is carried out in a low water environment i.e. less than about 1%.

One of the advantages working with transfereases instead of lipases is that the synthesis of MONO dose not correlates to excessive increased in the concentration of FFA. This fact is confirmed in present experiment. FIG. 1 shows that none of the reactions shows clear band of FFA (FFA band was expected to be visible between 1,3 DAGs and TAGs).

From this experiment it can be summarized that the optimal concentration of glycerol and water for Transferase #196 is as following:

Transferase #196: 5% GL:0.5% H$_2$O

The sample procedure in HPTLC analysis did not include specific weighing, because of that it was not possible to calculate the concentrations of the different components in the reaction mixtures. Because of that the observation is solely based on visual evaluation.

Result GC

Based on the HPTLC results sample No. 2 was selected for GC analysis. To find out whether the visual evaluation of the HPTLC plates could be confirmed by quantitative analyses of DAG. Before analysis glycerol was removed from the sample by centrifugation and only the lipid phase was exposed to GC analysis The GC results are presented in Table 3 below.

TABLE 3

Result of GC on selected reaction in Experiment I

| Sample No. | Ref. 1 | #196 2 |
|---|---|---|
| Gl (%)* | 5 | 5 |
| Water (%) | 0 | 0 |
| Oil phase (%) | 95 | 95 |
| GC results | | |
| MONO | <0.01 | 0.34 |
| DAG | 6.21 | 5.77 |

*Glycerol contains 10% water

Analyzing the result of the GC study it was found that the selected sample differ from the reference in higher MONO content and lower DAG yield. This observation supports the obtained results in the HPTLC analysis.

Conclusion: Experiment I

Concerning content of monoglycerides and diglycerides in the product of glycerolysis, the results of HPTLC analysis indicated that there is a correlation between the concentration of water and the amounts of MONO and DAGs, respectively: The lower concentration of water, the lower DAGs and higher MONO.

GC analysis confirmed degree of reduction in DAG. In this experiment the reduced amount of DAGs counts for 7.1% of the total amount of diglycerides palm oil (Table 4).

TABLE 4

Degree of reduction of DAGs

| Enz. No. | #196 |
|---|---|
| Sample no. | 2 |
| Reduction of DAGs (%) | 7.1 |

Experiment II:

The aim of this part was to continue the optimization of DAG reduction in palm oil and analyze the transferase-catalysed glycerolysis using Transferease #196. The primarily purpose is to reach a well-balanced reaction in which the amount of DAG has been reduced in time with increase concentration of MONO.

In this part of the experimental work six different sample compositions were tested and compared to a reference of palm oil mixed with 5% glycerol (Table 2). The reference was exposed to the same heating profile as the enzyme reactions, which makes it possible to observe and determine the degree of thermal degradation during reduction. FIG. 48 shows the result of the HPTLC analysis.

It appears from the results in FIG. 48 that especially the amount of MAG is varying. The HPTLC analysis shows that in samples containing 5% glycerol (Lane: 1-3) there is continuous relation between water concentration and MAG yield: Decreased amount of water in the reaction mixture is followed by increased MAG yield. The same tendency is observed in the reactions containing 10% glycerol (Lane: 5-7).

According to the amount of diglycerides, it was not possible to differentiate the samples solely based on visual evaluation of the HPTLC plate. Therefore, to be able to distinguish between the samples, components were quantified by analyzing standard materials with known composition of MAG and DAG. The HPTLC plates were scanned and handle by Adobe Photoshop 6.0 and further calculated by help from a constructed calculation macro (Microsoft Excel 2000). The quantitative analysis of the components analyzed by HPTLC is presented in Table 5 below.

TABLE 5

| Enz. No. | Transferase #196 | | | | | | |
|---|---|---|---|---|---|---|---|
| Run order: HPTLC | 1 | 2 | 3 | 4 | 5 | 6 | 7 |
| MONO (%) | 0.38 | 0.01 | Nm*. | 0.01 | 0.15 | 0.07 | 0.03 |
| DAG (%) | 7.24 | 8.13 | Nm*. | 8.35 | 8.26 | 7.88 | 7.62 |
| Reduction of DAG (%) | 13.29 | 2.63 | — | — | 1.08 | 5.63 | 8.74 |

Nm* Not measured
— not calculated.

The investigation supports the visual evaluation and gives a fine picture of the varying level of diglycerides. It is seen from the results that the highest degree of reduction in the amount of DAGs was achieved in sample no. 1 (5% GL:1.5% $H_2O$). Further it is observed that this sample also contains the highest amount of MAG.

Conclusion: Experiment II

Experiment II confirmed the observations that a lipid acyltransferase GCAT from *Aeromonas salmonicida* was able to reduce the amount of diglycerides in palm oil. For the experiments with 5% glycerol a correlation was found between the concentration of water in the reaction mixture and the amounts of MAG and DAGs, respectively: The lower concentration of water, the lower DAGs and higher MAG.

HPTLC quantified the degree of reduction (see Table 5). It appears from the results, that the reduced amount of DAGs counts for 13.29% of the total amount of diglycerides in palm oil and the amount of synthesized MONO raised from 0.01% (ref.) to 0.38% (sample No. 1).

From this experiment it can be summarized that the optimal concentration of glycerol and water for Transferase #196 is as following:

Transferase #196: 5% GL:1.5% $H_2O$

Comparing these observations with the result gained in Experiment I, it is confirmed that good consistency in the results is obtained. The optimal concentration of water is presumably between 0-1% $H_2O$ depending on enzyme activity and content of glycerol.

Based on the two experiments conducted, it can be concluded that it is possible to reduce the amount of DAGs in palm oil by a transferase-catalysed reaction, where the enzyme uses DAGs as donor molecules and glycerol as acceptor molecule, in a glycerolysis reaction in which monoglycerides is synthesized. This is in strong contrast to the glycerolysis reaction with conventional triglycerides hydrolyzing lipases where the amount of DAG increases due to the partial hydrolysis activity of the triglycerides hydrolyzing lipase.

Based on the fact that the structure of diglycerides is a mixture 1,2- and 1,3-isomers and that the transferase is specific to the sn2-position, even a small reduction in the amount of diglyceride will have a huge physical impact on palm-based products.

EXAMPLE 7

Immobilisation of a Diacylglycerol:Glycerol Transferase (an Lipid Acyltransferase According to the Present Invention) from *Aeromonas salmonicida*

The diacylglycerol:glycerol transferase is immobilised on Celite by acetone precipitation. 10 ml enzyme solution in 20 mM TEA buffer pH 7 is agitated slowly with 0.1 gram Celite 535 (from Fluka) for 2 hours at room temperature. 50 ml cool acetone is added during continued agitation.

The precipitate is isolated by centrifugation 5000 g for 1 minute.

The precipitate is washed 2 times with 20 ml cold acetone.
The Celite is tried at ambient temperature for about 1 hour.
The immobilised transferase is tested in palm oil (see table below):

TABLE

| | % |
|---|---|
| Palm oil | 92.5 |
| Glycerol | 5 |
| Immobilised diacylglycerol:glycerol On Celite, #178, 45 U/g | 2.0 |
| Water | 0.5 |

Palm oil and glycerol is heated to 42° C. The immobilised transferase was added.

The transferase reaction continued at 42° C. during gentle agitation with a magnetic stirrer. Samples are taken out for analyses after ½, 1, 3, 6 and 24 hours and analysed by HPTLC. The reaction is stopped after 24 hours reaction time and the immobilised enzyme was filtered off.

The HPTLC analysis clearly shows the effect of the immobilised diacylglycerol:glycerol from *A. salmonicida* by the formation of monoglyceride and reduction of diglyceride in palm oil.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention will now be further described by the following numbered paragraphs:

1. A method of reducing and/or removing diglyceride from an edible oil, comprising a) admixing an edible oil with an acyl acceptor substrate and a diglyceride:glycerol acyltransferase, wherein the diglyceride:glycerol acyltransferase is characterized as an enzyme which in an edible oil is capable of transferring an acyl group from a diglyceride to glycerol.

2. A method according to paragraph 1 wherein the diglyceride:glycerol acyltransferase comprises the amino acid sequence motif GDSX, wherein X is one or more of the following amino acid residues L, A, V, I, F, Y, H, Q, T, N, M or S.

3. A method according to paragraph 1 wherein the amount of diglyceride in the edible oil is reduced.

4. A method according to paragraph 1 or paragraph 2 wherein the diglyceride:glycerol acyltransferase transfers an acyl group from a diglyceride to an acyl acceptor, wherein the acyl acceptor is any compound comprising a hydroxy group (—OH).

5. A method according any one of paragraphs 1 to 4, wherein the diglyceride is a 1,2-diglyceride.

6. A method according to any one of the preceding paragraphs wherein acyl acceptor is one which is soluble in an edible oil.

7. A method according to any one of the preceding paragraphs wherein the acyl acceptor is an alcohol.

8. A method according to paragraph 7 wherein the acyl acceptor is an alcohol.

9. A method according to paragraph 8 wherein the acyl acceptor is glycerol.

10. A method according to any one of the preceding paragraphs wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

11. A method according to any one of the preceding paragraphs wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

12. A method according to any one of the preceding paragraphs wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SED ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, (xv) the amino acid sequence shown as SEQ ID no. 55; (xvi) the amino acid sequence shown as SEQ ID No. 58; (xvii) the amino acid sequence shown as SEQ ID No. 60; (xviii) the amino acid sequence shown as SEQ ID No. 61; (xix) the amino acid sequence shown as SEQ ID No. 63; (xx) the amino acid sequence shown as SEQ ID No. 65; (xxi) the amino acid sequence shown as SEQ ID No. 67; (xxii) the amino acid sequence shown as SEQ ID No. 70 or (xxiii) an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ BD No. 28, SEQ ID No. 30, SEQ ID No. 32, SEQ ID No. 34, SEQ ID No. 55, SEQ ID No. 58, SEQ ID No. 60, SEQ ID No. 61, SEQ ID No. 63, SEQ ID No. 65, SEQ ID No. 67 or SEQ ID No. 70.

13. A method according to any one of the preceding paragraphs wherein the lipid acyltransferase comprises an amino acid sequence encoded by one or more of the following nucleotide sequences:
a) the nucleotide sequence shown as SEQ ID No. 7;
b) the nucleotide sequence shown as SEQ ID No. 8;
c) the nucleotide sequence shown as SEQ ID No. 9;
d) the nucleotide sequence shown as SEQ ID No. 10;
e) the nucleotide sequence shown as SEQ ID No. 11;
f) the nucleotide sequence shown as SEQ ID No. 13;
g) the nucleotide sequence shown as SEQ ID No. 21;
h) the nucleotide sequence shown as SEQ ID No. 23;
i) the nucleotide sequence shown as SEQ ID No. 25;
j) the nucleotide sequence shown as SEQ ID No. 27;
k) the nucleotide sequence shown as SEQ ID No. 29;
l) the nucleotide sequence shown as SEQ ID No. 31;
m) the nucleotide sequence shown as SEQ ID No. 33;
n) the nucleotide sequence shown as SEQ ID No. 35;
o) the nucleotide sequence shown as SEQ ID No. 54;
p) the nucleotide sequence shown as SEQ ID No. 59;
q) the nucleotide sequence shown as SEQ ID No. 62;
r) the nucleotide sequence shown as SEQ ID No. 64;
s) the nucleotide sequence shown as SEQ ID No. 66;
t) the nucleotide sequence shown as SEQ ID No. 68
u) the nucleotide sequence shown as SEQ ID No. 69 or
v) a nucleotide sequence which has 75% or more identity with any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 54, SEQ ID No. 59, SEQ ID No. 62, SEQ ID No. 64, SEQ ID No. 66, SEQ ID No. 68 or SEQ ID No. 69.

14. Use of a diglyceride:glycerol acyltransferase characterized as an enzyme which in an edible oil is capable of transferring an acyl group from a diglyceride to glycerol, in the manufacture of an edible oil, for reducing and/or removing (preferably selectively reducing and/or removing) diglyceride from said edible oil.

15. Use of a diglyceride:glycerol acyltransferase characterized as an enzyme which in an edible oil is capable of transferring an acyl group from a diglyceride to glycerol, in the manufacture of a foodstuff comprising an edible oil for improving the crystallization properties of said foodstuff.

16. Use according paragraph 14 or paragraph 15 wherein the diglyceride:glycerol acyltransferase comprises the amino acid sequence motif GDSX, wherein X is one or more of the following amino acid residues L, A, V, I, F, Y, H, Q, T, N, M or S.

17. Use according to any one of paragraphs 14, 15 or 16 wherein the amount of diglyceride in the edible oil is reduced.

18. Use according to any one of paragraphs 14 to 17 wherein the diglyceride:glycerol acyltransferase is capable of transferring an acyl group from a diglyceride to an acyl acceptor, wherein the acyl acceptor is any compound comprising a hydroxy group (—OH).

19. Use according any one of paragraphs 14 to 18, wherein the diglyceride is a 1,2-diglyceride.

20. Use according to any one of paragraphs 14 to 19 wherein acyl acceptor is one which is soluble in an edible oil.

21. Use according to any one of paragraphs 13-17 wherein the acyl acceptor is an alcohol.

22. Use according to paragraph 21 wherein the acyl acceptor is an alcohol.

23. Use according to paragraph 22 wherein the acyl acceptor is glycerol.

24. Use according to any one of paragraphs 14-23 wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

25. Use according to any one of paragraphs 14-24 wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

26. Use according to any one of paragraphs 14-25 wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SED ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, (xv) the amino acid sequence shown as SEQ ID No. 55; (xvi) the amino acid sequence shown as SEQ ID No. 58; (xvii) the amino acid sequence shown as SEQ ID No. 60; (xviii) the amino acid sequence shown as SEQ ID No. 61; (xix) the amino acid sequence shown as SEQ ID No. 63; (xx) the amino acid sequence shown as SEQ ID No. 65; (xxi) the amino acid sequence shown as SEQ ID No. 67; (xxii) the amino acid sequence shown as SEQ ID No. 70 or (xxiii) an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 55, SEQ ID No. 58, SEQ ID No. 60, SEQ ID No. 61, SEQ ID No. 63, SEQ ID No. 65, SEQ ID No. 67 or SEQ ID No. 70.

27. Use according to any one of paragraphs 14-26 wherein the lipid acyltransferase comprises an amino acid sequence encoded by one or more of the following nucleotide sequences:
a) the nucleotide sequence shown as SEQ ID No. 7;
b) the nucleotide sequence shown as SEQ ID No. 8;
c) the nucleotide sequence shown as SEQ ID No. 9;
d) the nucleotide sequence shown as SEQ ID No. 10;
e) the nucleotide sequence shown as SEQ ID No. 11;
f) the nucleotide sequence shown as SEQ ID No. 13;
g) the nucleotide sequence shown as SEQ ID No. 21;
h) the nucleotide sequence shown as SEQ ID No. 23;
i) the nucleotide sequence shown as SEQ ID No. 25;
j) the nucleotide sequence shown as SEQ ID No. 27;
k) the nucleotide sequence shown as SEQ ID No. 29;
l) the nucleotide sequence shown as SEQ ID No. 31;
m) the nucleotide sequence shown as SEQ ID No. 33;
n) the nucleotide sequence shown as SEQ ID No. 35;
o) the nucleotide sequence shown as SEQ ID No. 54;
p) the nucleotide sequence shown as SEQ ID No. 59;
q) the nucleotide sequence shown as SEQ ID No. 62;
r) the nucleotide sequence shown as SEQ ID No. 64;
s) the nucleotide sequence shown as SEQ ID No. 66;
t) the nucleotide sequence shown as SEQ ID No. 68
u) the nucleotide sequence shown as SEQ ID No. 69 or
v) a nucleotide sequence which has 75% or more identity with any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 54, SEQ ID No. 59, SEQ ID No. 62, SEQ ID No. 64, SEQ ID No. 66, SEQ ID No. 68 or SEQ ID No. 69.

28. Use according to any one of paragraphs 14-27 wherein the diglyceride:glycerol acyltransferase is used in combination with a crystallization inhibitor.

29. A method substantially as hereinbefore described with reference to the accompanying description and the figures.

30. A use substantially as hereinbefore described with reference to the accompanying description and figures.

REFERENCES

Amano Enzyme Inc. (2004). Product description available at Amano Enzyme website. Dated: Jun. 21, 2004

Fødevareministeriet (2003). Bekendtgørelse om indhold af transfedtsyrer i olier og fedtstoffer. Bekendtgørelse nr. 160 af Nov. 3, 2003

Directive 2000/36/EC. Available at ScadPlus website. Dated: Jun. 16, 2004

Karlshamns, (2004). Press information available at Aarhaus Karlshamns website Dated: Jun. 16, 2004

Berger, K. G. (1990). Recent developments in palm oil. In *Oleagineux* 45: 437-443

Drozdowski, B. (1994). General characteristics of eatable fats. WNT, Warszawa, Poland, pp. 240-243 (In polish)

Hernquist, L. & Anjou, K. (1983). Diglycerides as a stabilizer of the β'-crystal Form in Margarines and Fats. In *Fette Seifen Anstrichmittel*. 2: 64-66

Hernquist, L. Herslof, B. Larsson, K. & Podlaha, O (1981). Polymorphism of rapeseed oil with low content of erucic acid and possibilities to stabilize the β' crystal form in fats. In *Journal of Science and Food Agriculture*. 32: 1197-1202

Jacobsberg, B. & Oh, C. H. (1976). Studies in Palm Oil Crystallisation. In *Journal of the American Oil Chemist Society*. 53: 609-616

Kristensen, A. C. J. (2004). Preparation of margarine and spreads by enzyme-generated emulsifiers. Master thesis, The Royal Veterinary and Agricultural University, Frederiksberg, Copenhagen McNeill, G. P. & Berger, R. G. (1993). Enzymatic glycerolysis of palm oil fractions and palm oil based model mixture: Relationship between fatty acid composition and monoglyceride yield. In *Food Biotechnology* 7: 75-87

Okiy, D. A. (1977). Partial glycerides and palm oil Crystallisation. In *Journal of Science and Food Agriculture*. 28: 955

Okiy, D. A. (1978). Interaction of triglycerides and diglycerides of palm oil. In *Oleagineux*. 33: 625-628

Okiy, D. A., Wright, W. B., Berger, K. G. & Morton, I. D. (1978). The physical properties of modified palm oil. In *Journal of Science of Food and Agriculture*. 29: 625-628

Walnett, S. V., Meusel, D. & Tülsner, M. (1991). Zur kenntnis des diglyceride influsses auf das kristallisationsverhalten von Fetten. In *Fat Science Technology*. 4: 117-121

Siew, N. L. (2001). Understanding the Interactions of Diacylglycerols with oil for better Product performance. Paper presented at the 2001 PIPOC International Palm Oil Congress—Chemistry and Technology Conference. 20-23 Aug. 2001, Kuala Lumpur, Malaysia Siew, N. L. & Ng, W. L. (2000). Differential scanning thermograms of palm oil triglycerides in the presence of diglycerides. In *Journal of Oil Palm Research*. 12: 1-7

Siew, N. L. & Ng, W. L. (1999). Influence of diglycerides on crystalisation of palm oil. In *Journal of Science of Food and Agriculture*. 79: 722-726

Sonntag, N. O. V. (1982a). Fat splitting, esterification and interesterification. Bailey's Industrial Oils and Fat products, Vol. 2, $4^{th}$ edn. John Wiley and Sons, New york pp. 97-173

Sonntag, N. O. V. (1982b). Glycerolysis of Fats and methyl esters—status, review and critique. In *Journal of American Oil Chemist Society*. 59: 795A-802A Timms, R. (2004). Oral presentation (Lecture: Trends & delvlopment) at Danisco A/S, Brabrand, Denmark.

The invention claimed is:

1. A method of reducing and/or removing diglyceride from an edible oil, comprising admixing an edible oil with an acyl acceptor substrate and a diglyceride:glycerol acyltransferase, wherein the diglyceride:glycerol acyltransferase comprises the amino acid sequence encoded by a nucleotide sequence having at least 95% identity with SEQ ID NO: 8; and is characterized as an enzyme which in an edible oil is capable of transferring an acyl group from a diglyceride to glycerol, and wherein the acyl acceptor substrate has a hydroxy group (—OH).

2. The method according to claim 1, wherein the diglyceride:glycerol acyltransferase is used in combination with a crystallization inhibitor.

3. The method according to claim 1, wherein the edible oil is one or more of the following oils:oils extracted from or derived from palm oil, palm olein, palm stearin, palm mid fraction or olive oil.

4. The method according to claim 1, wherein the edible oil is palm oil.

5. The method according to claim 1, wherein the amount of diglyceride in the edible oil after admixing with the acyl acceptor substrate and the diglyceride:glycerol acyl transferase is reduced as compared to said edible oil before so admixing.

6. The method according to claim 1, wherein the diglyceride is a 1,2-diglyceride.

7. The method according to claim 1, wherein the acyl acceptor is one which is soluble in an edible oil.

8. The method according to claim 1, wherein the acyl acceptor substrate is an alcohol.

9. The method according to claim 8, wherein the acyl acceptor substrate is glycerol.

10. The method according to claim 1, wherein the acyltransferase enzyme comprises H-309 or comprises a histidine residue at a position corresponding to His-309 in the amino acid sequence of the *Aeromonas hydrophila* lipolytic enzyme shown as SEQ ID NO: 2.

11. The method according to claim 1, wherein the acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

12. The method according to claim 1, wherein the edible oil is a palm oil fraction.

* * * * *